US012545687B2

(12) United States Patent
Sato et al.

(10) Patent No.: US 12,545,687 B2
(45) Date of Patent: Feb. 10, 2026

(54) URACIL DERIVATIVES HAVING VIRUS REPLICATION INHIBITORY ACTIVITY AND PHARMACEUTICAL COMPOSITION COMPRISING THE SAME

(71) Applicant: Shionogi & Co., Ltd., Osaka (JP)

(72) Inventors: Jun Sato, Osaka (JP); Hiromitsu Shibayama, Osaka (JP); Keiichiro Hirai, Osaka (JP); Yuto Unoh, Osaka (JP); Shota Uehara, Osaka (JP); Shuji Yonezawa, Osaka (JP); Kana Kurahashi, Osaka (JP); Eiichi Kojima, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 18/554,130

(22) PCT Filed: Apr. 7, 2023

(86) PCT No.: PCT/JP2023/014316
§ 371 (c)(1),
(2) Date: Oct. 5, 2023

(87) PCT Pub. No.: WO2023/195529
PCT Pub. Date: Oct. 12, 2023

(65) Prior Publication Data

US 2025/0092056 A1 Mar. 20, 2025

(30) Foreign Application Priority Data

| | | |
|---|---|---|
| Apr. 8, 2022 | (JP) | 2022-064593 |
| Jun. 10, 2022 | (JP) | 2022-094627 |
| Dec. 23, 2022 | (JP) | 2022-207187 |

(51) Int. Cl.
*C07D 491/107* (2006.01)
*A61K 31/513* (2006.01)
(Continued)

(52) U.S. Cl.
CPC ........ *C07D 491/107* (2013.01); *A61K 31/513* (2013.01); *A61K 31/527* (2013.01);
(Continued)

(58) Field of Classification Search
CPC ......................... C07D 491/107; C07D 401/04; C07D 401/14; A61P 31/14; A61P 31/513; A61P 31/527
(Continued)

(56) References Cited

U.S. PATENT DOCUMENTS

| | | |
|---|---|---|
| 8,106,064 B2 | 1/2012 | Guo et al. |
| 2011/0076276 A1 | 3/2011 | Guo et al. |

(Continued)

FOREIGN PATENT DOCUMENTS

| | | |
|---|---|---|
| CN | 113620888 | 11/2021 |
| CN | 113666914 | 11/2021 |

(Continued)

OTHER PUBLICATIONS

International Search Report issued Jun. 13, 2023 in International (PCT) Application No. PCT/JP2023/014316.

(Continued)

*Primary Examiner* — Kahsay Habte
(74) *Attorney, Agent, or Firm* — Wenderoth, Lind & Ponack, L.L.P.

(57) ABSTRACT

The present invention provides a compound exhibiting coronavirus 3CL protease inhibitory activity or a pharmaceutically acceptable salt thereof, and a pharmaceutical composition comprising the same.
Provided is a compound represented by Formula (I):

(I)

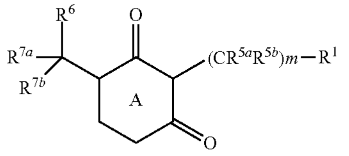

wherein Ring A is a ring represented by:

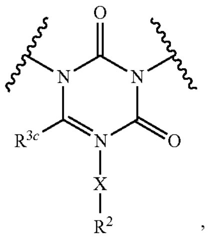

,

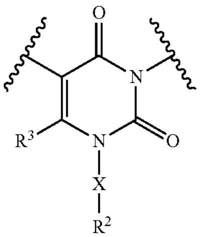

or

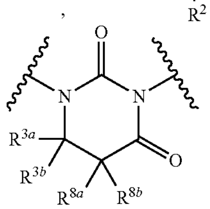

wherein X is a single bond or the like, $R^2$ is substituted or unsubstituted aromatic carbocyclyl or the like, $R^{3c}$ is substituted or unsubstituted aromatic carbocyclyl or the like, $R^3$ is substituted or unsubstituted aromatic carbocyclyl or the like, $R^{3a}$ is a hydrogen atom or the like, $R^{3b}$ is a hydrogen atom, $R^{8a}$ is substituted or unsubstituted aromatic carbocyclyl or the like, and $R^{8b}$ is a hydrogen atom or the like,
$R^1$ is a substituted or unsubstituted aromatic heterocyclyl, m is 0 or the like, $R^{5a}$ is each independently a hydrogen atom or the like, $R^{5b}$ is each independently a hydrogen
(Continued)

atom or the like, $R^6$ is cyano or the like, and $R^{7a}$ and $R^{7b}$ are each independently a hydrogen atom or the like, or a pharmaceutically acceptable salt of the compound.

6 Claims, No Drawings

Specification includes a Sequence Listing.

(51) Int. Cl.

| | |
|---|---|
| ***A61K 31/527*** | (2006.01) |
| ***A61P 31/14*** | (2006.01) |
| ***C07D 401/04*** | (2006.01) |
| ***C07D 401/14*** | (2006.01) |

(52) U.S. Cl.
CPC ............ *A61P 31/14* (2018.01); *C07D 401/04* (2013.01); *C07D 401/14* (2013.01)

(58) Field of Classification Search
USPC ........................................................ 514/260.1
See application file for complete search history.

(56) References Cited

U.S. PATENT DOCUMENTS

| | | | |
|---|---|---|---|
| 2016/0024072 | A1 | 1/2016 | Kai et al. |
| 2023/0128162 | A1 | 4/2023 | Tachibana et al. |
| 2023/0212154 | A1 | 7/2023 | Tachibana et al. |

FOREIGN PATENT DOCUMENTS

| | | |
|---|---|---|
| CN | 113735838 | 12/2021 |
| EP | 2 604 260 | 6/2013 |
| WO | 2005/095381 | 10/2005 |
| WO | 2021/205298 | 10/2021 |
| WO | 2021/250648 | 12/2021 |
| WO | 2022/224223 | 10/2022 |
| WO | 2023/002409 | 1/2023 |
| WO | 2023/046133 | 3/2023 |
| WO | 2023/046150 | 3/2023 |

OTHER PUBLICATIONS

"COVID-19 Dashboard by the Center for Systems Science and Engineering at Johns Hopkins University", [online], Johns Hopkins University, 1 page [Searched on Mar. 16, 2023], <URL:https://coronavirus.jhu.edu/map.html>.

Van Doremalen, N. et al., "Aerosol and Surface Stability of SARS-CoV-2 as Compared with SARS-CoV-1", The New England Journal of Medicine, Apr. 2020, vol. 382, No. 16, 4 pages.

"Report of the WHO-China Joint Mission on Coronavirus Disease 2019 (COVID-19)", [online], Feb. 28, 2020, WHO, 40 pages [Searched on Mar. 16, 2023], <URL:https://www.who.int/docs/default-source/coronaviruse/who-china-joint-mission-on-covid-19-final-report.pdf>.

Anand, Kanchan et al., "Coronavirus Main Proteinase ($3CL^{pro}$) Structure: Basis for Design of Anti-SARS Drugs", Science, Jun. 2003, vol. 300, pp. 1763-1767.

De Vries, Maren et al., "A Comparative Analysis of SARS-CoV-2 Antivirals Characterize $3CL^{pro}$ Inhibitor PF-00835231 as a Potential New Treatment for COVID-19", Journal of Virology, May 2021, vol. 95, Issue 10, 22 pages.

Ma, Chunlong et al., "Boceprevir, GC-376, and calpain inhibitors II, XII inhibit SARS-CoV-2 viral replication by targeting the viral main", Cell Research, Jun. 2020, vol. 30, pp. 678-692.

Zhang, Linlin et al., "Crystal structure of SARS-CoV-2 main protease provides a basis for design of improved α-ketoamide inhibitors", Science, Apr. 2020, vol. 368, pp. 409-412.

Zhang, Chun-Hui et al., "Potent Noncovalent Inhibitors of the Main Protease of SARS-CoV-2 from Molecular Sculpting of the Drug Perampanel Guided by Free Energy Perturbation Calculations", ACS Central Science, 2021, vol. 7, No. 3, pp. 467-475.

Owen, Dafydd, "Oral inhibitors of the SARS-CoV-2 main protease for the treatment of COVID-19", Am Chem Soc (ACS) Spring Meeting, Apr. 6-May 2, 2021, Virtual, Abstract only.

Owen, Dafydd R. et al., "An oral SARS-CoV-2 $M^{pro}$ inhibitor clinical candidate for the treatment of COVID-19", Science, Dec. 2021, vol. 374, pp. 1586-1593.

"Pfizer's Novel COVID-19 Oral Antiviral Treatment Candidate Reduced Risk of Hospitalization or Death by 89% in Interim Analysis of Phase 2/3 EPIC-HR Study", [online], Nov. 5, 2021, Pfizer Press Release, 21 pages.

Chen, Yanli et al., "Synthesis of I-(Alkoxymethyl)-5-benzyl-6-methyluracil as Potential Nonnucleoside HIV-1 RT Inhibitors", Synthetic Communications, 2006, vol. 36, No. 19, pp. 2913-2920.

"Discovery and Development of PBI-0451", [online], Mar. 24, 2022, 35th International Conference on Antiviral Research (ICAR), 29 pages [Searched on Mar. 16, 2023], <URL:https://ir.pardesbio.com/static-files/fc7c4f8c-e0bd-4b97-8c9c-eff09bafd4db>.

Olubiyi, Olujide O. et al., "High Throughput Virtual Screening to Discover Inhibitors of the Main Protease of the Coronavirus SARS-CoV-2", Molecules, 2020, vol. 25, No. 3193, 20 pages.

Akaji, Kenichi et al., "Design and Evaluation of Anti-SARS-Coronavirus Agents Based on Molecular Interactions with the Viral Protease", Molecules, 2020, vol. 25, No. 3920, 19 pages.

Liu, Yuzhi et al., "The development of Coronavirus 3C-Like protease ($3CL^{pro}$) inhibitors from 2010 to 2020", European Journal of Medicinal Chemistry, 2020, vol. 206, No. 112711, 18 pages.

Luttens, Andreas et al., "Ultralarge Virtual Screening Identifies SARS-CoV-2 Main Protease Inhibitors with Broad-Spectrum Activity against Coronavirus", Journal of the American Chemical Society, 2022, vol. 144, pp. 2905-2920.

"Xocova® (Ensitrelvir Fumaric Acid) Tablets 125mg Approved in Japan for the Treatment of SARS-CoV-2 Infection, under the Emergency Regulatory Approval System", Shionogi Press Release, Nov. 22, 2022, 6 pages.

Čaplar, Vesna et al., "A Novel Type of Rigid Macrocycle with Bis(3-uracilyl)methane and Hexadiyne Units. The Uracilophane", Croatica Chemica Acta, 1996, vol. 69, No. 4, pp. 1617-1631.

International Preliminary Report on Patentability issued Oct. 8, 2024 in the corresponding PCT application No. PCT/JP2023/014316, with English-language translation.

International Preliminary Report on Patentability issued Oct. 8, 2024 in application No. PCT/JP2023/014318, with English-language translation.

URACIL DERIVATIVES HAVING VIRUS REPLICATION INHIBITORY ACTIVITY AND PHARMACEUTICAL COMPOSITION COMPRISING THE SAME

SEQUENCE LISTING

A sequence listing in electronic (XML file) format is filed with this application and incorporated herein by reference. The name of the XML file is "ATTACHF_Sequence_Listing-1402.xml"; the file was created on Sep. 27, 2023; the size of the file is 3,574 bytes.

TECHNICAL FIELD

The present invention relates to a compound exhibiting coronavirus 3CL protease inhibitory activity and a pharmaceutical composition comprising a compound exhibiting coronavirus 3CL protease inhibitory activity.

BACKGROUND ART

Coronaviruses, which belong to the order Nidovirales, family Coronaviridae, and the subfamily Coronavirinae, are positive-sense single-stranded RNA viruses that have a genome size of about 30 kilobases and are the largest among the known RNA viruses. Coronaviruses are classified into four genera, namely, the genus Alphacoronavirus, Betacoronavirus, Gammacoronavirus, and Deltacoronavirus, and a total of seven types of coronaviruses, including two kinds in the genus Alphacoronavirus (HCoV-229E and HCoV-NL63) and five kinds in the genus Betacoronavirus (HCoV-HKU1, HCoV-OC43, SARS-CoV, MERS-CoV, and SARS-CoV-2), are known as coronaviruses that infect humans. Among these, four kinds (HCoV-229E, HCoV-NL63, HCoV-HKU1, and HCoV-OC43) are pathogens of common cold, while the other three kinds are severe acute respiratory syndrome (SARS) coronavirus (SARS-CoV), Middle East respiratory syndrome (MERS) coronavirus (MERS-CoV), and a novel coronavirus (SARS-CoV-2), all of which cause severe pneumonia.

Novel coronavirus infections (COVID-19) that occurred in December 2019, rapidly spread to the international community, and the pandemic was announced by the WHO on Mar. 11, 2020. The number of infected people confirmed as of Mar. 10, 2023, was more than 670 million, and the number of deaths reached more than 6.88 million (Non-patent Document 1). Droplet infection, contact infection, and aerosol infection have been reported as main routes of infection of SARS-CoV-2, and it has been confirmed that SARS-CoV-2 continues to drift in air together with aerosols and maintains infectivity for about 3 hours (Non-patent Document 2). The incubation period is about 2 to 14 days, and cold-like symptoms such as fever (87.9%), dry cough (67.7%), malaise (38.1%), and phlegm (33.4%) are typical (Non-patent Document 3). In severe cases, respiratory failure due to acute respiratory distress syndrome, acute lung injury, interstitial pneumonia, and the like occurs. Furthermore, multiple organ failure such as renal failure and hepatic failure has also been reported.

In Japan, as a result of drug repositioning of existing drugs, remdesivir, which is an antiviral drug, dexamethasone, which is an anti-inflammatory drug, and baricitinib, which is an antirheumatic drug, have been approved as therapeutic agents against COVID-19, and in January 2022, tocilizumab, which is an anti-IL-6 receptor antibody, have been received additional approval. Furthermore, in July 2021, ronapreve (casirivimab/imdevimab), which is an antibody cocktail therapy, was approved as special case approval, in September 2021, sotrovimab was approved as special case approval, and in December 2021, molnupiravir was approved as special case approval. Sufficient evidence has not been obtained on the efficacy and safety of these drugs. Accordingly, it is imperative to create therapeutic agents against COVID-19.

Upon infection of cells, coronaviruses synthesize two polyproteins. In these two polyproteins, replication complexes producing viral genomes, and two proteases are included. Proteases play an indispensable role for cleaving the polyproteins synthesized by viruses and causing each of the proteins to function. Between these two proteases, 3CL protease (main protease) bears most of the cleavage of the polyproteins (Non-patent Document 4).

Regarding COVID-19 therapeutic agents targeting 3CL proteases, it was published in ClinicalTrials.gov that Phase 1b trials for Lufotrelvir (PF-07304814), which is a prodrug of PF-00835231, have completed by Pfizer Inc (NCT04535167). Furthermore, in March 2021, Pfizer Inc. announced that Phase 1 trials for PF-07321332, a therapeutic agent against novel coronavirus infections, will be initiated. The structural formulae of PF-00835231, Lufotrelvir and PF-07321332 are as shown below, and these agents are different from the compound of the present invention in chemical structure (Non-patent Documents 5, 9 and 10 and Patent Documents 1 and 2).

[Chemical Formula 1]

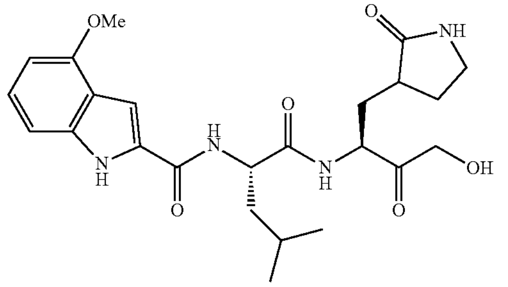

PF-00835231

[Chemical Formula 2]

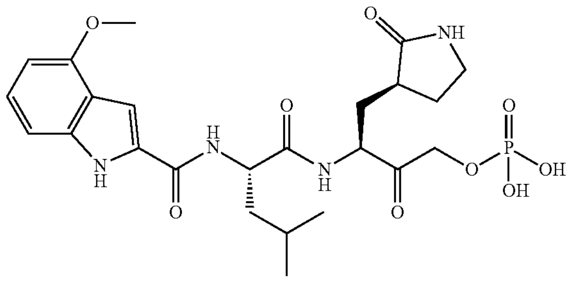

Lufotrelvir (PF-07304814)

-continued

[Chemical Formula 3]

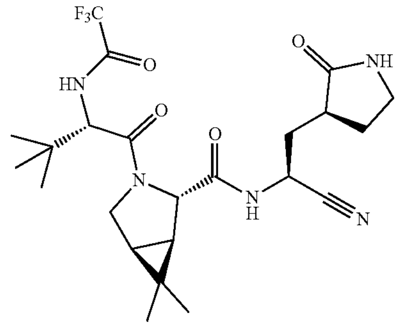

PF-07321332

In December 2021, PAXLOVID (trademark) was approved for emergency use in the United States, and on Feb. 10, 2022, the Paxlovid (registered trademark) PACK was approved as special case approval in Japan.

Furthermore, regarding COVID-19 therapeutic agents targeting 3CL proteases, the start of Phase 1 trials for PBI-0451 by Pardes Biosciences was reported in ClinicalTrials.gov on August 2021 (NCT05011812). The structural formula of PBI-0451 is as shown below, and these agents are different from the compound of the present invention in chemical structure (Non-patent Document 13).

[Chemical Formula 4]

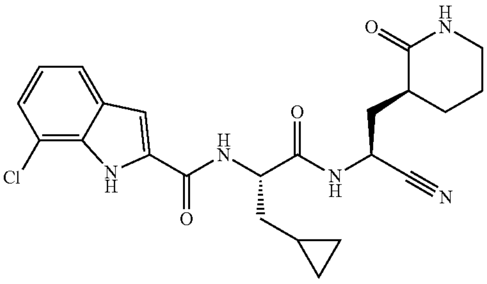

Furthermore, Xocova (registered trademark) was emergently approved in Japan on Nov. 22, 2022 as a COVID-19 therapeutic agent targeting 3CL protease (Non-Patent Document 18).

The active ingredient of Xocova is ensitrelvir fumaric acid, and the structural formula thereof is as shown below and is different in chemical structure from the compound of the present invention (Patent Documents 10 and 11).

[Chemical Formula 5]

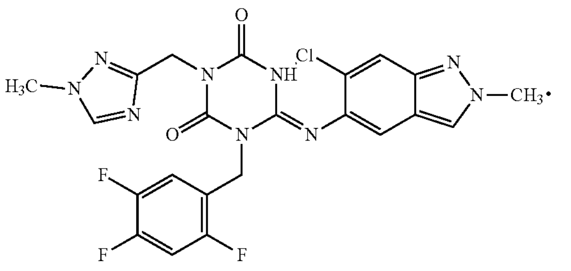

-continued

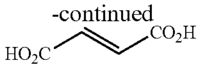

No sufficient evidence has been obtained for mutations resistant to COVID-19 therapeutic agents targeting 3CL proteases.

Compounds having 3CL protease inhibitory activity are disclosed in Non-patent Documents 5 to 8 and 14 to 17; however, the compounds related to the present invention are neither described nor suggested in any of the documents.

Compounds having $P2X_3$ and/or $P2X_{2/3}$ receptor inhibitory activity have been disclosed in Patent Documents 3 to 9; however, the 3CL protease inhibitory activity and the antiviral effect are neither described nor suggested in any of the documents.

Although compounds having an inhibitory action on HIV-1 reverse transcriptase are disclosed in Non-patent Document 12, 3CL protease inhibitory activity and anti-coronavirus effect have neither been described nor suggested.

PRIOR ART REFERENCES

Patent Document

[Patent Document 1] International Publication WO 2021/205298A

[Patent Document 2] International Publication WO 2021/250648A

[Patent Document 3] International Publication WO 2012/020742A

[Patent Document 4] International Publication WO 2013/118855A

[Patent Document 5] China Patent Application Publication CN 113620888A

[Patent Document 6] China Patent Application Publication CN 113666914A

[Patent Document 7] China Patent Application Publication CN 113735838A

[Patent Document 8] Chinese Patent Application Publication CN 113773300A

[Patent Document 9] Chinese Patent Application Publication CN 113801097A

[Patent Document 10] International Publication WO 2022/138987A

[Patent Document 11] International Publication WO 2022/138988A

Non-Patent Document

[Non-patent Document 1] "COVID-19 Dashboard by the Center for Systems Science and Engineering at Johns Hopkins University", [online], Johns Hopkins University, [retrieved on Mar. 16, 2023], Internet <URL: https://coronavirus.jhu.edu/map.html>.

[Non-patent Document 2] The NEW ENGLAND JOURNAL of MEDICINE (2020), Vol. 382, pp. 1564-1567.

[Non-patent Document 3] "Report of the WHO-China Joint Mission on Coronavirus Disease 2019 (COVID-19)", [online], Feb. 28, 2020, WHO, [retrieved on Mar. 16, 2023], Internet <URL: https://www.who.int/docs/default-source/coronaviruse/who-china-joint-mission-on-covid-19-final-report.pdf>.

[Non-patent Document 4] Science (2003), Vol. 300, pp. 1763-1767.

[Non-patent Document 5] "A comparative analysis of SARS-CoV-2 antivirals characterizes 3CLpro inhibitor PF-00835231 as a potential new treatment for COVID-19", Journal of Virology, 2021 Mar. 10; 95(7), e01819-20
[Non-patent Document 6] Cell Research (2020), Vol. 30, pp. 678-692.
[Non-patent Document 7] Science (2020), Vol. 368, pp. 409-412.
[Non-patent Document 8] ACS Central Science (2021), Vol. 7, No. 3, pp. 467-475.
[Non-patent Document 9] 261st Am Chem Soc (ACS) Natl Meet—2021 Apr. 5/2021 Apr. 16—Virtual, N/A—Abst 243
[Non-patent Document 10] Science (2021), Vol. 374, pp. 1586-1593.
[Non-patent Document 11] Pfizer's Novel COVID-19 Oral Antiviral Treatment Candidate Reduced Risk Of Hospitalization Or Death By 89% In Interim Analysis Of Phase 2/3 EPIC-HR Study, [online], Nov. 5, 2021, Pfizer Press Release, [retrieved on Mar. 16, 2023], Internet <URL: https://www.pfizer.com/news/press-release/press-release-detail/pfizers-novel-covid-19-oral-antiviral-treatment-candidate>
[Non-patent Document 12] Synthetic Communications (2006), Vol. 36, No. 19, pp. 2913-2920
[Non-patent Document 13] "Discovery and Development of PBI-0451", [online], Mar. 24, 2022, 35th International Conference on Antiviral Research (ICAR), [retrieved on Mar. 16, 2023], Internet <URL: https://ir.pardesbio.com/static-files/fc7c4f8c-e0bd-4b97-8c9c-eff09bafd4db>
[Non-patent Document 14] Molecules (2020), vol. 25, p. 3193
[Non-patent Document 15] Molecules (2020), vol. 25, p. 3920
[Non-patent Document 16] European Journal of Medicinal Chemistry (2020), Vol. 206, p. 112711
[Non-patent Document 17] Journal of the American Chemical Society (2022), vol. 144, pp. 2905-2920.
[Non-patent Document 18] Shionogi & Co., Ltd. Press Release (Nov. 22, 2022)

SUMMARY OF THE INVENTION

Problems to be Solved by the Invention

An object of the present invention is to provide a compound having coronavirus 3CL protease inhibitory activity. Preferably, the present invention provides a compound having an antiviral activity, particularly a coronavirus replication inhibitory activity, and a medicament comprising the compound.

Means for Solving the Problem

The present invention relates to the following.

(1") A compound represented by Formula (I):

[Chemical Formula 6]

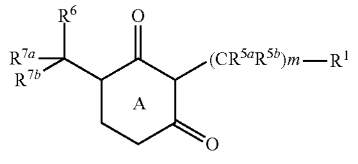

(I)

wherein

Ring A is a ring represented by:

[Chemical Formula 7]

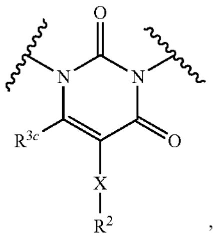

,

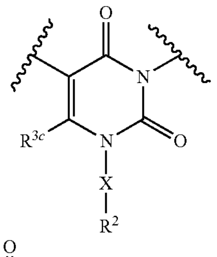

or

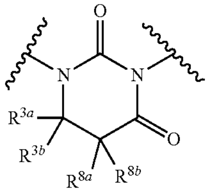

wherein

X is a single bond, —$CR^{4a}R^{4b}$—, —C(═O)—, —O—, or —S—;

$R^{4a}$ and $R^{4b}$ are each independently a hydrogen atom, or substituted or unsubstituted alkyl;

$R^2$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or substituted or unsubstituted alkyl;

$R^{3c}$ is a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, substituted or unsubstituted amino, substituted or unsubstituted carbamoyl, or substituted or unsubstituted alkyloxy;

$R^3$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, substituted or unsubstituted amino, substituted or unsubstituted carbamoyl, or substituted or unsubstituted alkyloxy;

$R^{3a}$ is a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, or substituted or unsubstituted alkyloxy;

$R^{3b}$ is a hydrogen atom;

$R^{8a}$ is substituted or unsubstituted aromatic carbocyclyl or substituted or unsubstituted aromatic heterocyclyl; and $R^{8b}$ is a hydrogen atom, or substituted or unsubstituted alkyl;

or, $R^{8a}$ and $R^{8b}$ may be taken together with a carbon atom to which $R^{8a}$ and $R^{8b}$ are bonded to form a substituted or unsubstituted non-aromatic carbocycle or a substituted or unsubstituted non-aromatic heterocycle;

$R^1$ is substituted or unsubstituted aromatic heterocyclyl, substituted or unsubstituted non-aromatic heterocyclyl, substituted or unsubstituted carbamoyl, substituted or unsubstituted amino or cyano;

m is 0, 1, or 2;

$R^{5a}$ is each independently a hydrogen atom, or substituted or unsubstituted alkyl;

$R^{5b}$ is each independently a hydrogen atom, or substituted or unsubstituted alkyl;

$R^6$ is cyano, halogen, or substituted or unsubstituted alkynyl;

$R^{7a}$ and $R^{7b}$ are each independently a hydrogen atom, halogen, carboxy, substituted or unsubstituted alkyl, substituted or unsubstituted alkyloxycarbonyl;

or, $R^{7a}$ and $R^{7b}$ may be taken together with a carbon atom to which $R^{7a}$ and $R^{7b}$ are bonded to form a substituted or unsubstituted non-aromatic carbocycle or a substituted or unsubstituted non-aromatic heterocycle, or a pharmaceutically acceptable salt thereof.

(1''') A compound represented by Formula (I):

[Chemical Formula 8]

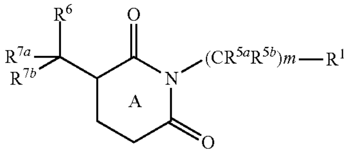

(I)

wherein

Ring A is a ring represented by:

[Chemical Formula 9]

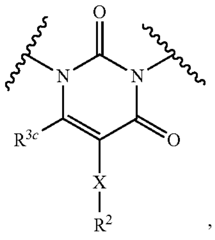

,

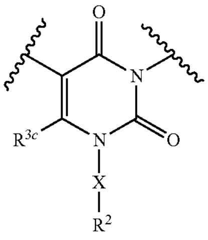

or

-continued

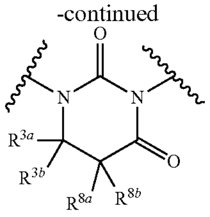

wherein

X is a single bond, —$CR^{4a}R^{4b}$—, —C(═O)—, —O—, or —S—;

$R^{4a}$ and $R^{4b}$ are each independently a hydrogen atom, or substituted or unsubstituted alkyl;

$R^2$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or substituted or unsubstituted alkyl;

$R^{3c}$ is a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, substituted or unsubstituted amino, substituted or unsubstituted carbamoyl, or substituted or unsubstituted alkyloxy;

$R^3$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, substituted or unsubstituted amino, substituted or unsubstituted carbamoyl, or substituted or unsubstituted alkyloxy;

$R^{3a}$ is a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, or substituted or unsubstituted alkyloxy;

$R^{3b}$ is a hydrogen atom;

$R^{8a}$ is substituted or unsubstituted aromatic carbocyclyl or substituted or unsubstituted aromatic heterocyclyl; and $R^{8b}$ is a hydrogen atom, or substituted or unsubstituted alkyl;

or, $R^{8a}$ and $R^{8b}$ may be taken together with a carbon atom to which $R^{8a}$ and $R^{8b}$ are bonded to form a substituted or unsubstituted non-aromatic carbocycle or a substituted or unsubstituted non-aromatic heterocycle;

$R^1$ is substituted or unsubstituted aromatic heterocyclyl, substituted or unsubstituted non-aromatic heterocyclyl, substituted or unsubstituted carbamoyl, substituted or unsubstituted amino or cyano;

m is 0, 1, or 2;

$R^{5a}$ is each independently a hydrogen atom, or substituted or unsubstituted alkyl;

$R^{5b}$ is each independently a hydrogen atom, or substituted or unsubstituted alkyl;

$R^6$ is cyano, halogen, or substituted or unsubstituted alkynyl;

$R^{7a}$ and $R^{7b}$ are each independently a hydrogen atom, halogen, carboxy, substituted or unsubstituted alkyl, substituted or unsubstituted alkyloxycarbonyl;

or, $R^{7a}$ and $R^{7b}$ may be taken together with a carbon atom to which $R^{7a}$ and $R^{7b}$ are bonded to form a substituted or unsubstituted non-aromatic carbocycle or a substituted or unsubstituted non-aromatic heterocycle, provided that the following compounds are excluded:

[Chemical Formula 10]

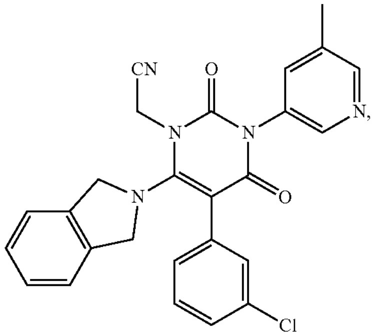

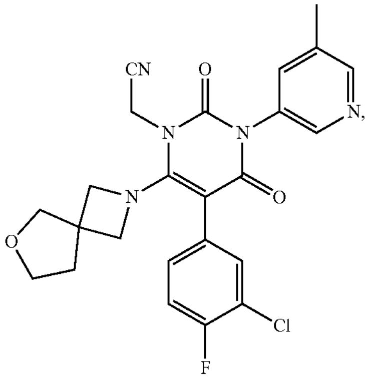

-continued

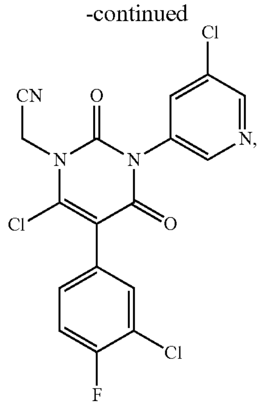

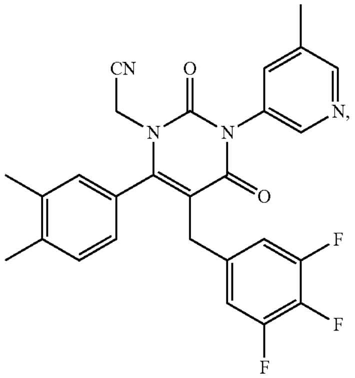

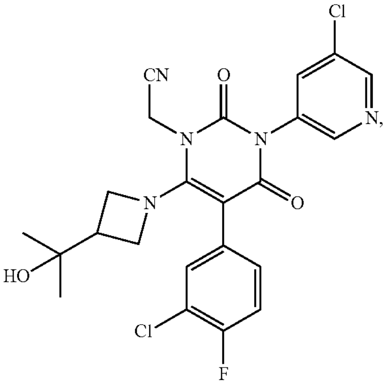

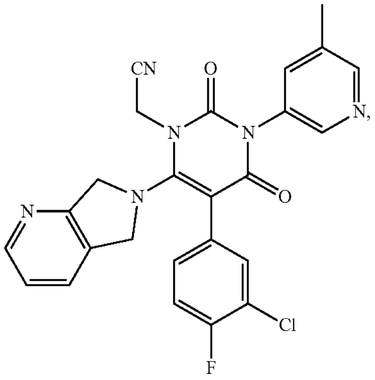

-continued
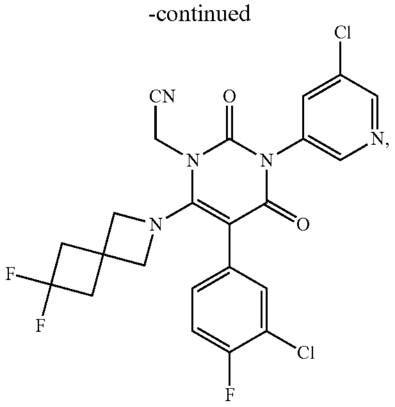
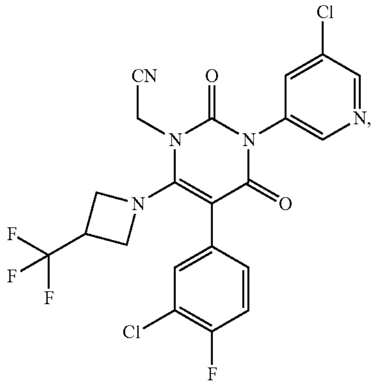
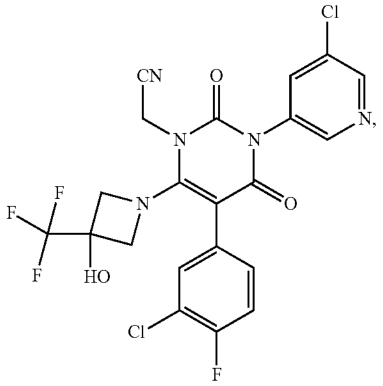
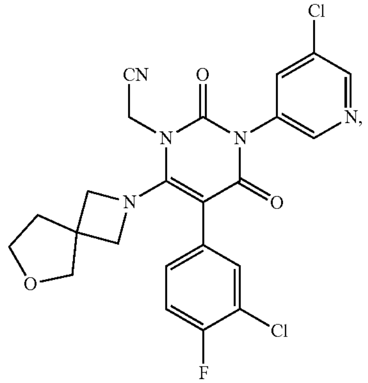
-continued
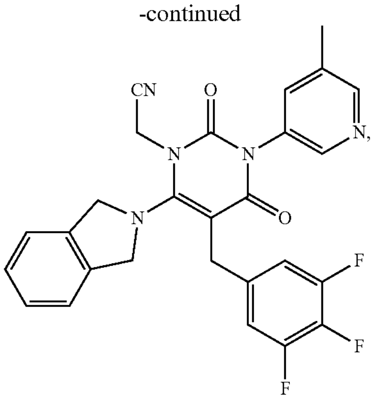
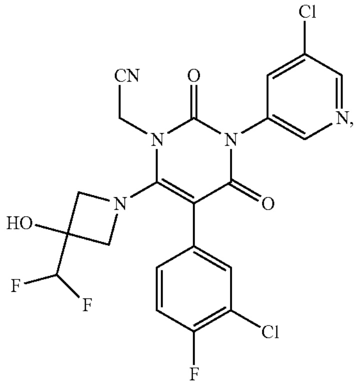
[Chemical Formula 11]
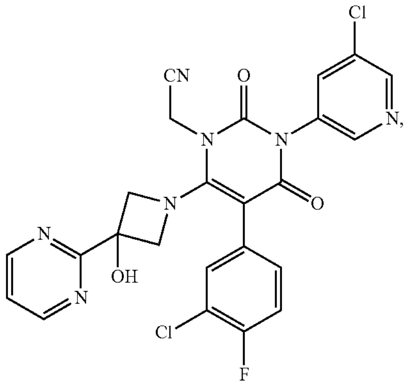
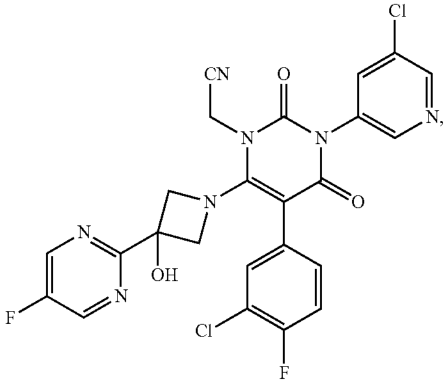

-continued
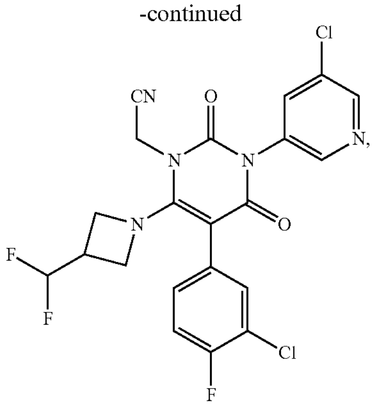
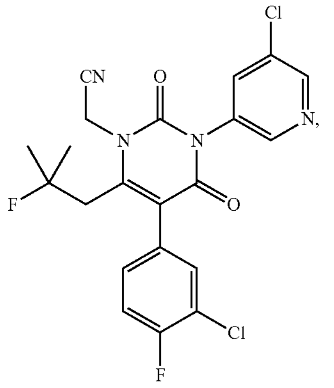
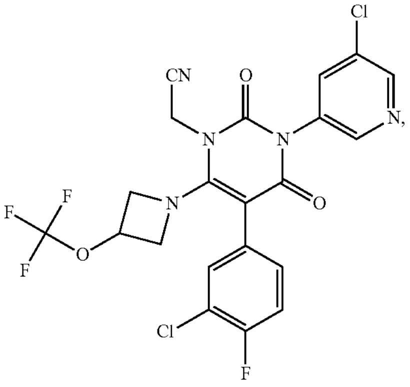
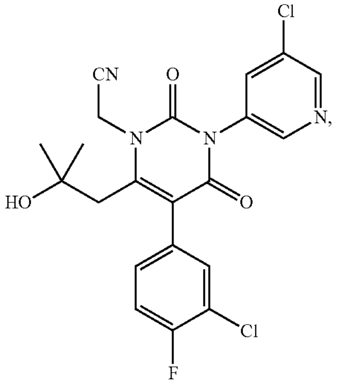
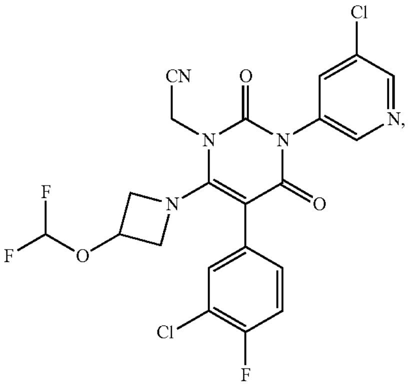
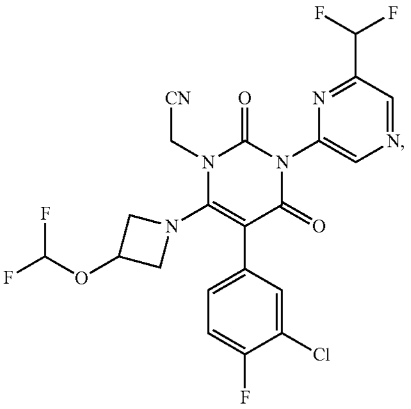
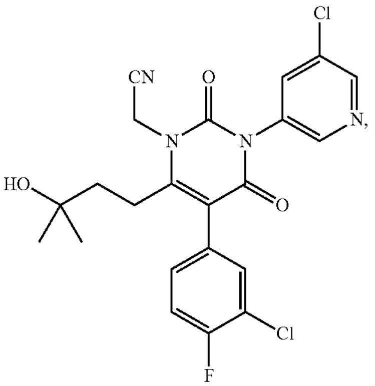
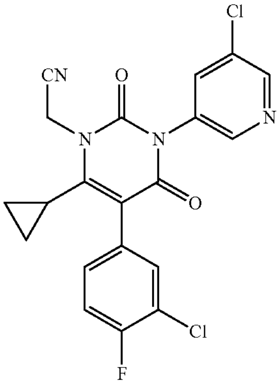
and -continued

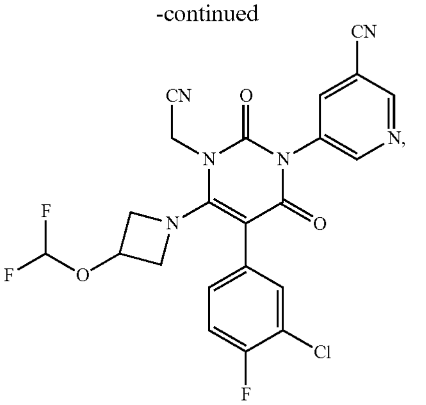

or a pharmaceutically acceptable salt thereof.

(2") The compound according to the above item (1") or (1'''), wherein Ring A is a ring represented by:

[Chemical Formula 12]

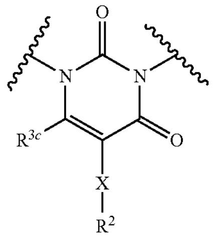

or

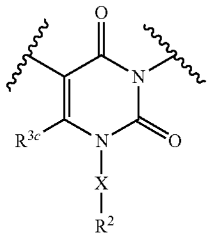

wherein $R^{3c}$, $R^3$, X, and $R^2$ have the same meanings as those in the above item (1") or (1''), or a pharmaceutically acceptable salt thereof.

(3") The compound according to any one of the above items (1") to (2") and (1''')

wherein Ring A is a ring represented by:

[Chemical Formula 13]

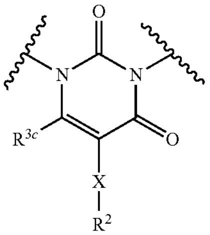

wherein $R^{3c}$, X, and $R^2$ have the same meanings as those in the above item (1") or (1'''), or a pharmaceutically acceptable salt thereof.

(4") The compound according to any one of the above items (1") to (3") and (1''') wherein $R^1$ is substituted or unsubstituted aromatic heterocyclyl or substituted or unsubstituted non-aromatic heterocyclyl, or a pharmaceutically acceptable salt thereof.

(5") The compound according to any one of the above items (1") to (4") and (1''') wherein X is a single bond or $—CH_2—$, or a pharmaceutically acceptable salt thereof.

(6") The compound according to any one of the above items (1") to (5") and (1''') wherein $R^2$ is substituted or unsubstituted aromatic carbocyclyl, or a pharmaceutically acceptable salt thereof.

(7") The compound according to any one of the above items (1") to (6") and (1''') wherein $R^{3c}$ and $R^3$ are each independently substituted or unsubstituted aromatic carbocyclyl, substituted or unsubstituted aromatic heterocyclyl, substituted or unsubstituted non-aromatic heterocyclyl, substituted or unsubstituted aromatic carbocyclyloxy, halogen, substituted or unsubstituted alkyl, or substituted or unsubstituted alkyloxy, or a pharmaceutically acceptable salt thereof.

(8") The compound according to any one of the above items (1") to (7") and (1''') wherein m is 0 or 1, or a pharmaceutically acceptable salt thereof.

(9") The compound according to any one of the above items (1") to (8") and (1''') wherein $R^{5a}$ is each independently a hydrogen atom, and $R^{5b}$ is each independently a hydrogen atom, or a pharmaceutically acceptable salt thereof.

(10") The compound according to any one of the above items (1") to (9") and (1'''), wherein $R^6$ is cyano, or a pharmaceutically acceptable salt thereof.

(11") The compound according to any one of the above items (1") to (10") and (1'''), wherein $R^{7a}$ and $R^{7b}$ are each independently a hydrogen atom, or substituted or unsubstituted alkyl, or a pharmaceutically acceptable salt thereof.

(12")

The compound according to the above items (1") to (11"), wherein the compound is selected from the group consisting of:

[Chemical Formula 14]

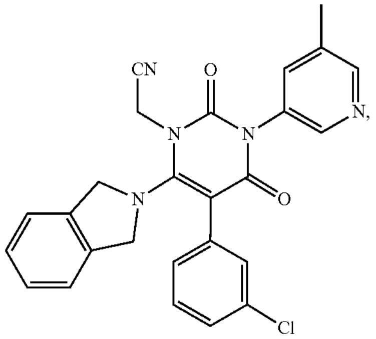

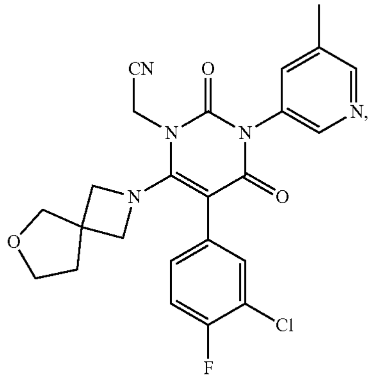

-continued
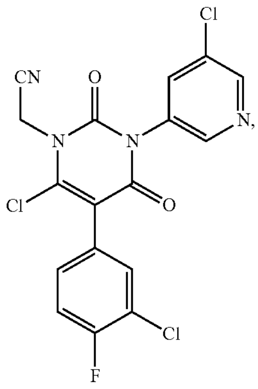
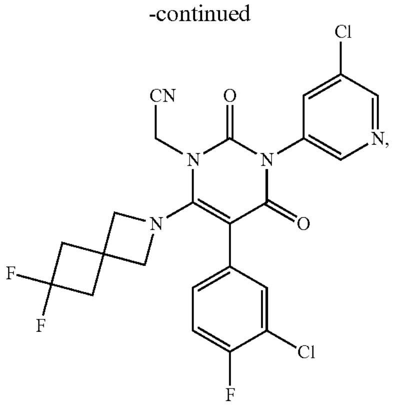
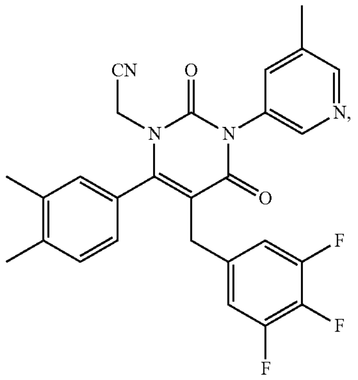
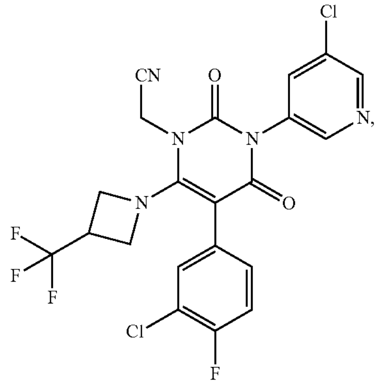
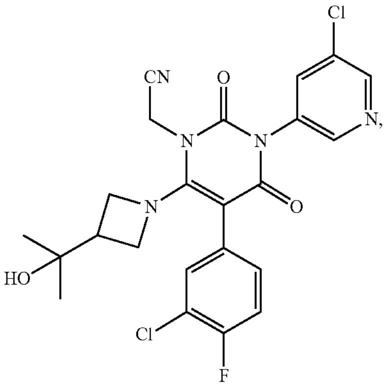
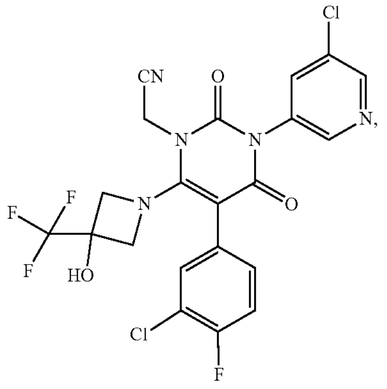
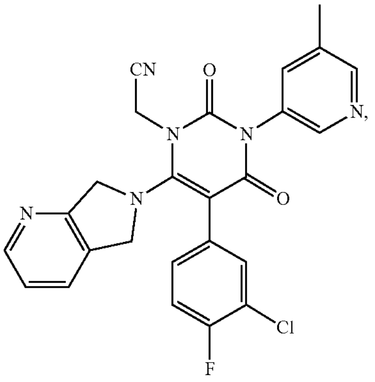
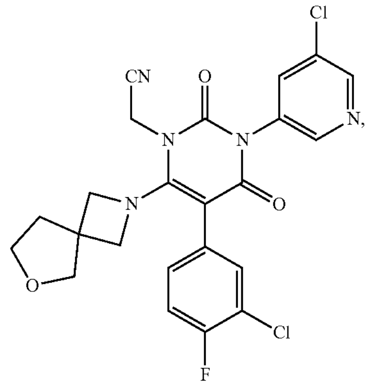

-continued
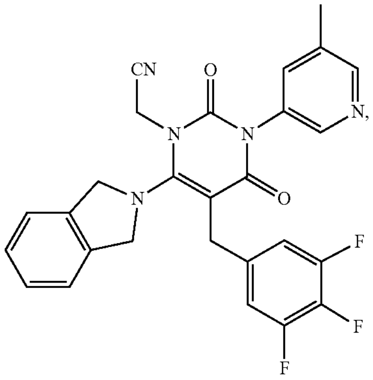
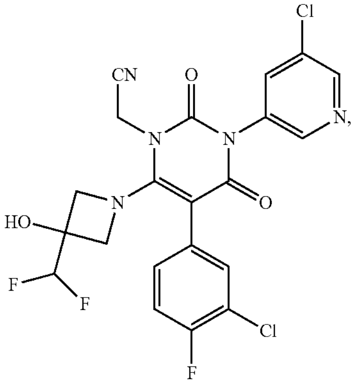
[Chemical Formula 15]
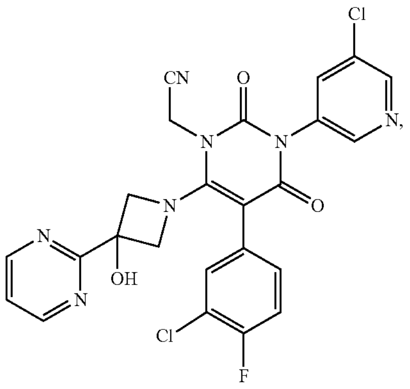
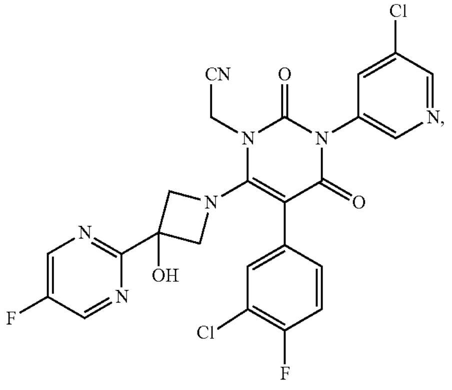
-continued
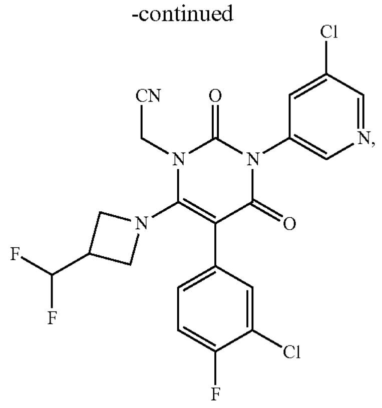
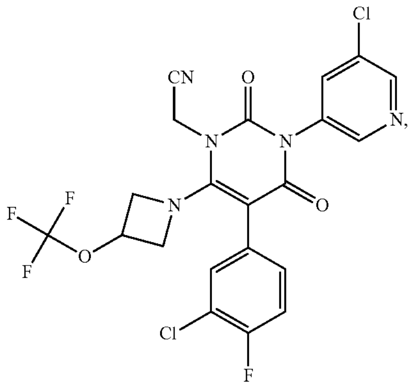
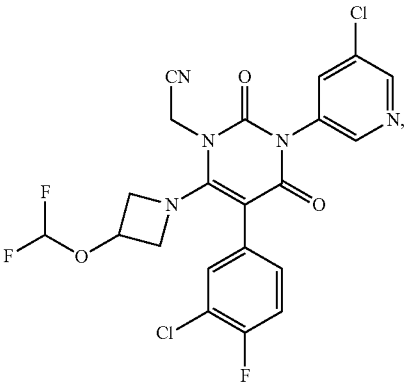
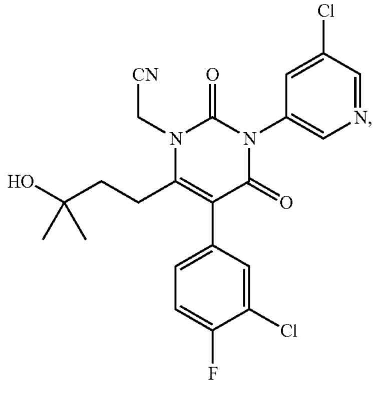

-continued
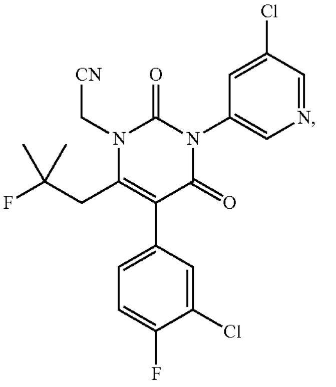
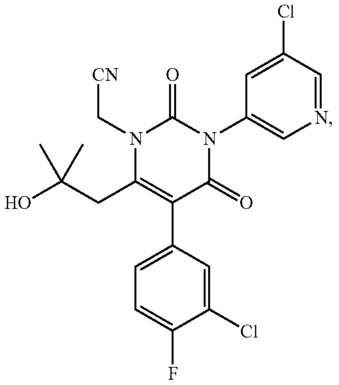
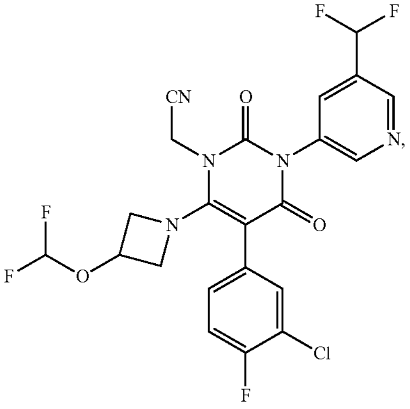
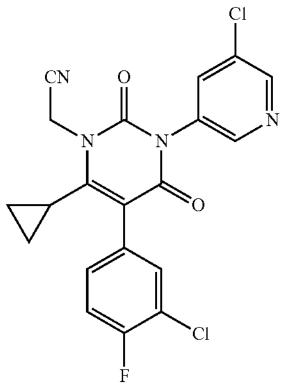
and
-continued
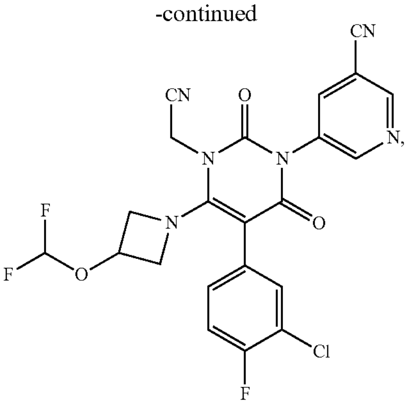
or a pharmaceutically acceptable salt thereof.
(13") The compound according to the above items (1") to (11"), wherein the compound is selected from the group consisting of:
[Chemical Formula 16]
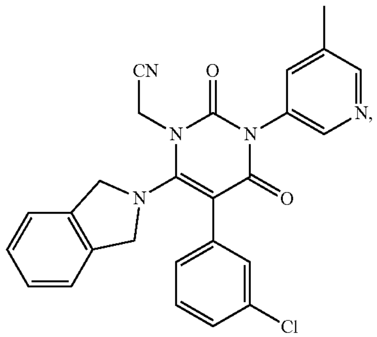
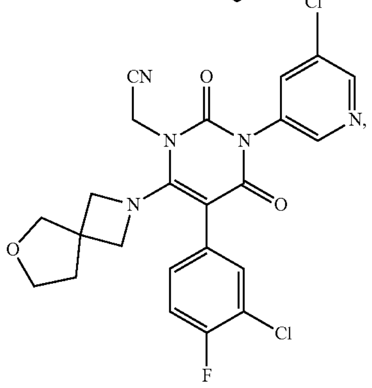
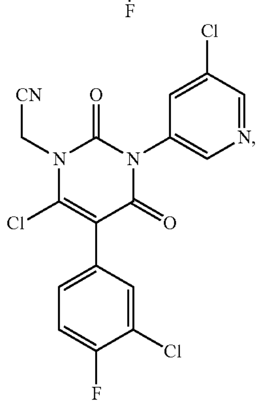

-continued
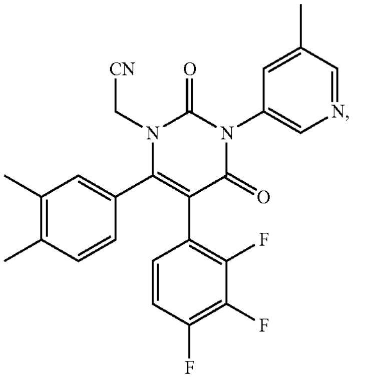
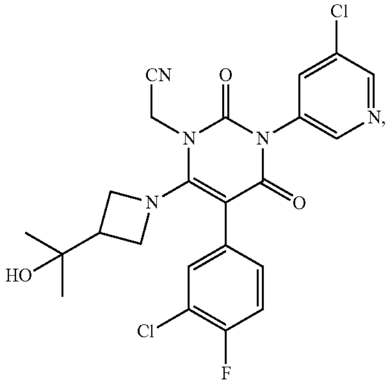
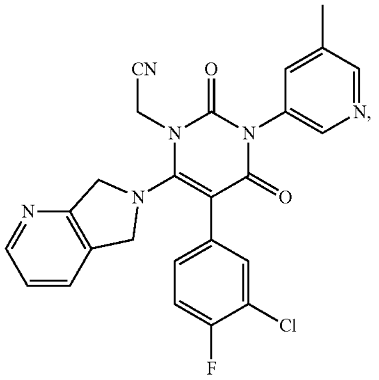
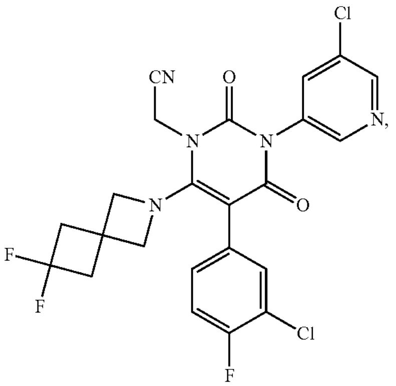
-continued
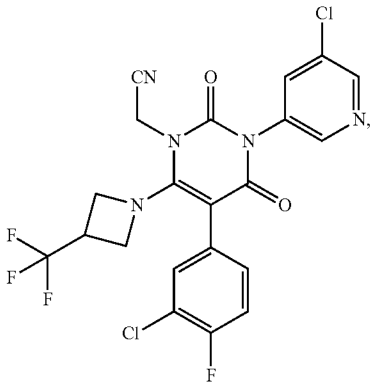
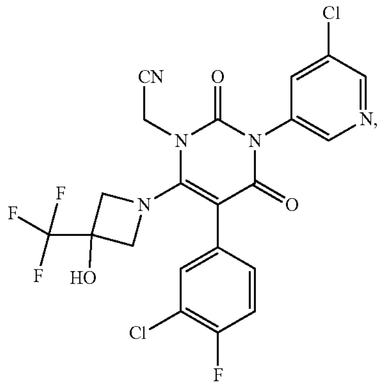
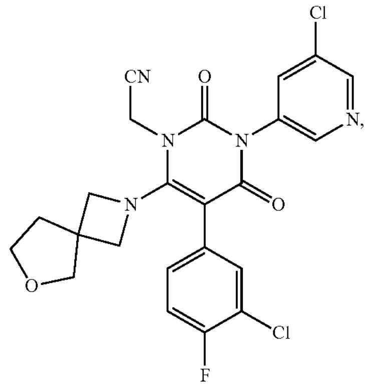
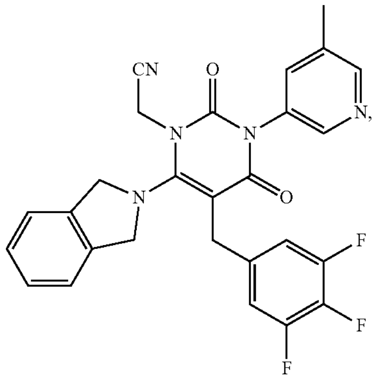

-continued
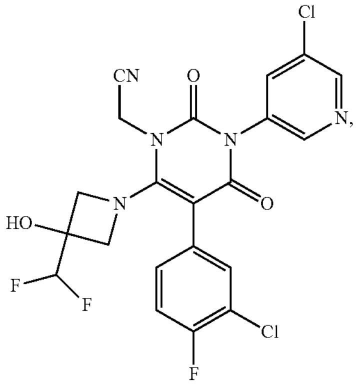
[Chemical Formula 17]
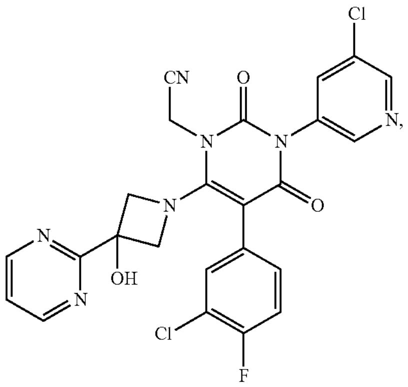
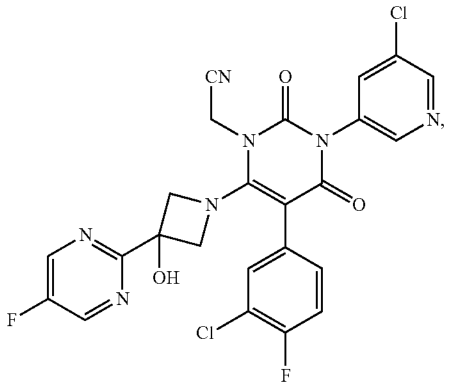
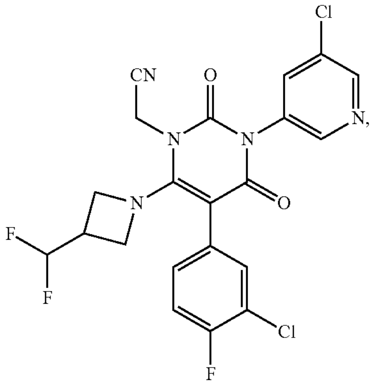
-continued
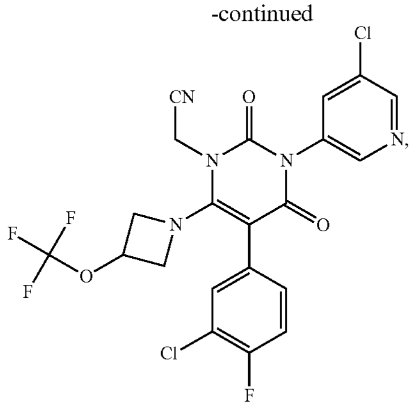
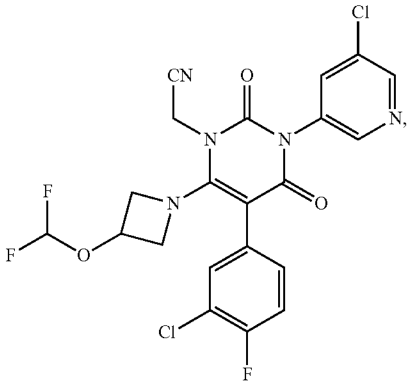
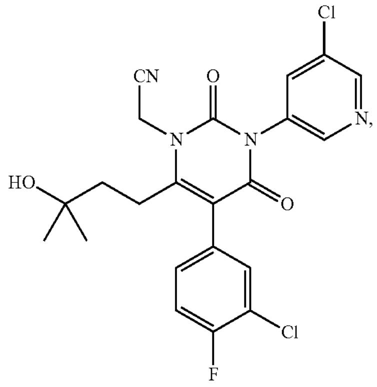
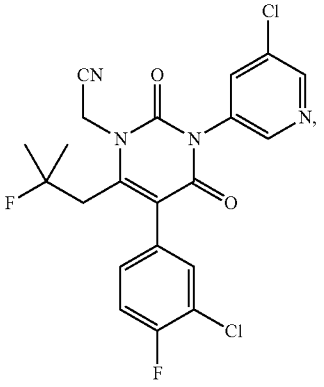

-continued

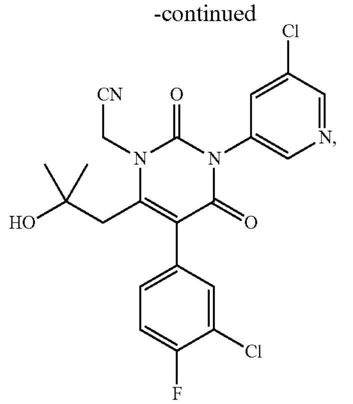

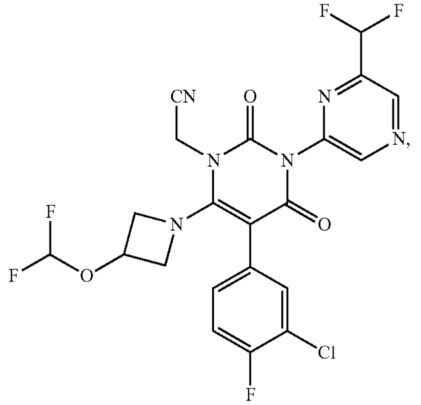

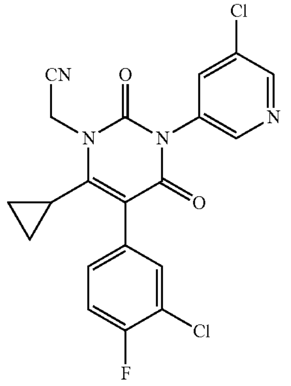

and

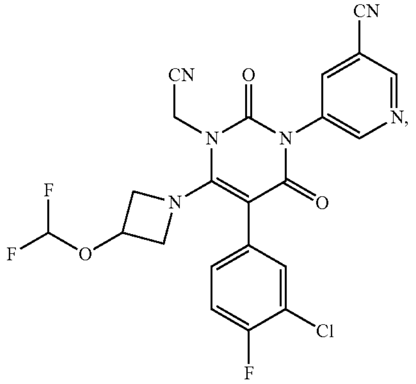

or deuterated compound thereof, or a pharmaceutically acceptable salt thereof.

(14") A pharmaceutical composition comprising the compound according to any one of the above items (1") to (12") and (1'") or a pharmaceutically acceptable salt thereof.

(14'") A pharmaceutical composition comprising the compound according to the above item (13") or deuterated compound thereof, or a pharmaceutically acceptable salt thereof.

(15") A coronavirus 3CL protease inhibitor comprising the compound according to any one of the above items (1") to (12") and (1'") or a pharmaceutically acceptable salt thereof.

(15'") A coronavirus 3CL protease inhibitor comprising the compound according to the above item (13") or deuterated compound thereof, or a pharmaceutically acceptable salt thereof.

(16") A coronavirus replication inhibitor comprising the compound according to any one of the above items (1") to (12") and (1'") or a pharmaceutically acceptable salt thereof.

(16'") A coronavirus replication inhibitor comprising the compound according to the above item (13") or deuterated compound thereof, or a pharmaceutically acceptable salt thereof.

(17") The coronavirus replication inhibitor according to the above item (16") or (16'"), wherein the coronavirus is an alpha coronavirus and/or beta coronavirus.

(18") The coronavirus replication inhibitor according to the above item (16") or (16'"), wherein the coronavirus is SARS-CoV-2.

Furthermore, the present invention relates to the following.

(1') A compound represented by Formula (I):

[Chemical Formula 18]

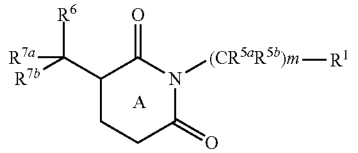

(I)

wherein

Ring A is a ring represented by:

[Chemical Formula 19]

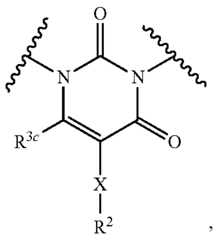

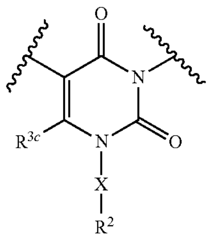

, or

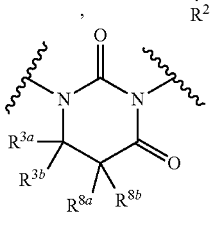

wherein

X is a single bond, —$CR^{4a}R^{4b}$—, —C(═O)—, —O—, or —S—;

$R^{4a}$ and $R^{4b}$ are each independently a hydrogen atom, or substituted or unsubstituted alkyl;

$R^2$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or substituted or unsubstituted alkyl;

$R^{3c}$ is a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, substituted or unsubstituted amino, substituted or unsubstituted carbamoyl, or substituted or unsubstituted alkyloxy;

$R^3$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, substituted or unsubstituted amino, substituted or unsubstituted carbamoyl, or substituted or unsubstituted alkyloxy;

$R^{3a}$ is a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, or substituted or unsubstituted alkyloxy;

$R^{3b}$ is a hydrogen atom;

$R^{8a}$ is substituted or unsubstituted aromatic carbocyclyl or substituted or unsubstituted aromatic heterocyclyl; and $R^{8b}$ is a hydrogen atom, or substituted or unsubstituted alkyl;

or, $R^{8a}$ and $R^{8b}$ may be taken together with a carbon atom to which $R^{8a}$ and $R^{8b}$ are bonded to form a substituted or unsubstituted non-aromatic carbocycle or a substituted or unsubstituted non-aromatic heterocycle;

$R^1$ is substituted or unsubstituted aromatic heterocyclyl, substituted or unsubstituted non-aromatic heterocyclyl, substituted or unsubstituted carbamoyl, substituted or unsubstituted amino or cyano;

m is 0, 1, or 2;

$R^{5a}$ is each independently a hydrogen atom, or substituted or unsubstituted alkyl;

$R^{5b}$ is each independently a hydrogen atom, or substituted or unsubstituted alkyl;

$R^6$ is cyano, halogen, or substituted or unsubstituted alkynyl;

$R^{7a}$ and $R^{7b}$ are each independently a hydrogen atom, halogen, carboxy, substituted or unsubstituted alkyl, substituted or unsubstituted alkyloxycarbonyl;

or, $R^{7a}$ and $R^{7b}$ may be taken together with a carbon atom to which $R^{7a}$ and $R^{7b}$ are bonded to form a substituted or unsubstituted non-aromatic carbocycle or a substituted or unsubstituted non-aromatic heterocycle, or a pharmaceutically acceptable salt thereof.

(2') The compound according to the above item (1'), wherein Ring A is a ring represented by:

[Chemical Formula 20]

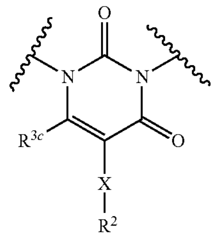

or

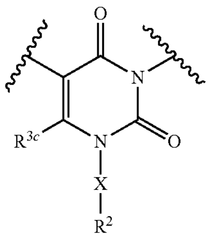

wherein $R^{3c}$, $R^3$, X, and $R^2$ have the same meanings as those in the above item (1'), or a pharmaceutically acceptable salt thereof.

(3') The compound according to the above item (1') or (2'), wherein Ring A is a ring represented by:

[Chemical Formula 21]

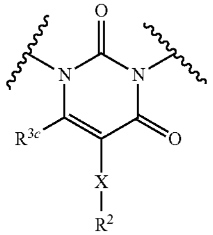

wherein $R^{3c}$, X, and $R^2$ have the same meanings as those in the above item (1'), or a pharmaceutically acceptable salt thereof.

(4') The compound according to any one of the above items (1') to (3'), wherein $R^1$ is substituted or unsubstituted aromatic heterocyclyl or substituted or unsubstituted non-aromatic heterocyclyl, or a pharmaceutically acceptable salt thereof.

(5') The compound according to any one of the above items (1') to (4'), wherein X is a single bond or —$CH_2$—, or a pharmaceutically acceptable salt thereof.

(6') The compound according to any one of the above items (1') to (5'), wherein $R^2$ is substituted or unsubstituted aromatic carbocyclyl, or a pharmaceutically acceptable salt thereof.

(7') The compound according to any one of the above items (1') to (6'), wherein $R^{3c}$ and $R^3$ are each independently substituted or unsubstituted aromatic carbocyclyl, substituted or unsubstituted aromatic heterocyclyl, substituted or unsubstituted non-aromatic heterocyclyl, substituted or unsubstituted aromatic carbocyclyloxy, halogen, substituted or unsubstituted alkyl, or substituted or unsubstituted alkyloxy, or a pharmaceutically acceptable salt thereof.

(8') The compound according to any one of the above items (1') to (7'), wherein m is 0 or 1, or a pharmaceutically acceptable salt thereof.

(9') The compound according to any one of the above items (1') to (8'), wherein $R^{5a}$ is each independently a hydrogen atom, and $R^{5b}$ is each independently a hydrogen atom, or a pharmaceutically acceptable salt thereof.

(10') The compound according to any one of the above items (1') to (9'), wherein $R^6$ is cyano, or a pharmaceutically acceptable salt thereof.

(11') The compound according to any one of the above items (1') to (10'), wherein $R^{7a}$ and $R^{7b}$ are each independently a hydrogen atom, or substituted or unsubstituted alkyl, or a pharmaceutically acceptable salt thereof.

(12') A pharmaceutical composition comprising the compound according to any one of the above items (1') to (11') or a pharmaceutically acceptable salt thereof.

(13') A coronavirus 3CL protease inhibitor comprising the compound according to any one of the above items (1') to (11') or a pharmaceutically acceptable salt thereof.

(14') A coronavirus replication inhibitor comprising the compound according to any one of the above items (1') to (11') or a pharmaceutically acceptable salt thereof.

(15') The coronavirus replication inhibitor according to the above item (14'), wherein the coronavirus is an alpha coronavirus and/or beta coronavirus.

(16') The coronavirus replication inhibitor according to the above item (14'), wherein the coronavirus is SARS-CoV-2.

Furthermore, the present invention relates to the following.

(1) A compound represented by Formula (I):

[Chemical Formula 22]

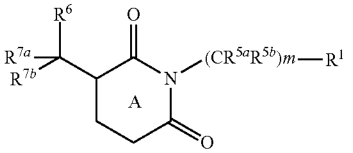

(I)

wherein

Ring A is a ring represented by:

[Chemical Formula 23]

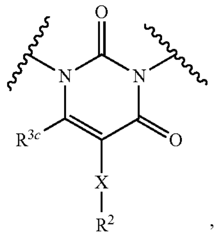

,

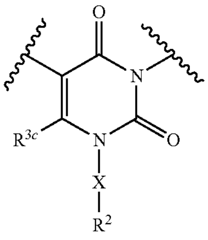

or

-continued

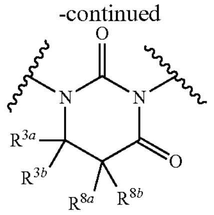

wherein

X is a single bond, $—CR^{4a}R^{4b}—$, —C(═O)—, —O—, or —S—;

$R^{4a}$ and $R^{4b}$ are each independently a hydrogen atom, or substituted or unsubstituted alkyl;

$R^2$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^3$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, substituted or unsubstituted amino, or substituted or unsubstituted alkyloxy;

$R^{3a}$ is a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, or substituted or unsubstituted alkyloxy;

$R^{3b}$ is a hydrogen atom;

$R^{8a}$ is substituted or unsubstituted aromatic carbocyclyl or substituted or unsubstituted aromatic heterocyclyl; and $R^{8b}$ is a hydrogen atom, or substituted or unsubstituted alkyl;

or, $R^{8a}$ and $R^{8b}$ may be taken together with a carbon atom to which $R^{8a}$ and $R^{8b}$ are bonded to form a substituted or unsubstituted non-aromatic carbocycle or a substituted or unsubstituted non-aromatic heterocycle;

$R^1$ is substituted or unsubstituted aromatic heterocyclyl, substituted or unsubstituted non-aromatic heterocyclyl, substituted or unsubstituted carbamoyl, or substituted or unsubstituted amino;

m is 0, 1, or 2;

$R^{5a}$ is each independently a hydrogen atom, or substituted or unsubstituted alkyl;

$R^{5b}$ is each independently a hydrogen atom, or substituted or unsubstituted alkyl;

$R^6$ is cyano, halogen, or substituted or unsubstituted alkynyl;

$R^{7a}$ and $R^{7b}$ are each independently a hydrogen atom, halogen, carboxy, substituted or unsubstituted alkyl, substituted or unsubstituted alkyloxycarbonyl;

or, $R^{7a}$ and $R^{7b}$ may be taken together with a carbon atom to which $R^{7a}$ and $R^{7b}$ are bonded to form a substituted or unsubstituted non-aromatic carbocycle or a substituted or unsubstituted non-aromatic heterocycle, or a pharmaceutically acceptable salt thereof.

(2) The compound according to the above item (1), wherein Ring A is a ring represented by:

[Chemical Formula 24]

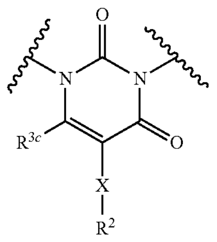

or

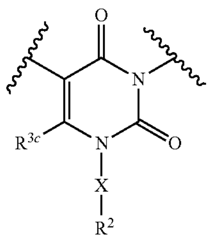

wherein $R^3$, X, and $R^2$ have the same meanings as those in the above item (1), or a pharmaceutically acceptable salt thereof.

(3) The compound according to the above item (1) or (2), wherein Ring A is a ring represented by:

[Chemical Formula 25]

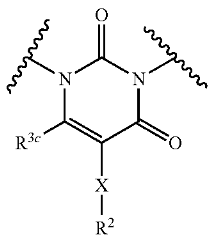

wherein $R^3$, X, and $R^2$ have the same meanings as those in the above item (1), or a pharmaceutically acceptable salt thereof.

(4) The compound according to any one of the above items (1) to (3), wherein $R^1$ is substituted or unsubstituted aromatic heterocyclyl, or substituted or unsubstituted non-aromatic heterocyclyl, or a pharmaceutically acceptable salt thereof.

(5) The compound according to any one of the above items (1) to (4), wherein X is a single bond or $—CH_2—$, or a pharmaceutically acceptable salt thereof.

(6) The compound according to any one of the above items (1) to (5), wherein $R^2$ is substituted or unsubstituted aromatic carbocyclyl, or a pharmaceutically acceptable salt thereof.

(7) The compound according to any one of the above items (1) to (6), wherein $R^3$ is substituted or unsubstituted aromatic carbocyclyl, substituted or unsubstituted aromatic heterocyclyl, substituted or unsubstituted non-aromatic heterocyclyl, substituted or unsubstituted aromatic carbocyclyloxy, halogen, substituted or unsubstituted alkyl, or substituted or unsubstituted alkyloxy, or a pharmaceutically acceptable salt thereof.

(8) The compound according to any one of the above items (1) to (7), wherein m is 0 or 1, or a pharmaceutically acceptable salt thereof.

(9) The compound according to any one of the above items (1) to (8), wherein $R^{5a}$ is each independently a hydrogen atom, and $R^{5b}$ is each independently a hydrogen atom, or a pharmaceutically acceptable salt thereof.

(10) The compound according to any one of the above items (1) to (9), wherein $R^6$ is cyano, or a pharmaceutically acceptable salt thereof.

(11) The compound according to any one of the above items (1) to (10), wherein $R^{7a}$ and $R^{7b}$ are each independently a hydrogen atom, or substituted or unsubstituted alkyl, or a pharmaceutically acceptable salt thereof.

(12) A pharmaceutical composition comprising the compound according to any one of the above items (1) to (11) or a pharmaceutically acceptable salt thereof.

(13) A coronavirus 3CL protease inhibitor comprising the compound according to any one of the above items (1) to (11) or a pharmaceutically acceptable salt thereof.

(14) A coronavirus replication inhibitor comprising the compound according to any one of the above items (1) to (11) or a pharmaceutically acceptable salt thereof.

(15) The coronavirus replication inhibitor according to the above item (14), wherein the coronavirus is an alpha coronavirus and/or beta coronavirus.

(16) The coronavirus replication inhibitor according to the above item (14), wherein the coronavirus is SARS-CoV-2.

(100) A pharmaceutical composition for preventing and/or treating coronavirus infections, the pharmaceutical composition comprising the compound according to any one of the above items (1) to (11), (1') to (11'), (1") to (12"), and (1"') or a pharmaceutically acceptable salt thereof.

(100') A pharmaceutical composition for preventing and/or treating coronavirus infections, the pharmaceutical composition comprising the compound according to the above item (13") or deuterated compound thereof, or a pharmaceutically acceptable salt thereof.

(101) The pharmaceutical composition according to the above item (100) or (100'), for preventing and/or treating novel coronavirus infections (COVID-19).

(102) The pharmaceutical composition according to the above item (100) or (100'), for preventing and/or treating infections caused by SARS-CoV-2.

(103) A method for inhibiting replication of coronavirus, the method comprising administering the compound according to any one of the above items (1) to (11), (1') to (11'), (1") to (12"), and (1"') or a pharmaceutically acceptable salt thereof.

(103') A method for inhibiting replication of coronavirus, the method comprising the compound according to the above item (13") or deuterated compound thereof, or a pharmaceutically acceptable salt thereof.

(104) The method for inhibiting replication according to the above item (103) or (103'), wherein the coronavirus is alphacoronavirus and/or betacoronavirus.

(105) The method for inhibiting replication according to the above item (103) or (103'), wherein the coronavirus is SARS-CoV-2.

(106) A method for treating and/or preventing a disease associated with coronavirus 3CL proteases, the method comprising administering the compound according to any one of the above items (1) to (11), (1') to (11'), (1") to (12"), and (1"') or a pharmaceutically acceptable salt thereof.

(106') A method for treating and/or preventing a disease associated with coronavirus 3CL proteases, the method comprising administering the compound according to the above item (13") or deuterated compound thereof, or a pharmaceutically acceptable salt thereof.

(107) A method for treating and/or preventing coronavirus infections, the method comprising administering the compound according to any one of the above items (1) to (11), (1') to (11'), (1") to (12"), and (1"') or a pharmaceutically acceptable salt thereof.

(107') A method for treating and/or preventing coronavirus infections, the method comprising administering the compound according to the above item (13") or deuterated compound thereof, or a pharmaceutically acceptable salt thereof.

(108) The method for preventing and/or treating coronavirus infections according to the above item (107) or (107'), wherein the coronavirus infections are novel coronavirus infections (COVID-19).

(109) The method for treating and/or preventing coronavirus infections according to the above item (107) or (107'), wherein the coronavirus infections are infections caused by SARS-CoV-2.

(110) Use of the compound according to any one of the above items (1) to (11), (1') to (11'), (1") to (12"), and (1"') or a pharmaceutically acceptable salt thereof, for producing a therapeutic and/or prophylactic agent for a disease associated with coronavirus 3CL protease.

(110') Use of the compound according to the above item (13") or deuterated compound thereof, or a pharmaceutically acceptable salt thereof, for producing a therapeutic and/or prophylactic agent for a disease associated with coronavirus 3CL proteases.

(111) Use of the compound according to any one of the above items (1) to (11), (1') to (11'), (1") to (12"), and (1"') or a pharmaceutically acceptable salt thereof, for producing a replication inhibitor for coronavirus.

(111') Use of the compound according to the above item (13"), a deuterium body thereof, or a pharmaceutically acceptable salt thereof, for producing a replication inhibitor for coronavirus.

(112) The use according to the above item (111) or (111'), wherein the coronavirus is alphacoronavirus and/or betacoronavirus.

(113) The use according to the above item (111) or (111'), wherein the coronavirus is SARS-CoV-2.

(114) Use of the compound according to any one of the above items (1) to (11), (1') to (11'), (1") to (12"), and (1"') or a pharmaceutically acceptable salt thereof, for producing a therapeutic and/or prophylactic agent for coronavirus infections.

(114') Use of the compound according to the above item (13") or deuterated compound thereof, or a pharmaceutically acceptable salt thereof, for producing a therapeutic and/or prophylactic agent for coronavirus infections.

(115) The use according to the above item (114) or (114'), wherein the coronavirus infections are novel coronavirus infections (COVID-19).

(116) The use according to the above item (114) or (114'), wherein the coronavirus infections are infections caused by SARS-CoV-2.

(117) The compound according to any one of the above items (1) to (11), (1') to (11'), (1") to (12"), and (1"') or a pharmaceutically acceptable salt thereof, for use in the treatment and/or prevention of a disease associated with coronavirus 3CL proteases.

(117') The compound according to the above item (13") or deuterated compound thereof, or a pharmaceutically acceptable salt thereof, for use in treating and/or preventing a disease associated with coronavirus 3CL proteases.

(118) The compound according to any one of the above items (1) to (11), (1') to (11'), (1") to (12"), and (1"') or a pharmaceutically acceptable salt thereof, for use in the inhibition of replication of coronavirus.

(118') The compound according to the above item (13") or deuterated compound thereof, or a pharmaceutically acceptable salt thereof, for use in the inhibition of replication of coronavirus.

(119) The compound according to the above item (118) or a pharmaceutically acceptable salt thereof, wherein the coronavirus is alphacoronavirus and/or betacoronavirus.

(119') The compound according to the above item (118') or deuterated compound thereof, or a pharmaceutically acceptable salt thereof, wherein the coronavirus is alphacoronavirus and/or betacoronavirus.

(120) The compound according to the above item (118) or a pharmaceutically acceptable salt thereof, wherein the coronavirus is SARS-CoV-2.

(120') The compound according to the above item (118') or deuterated compound thereof, or a pharmaceutically acceptable salt thereof, wherein the coronavirus is SARS-CoV-2.

(121) The compound according to any one of the above items (1) to (11), (1') to (11'), (1") to (12"), and (1"') or a pharmaceutically acceptable salt thereof, for use in treating and/or preventing coronavirus infections.

(121') The compound according to the above item (13") or deuterated compound thereof, or a pharmaceutically acceptable salt thereof, for use in treating and/or preventing coronavirus infections.

(122) The compound according to the above item (121) or a pharmaceutically acceptable salt thereof, wherein the coronavirus infections are novel coronavirus infections (COVID-19).

(122') The compound according to the above item (121') or deuterated compound thereof, or a pharmaceutically acceptable salt thereof, wherein the coronavirus infections are novel coronavirus infections (COVID-19).

(123) The compound according to the above item (121) or a pharmaceutically acceptable salt thereof, wherein the coronavirus infections are infections caused by SARS-CoV-2.

(123') The compound according to the above item (121') or deuterated compound thereof, or a pharmaceutically acceptable salt thereof, wherein the coronavirus infections are infections caused by SARS-CoV-2.

Effect of the Invention

The compound of the present invention has inhibitory activity against coronavirus 3CL proteases and is useful as a therapeutic (treating) agent and/or prophylactic (preventing) agent for coronavirus infections.

MODE FOR CARRYING OUT THE INVENTION

Hereinafter, the meaning of each term used in the present specification will be described. Unless particularly stated otherwise, each term is used in the same sense, either alone or in combination with other terms.

The term "consist of" means having only the constituent elements.

The term "comprise" means that elements are not limited to the constituent elements, and elements that are not described are not excluded.

Hereinafter, the present invention will be described while showing exemplary embodiments. Throughout the present specification, it should be understood that, unless particularly stated otherwise, an expression of a singular form also includes the concept of a plural form thereof. Therefore, it should be understood that, unless particularly stated otherwise, an article for a singular form (for example, in the case of English, "a", "an", "the", or the like) also includes the concept of a plural form thereof.

Furthermore, it should be understood that, unless particularly stated otherwise, the terms used in the present specification are used in the meanings normally used in the above-described art. Accordingly, unless otherwise defined, all terminologies and scientific and technical terms used in the present specification have the same meanings as commonly understood by those having ordinary skill in the art to which the present invention belongs. In a case of contradiction, priority is given to the present specification (including definitions).

"Halogen" includes a fluorine atom, a chlorine atom, a bromine atom, and an iodine atom. Particularly, a fluorine atom and a chlorine atom are preferred.

"Alkyl" includes linear or branched hydrocarbon groups each having 1 to 15 carbon atoms, preferably 1 to 10 carbon atoms, more preferably 1 to 6 carbon atoms, and even more preferably 1 to 4 carbon atoms. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

Preferred embodiments of "alkyl" include methyl, ethyl, n-propyl, isopropyl, n-butyl, isobutyl, sec-butyl, tert-butyl, and n-pentyl. More preferred embodiments include methyl, ethyl, n-propyl, isopropyl, and tert-butyl.

"Alkenyl" includes linear or branched hydrocarbon groups each having one or more double bonds at any position and having 2 to 15 carbon atoms, preferably 2 to 10 carbon atoms, more preferably 2 to 6 carbon atoms, and even more preferably 2 to 4 carbon atoms. Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, and pentadecenyl.

Preferred embodiments of "alkenyl" include vinyl, allyl, propenyl, isopropenyl, and butenyl. More preferred embodiments include vinyl, and n-propenyl.

"Alkynyl" includes linear or branched hydrocarbon groups each having one or more triple bonds at any position and having 2 to 10 carbon atoms, preferably 2 to 8 carbon atoms, more preferably 2 to 6 carbon atoms, and even more preferably 2 to 4 carbon atoms. Alkynyl may further have a double bond at any position. Examples include ethynyl, propynyl, butynyl, pentynyl, hexynyl, heptynyl, octynyl, nonynyl, and decynyl.

Preferred embodiments of "alkynyl" include ethynyl, propynyl, butynyl, and pentynyl. More preferred embodiments include ethynyl and propynyl.

"Aromatic carbocyclyl" means a cyclic aromatic hydrocarbon group having a single ring or two or more rings. Examples include phenyl, naphthyl, anthryl, and phenanthryl.

Preferred embodiments of the "aromatic carbocyclyl" include phenyl.

"Aromatic carbocycle" means a ring derived from the above-described "aromatic carbocyclyl".

Examples of "substituted or unsubstituted aromatic carbocycle formed by $R^{31'}$ and $R^{35'}$ together with a carbon atom to which $R^{31'}$ is bonded and a carbon atom to which $R^{35'}$ is bonded include the following rings.

[Chemical Formula 26]

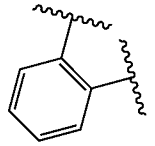

"Non-aromatic carbocyclyl" means a cyclic saturated hydrocarbon group or a cyclic non-aromatic unsaturated hydrocarbon group, both having a single ring or two or more rings. The "non-aromatic carbocyclyl" having two or more rings also includes a non-aromatic carbocyclyl having a single ring or two or more rings, to which the ring in the "aromatic carbocyclyl" is fused.

Furthermore, the "non-aromatic carbocyclyl" also includes a bridged group or a group forming a spiro ring, such as follows.

[Chemical Formula 27]

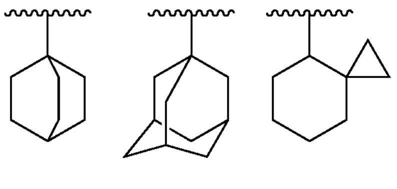

A non-aromatic carbocyclyl having a single ring preferably has 3 to 16 carbon atoms, more preferably 3 to 12 carbon atoms, and even more preferably 4 to 8 carbon atoms. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl.

The non-aromatic carbocyclyl which is polycyclic having two or more rings preferably has 8 to 20 carbon atoms, and more preferably 8 to 16 carbon atoms. Examples include indanyl, indenyl, acenaphthyl, tetrahydronaphthyl, and fluorenyl.

"Non-aromatic carbocycle" means a ring derived from the above-described "non-aromatic carbocyclyl".

Examples of "non-aromatic carbocycle formed by $R^{8a}$ and $R^{8b}$ together with a carbon atom to which $R^{8a}$ and $R^{8b}$ are bonded" include the following rings.

[Chemical Formula 28]

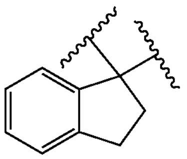

Examples of "non-aromatic carbocycle formed by $R^{7a}$ and $R^{7b}$ together with a carbon atom to which $R^{7a}$ and $R^{7b}$ are bonded" include the following rings.

[Chemical Formula 29]

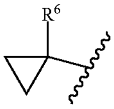

Examples of "non-aromatic carbocycle formed by $R^{31}$ and $R^{32}$ together with a carbon atom to which $R^{31}$ and $R^{32}$ are bonded" include the following rings.

[Chemical Formula 30]

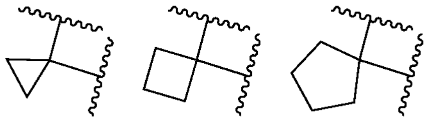

Examples of "non-aromatic carbocycle formed by $R^{31'}$ and $R^{35'}$ together with a carbon atom to which $R^{31'}$ is bonded and a carbon atom to which $R^{35'}$ is bonded" include the following rings.

[Chemical Formula 31]

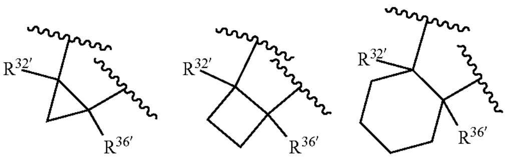

"Aromatic heterocyclyl" means an aromatic cyclyl having a single ring or two or more rings, which has one or more identical or different heteroatoms optionally selected from O, S, and N in the ring(s).

An aromatic heterocyclyl having two or more rings also includes an aromatic heterocyclyl having a single ring or two or more rings, to which a ring in the "aromatic carbocyclyl" is fused, and the linking bond may be carried by any of the rings.

The aromatic heterocyclyl having a single ring is preferably a 5- to 8-membered ring, and more preferably a 5-membered or 6-membered ring. Examples of 5-membered aromatic heterocyclyl include pyrrolyl, imidazolyl, pyrazolyl, triazolyl, tetrazolyl, furyl, thienyl, isoxazolyl, oxazolyl, oxadiazolyl, isothiazolyl, thiazolyl, and thiadiazolyl. Examples of 6-membered aromatic heterocyclyl include pyridyl, pyridazinyl, pyrimidinyl, pyrazinyl, and triazinyl.

The aromatic heterocyclyl having two rings is preferably an 8- to 10-membered ring, and more preferably a 9-membered or 10-membered ring. Examples include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, and thiazolopyridyl.

Examples of 9-membered aromatic heterocyclyl include indolyl, isoindolyl, indazolyl, indolizinyl, purinyl, benzimidazolyl, benzisoxazolyl, benzoxazolyl, benzoxadiazolyl, benzisothiazolyl, benzothiazolyl, benzothiadiazolyl, benzotriazolyl, benzofuryl, imidazopyridyl, triazolopyridyl, oxazolopyridyl, and thiazolopyridyl.

Examples of 10-membered aromatic heterocyclyl include quinolinyl, isoquinolinyl, cinnolinyl, phthalazinyl, quinazolinyl, naphthyridinyl, quinoxalinyl, pteridinyl, and pyrazinopyridazinyl.

An aromatic heterocyclyl having three or more rings is preferably a 13- to 15-membered group. Examples include carbazolyl, acridinyl, xanthenyl, phenothiazinyl, phenoxathiinyl, phenoxazinyl, and dibenzofuryl.

"Aromatic heterocycle" means a ring derived from the above-described "aromatic heterocyclyl".

Examples of "aromatic heterocycle formed by $R^{31'}$ and $R^{35'}$ together with a carbon atom to which $R^{31'}$ is bonded and a carbon atom to which $R^{35'}$ is bonded" include the following rings.

[Chemical Formula 32]

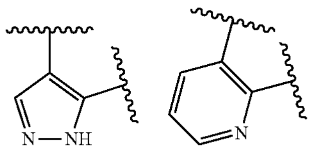

"Non-aromatic heterocyclyl" means a non-aromatic cyclyl having a single ring or two or more rings, which has one or more identical or different heteroatoms optionally selected from O, S, and N in the ring(s). A non-aromatic heterocyclyl having two or more rings also includes a non-aromatic heterocyclyl having a single ring or two or more rings, to which a ring in each of the "aromatic carbocyclyl", "non-aromatic carbocyclyl", and/or "aromatic heterocyclyl" is fused, as well as a non-aromatic carbocyclyl having a single ring or two or more rings, to which a ring in the "aromatic heterocyclyl" is fused, and the linking bond may be carried by any of the rings.

Furthermore, the "non-aromatic heterocyclyl" also includes a bridged group or a group forming a spiro ring, such as follows.

[Chemical Formula 33]

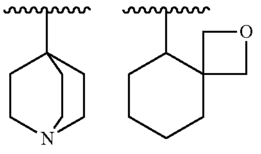

The non-aromatic heterocyclyl having a single ring is preferably a 3- to 8-membered ring, and more preferably a 5-membered or 6-membered ring.

Examples of 3-membered non-aromatic heterocyclyl include thiiranyl, oxiranyl, and aziridinyl. Examples of 4-membered non-aromatic heterocyclyl include oxetanyl and azetidinyl. Examples of 5-membered non-aromatic heterocyclyl include oxathiolanyl, thiazolidinyl, pyrrolidinyl, pyrrolinyl, imidazolidinyl, imidazolinyl, pyrazolidinyl, pyrazolinyl, tetrahydrofuryl, dihydrothiazolyl, tetrahydroisothiazolyl, dioxolanyl, dioxolyl, and thiolanyl. Examples of 6-membered non-aromatic heterocyclyl include dioxanyl, thianyl, piperidyl, piperazinyl, morpholinyl, morpholino, thiomorpholinyl, thiomorpholino, dihydropyridyl, tetrahydropyridyl, tetrahydropyranyl, dihydroxazinyl, tetrahydropyridazinyl, hexahydropyrimidinyl, dioxazinyl, thiinyl, and thiazinyl. Examples of the 7-membered non-aromatic heterocyclyl include hexahydroazepinyl, tetrahydrodiazepinyl, and oxepanyl.

The non-aromatic heterocyclyl having two or more rings is preferably an 8- to 20-membered ring, more preferably an 8- to 13-membered ring, and even more preferably an 8- to 10-membered ring. Examples include indolinyl, isoindolinyl, chromanyl, and isochromanyl.

The term "nitrogen-containing non-aromatic heterocyclyl" means a non-aromatic heterocyclyl, which is monocyclic or polycyclic having two or more rings, containing one or more nitrogen atoms. The nitrogen-containing non-aromatic heterocyclyl, which is polycyclic having two or more rings, includes a fused ring group wherein a nitrogen-containing non-aromatic heterocyclyl, which is monocyclic or polycyclic having two or more rings, is fused with a ring of the above "aromatic carbocyclyl", "non-aromatic carbocyclyl" and/or "aromatic heterocyclyl", and the bond may be held in any ring. The nitrogen-containing non-aromatic heterocyclyl, which is polycyclic having two or more rings, includes a fused ring group wherein a non-aromatic carbocyclyl, which is monocyclic or polycyclic having two or more rings, is fused with a ring of an aromatic heterocyclyl which is monocyclic or polycyclic having two or more rings, containing one or more nitrogen atoms, and the bond may be held in any ring.

Examples of the same include the following groups.

[Chemical Formula 34]

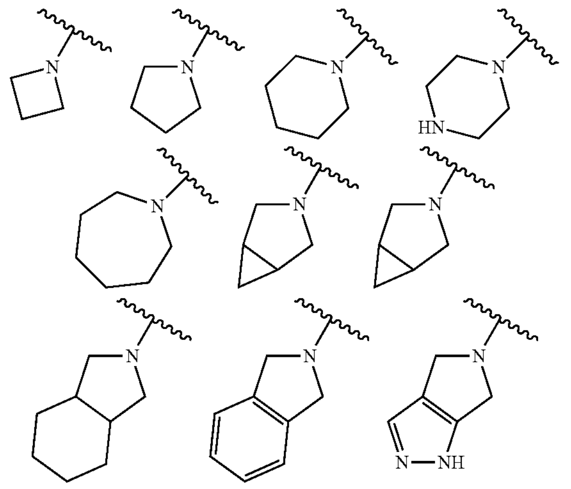

-continued

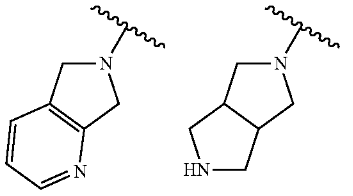

Furthermore, the "nitrogen-containing non-aromatic heterocyclyl" also include a group having a bridge or a group to form a spiro ring as follows.

[Chemical Formula 35]

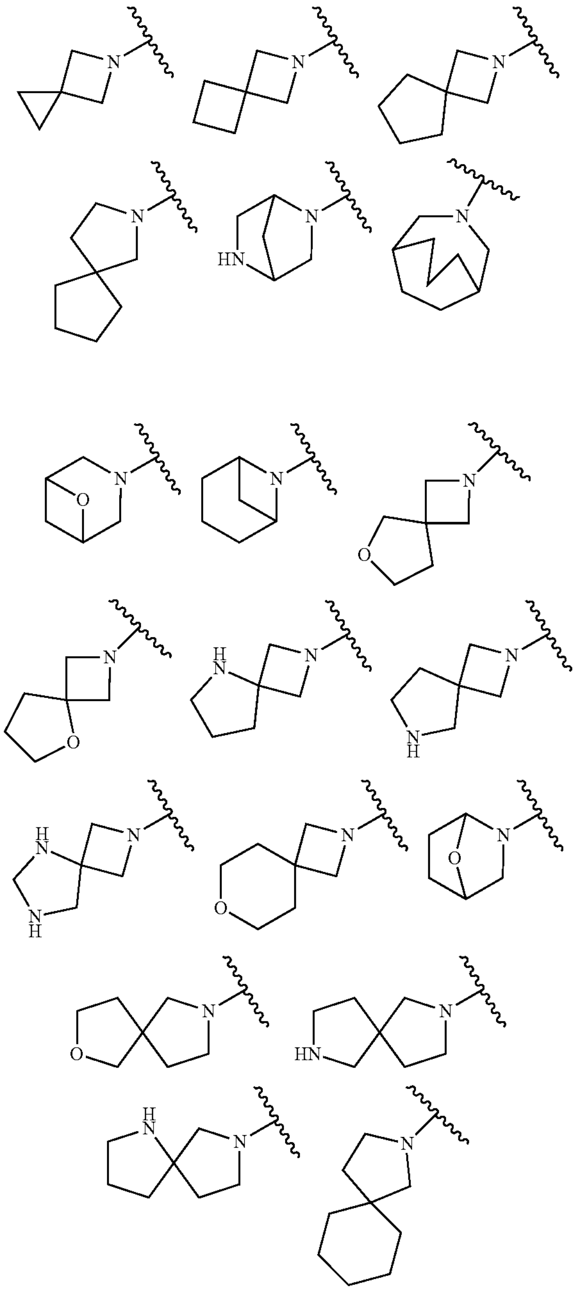

-continued

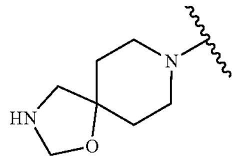

"Non-aromatic heterocycle" means a ring derived from the above-described "non-aromatic heterocyclyl".

Examples of "non-aromatic heterocycle formed by $R^{8a}$ and $R^{8b}$ together with a carbon atom to which $R^{8a}$ and $R^{8b}$ are bonded" include the following rings.

[Chemical Formula 36]

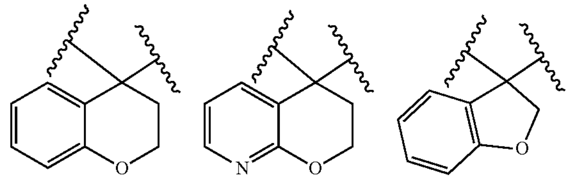

Examples of "non-aromatic heterocycle formed by $R^{7a}$ and $R^{7b}$ together with a carbon atom to which $R^{7a}$ and $R^{7b}$ are bonded" include the following rings.

[Chemical Formula 37]

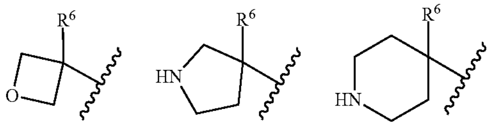

Examples of "non-aromatic heterocycle formed by $R^{31}$ and $R^{32}$ together with a carbon atom to which $R^{31}$ and $R^{32}$ are bonded" include the following rings.

[Chemical Formula 38]

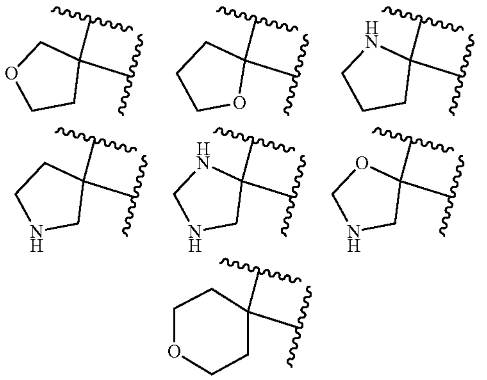

Examples of "non-aromatic heterocycle formed by $R^{31'}$ and $R^{35'}$ together with a carbon atom to which $R^{31'}$ is bonded and a carbon atom to which $R^{35'}$ is bonded" include the following rings.

[Chemical Formula 39]

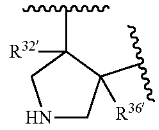

"Trialkylsilyl" means a group in which three moieties of the above-described "alkyl" are bonded to a silicon atom. The three alkyl groups may be identical or different. Examples include trimethylsilyl, triethylsilyl, and tert-butyldimethylsilyl.

In the present specification, the phrase "may be substituted with substituent group α" means that "an arbitrary substitutable hydrogen atom may be substituted with one or more group(s) selected from substituent group α". The same also applies to substituent groups ß, γ, and γ'.

Examples of the substituents for the "substituted alkyl", the "substituted alkynyl", the "substituted alkyloxy", the "substituted alkenyloxy", the "substituted alkynyloxy", and the "substituted alkyloxycarbonyl" include substituent group A given below. A carbon atom at any position may be bonded to one or more group(s) selected from the following substituent group A.

Substituent group A: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azide, hydrazino, ureido, amidino, guanidino, pentafluorothio, trialkylsilyl, alkyloxy which may be substituted with substituent group α, alkenyloxy which may be substituted with substituent group α, alkynyloxy which may be substituted with substituent group α, alkylcarbonyloxy which may be substituted with substituent group α, alkenylcarbonyloxy which may be substituted with substituent group α, alkynylcarbonyloxy which may be substituted with substituent group α, alkylcarbonyl which may be substituted with substituent group α, alkenylcarbonyl which may be substituted with substituent group α, alkynylcarbonyl which may be substituted with substituent group α, alkyloxycarbonyl which may be substituted with substituent group α, alkenyloxycarbonyl which may be substituted with substituent group α, alkynyloxycarbonyl which may be substituted with substituent group α, alkylsulfanyl which may be substituted with substituent group α, alkenylsulfanyl which may be substituted with substituent group α, alkynylsulfanyl which may be substituted with substituent group α, alkylsulfinyl which may be substituted with substituent group α, alkenylsulfinyl which may be substituted with substituent group α, alkynylsulfinyl which may be substituted with substituent group α, alkylsulfonyl which may be substituted with substituent group α, alkenylsulfonyl which may be substituted with substituent group α, alkynylsulfonyl which may be substituted with substituent group α, amino which may be substituted with substituent group ß, imino which may be substituted with substituent group ß, carbamoyl which may be substituted with substituent group ß, sulfamoyl which may be substituted with substituent group ß, aromatic carbocyclyl which may be substituted with substituent group γ, non-aromatic carbocyclyl which may be substituted with substituent group γ', aromatic heterocyclyl which may be substituted with substituent group γ, non-aromatic heterocyclyl which may be substituted with substituent group γ', aromatic carbocyclyloxy which may be substituted with substituent group γ, non-aromatic carbocyclyloxy which may be substituted with substituent group γ', aromatic heterocyclyloxy which may be substituted with substituent group γ, non-aromatic heterocyclyloxy which may be substituted with substituent group γ', aromatic carbocyclylcarbonyloxy which may be substituted with substituent group γ, non-aromatic carbocyclylcarbonyloxy which may be substituted with substituent group γ', aromatic heterocyclylcarbonyloxy which may be substituted with substituent group γ, non-aromatic heterocyclylcarbonyloxy which may be substituted with substituent group γ', aromatic carbocyclylcarbonyl which may be substituted with substituent group γ, non-aromatic carbocyclylcarbonyl which may be substituted with substituent group γ', aromatic heterocyclylcarbonyl which may be substituted with substituent group γ, non-aromatic heterocyclylcarbonyl which may be substituted with substituent group γ', aromatic carbocyclyloxycarbonyl which may be substituted with substituent group γ, non-aromatic carbocyclyloxycarbonyl which may be substituted with substituent group γ', aromatic heterocyclyloxycarbonyl which may be substituted with substituent group γ, non-aromatic heterocyclyloxycarbonyl which may be substituted with substituent group γ', aromatic carbocyclylalkyloxy which may be substituted with substituent group γ, non-aromatic carbocyclylalkyloxy which may be substituted with substituent group γ', aromatic heterocyclylalkyloxy which may be substituted with substituent group γ, non-aromatic heterocyclylalkyloxy which may be substituted with substituent group γ', aromatic carbocyclylalkyloxycarbonyl which may be substituted with substituent group γ, non-aromatic carbocyclylalkyloxycarbonyl which may be substituted with substituent group γ', aromatic heterocyclylalkyloxycarbonyl which may be substituted with substituent group γ, non-aromatic heterocyclylalkyloxycarbonyl which may be substituted with substituent group γ', aromatic carbocyclylsulfanyl which may be substituted with substituent group γ, non-aromatic carbocyclylsulfanyl which may be substituted with substituent group γ', aromatic heterocyclylsulfanyl which may be substituted with substituent group γ, non-aromatic heterocyclylsulfanyl which may be substituted with substituent group γ', aromatic carbocyclylsulfinyl which may be substituted with substituent group γ, non-aromatic carbocyclylsulfinyl which may be substituted with substituent group γ', aromatic heterocyclylsulfinyl which may be substituted with substituent group γ, non-aromatic heterocyclylsulfinyl which may be substituted with substituent group γ', aromatic carbocyclylsulfonyl which may be substituted with substituent group γ, non-aromatic carbocyclylsulfonyl which may be substituted with substituent group γ', aromatic heterocyclylsulfonyl which may be substituted with substituent group γ, and non-aromatic heterocyclylsulfonyl which may be substituted with substituent group γ'.

Substituent group α: halogen, hydroxy, carboxy, alkyloxy, haloalkyloxy, alkenyloxy, alkynyloxy, sulfanyl, and cyano.

Substituent group ß: halogen, hydroxy, carboxy, cyano, alkyl which may be substituted with substituent group α, alkenyl which may be substituted with substituent group α, alkynyl which may be substituted with substituent group α, alkylcarbonyl which may be substituted with substituent group α, alkenylcarbonyl which may be substituted with substituent group α, alkynylcarbonyl which may be substituted with substituent group α, alkyloxycarbonyl which may be substituted with substituent group α, alkenyloxycarbonyl which may be substituted with substituent group α, alkynyloxycarbonyl which may be substituted with substituent group α, alkylsulfanyl which may be substituted with substituent group α, alkenylsulfanyl which may be substituted with substituent group α, alkynylsulfanyl which may be substituted with substituent group α, alkylsulfinyl which may be substituted with substituent group α, alkenylsulfinyl which may be substituted with substituent group α, alkynylsulfinyl which may be substituted with substituent group α, alkylsulfonyl which may be substituted with substituent group α, alkenylsulfonyl which may be substituted with substituent group α, alkynylsulfonyl which may be substituted with substituent group α, aromatic carbocyclyl which may be substituted with substituent group γ, non-aromatic carbocyclyl which may be substituted with substituent group γ', aromatic heterocyclyl which may be substituted with substituent group γ, non-aromatic heterocyclyl which may be substituted with substituent group γ', aromatic carbocyclylalkyl which may be substituted with substituent group γ, non-aromatic carbocyclylalkyl which may be substituted with substituent group γ', aromatic heterocyclylalkyl which may be substituted with substituent group γ, non-aromatic heterocyclylalkyl which may be substituted with substituent group γ', aromatic carbocyclylcarbonyl which may be substituted with substituent group γ, non-aromatic carbocyclylcarbonyl which may be substituted with substituent group γ', aromatic heterocyclylcarbonyl which may be substituted with substituent group γ, non-aromatic heterocyclylcarbonyl which may be substituted with substituent group γ', aromatic carbocyclyloxycarbonyl which may be substituted with substituent group γ, non-aromatic carbocyclyloxycarbonyl which may be substituted with substituent group γ', aromatic heterocyclyloxycarbonyl which may be substituted with substituent group γ, non-aromatic heterocyclyloxycarbonyl which may be substituted with substituent group γ', aromatic carbocyclylsulfanyl which may be substituted with substituent group γ, non-aromatic carbocyclylsulfanyl which may be substituted with substituent group γ', aromatic heterocyclylsulfanyl which may be substituted with substituent group γ, non-aromatic heterocyclylsulfanyl which may be substituted with substituent group γ', aromatic carbocyclylsulfinyl which may be substituted with substituent group γ, non-aromatic carbocyclylsulfinyl which may be substituted with substituent group γ', aromatic heterocyclylsulfinyl which may be substituted with substituent group γ, non-aromatic heterocyclylsulfinyl which may be substituted with substituent group γ', aromatic carbocyclylsulfonyl which may be substituted with substituent group γ, non-aromatic carbocyclylsulfonyl which may be substituted with substituent group γ', aromatic heterocyclylsulfonyl which may be substituted with substituent group γ, and non-aromatic heterocyclylsulfonyl which may be substituted with substituent group γ'.

Substituent group γ: substituent group α, alkyl, haloalkyl, hydroxyalkyl, alkenyl, alkynyl, alkylcarbonyl, haloalkylcarbonyl, alkenylcarbonyl, and alkynylcarbonyl.

Substituent group γ': substituent group γ and oxo.

Examples of a substituent on a ring of "aromatic carbocycle", "aromatic heterocycle", "substituted or unsubstituted aromatic carbocycle formed by $R^{31'}$ and $R^{35'}$ together with a carbon atom to which $R^{31'}$ is bonded and a carbon atom to which $R^{35'}$ is bonded", and "substituted or unsubstituted aromatic heterocycle formed by $R^{31'}$ and $R^{35'}$ together with a carbon atom to which $R^{31'}$ is bonded and a carbon atom to which $R^{35'}$ is bonded", such as "substituted aromatic carbocyclyl", "substituted aromatic heterocyclyl", "substituted aromatic carbocyclyloxy", "substituted aromatic heterocyclyloxy", include the following substituent group B. An atom at any position on the ring may be bonded to one or more group(s) selected from the following substituent group B.

Substituent group B: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azide, hydrazino, ureido, amidino, guanidino, pentafluorothio, trialkylsilyl, alkyl which may be substituted with substituent group α, alkenyl which may be substituted with substituent group α, alkynyl which may be substituted with substituent group α, alkyloxy which may be substituted with substituent group α, alkenyloxy which may be substituted with substituent group α, alkynyloxy which may be substituted with substituent group α, alkylcarbonyloxy which may be substituted with substituent group α, alkenylcarbonyloxy which may be substituted with substituent group α, alkynylcarbonyloxy which may be substituted with substituent group α, alkylcarbonyl which may be substituted with substituent group α, alkenylcarbonyl which may be substituted with substituent group α, alkynylcarbonyl which may be substituted with substituent group α, alkyloxycarbonyl which may be substituted with substituent group α, alkenyloxycarbonyl which may be substituted with substituent group α, alkynyloxycarbonyl which may be substituted with substituent group α, alkylsulfanyl which may be substituted with substituent group α, alkenylsulfanyl which may be substituted with substituent group α, alkynylsulfanyl which may be substituted with substituent group α, alkylsulfinyl which may be substituted with substituent group α, alkenylsulfinyl which may be substituted with substituent group α, alkynylsulfinyl which may be substituted with substituent group α, alkylsulfonyl which may be substituted with substituent group α, alkenylsulfonyl which may be substituted with substituent group α, alkynylsulfonyl which may be substituted with substituent group α, amino which may be substituted with substituent group ß, imino which may be substituted with substituent group ß, carbamoyl which may be substituted with substituent group ß, sulfamoyl which may be substituted with substituent group ß, aromatic carbocyclyl which may be substituted with substituent group γ, non-aromatic carbocyclyl which may be substituted with substituent group γ', aromatic heterocyclyl which may be substituted with substituent group γ, non-aromatic heterocyclyl which may be substituted with substituent group γ', aromatic carbocyclyloxy which may be substituted with substituent group γ, non-aromatic carbocyclyloxy which may be substituted with substituent group γ', aromatic heterocyclyloxy which may be substituted with substituent group γ, non-aromatic heterocyclyloxy which may be substituted with substituent group γ', aromatic carbocyclylcarbonyloxy which may be substituted with substituent group γ, non-aromatic carbocyclylcarbonyloxy which may be substituted with substituent group γ', aromatic heterocyclylcarbonyloxy which may be substituted with substituent group γ, non-aromatic heterocyclylcarbonyloxy which may be substituted with substituent group γ', aromatic carbocyclylcarbonyl which may be substituted with substituent group γ, non-aromatic carbocyclylcarbonyl which may be substituted with substituent group γ', aromatic heterocyclylcarbonyl which may be substituted with substituent group γ, non-aromatic heterocyclylcarbonyl which may be substituted with substituent group γ', aromatic carbocyclyloxycarbonyl which may be substituted with substituent group γ, non-aromatic carbocyclyloxycarbonyl which may be substituted with substituent group γ', aromatic heterocyclyloxycarbonyl which may be substituted with substituent group γ, non-aromatic heterocyclyloxycarbonyl which may be substituted with substituent group γ', aromatic carbocyclylalkyl which may be substituted with substituent group γ, non-aromatic carbocyclylalkyl which may be substituted with substituent group γ', aromatic heterocyclylalkyl which may be substituted with substituent group γ, non-aromatic heterocyclylalkyl which may be substituted with substituent group γ', aromatic carbocyclylalkyloxy which may be substituted with substituent group γ, non-aromatic carbocyclylalkyloxy which may be substituted with substituent group γ', aromatic heterocyclylalkyloxy which may be substituted with substituent group γ, non-aromatic heterocyclylalkyloxy which may be substituted with substituent group γ', aromatic carbocyclylalkyloxycarbonyl which may be substituted with substituent group γ, non-aromatic carbocyclylalkyloxycarbonyl which may be substituted with substituent group γ', aromatic heterocyclylalkyloxycarbonyl which may be substituted with substituent group γ, non-aromatic heterocyclylalkyloxycarbonyl which may be substituted with substituent group γ', aromatic carbocyclylalkyloxyalkyl which may be substituted with substituent group γ, non-aromatic carbocyclylalkyloxyalkyl which may be substituted with substituent group γ', aromatic heterocyclylalkyloxyalkyl which may be substituted with substituent group γ, non-aromatic heterocyclylalkyloxyalkyl which may be substituted with substituent group γ', aromatic carbocyclylsulfanyl which may be substituted with substituent group γ, non-aromatic carbocyclylsulfanyl which may be substituted with substituent group γ', aromatic heterocyclylsulfanyl which may be substituted with substituent group γ, non-aromatic heterocyclylsulfanyl which may be substituted with substituent group γ', aromatic carbocyclylsulfinyl which may be substituted with substituent group γ, non-aromatic carbocyclylsulfinyl which may be substituted with substituent group γ', aromatic heterocyclylsulfinyl which may be substituted with substituent group γ, non-aromatic heterocyclylsulfinyl which may be substituted with substituent group γ', aromatic carbocyclylsulfonyl which may be substituted with substituent group γ, non-aromatic carbocyclylsulfonyl which may be substituted with substituent group γ', aromatic heterocyclylsulfonyl which may be substituted with substituent group γ, and non-aromatic heterocyclylsulfonyl which may be substituted with substituent group γ'.

Examples of a substituent on a ring of "non-aromatic carbocycle" and "non-aromatic heterocycle" of "substituted non-aromatic carbocyclyl", "substituted non-aromatic heterocyclyl", "substituted non-aromatic carbocyclyloxy", "substituted non-aromatic heterocyclyloxy", "nitrogen-containing non-aromatic heterocyclyl", "non-aromatic carbocycle formed by $R^{8a}$ and $R^{8b}$ together with a carbon atom to which $R^{8a}$ and $R^{8b}$ are bonded", "non-aromatic carbocycle formed by $R^{7a}$ and $R^{7b}$ together with a carbon atom to which $R^{7a}$ and $R^{7b}$ are bonded", "non-aromatic carbocycle formed by $R^{31}$ and $R^{32}$ together with a carbon atom to which $R^{31}$ and $R^{32}$ are bonded", "non-aromatic carbocycle formed by $R^{31'}$ and $R^{35'}$ together with a carbon atom to which $R^{31'}$ is bonded and a carbon atom to which $R^{35'}$ is bonded", "non-aromatic heterocycle formed by $R^{8a}$ and $R^{8b}$ together with a carbon atom to which $R^{8a}$ and $R^{8b}$ are bonded", "non-aromatic heterocycle formed by $R^{7a}$ and $R^{7b}$ together with a carbon atom to which $R^{7a}$ and $R^{7b}$ are bonded", "non-aromatic heterocycle formed by $R^{31}$ and $R^{32}$ together with a carbon atom to which $R^{31}$ and $R^{32}$ are bonded", "non-aromatic heterocycle formed by $R^{31'}$ and $R^{35'}$ together with a carbon atom to which $R^{31'}$ is bonded and a carbon atom to which $R^{35'}$ is bonded" include the following substituent group C. An atom at any position on the ring may be bonded to one or more group(s) selected from the following substituent group C.

Substituent group C: substituent group B and oxo.

When the "non-aromatic carbocycle" and the "non-aromatic heterocycle" are substituted with "oxo", this means a ring in which two hydrogen atoms on a carbon atom are substituted as follows.

[Chemical Formula 40]

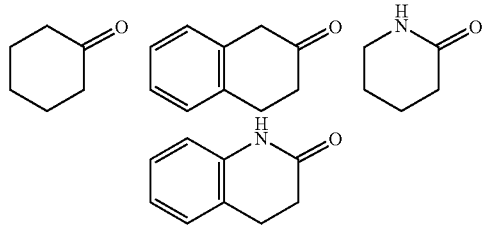

Examples of the ring in which the "non-aromatic heterocycle formed by $R^{31}$ and $R^{32}$ together with a carbon atom to which $R^{31}$ and $R^{32}$ are bonded" is substituted with oxo" include the following rings.

[Chemical Formula 41]

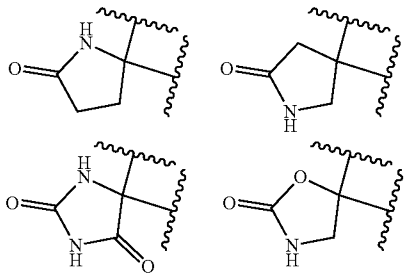

The substituents for "substituted amino", "substituted carbamoyl", and "substituted sulfamoyl" include the following substituent group D. These moieties may be substituted with one or two group(s) selected from substituent group D.

Substituent group D: halogen, hydroxy, carboxy, cyano, alkyl which may be substituted with substituent group α, alkenyl which may be substituted with substituent group α, alkynyl which may be substituted with substituent group α, alkylcarbonyl which may be substituted with substituent group α, alkenylcarbonyl which may be substituted with substituent group α, alkynylcarbonyl which may be substituted with substituent group α, alkylsulfanyl which may be substituted with substituent group α, alkenylsulfanyl which may be substituted with substituent group α, alkynylsulfanyl which may be substituted with substituent group α, alkylsulfinyl which may be substituted with substituent group α, alkenylsulfinyl which may be substituted with substituent group α, alkynylsulfinyl which may be substituted with substituent group α, alkylsulfonyl which may be substituted with substituent group α, alkenylsulfonyl which may be substituted with substituent group α, alkynylsulfonyl which may be substituted with substituent group α, amino which may be substituted with substituent group ß, imino which may be substituted with substituent group ß, carbamoyl which may be substituted with substituent group ß, sulfamoyl which may be substituted with substituent group ß, aromatic carbocyclyl which may be substituted with substituent group γ, non-aromatic carbocyclyl which may be substituted with substituent group γ', aromatic heterocyclyl which may be substituted with substituent group γ, non-aromatic heterocyclyl which may be substituted with substituent group γ', aromatic carbocyclylalkyl which may be substituted with substituent group γ, non-aromatic carbocyclylalkyl which may be substituted with substituent group γ', aromatic heterocyclylalkyl which may be substituted with substituent group γ, non-aromatic heterocyclylalkyl which may be substituted with substituent group γ', aromatic carbocyclylcarbonyl which may be substituted with substituent group γ, non-aromatic carbocyclylcarbonyl which may be substituted with substituent group γ', aromatic heterocyclylcarbonyl which may be substituted with substituent group γ, non-aromatic heterocyclylcarbonyl which may be substituted with substituent group γ', aromatic carbocyclyloxycarbonyl which may be substituted with substituent group γ, non-aromatic carbocyclyloxycarbonyl which may be substituted with substituent group γ', aromatic heterocyclyloxycarbonyl which may be substituted with substituent group γ, non-aromatic heterocyclyloxycarbonyl which may be substituted with substituent group γ', aromatic carbocyclylsulfanyl which may be substituted with substituent group γ, non-aromatic carbocyclylsulfanyl which may be substituted with substituent group γ', aromatic heterocyclylsulfanyl which may be substituted with substituent group γ, non-aromatic heterocyclylsulfanyl which may be substituted with substituent group γ', aromatic carbocyclylsulfinyl which may be substituted with substituent group γ, non-aromatic carbocyclylsulfinyl which may be substituted with substituent group γ', aromatic heterocyclylsulfinyl which may be substituted with substituent group γ, non-aromatic heterocyclylsulfinyl which may be substituted with substituent group γ', aromatic carbocyclylsulfonyl which may be substituted with substituent group γ, non-aromatic carbocyclylsulfonyl which may be substituted with substituent group γ', aromatic heterocyclylsulfonyl which may be substituted with substituent group γ, and non-aromatic heterocyclylsulfonyl which may be substituted with substituent group γ'.

Examples of the substituents for the "substituted or unsubstituted aromatic carbocyclyl" in $R^2$ include:

halogen;

cyano;

substituted or unsubstituted alkyl; and substituted or unsubstituted alkyloxy. It may be substituted with one or more group(s) selected from these.

Examples of the substituents for the "substituted or unsubstituted aromatic carbocyclyl" in $R^2$ include:

halogen;

cyano;

substituted alkyl (Examples of the substituents include halogen; optionally substituted with one or more group(s) selected from these); and unsubstituted alkyloxy. It may be substituted with one or more group(s) selected from these.

Examples of the substituents for the "substituted or unsubstituted aromatic carbocyclyl" in $R^2$ include:

halogen;

cyano;

substituted or unsubstituted alkyl;

substituted or unsubstituted alkyloxy; and substituted or unsubstituted amino. It may be substituted with one or more group(s) selected from these.

Examples of the substituents for the "substituted or unsubstituted aromatic carbocyclyl" in $R^2$ include:

halogen;

cyano;

substituted alkyl (Examples of the substituents include halogen; optionally substituted with one or more group(s) selected from these);

unsubstituted alkyloxy; and substituted amino (Example of the substituents include alkylcarbonyl; optionally substituted with one or more group(s) selected from these). It may be substituted with one or more group(s) selected from these.

Examples of the substituents for the "substituted or unsubstituted aromatic heterocyclyl" in $R^2$ include:

halogen; and substituted or unsubstituted alkyl. It may be substituted with one or more group(s) selected from these.

Examples of the substituent for the "substituted or unsubstituted aromatic heterocyclyl" in $R^2$ include:

halogen; and substituted alkyl (Examples of the substituents include halogen; optionally substituted with one or more group(s) selected from these). It may be substituted with one or more group(s) selected from these.

Examples of substituents for the "substituted or unsubstituted non-aromatic carbocyclyl" and the "substituted or unsubstituted non-aromatic heterocyclyl" in $R^2$ include: halogen; and substituted alkyl (Examples of the substituents include halogen). It may be substituted with one or more group(s) selected from these.

Examples of substituents for the "substituted or unsubstituted alkyl" in $R^2$ include: halogen; substituted alkyl (Examples of the substituents include halogen; optionally substituted with one or more group(s) selected from these). It may be substituted with one or more group(s) selected from these.

Examples of the substituents for the "substituted or unsubstituted aromatic carbocyclyl" in $R^{8a}$ include:

halogen;

cyano;

substituted alkyl (Examples of the substituents include halogen; optionally substituted with one or more group(s) selected from these); and unsubstituted alkyloxy. It may be substituted with one or more group(s) selected from these.

Examples of the substituents for the "substituted or unsubstituted aromatic carbocyclyl" in $R^{8a}$ include halogen. It may be substituted with one or more group(s) selected from these.

Examples of the substituents for the "substituted or unsubstituted aromatic heterocyclyl" in $R^{8a}$ include halogen. It may be substituted with one or more group(s) selected from these.

Examples of the "substituents for "substituted or unsubstituted non-aromatic heterocycle" and "substituted or unsubstituted non-aromatic carbocycle" formed by $R^{8a}$ and $R^{8b}$ together with a carbon atom to which $R^{8a}$ and $R^{8b}$ are bonded" include halogen. It may be substituted with one or more group(s) selected from these.

Examples of the substituents for the "substituted or unsubstituted alkyl" in $R^{8b}$ include halogen. It may be substituted with one or more group(s) selected from these.

Examples of the substituents for the "substituted or unsubstituted aromatic carbocyclyl" in $R^{3c}$ and $R^3$ include:

halogen;

cyano;

carboxy;

substituted or unsubstituted alkyl;

substituted or unsubstituted alkyloxycarbonyl; and substituted or unsubstituted non-aromatic carbocyclyl. It may be substituted with one or more group(s) selected from these.

Examples of the substituents for the "substituted or unsubstituted aromatic carbocyclyl" in $R^{3c}$ and $R^3$ include:

halogen;

cyano;

carboxy;

substituted alkyl (Examples of the substituents include halogen); unsubstituted alkyl;

unsubstituted alkyloxycarbonyl; and unsubstituted non-aromatic carbocyclyl. It may be substituted with one or more group(s) selected from these.

Examples of the substituents for the "substituted or unsubstituted aromatic carbocyclyl" in $R^{3c}$ and $R^3$ include:

halogen;

cyano;

carboxy;

substituted or unsubstituted alkyl;

substituted or unsubstituted alkyloxy;

substituted or unsubstituted alkyloxycarbonyl;

substituted or unsubstituted amino;

substituted or unsubstituted carbamoyl;

substituted or unsubstituted sulfamoyl; and substituted or unsubstituted non-aromatic carbocyclyl. It may be substituted with one or more group(s) selected from these.

Examples of the substituents for the "substituted or unsubstituted aromatic carbocyclyl" in $R^{3c}$ and $R^3$ include:

halogen;

cyano;

carboxy;

substituted alkyl (the substituent is halogen); unsubstituted alkyl;

unsubstituted alkyloxy;

unsubstituted alkyloxycarbonyl;

substituted amino (the substituent is alkyl);

unsubstituted carbamoyl;

unsubstituted sulfamoyl; and unsubstituted non-aromatic carbocyclyl. It may be substituted with one or more group(s) selected from these.

Examples of the substituents for the "substituted or unsubstituted aromatic heterocyclyl" in $R^{3c}$ and $R^3$ include substituted or unsubstituted alkyl. It may be substituted with one or more group(s) selected from these.

Examples of the substituents for the "substituted or unsubstituted aromatic heterocyclyl" in $R^{3c}$ and $R^3$ include unsubstituted alkyl. It may be substituted with one or more group(s) selected from these.

Examples of the substituents for the "substituted or unsubstituted aromatic heterocyclyl" in $R^{3c}$ and $R^3$ include substituted or unsubstituted alkyl; and substituted or unsubstituted non-aromatic carbocyclyl. It may be substituted with one or more group(s) selected from these.

Examples of the substituents for the "substituted or unsubstituted aromatic heterocyclyl" in $R^{3c}$ and $R^3$ include unsubstituted alkyl; and unsubstituted non-aromatic carbocyclyl. It may be substituted with one or more group(s) selected from these.

Examples of the substituents for the "substituted or unsubstituted non-aromatic heterocyclyl" in $R^{3c}$ and $R^3$ include:

oxo;

halogen;

cyano;

hydroxy;

substituted or unsubstituted carbamoyl;

substituted or unsubstituted sulfamoyl;

substituted or unsubstituted alkyl;

substituted or unsubstituted alkyloxy;

substituted or unsubstituted aromatic carbocyclyl;

substituted or unsubstituted non-aromatic carbocyclyl;

substituted or unsubstituted aromatic heterocyclyl; and substituted or unsubstituted non-aromatic heterocyclyl. It may be substituted with one or more group(s) selected from these.

Examples of the substituents for the "substituted or unsubstituted non-aromatic heterocyclyl" in $R^{3c}$ and $R^3$ include:

oxo;

halogen;

cyano;

hydroxy;

unsubstituted carbamoyl;

unsubstituted sulfamoyl;

substituted alkyl (Examples of the substituents include halogen and hydroxy;

optionally substituted with one or more group(s) selected from these); unsubstituted alkyl;

unsubstituted alkyloxy;

unsubstituted aromatic carbocyclyl;

unsubstituted non-aromatic carbocyclyl;

unsubstituted aromatic heterocyclyl; and unsubstituted non-aromatic heterocyclyl. It may be substituted with one or more group(s) selected from these.

Examples of the substituents for the "substituted or unsubstituted non-aromatic heterocyclyl" in $R^{3c}$ and $R^3$ include: oxo;

halogen;

cyano;

hydroxy;

substituted or unsubstituted carbamoyl;

substituted or unsubstituted sulfamoyl;

substituted or unsubstituted alkyl;

substituted or unsubstituted alkyloxy;

substituted or unsubstituted aromatic carbocyclyl;

substituted or unsubstituted non-aromatic carbocyclyl;

substituted or unsubstituted aromatic heterocyclyl;

substituted or unsubstituted non-aromatic heterocyclyl; and substituted or unsubstituted non-aromatic heterocyclylcarbonyl. It may be substituted with one or more group(s) selected from these.

Examples of the substituents for the "substituted or unsubstituted non-aromatic heterocyclyl" in $R^{3c}$ and $R^3$ include:

oxo;

halogen;

cyano;

hydroxy;

unsubstituted carbamoyl;

unsubstituted sulfamoyl;

substituted alkyl (Examples of the substituents include halogen and hydroxy;

optionally substituted with one or more group(s) selected from these); unsubstituted alkyl;

substituted alkyloxy (Examples of the substituents include halogen; optionally substituted with one or more group(s) selected from these); unsubstituted alkyloxy;

unsubstituted aromatic carbocyclyl;

unsubstituted non-aromatic carbocyclyl;

substituted aromatic heterocyclyl (Examples of the substituents include halogen;

optionally substituted with one or more group(s) selected from these); unsubstituted aromatic heterocyclyl;

unsubstituted non-aromatic heterocyclyl; and substituted non-aromatic heterocyclylcarbonyl (Examples of the substituents include halogen; optionally substituted with one or more group(s) selected from these). It may be substituted with one or more group(s) selected from these.

Examples of the substituents for the "substituted or unsubstituted non-aromatic carbocyclyl" in $R^{3c}$ and $R^3$ include hydroxy. It may be substituted with one or more group(s) selected from these.

Examples of the substituents for the "substituted or unsubstituted aromatic carbocyclyloxy" in $R^{3c}$ and $R^3$ include:

halogen; and substituted or unsubstituted alkyloxy. It may be substituted with one or more group(s) selected from these.

Examples of the substituents for the "substituted or unsubstituted aromatic carbocyclyloxy" in $R^{3c}$ and $R^3$ include:

halogen; and unsubstituted alkyloxy. It may be substituted with one or more group(s) selected from these.

Examples of the substituents for the "substituted or unsubstituted aromatic heterocyclyloxy" in $R^{3c}$ and $R^3$ include halogen. It may be substituted with one or more group(s) selected from these.

Examples of the substituents for the "substituted or unsubstituted non-aromatic carbocyclyloxy" in $R^{3c}$ and $R^3$ include halogen. It may be substituted with one or more group(s) selected from these.

Examples of the substituents for the "substituted or unsubstituted non-aromatic heterocyclyloxy" in $R^{3c}$ and $R^3$ include halogen. It may be substituted with one or more group(s) selected from these.

Examples of the substituents for the "substituted or unsubstituted alkyl" in $R^{3c}$ and $R^3$ include hydroxy. It may be substituted with one or more group(s) selected from these.

Examples of the substituents for the "substituted or unsubstituted alkyl" in $R^{3c}$ and $R^3$ include:

hydroxy;

halogen;

alkyloxy; and substituted non-aromatic carbocyclyl (Examples of the substituents include halogen; and hydroxy; optionally substituted with one or more group(s) selected from these). It may be substituted with one or more group(s) selected from these.

Examples of the substituents for the "substituted or unsubstituted alkenyl" in $R^3$ include hydroxy. It may be substituted with one or more group(s) selected from these.

Examples of the substituents for the "substituted or unsubstituted alkenyl" in $R^{3c}$ and $R^3$ include:

hydroxy; and substituted or unsubstituted aromatic carbocyclyl. It may be substituted with one or more group(s) selected from these.

Examples of the substituents for the "substituted or unsubstituted alkenyl" in $R^{3c}$ and $R^3$ include:

hydroxy; and substituted aromatic carbocyclyl (Examples of the substituents include haloalkyl; optionally substituted with one or more groups selected from these). It may be substituted with one or more group(s) selected from these.

Examples of the substituents for the "substituted or unsubstituted alkynyl" in $R^{3c}$ and $R^3$ include substituted or unsubstituted non-aromatic carbocyclyl.

It may be substituted with one or more group(s) selected from these.

Examples of the substituents for the "substituted or unsubstituted alkynyl" in $R^{3c}$ and $R^3$ include unsubstituted non-aromatic carbocyclyl. It may be substituted with one or more group(s) selected from these.

Examples of the substituents for the "substituted or unsubstituted amino" in $R^3$ include substituted or unsubstituted alkyl. It may be substituted with one or more group(s) selected from these.

Examples of the substituents for the "substituted or unsubstituted amino" in $R^3$ include substituted alkyl (Examples of the substituents include aromatic carbocyclyl); and unsubstituted alkyl. It may be substituted with one or more group(s) selected from these.

Examples of the substituents for the "substituted or unsubstituted amino" in $R^{3c}$ and $R^3$ include:

substituted or unsubstituted alkyl; and substituted or unsubstituted aromatic carbocyclylsulfonyl. It may be substituted with one or more group(s) selected from these.

Examples of the substituents for the "substituted or unsubstituted amino" in $R^{3c}$ and $R^3$ include:

substituted alkyl (Examples of the substituents include aromatic carbocyclyl);

unsubstituted alkyl; and unsubstituted aromatic carbocyclylsulfonyl. It may be substituted with one or more group(s) selected from these.

Examples of the substituents for the "substituted or unsubstituted alkyloxy" in $R^{3c}$ and $R^3$ include halogen. It may be substituted with one or more group(s) selected from these.

Examples of the substituents for the "substituted or unsubstituted carbamoyl" in $R^{3c}$ and $R^3$ include substituted alkyl (Examples of the substituents include halogen); and unsubstituted alkyl. It may be substituted with one or more group(s) selected from these.

The substituents in the "substituted or unsubstituted aromatic carbocyclyl", the "substituted or unsubstituted non-aromatic carbocyclyl", the "substituted or unsubstituted aromatic heterocyclyl", the "substituted or unsubstituted non-aromatic heterocyclyl", the "substituted or unsubstituted aromatic carbocyclyloxy", the "substituted or unsubstituted non-aromatic carbocyclyloxy", the "substituted or unsubstituted aromatic heterocyclyloxy", the "substituted or unsubstituted non-aromatic heterocyclyloxy", the "substituted or unsubstituted alkyl", the "substituted or unsubstituted alkenyl", the "substituted or unsubstituted alkynyl", or the "substituted or unsubstituted alkyloxy" in $R^{3a}$ have the same meanings as those in $R^{3c}$ Examples of the substituent for the "substituted or unsubstituted aromatic heterocyclyl" in $R^1$ include:

halogen; and substituted or unsubstituted alkyl. It may be substituted with one or more group(s) selected from these.

Examples of the substituent for the "substituted or unsubstituted aromatic heterocyclyl" in $R^1$ include:

halogen;

substituted alkyl (Examples of the substituents include halogen; optionally substituted with one or more group(s) selected from these); and unsubstituted alkyl.

It may be substituted with one or more group(s) selected from these.

Examples of the substituent for the "substituted or unsubstituted aromatic heterocyclyl" in $R^1$ include:

halogen; cyano; oxide;

substituted or unsubstituted alkyl;

substituted or unsubstituted alkyloxy; and substituted or unsubstituted amino. It may be substituted with one or more group(s) selected from these.

Examples of the substituent for the "substituted or unsubstituted aromatic heterocyclyl" in $R^1$ include:

halogen; cyano; oxide;

substituted alkyl (Examples of the substituents include halogen and cyano; optionally substituted with one or more group(s) selected from these); unsubstituted alkyl;

substituted alkyloxy (Examples of the substituents include halogen; optionally substituted with one or more group(s) selected from these); unsubstituted alkyloxy; and substituted amino (Examples of the substituent include alkyl; optionally substituted with one or more group(s) selected from these). It may be substituted with one or more group(s) selected from these.

Examples of the substituent for the "substituted or unsubstituted non-aromatic heterocyclyl" in $R^1$ include:

halogen;

oxo; and substituted or unsubstituted alkyl. It may be substituted with one or more group(s) selected from these.

Examples of the substituent for the "substituted or unsubstituted non-aromatic heterocyclyl" in $R^1$ include:

halogen;

oxo;

substituted alkyl (Examples of the substituents include halogen; optionally substituted with one or more group(s) selected from these); and unsubstituted alkyl. It may be substituted with one or more group(s) selected from these.

Examples of the substituents for the "substituted or unsubstituted carbamoyl", "substituted or unsubstituted amino" in $R^1$ include substituted alkyl (Examples of the substituents include halogen); and unsubstituted alkyl. It may be substituted with one or more group(s) selected from these.

Examples of substituents for the "substituted or unsubstituted alkyl" in $R^{4a}$ and $R^{4b}$ include halogen; oxo; substituted alkyl (Examples of the substituents include halogen; optionally substituted with one or more group(s) selected from these); and unsubstituted alkyl. It may be substituted with one or more group(s) selected from these.

Examples of the substituents of the "substituted or unsubstituted alkyl" in $R^{5a}$ and $R^{5b}$ include halogen. It may be substituted with one or more group(s) selected from these.

Examples of the substituents for the "substituted or unsubstituted alkynyl" in $R^6$ include hydroxy; substituted aromatic carbocyclyl (Examples of the substituents include halogen); unsubstituted aromatic carbocyclyl; substituted aromatic heterocyclyl (Examples of the substituents include halogen); and unsubstituted aromatic heterocyclyl. It may be substituted with one or more group(s) selected from these.

Examples of the substituents for the "substituted or unsubstituted alkyl" and the "substituted or unsubstituted alkyloxycarbonyl" in $R^{7a}$ and $R^{7b}$ include halogen. It may be substituted with one or more group(s) selected from these.

Examples of the substituents for the "substituted or unsubstituted non-aromatic carbocycle" and the "substituted or unsubstituted non-aromatic heterocycle" formed by $R^{7a}$ and $R^{7b}$ together with a carbon atom to which $R^{7a}$ and $R^{7b}$ are bonded include halogen; hydroxy; oxo; substituted alkyl (Examples of the substituents include halogen); and unsubstituted alkyl. It may be substituted with one or more group(s) selected from these.

Preferred embodiments of Ring A, X, $R^{4a}$, $R^{4b}$, $R^2$, $R^{3c}$, $R^3$, $R^{3a}$, $R^{3b}$, $R^{8a}$, $R^{8b}$, $R^1$, m, $R^{5a}$, $R^{5b}$, $R^6$, $R^{7a}$, and $R^{7b}$ in the compound represented by Formula (I) are described below. Regarding the compound represented by Formula (I), embodiments of all the combinations of specific examples shown below are mentioned as examples.

In the present specification, the phrase "may be substituted with substituent group G" means that "an arbitrary substitutable hydrogen atom may be substituted with one or more group(s) selected from substituent group G". The same also applies to substituent groups G', ω1, and ω1.

Examples of Ring A include those represented by:

[Chemical Formula 42]

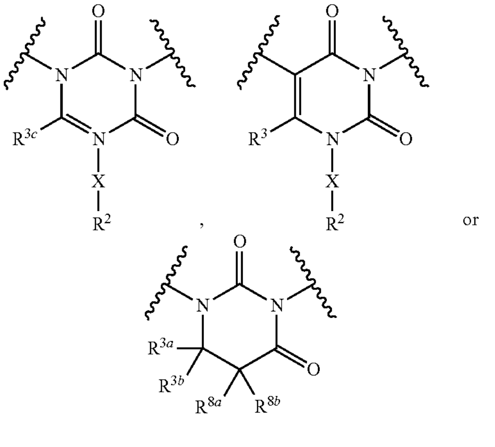

, or wherein each symbol has the same meaning as that in the above item (1) (hereinafter, referred to as A-6).

Examples of Ring A include those represented by:

[Chemical Formula 43]

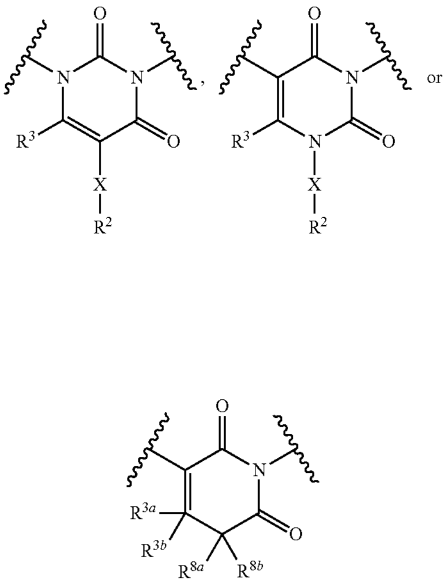

, or wherein each symbol has the same meaning as that in the above item (1) (hereinafter, referred to as A-1).

Examples of Ring A include those represented by:

[Chemical Formula 44]

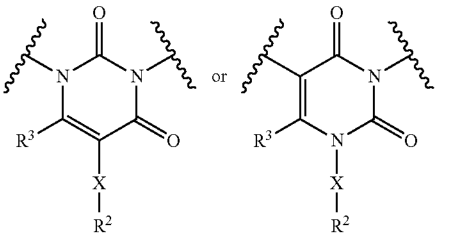

or wherein each symbol has the same meaning as that in the above item (1) (hereinafter, referred to as A-2).

Examples of Ring A include those represented by:

[Chemical Formula 45]

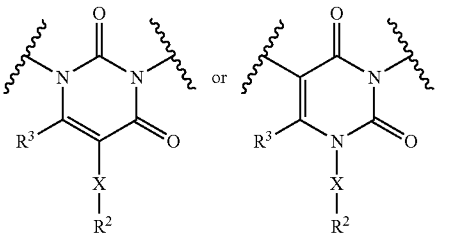

or wherein each symbol has the same meaning as that in the above item (1) (hereinafter, referred to as A-7).

Examples of Ring A include those represented by:

[Chemical Formula 46]

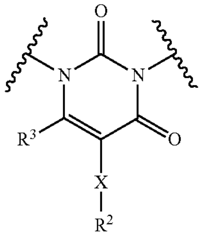

wherein each symbol has the same meaning as that in the above item (1) (hereinafter, referred to as A-3).

Examples of Ring A include those represented by:

[Chemical Formula 47]

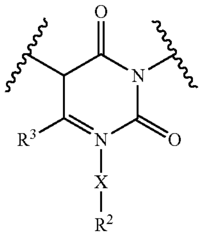

wherein each symbol has the same meaning as that in the above item (1) (hereinafter, referred to as A-8).

Examples of Ring A include those represented by:

[Chemical Formula 48]

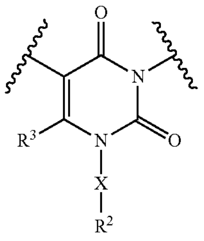

wherein each symbol has the same meaning as that in the above item (1) (hereinafter, referred to as A-4).

Examples of Ring A include those represented by:

[Chemical Formula 49]

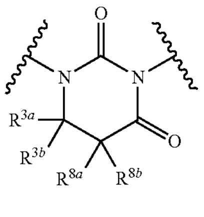

wherein each symbol has the same meaning as that in the above item (1) (hereinafter, referred to as A-5).

X may be a single bond, —$CR^{4a}R^{4b}$—, —C(═O)—, —O—, or —S— (hereinafter, referred to as B-1).

X may be a single bond, —$CH_2$—, —C(═O)—, —O—, or —S— (hereinafter, referred to as B-2).

X may be a single bond, —$CR^{4a}R^{4b}$—, or —C(═O)— (hereinafter, referred to as B-3).

X may be a single bond, —$CH_2$—, or —C(═O)— (hereinafter, referred to as B-4).

X may be a single bond, or —$CR^{4a}R^{4b}$— (hereinafter, referred to as B-5).

X may be a single bond, or —$CH_2$— (hereinafter, referred to as B-6).

X may be a single bond (hereinafter, referred to as B-7).

X may be —$CH_2$— (hereinafter, referred to as B-8).

$R^{4a}$ and $R^{4b}$ may be each independently a hydrogen atom, or substituted or unsubstituted alkyl (hereinafter, referred to as C-1).

$R^{4a}$ and $R^{4b}$ may be each independently a hydrogen atom (hereinafter, referred to as C-2).

$R^{4a}$ may be a hydrogen atom or substituted or unsubstituted alkyl (hereinafter, referred to as C-3).

$R^{4b}$ may be a hydrogen atom or substituted or unsubstituted alkyl (hereinafter, referred to as C-4).

$R^{4b}$ may be a hydrogen atom (hereinafter, referred to as C-5).

$R^2$ may be substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or substituted or unsubstituted alkyl (hereinafter, referred to as D-21).

$R^2$ may be substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl (hereinafter, referred to as D-1).

$R^2$ may be aromatic carbocyclyl which is substituted with substituent group G or unsubstituted aromatic carbocyclyl, non-aromatic carbocyclyl which is substituted with substituent group G or unsubstituted non-aromatic carbocyclyl, aromatic heterocyclyl which is substituted with substituent group G or unsubstituted aromatic heterocyclyl, or non-aromatic heterocyclyl which is substituted with substituent group G or unsubstituted non-aromatic heterocyclyl (hereinafter, referred to as D-20).

Substituent group G: halogen, cyano, alkyl, alkenyl, alkynyl, haloalkyl, alkyloxy, alkenyloxy, alkynyloxy, and haloalkyloxy.

$R^2$ may be substituted or unsubstituted aromatic carbocyclyl, or substituted or unsubstituted aromatic heterocyclyl (hereinafter, referred to as D-2).

$R^2$ may be substituted or unsubstituted aromatic carbocyclyl (hereinafter, referred to as D-3).

$R^2$ may be substituted or unsubstituted 6-membered or 10-membered aromatic carbocyclyl (hereinafter, referred to as D-4).

$R^2$ may be substituted or unsubstituted 6-membered aromatic carbocyclyl (hereinafter, referred to as D-5).

$R^2$ may be 6-membered aromatic carbocyclyl which is substituted with one, two, three, four, or five substituents selected from substituent group G, or 6-membered aromatic heterocyclyl which is substituted with one or two substituents selected from substituent group G (hereinafter, referred to as D-6).

$R^2$ may be 6-membered aromatic carbocyclyl which is substituted with one, two, or three substituents selected from substituent group G, or unsubstituted 6-membered aromatic carbocyclyl (hereinafter, referred to as D-7).

$R^2$ may be 6-membered aromatic carbocyclyl which is substituted with one, two, or three substituents selected from substituent group G', or unsubstituted 6-membered aromatic carbocyclyl (hereinafter, referred to as D-8).

Substituent group G': halogen, haloalkyl, and cyano.

$R^2$ may be 6-membered aromatic carbocyclyl which is substituted with one or two substituents selected from substituent group G, or unsubstituted 6-membered aromatic carbocyclyl (hereinafter, referred to as D-9).

$R^2$ may be 6-membered aromatic carbocyclyl which is substituted with one or two substituents selected from substituent group G (hereinafter, referred to as D-10).

$R^2$ may be 6-membered aromatic carbocyclyl which is substituted with one substituent selected from substituent group G (hereinafter, referred to as D-11).

$R^2$ may be 6-membered aromatic carbocyclyl which is substituted with two substituents selected from substituent group G (hereinafter, referred to as D-12).

$R^2$ may be 6-membered aromatic carbocyclyl which is substituted with three substituents selected from substituent group G (hereinafter, referred to as D-13).

$R^2$ may be 6-membered aromatic carbocyclyl which is substituted with one or two substituents selected from substituent group G', or unsubstituted 6-membered aromatic carbocyclyl (hereinafter, referred to as D-14).

$R^2$ may be 6-membered aromatic carbocyclyl which is substituted with one or two substituents selected from substituent group G' (hereinafter, referred to as D-15).

$R^2$ may be 6-membered aromatic carbocyclyl which is substituted with one substituent selected from substituent group G' (hereinafter, referred to as D-16).

$R^2$ may be 6-membered aromatic carbocyclyl which is substituted with two substituents selected from substituent group G' (hereinafter, referred to as D-17).

$R^2$ may be 6-membered aromatic carbocyclyl which is substituted with three substituents selected from substituent group G' (hereinafter, referred to as D-18).

$R^2$ may be unsubstituted 6-membered aromatic carbocyclyl (hereinafter, referred to as D-19).

$R^{3c}$ may be a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, substituted or unsubstituted amino, substituted or unsubstituted carbamoyl, or substituted or unsubstituted alkyloxy (hereinafter, referred to as E-9).

$R^3$ may be substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, substituted or unsubstituted amino, substituted or unsubstituted carbamoyl, or substituted or unsubstituted alkyloxy (hereinafter, referred to as E-10).

$R^{3c}$ and $R^3$ may be each independently substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, substituted or unsubstituted amino, or substituted or unsubstituted alkyloxy (hereinafter, referred to as E-1).

$R^{3c}$ and $R^3$ may be each independently substituted or unsubstituted aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted aromatic heterocyclyloxy, halogen, substituted or unsubstituted alkyl, substituted or unsubstituted alkenyl, substituted or unsubstituted alkynyl, substituted or unsubstituted amino, or substituted or unsubstituted alkyloxy (hereinafter, referred to as E-2).

$R^{3c}$ and $R^3$ may be each independently substituted or unsubstituted 6-membered aromatic carbocyclyl, substituted or unsubstituted 5- to 10-membered aromatic heterocyclyl, substituted or unsubstituted 4- to 10-membered non-aromatic heterocyclyl, substituted or unsubstituted 6- or 10-membered aromatic carbocyclyloxy, substituted or unsubstituted 5- to 10-membered aromatic heterocyclyloxy, halogen, substituted or unsubstituted alkyl, substituted or unsubstituted alkenyl, substituted or unsubstituted alkynyl, substituted or unsubstituted amino, or substituted or unsubstituted alkyloxy (hereinafter, referred to as E-3).

$R^{3c}$ and $R^3$ may be each independently substituted or unsubstituted 6-membered aromatic carbocyclyl, substituted or unsubstituted 5- to 10-membered aromatic heterocyclyl, or substituted or unsubstituted 4- to 10-membered non-aromatic heterocyclyl (hereinafter, referred to as E-4).

$R^{3c}$ and $R^3$ may be each independently substituted or unsubstituted 6-membered aromatic carbocyclyl, or substituted or unsubstituted 5- to 10-membered aromatic heterocyclyl (hereinafter, referred to as E-5).

$R^{3c}$ and $R^3$ may be each independently substituted or unsubstituted 5- to 10-membered aromatic heterocyclyl (hereinafter, referred to as E-8).

$R^{3c}$ and $R^3$ may be each independently substituted or unsubstituted 4- to 10-membered nitrogen-containing non-aromatic heterocyclyl, or substituted or unsubstituted amino (hereinafter, referred to as E-6).

$R^{3c}$ and $R^3$ may be each independently substituted or unsubstituted 4- to 10-membered nitrogen-containing non-aromatic heterocyclyl (hereinafter, referred to as E-7).

$R^{3c}$ and $R^3$ may be each independently substituted or unsubstituted C1-C4 alkyl (hereinafter, referred to as E-8).

$R^{3c}$ and $R^3$ may be each independently substituted or unsubstituted C2-C4 alkyl (hereinafter, referred to as E-9).

$R^{3c}$ and $R^3$ may be each independently substituted or unsubstituted C2-C5 alkenyl (hereinafter, referred to as E-10).

$R^{3c}$ and $R^3$ may be each independently substituted or unsubstituted non-aromatic carbocyclyl (hereinafter, referred to as E-11).

$R^{3c}$ and $R^3$ may be each independently substituted C1-C4 alkyl (Examples of the substituents include halogen and hydroxy; optionally substituted with one or more group(s) selected from these) (hereinafter, referred to as E-12).

$R^{3c}$ and $R^3$ may be each independently substituted or unsubstituted 6-membered aromatic carbocyclyl (hereinafter, referred to as E-13).

$R^{3c}$ and $R^3$ may be each independently halogen (hereinafter, referred to as E-14).

A group represented by Formula:

[Chemical Formula 50]

 and 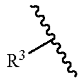

may be each independently a group represented by:

[Chemical Formula 51]

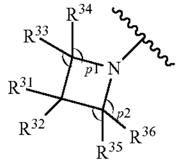 or 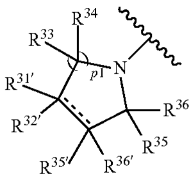

wherein a dotted line represents the presence or absence of a bond;

when the dotted line indicates the presence of a bond, $R^{32'}$ and $R^{36'}$ are not present;

p1 is an integer from 1 to 3;

p2 is 1 or 2;

$R^{31}$ and $R^{32}$ are each independently a hydrogen atom, halogen, cyano, hydroxy, substituted or unsubstituted carbamoyl, substituted or unsubstituted sulfamoyl, substituted or unsubstituted alkyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, $R^{33}$ is each independently a hydrogen atom;

$R^{34}$ is each independently a hydrogen atom;

$R^{35}$ is each independently a hydrogen atom;

$R^{36}$ is each independently a hydrogen atom;

$R^{32'}$ is a hydrogen atom; $R^{36'}$ is a hydrogen atom;

$R^{33}$ and $R^{34}$ may be taken together to form oxo;

$R^{35}$ and $R^{36}$ may be taken together to form oxo;

$R^{33}$ and $R^{35}$ may be taken together to form a (C1-C3) bridge, wherein one of the carbon atoms constituting the bridge may be replaced with an oxygen atom;

$R^{31}$ and $R^{32}$ may be taken together with a carbon atom to which $R^{31}$ and $R^{32}$ are bonded to form a substituted or unsubstituted non-aromatic carbocycle or a substituted or unsubstituted non-aromatic heterocycle; and $R^{31'}$ and $R^{35'}$ may be taken together with a carbon atom to which $R^{31'}$ is bonded and a carbon atom to which $R^{35'}$ is bonded to form a substituted or unsubstituted aromatic carbocycle, a substituted or unsubstituted aromatic heterocycle, a substituted or unsubstituted non-aromatic carbocycle, or a substituted or unsubstituted non-aromatic heterocycle (hereinafter referred to as E-1-1).

A group represented by Formula:

[Chemical Formula 52]

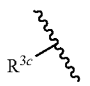 and 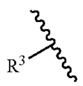

may be each independently a group represented by:

[Chemical Formula 53]

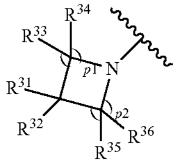

wherein each symbol has the same meaning as that in the above E-1-1 (hereinafter, referred to as E-1-2).

p1 may be an integer of 1 to 3 (hereinafter, referred to as E-2-1).

p1 may be 1 or 2 (hereinafter, referred to as E-2-2).

p1 may be 1 (hereinafter, referred to as E-2-3).

p1 may be 2 (hereinafter, referred to as E-2-4).

p2 may be 1 or 2 (hereinafter, referred to as E-3-1).

p2 may be 1 (hereinafter, referred to as E-3-2).

p2 may be 2 (hereinafter, referred to as E-3-3).

$R^{31}$ and $R^{32}$ may be each independently a hydrogen atom, halogen, hydroxy, substituted alkyl (Examples of the substituents include halogen and hydroxy; optionally substituted with one or more group(s) selected from these), unsubstituted alkyl, substituted alkyloxy (Examples of the substituents include halogen), substituted aromatic heterocyclyl (Examples of the substituents include halogen), unsubstituted aromatic heterocyclyl, substituted 6-membered aromatic heterocyclyl (Examples of the substituents include halogen; optionally substituted with one or more group(s) selected from these), or unsubstituted 6-membered aromatic heterocyclyl;

or alternatively, $R^{31}$ and $R^{32}$ may be taken together with a carbon atom to which $R^{31}$ and $R^{32}$ are bonded to form a substituted 4-membered non-aromatic carbocycle (Examples of the substituents include halogen, alkyl, and hydroxy; optionally substituted with one or more group(s) selected from these) or a unsubstituted 5-membered non-aromatic heterocycle (hereinafter, referred to as E-4-1).

$R^{31}$ and $R^{32}$ may be each independently a hydrogen atom, halogen, hydroxy, substituted alkyl (Examples of the substituents include halogen and hydroxy; optionally substituted with one or more group(s) selected from these), unsubstituted alkyl, substituted 6-membered aromatic heterocyclyl (Examples of the substituents include halogen; optionally substituted with one or more group(s) selected from these), or unsubstituted 6-membered aromatic heterocyclyl; or alternatively, $R^{31}$ and $R^{32}$ may be taken together with a carbon atom to which $R^{31}$ and $R^{32}$ are bonded to form a substituted 4-membered non-aromatic carbocycle (Examples of the substituents include halogen, alkyl, and hydroxy; optionally substituted with one or more group(s) selected from these) (hereinafter, referred to as E-4-2).

$R^{31}$ and $R^{32}$ may be each independently a hydrogen atom, halogen, hydroxy, substituted alkyl (Examples of the substituents include halogen and hydroxy; optionally substituted with one or more group(s) selected from these), unsubstituted alkyl, substituted alkyloxy (Examples of the substituents include halogen), substituted aromatic heterocyclyl (Examples of the substituents include halogen), unsubstituted aromatic heterocyclyl, substituted 6-membered aromatic heterocyclyl (Examples of the substituents include halogen; optionally substituted with one or more group(s) selected from these), or unsubstituted 6-membered aromatic heterocyclyl (hereinafter, referred to as E-4-3).

$R^{31}$ and $R^{32}$ may be taken together with a carbon atom to which $R^{31}$ and $R^{32}$ are bonded to form a substituted 4-membered non-aromatic carbocycle (Examples of the substituents include halogen, alkyl, and hydroxy; optionally substituted with one or more group(s) selected from these), or a unsubstituted 5-membered non-aromatic heterocycle (hereinafter, referred to as E-4-4).

$R^{31}$ and $R^{32}$ may be taken together with a carbon atom to which $R^{31}$ and $R^{32}$ are bonded to form a substituted 4-membered non-aromatic carbocycle (Examples of the substituents include halogen, alkyl, and hydroxy; optionally substituted with one or more group(s) selected from these) (hereinafter, referred to as E-4-5).

$R^{31}$ and $R^{32}$ may be taken together with a carbon atom to which $R^{31}$ and $R^{32}$ are bonded to form a unsubstituted 5-membered non-aromatic heterocycle (hereinafter, referred to as E-4-6).

$R^{33}$ and $R^{34}$ may be each independently a hydrogen atom (hereinafter, referred to as E-5-1).

$R^{35}$ and $R^{36}$ may be each independently a hydrogen atom (hereinafter, referred to as E-6-1).

A group represented by Formula:

[Chemical Formula 54]

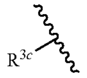 and 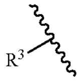

may be each independently a group represented by:

[Chemical Formula 55]

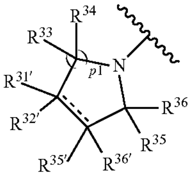

wherein a dotted line represents the presence of a bond, and $R^{32'}$ and $R^{36'}$ are not present (hereinafter, referred to as E-1-3).

p1 may be an integer of 1 to 3 (hereinafter, referred to as E-2'-1).

p1 may be 1 or 2 (hereinafter, referred to as E-2'-2).

p1 may be 1 (hereinafter, referred to as E-2'-3).

p1 may be 2 (hereinafter, referred to as E-2'-4).

$R^{31'}$ and $R^{35'}$ may be taken together with a carbon atom to which $R^{31'}$ is bonded and a carbon atom to which $R^{35'}$ is bonded to form a substituted or unsubstituted aromatic carbocycle, or a substituted or unsubstituted aromatic heterocycle (hereinafter referred to as E-7-1).

$R^{31'}$ and $R^{35'}$ may be taken together with a carbon atom to which $R^{31'}$ is bonded and a carbon atom to which $R^{35'}$ is bonded to form a substituted or unsubstituted aromatic carbocycle (hereinafter referred to as E-7-2).

$R^{31'}$ and $R^{35'}$ may be taken together with a carbon atom to which $R^{31'}$ is bonded and a carbon atom to which $R^{35'}$ is bonded to form a substituted or unsubstituted aromatic heterocycle (hereinafter referred to as E-7-3).

$R^{33}$ and $R^{34}$ may be each independently a hydrogen atom (hereinafter, referred to as E-5'-1).

$R^{35}$ and $R^{36}$ may be each independently a hydrogen atom (hereinafter, referred to as E-6'-1).

$R^{3a}$ may be a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, halogen, substituted or unsubstituted alkyl, substituted or unsubstituted alkenyl, substituted or unsubstituted alkynyl, or substituted or unsubstituted alkyloxy (hereinafter, referred to as F-1).

$R^{3a}$ may be a hydrogen atom (hereinafter, referred to as F-2).

$R^{3b}$ may be a hydrogen atom (hereinafter, also referred to as G-1).

$R^{8a}$ is substituted or unsubstituted aromatic carbocyclyl or substituted or unsubstituted aromatic heterocyclyl;

$R^{8b}$ is a hydrogen atom, or substituted or unsubstituted alkyl;

or, $R^{8a}$ and $R^{8b}$ may be taken together with a carbon atom to which $R^{8a}$ and $R^{8b}$ are bonded to form a substituted or unsubstituted non-aromatic carbocycle or a substituted or unsubstituted non-aromatic heterocycle (hereinafter, referred to as G-1).

$R^{8a}$ and $R^{8b}$ are taken together with a carbon atom to which $R^{8a}$ and $R^{8b}$ are bonded to form a substituted or unsubstituted non-aromatic carbocycle or a substituted or unsubstituted non-aromatic heterocycle (hereinafter, referred to as G-2).

$R^{8a}$ may be substituted or unsubstituted aromatic carbocyclyl, or substituted or unsubstituted aromatic heterocyclyl (hereinafter, referred to as G-3).

$R^{8a}$ may be substituted or unsubstituted 6-membered aromatic carbocyclyl, or substituted or unsubstituted 5- to 6-membered aromatic heterocyclyl (hereinafter, referred to as G-4).

$R^{8a}$ may be 6-membered aromatic carbocyclyl which is substituted with halogen or unsubstituted 6-membered aromatic carbocyclyl, or 5- to 6-membered aromatic heterocyclyl which is substituted with halogen or unsubstituted 5- to 6-membered aromatic heterocyclyl (hereinafter, referred to as G-5).

$R^{8b}$ may be a hydrogen atom or substituted or unsubstituted alkyl (hereinafter, referred to as G-6).

$R^{8b}$ may be unsubstituted alkyl (hereinafter, referred to as G-7).

The ring formed by $R^{8a}$ and $R^{8b}$ together with a carbon atom to which $R^{8a}$ and $R^{8b}$ are bonded may be a substituted or unsubstituted non-aromatic carbocycle or a substituted or unsubstituted non-aromatic heterocycle (hereinafter, referred to as G-8).

The ring formed by $R^{8a}$ and $R^{8b}$ together with a carbon atom to which $R^{8a}$ and $R^{8b}$ are bonded may be a substituted or unsubstituted 10-membered non-aromatic carbocycle or a substituted or unsubstituted 10-membered non-aromatic heterocycle (hereinafter, referred to as G-9).

The ring formed by $R^{8a}$ and $R^{8b}$ together with a carbon atom to which $R^{8a}$ and $R^{8b}$ are bonded may be a 10-membered non-aromatic carbocycle which is substituted with halogen or a unsubstituted 10-membered non-aromatic carbocycle, or a 10-membered non-aromatic heterocycle which is substituted with halogen or a unsubstituted 10-membered non-aromatic heterocycle (hereinafter, referred to as G-10).

$R^1$ may be substituted or unsubstituted aromatic heterocyclyl, substituted or unsubstituted non-aromatic heterocyclyl, substituted or unsubstituted carbamoyl, substituted or unsubstituted amino or cyano (hereinafter, referred to as H-21).

$R^1$ may be substituted or unsubstituted aromatic heterocyclyl, substituted or unsubstituted non-aromatic heterocyclyl, substituted or unsubstituted carbamoyl, or substituted or unsubstituted amino (hereinafter, referred to as H-1).

$R^1$ may be substituted or unsubstituted aromatic heterocyclyl, substituted or unsubstituted non-aromatic heterocyclyl, or substituted or unsubstituted carbamoyl (hereinafter, referred to as H-2).

$R^1$ may be substituted or unsubstituted aromatic heterocyclyl, or substituted or unsubstituted non-aromatic heterocyclyl (hereinafter, referred to as H-3).

$R^1$ may be substituted or unsubstituted 5- to 9-membered aromatic heterocyclyl, substituted or unsubstituted 5- to 9-membered non-aromatic heterocyclyl, or substituted or unsubstituted carbamoyl (hereinafter, referred to as H-4).

$R^1$ may be 5- to 9-membered aromatic heterocyclyl which is substituted with substituent group ω1 or unsubstituted 5- to 9-membered aromatic heterocyclyl, 5- to 9-membered non-aromatic heterocyclyl which is substituted with substituent group ω2 or unsubstituted 5- to 9-membered non-aromatic heterocyclyl, or unsubstituted carbamoyl (hereinafter, referred to as H-5).

Substituent group ω1: cyano, halogen, alkyl, haloalkyl, and alkyloxy.

Substituent group ω2: substituent group ω1 and oxo.

$R^1$ may be substituted or unsubstituted 5- to 9-membered aromatic heterocyclyl, or substituted or unsubstituted 5- to 9-membered non-aromatic heterocyclyl (hereinafter, referred to as H-6).

$R^1$ may be 5- to 9-membered aromatic heterocyclyl which is substituted with substituent group ω1 or unsubstituted 5- to 9-membered aromatic heterocyclyl, or 5- to 9-membered non-aromatic heterocyclyl which is substituted with substituent group ω2 or unsubstituted 5- to 9-membered non-aromatic heterocyclyl (hereinafter, referred to as H-7).

$R^1$ may be substituted or unsubstituted 5- or 6-membered aromatic heterocyclyl, or substituted or unsubstituted 6-membered non-aromatic heterocyclyl (hereinafter, referred to as H-8).

$R^1$ may be 5- or 6-membered aromatic heterocyclyl which is substituted with substituent group ω1 or unsubstituted 5- or 6-membered aromatic heterocyclyl, or 6-membered non-aromatic heterocyclyl which is substituted with substituent group ω2 or unsubstituted 6-membered non-aromatic heterocyclyl (hereinafter, referred to as H-9).

$R^1$ may be substituted or unsubstituted 9-membered aromatic heterocyclyl (hereinafter, referred to as H-10).

$R^1$ may be 9-membered aromatic heterocyclyl which is substituted with substituent group ω1 or unsubstituted 9-membered aromatic heterocyclyl, (hereinafter, referred to as H-11).

$R^1$ may be substituted or unsubstituted pyrazolyl, substituted or unsubstituted triazolyl, substituted or unsubstituted pyridinyl, substituted or unsubstituted pyridazinyl, substituted or unsubstituted pyrimidinyl, substituted or unsubstituted pyrazinyl, substituted or unsubstituted imidazopyridinyl, substituted or unsubstituted pyrazolopyridinyl, substituted or unsubstituted triazolopyridinyl, substituted or unsubstituted imidazopyridazinyl, substituted or unsubstituted imidazopyrazinyl, substituted or unsubstituted benzisothiazolyl, substituted or unsubstituted dihydropyrazolyl, substituted or unsubstituted piperidinyl, substituted or unsubstituted dihydropyridinyl, substituted or unsubstituted dihydropyrrolotriazolyl, or substituted or unsubstituted tetrahydroindolizinyl (hereinafter, referred to as H-12).

$R^1$ may be pyrazolyl which is substituted with substituent group ω1 or unsubstituted pyrazolyl, triazolyl which is substituted with substituent group ω1 or unsubstituted triazolyl, pyridinyl which is substituted with substituent group ω1 or unsubstituted pyridinyl, pyridazinyl which is substituted with substituent group ω1 or unsubstituted pyridazinyl, pyrimidinyl which is substituted with substituent group ω1 or unsubstituted pyrimidinyl, pyrazinyl which is substituted with substituent group ω1 or unsubstituted pyrazinyl, imidazopyridinyl which is substituted with substituent group ω1 or unsubstituted imidazopyridinyl, pyrazolopyridinyl which is substituted with substituent group ω1 or unsubstituted pyrazolopyridinyl, triazolopyridinyl which is substituted with substituent group ω1 or unsubstituted triazolopyridinyl, imidazopyridazinyl which is substituted with substituent group ω1 or unsubstituted imidazopyridazinyl, imidazopyrazinyl which is substituted with substituent group ω1 or unsubstituted imidazopyrazinyl, benzisothiazolyl which is substituted with substituent group ω1 or unsubstituted benzisothiazolyl, dihydropyrazolyl which is substituted with substituent group ω2 or unsubstituted dihydropyrazolyl, piperidinyl which is substituted with substituent group ω2 or unsubstituted piperidinyl, dihydropyridinyl which is substituted with substituent group ω2 or unsubstituted dihydropyridinyl, dihydropyrrolotriazolyl which is substituted with substituent group ω2 or unsubstituted dihydropyrrolotriazolyl, or tetrahydroindolizinyl which is substituted with substituent group ω2 or unsubstituted tetrahydroindolizinyl (hereinafter, referred to as H-13).

$R^1$ may be triazolyl which is substituted with substituent group ω1 or unsubstituted triazolyl, pyridinyl which is substituted with substituent group ω1 or unsubstituted pyridinyl, pyridazinyl which is substituted with substituent group ω1 or unsubstituted pyridazinyl, pyrazinyl which is substituted with substituent group ω1 or unsubstituted pyrazinyl, imidazopyridinyl which is substituted with substituent group ω1 or unsubstituted imidazopyridinyl, or dihydropyridinyl which is substituted with substituent group ω2 or unsubstituted dihydropyridinyl (hereinafter, referred to as H-14).

$R^1$ may be triazolyl substituted with methyl (hereinafter, referred to as H-15).

$R^1$ may be pyridinyl substituted with substituent group ω1 (hereinafter, referred to as H-16).

$R^1$ may be pyridazinyl substituted with substituent group ω1 (hereinafter, referred to as H-17).

$R^1$ may be pyrazinyl substituted with substituent group ω1 (hereinafter, referred to as H-18).

$R^1$ may be imidazopyridinyl which is substituted with substituent group ω1 or unsubstituted imidazopyridinyl (hereinafter, referred to as H-19).

$R^1$ may be dihydropyridinyl which is substituted with oxo and is further substituted with substituent group ω1 (hereinafter, referred to as H-20).

$R^1$ may be pyridinyl substituted with halogen (hereinafter, referred to as H-21).

$R^1$ may be pyridinyl substituted with cyano (hereinafter, referred to as H-22).

$R^1$ may be pyridinyl substituted with methyl (hereinafter, referred to as H-23).

$R^1$ may be substituted pyridinyl (Examples of the substituents include halogen, cyano, and methyl) (hereinafter, referred to as H-24).

$R^1$ may be substituted 6-membered aromatic heterocyclyl (Examples of the substituents include halogen, cyano, and methyl) (hereinafter, referred to as H-25).

m may be 0, 1, or 2 (hereinafter, referred to as J-1).

m may be 0 or 1 (hereinafter, referred to as J-2).

m may be 0 (hereinafter, referred to as J-3).

m may be 1 (hereinafter, referred to as J-4).

m may be 2 (hereinafter, referred to as J-5).

$R^{5a}$ may be each independently a hydrogen atom or substituted or unsubstituted alkyl (hereinafter, referred to as K-1).

$R^{5a}$ may be each independently a hydrogen atom (hereinafter, referred to as K-2).

$R^{5b}$ may be each independently a hydrogen atom or substituted or unsubstituted alkyl (hereinafter, referred to as L-1).

$R^{5b}$ may be each independently a hydrogen atom (hereinafter, referred to as L-2).

A group represented by Formula:

[Chemical Formula 56]

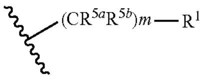

may be a group represented by Formula:

[Chemical Formula 57]

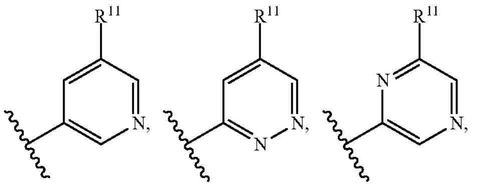

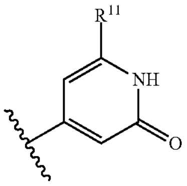

or

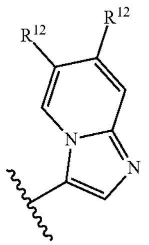

wherein $R^{11}$ is halogen, alkyl, or haloalkyl; and $R^{12}$ is each independently a hydrogen atom or halogen (hereinafter, referred to as M-1).

A group represented by Formula:

[Chemical Formula 58]

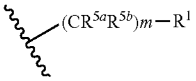

may be a group represented by Formula:

[Chemical Formula 59]

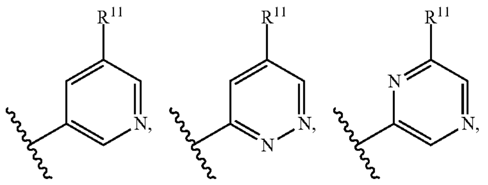

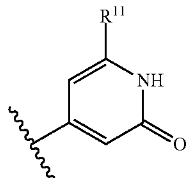

or

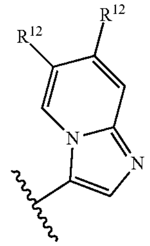

wherein $R^{11}$ is halogen, cyano, alkyl, or haloalkyl; and $R^{12}$ is each independently a hydrogen atom or halogen (hereinafter, referred to as M-7).

A group represented by Formula:

[Chemical Formula 60]

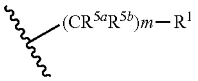

may be a group represented by Formula:

[Chemical Formula 61]

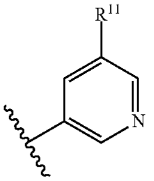

wherein $R^{11}$ has the same meaning as that in the above (M-1) (hereinafter, referred to as M-2).

A group represented by Formula:

[Chemical Formula 62]

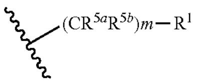

may be a group represented by Formula:

[Chemical Formula 63]

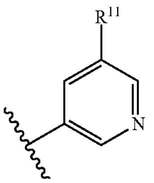

wherein $R^{11}$ has the same meaning as that in the above (M-2) (hereinafter, referred to as M-8).

A group represented by Formula:

[Chemical Formula 64]

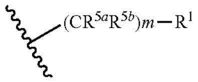

may be a group represented by Formula:

[Chemical Formula 65]

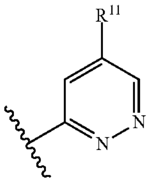

wherein $R^{11}$ has the same meaning as that in the above (M-1) (hereinafter, referred to as M-3).

A group represented by Formula:

[Chemical Formula 66]

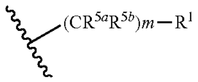

may be a group represented by Formula:

[Chemical Formula 67]

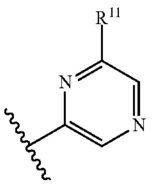

wherein $R^{11}$ has the same meaning as that in the above (M-1) (hereinafter, referred to as M-4).

A group represented by Formula:

[Chemical Formula 68]

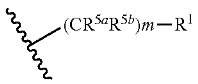

may be a group represented by Formula:

[Chemical Formula 69]

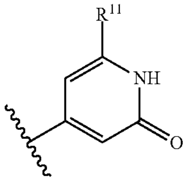

wherein $R^{11}$ has the same meaning as that in the above (M-1) (hereinafter, referred to as M-5).

A group represented by Formula:

[Chemical Formula 70]

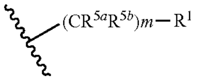

may be a group represented by Formula:

[Chemical Formula 71]

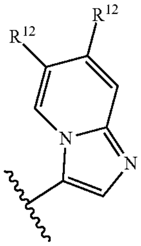

wherein $R^{12}$ has the same meaning as that in the above (M-1) (hereinafter, referred to as M-6).

$R^6$ may be cyano, halogen, or substituted or unsubstituted alkynyl (hereinafter, referred to as N-1).

$R^6$ may be cyano (hereinafter, referred to as N-2).

$R^6$ may be substituted or unsubstituted alkylcarbonyl, or substituted or unsubstituted carbamoyl (hereinafter, referred to as N-3).

$R^6$ may be substituted or unsubstituted alkylcarbonyl (the substituent is hydroxy or alkylcarbonyloxy) or unsubstituted carbamoyl (hereinafter, referred to as N-4).

$R^{7a}$ and $R^{7b}$ may be each independently a hydrogen atom, halogen, carboxy, substituted or unsubstituted alkyl, substituted or unsubstituted alkyloxycarbonyl;

or, $R^{7a}$ and $R^{7b}$ may be taken together with a carbon atom to which $R^{7a}$ and $R^{7b}$ are bonded to forma substituted or unsubstituted non-aromatic carbocycle or a substituted or unsubstituted non-aromatic heterocycle (hereinafter, referred to as O-1).

$R^{7a}$ and $R^{7b}$ may be each independently a hydrogen atom, halogen, carboxy, substituted or unsubstituted alkyl, or substituted or unsubstituted alkyloxycarbonyl (hereinafter, referred to as O-2).

$R^{7a}$ and $R^{7b}$ may be each independently a hydrogen atom, halogen, carboxy, unsubstituted alkyl, or unsubstituted alkyloxycarbonyl (hereinafter, referred to as O-3).

$R^{7a}$ and $R^{7b}$ may be each independently a hydrogen atom, or substituted or unsubstituted alkyl (hereinafter, referred to as O-8).

$R^{7a}$ and $R^{7b}$ may be each independently a hydrogen atom or unsubstituted alkyl (hereinafter, referred to as O-9).

$R^{7a}$ and $R^{7b}$ may be each independently a hydrogen atom (hereinafter, referred to as O-4).

A ring formed by $R^{7a}$ and $R^{7b}$ together with a carbon atom to which $R^{7a}$ and $R^{7b}$ are bonded may be a substituted or unsubstituted non-aromatic carbocycle or a substituted or unsubstituted non-aromatic heterocycle (hereinafter, referred to as O-5).

A ring formed by $R^{7a}$ and $R^{7b}$ together with a carbon atom to which $R^{7a}$ and $R^{7b}$ are bonded may be a substituted or unsubstituted non-aromatic carbocycle (hereinafter, referred to as O-6).

A ring formed by $R^{7a}$ and $R^{7b}$ together with a carbon atom to which $R^{7a}$ and $R^{7b}$ are bonded may be a unsubstituted 3-membered non-aromatic carbocycle (hereinafter, referred to as O-7).

Furthermore, examples of the compound represented by Formula (I) include a compound represented by the following Formula (I'):

[Chemical Formula 72]

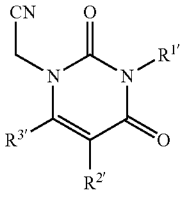

(I')

wherein $R^1$ is a group represented by:

[Chemical Formula 73]

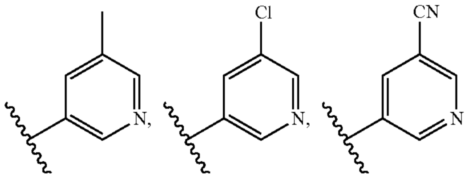

or

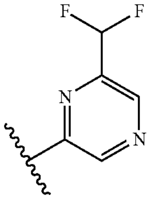

$R^2$ is a group represented by

[Chemical Formula 74]

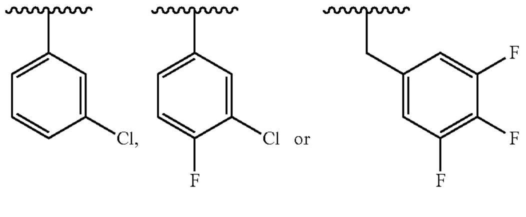

and $R^3$ is a group represented by:

[Chemical Formula 75]

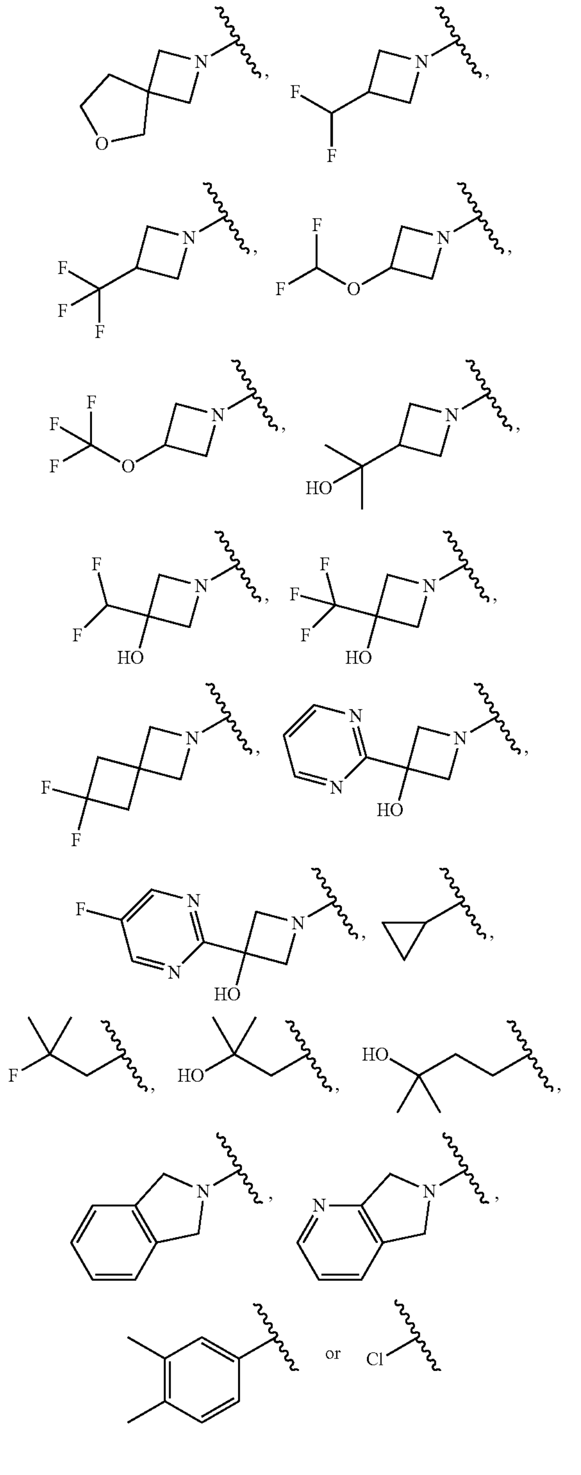

Furthermore, in the compound represented by the above Formula (I'), examples of the embodiment regarding $R^{1'}$, $R^{2'}$, and $R^{3'}$ include the following combinations. As the definitions of $R^{1'}$, $R^{2'}$, and $R^{3'}$ in Formula (I'), the definitions of $R^1$, $R^2$, and $R^{3c}$ in Formula (I) can be used.

(a1)

$R^{1'}$ is M-2 or M-4;

$R^{2'}$ is D-16, D-17, or D-18; and $R^{3'}$ is E-7, E-11, E-12, E-13, or E-14.

(a2)

$R^{1'}$ is M-2 or M-4;

$R^{2'}$ is D-16, D-17, or D-18;

$R^{3'}$ is E-1-2 in which p1 is 1 and p2 is 1;

$R^{31}$ and $R^{32}$ is E-4-1, E-4-2, E-4-5, or E-4-6;

$R^{33}$ and $R^{34}$ are each E-5-1; and $R^{35}$ and $R^{36}$ are each E-6-1.

(a3)

$R^{1'}$ is M-2 or M-4;

$R^{2'}$ is D-16, D-17, or D-18;

$R^{3'}$ is E-1-3 in which p1 is 1;

$R^{31'}$ and $R^{35'}$ are each E-7-2, or E-7-3;

$R^{33}$ and $R^{34}$ are each E-5'-1; and $R^{35}$ and $R^{36}$ are each E-6'-1.

(a4)

$R^{1'}$ is H-18, H-21, H-22, H-23, H-24, or H-25; and $R^{2'}$ has the same meaning as that in the above (a1), (a2), or (a3).

$R^{3'}$ has the same meaning as that in the above (a1), (a2), or (a3).

The compounds represented by Formula (I) are not limited to specific isomers but include all possible isomers (e.g., keto-enol isomers, imine-enamine isomers, diastereoisomers, enantiomers, rotamers or the like), racemates or mixtures thereof.

One or more hydrogen, carbon and/or other atoms in the compounds represented by Formula (I) may be replaced with isotopes of hydrogen, carbon and/or other atoms respectively. Examples of such isotopes include hydrogen, carbon, nitrogen, oxygen, phosphorus, sulfur, fluorine, iodine, and chlorine, as in the cases of $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$, and $^{36}Cl$, respectively. The compounds represented by Formula (I) include the compounds replaced with these isotopes. The compounds replaced with the isotopes are also useful as pharmaceutical products. The compounds represented by Formula (I) encompass all of radiolabeled forms replaced with radioactive isotopes included in the above isotopes. Furthermore, a "radiolabeling method" for producing the "radiolabeled forms" is also included in the present invention, and the "radiolabeled forms" are useful as tools for metabolic pharmacokinetics studies, studies on binding assay, and/or diagnostics.

The radiolabeled form of the compound represented by Formula (I) can be prepared using well-known methods in the art. For example, a tritium-labeled compound represented by Formula (I) can be prepared by introducing tritium into a specific compound represented by Formula (I) by catalytic dehalogenation reaction using tritium. This method includes reacting an appropriately halogenated precursor of the compound represented by Formula (I) with tritium gas in the presence of an appropriate catalyst, such as Pd/C, and in the presence or absence of a base. Regarding other appropriate methods for preparing tritium-labeled compounds, "Isotopes in the Physical and Biomedical Sciences, Vol. 1, Labeled Compounds (Part A), Chapter 6 (1987)" can be referred to. A $^{14}C$-labeled compound can be prepared by using a raw material having $^{14}C$ carbon.

Examples of the pharmaceutically acceptable salt of the compound represented by Formula (I) include salts of the compound represented by Formula (I) with alkali metals (e.g., lithium, sodium, potassium, and the like), alkaline earth metals (e.g., calcium, barium, and the like), magnesium, transition metals (e.g., zinc, iron, and the like), ammonia, organic bases (e.g., trimethylamine, triethylamine, dicyclohexylamine, ethanolamine, diethanolamine, triethanolamine, meglumine, ethylenediamine, pyridine, picoline, quinoline, and the like), and amino acids, or salts of the compound represented by Formula (I) with inorganic acids (e.g., hydrochloric acid, sulfuric acid, nitric acid, carbonic acid, hydrobromic acid, phosphoric acid, hydroiodic acid, and the like), and organic acids (e.g., formic acid, acetic acid, propionic acid, trifluoroacetic acid, citric acid, lactic acid, tartaric acid, oxalic acid, maleic acid, fumaric acid, succinic acid, mandelic acid, glutaric acid, malic acid, benzoic acid, phthalic acid, ascorbic acid, benzenesulfonic acid, p-toluenesulfonic acid, methanesulfonic acid, ethanesulfonic acid, trifluoroacetic acid, and the like). These salts can be formed according to methods that are conventionally carried out.

The compounds represented by Formula (I) or pharmaceutically acceptable salts thereof of the present invention may form solvates (e.g., hydrates), co-crystal and/or crystal polymorphs. The compounds represented by Formula (I) or pharmaceutically acceptable salts thereof of the present invention encompass those various solvates, co-crystal and crystal polymorphs. "Solvates" may be those wherein any numbers of solvent molecules (e.g., water molecules or the like) are coordinated with the compounds represented by Formula (I). When the compound represented by Formula (I) or a pharmaceutically acceptable salt thereof is allowed to stand in the atmosphere, the compound may absorb water, resulting in attachment of adsorbed water or formation of a hydrate. Furthermore, crystalline polymorphs may be formed by recrystallizing the compounds represented by Formula (I) or pharmaceutically acceptable salts thereof. The term "co-crystal" means that the compound represented by Formula (I) or a salt thereof and a counter molecule are present in the same crystal lattice, and may contain any number of counter molecules.

The compounds represented by Formula (I) or pharmaceutically acceptable salts thereof of the present invention may form prodrugs, and the present invention also encompasses such various prodrugs. A prodrug is a derivative of a compound of the present invention having a group that can be chemically or metabolically degraded, and is a compound which becomes a pharmaceutically active compound of the present invention in vivo as a result of solvolysis or under physiological conditions. Prodrugs encompass compounds that are converted to the compounds represented by Formula (I) through enzymatic oxidation, reduction, hydrolysis or the like under physiological conditions and in vivo, compounds that are converted to the compounds represented by Formula (I) through hydrolysis by gastric acid etc., and the like. Methods for selecting and producing an appropriate prodrug derivative are described in, for example, "Design of Prodrugs, Elsevier, Amsterdam, 1985". A prodrug may have activity per se.

When the compounds represented by Formula (I) or pharmaceutically acceptable salts thereof have hydroxy group(s), examples of the prodrug include acyloxy derivatives and sulfonyloxy derivatives that are prepared by, for example, reacting compounds having hydroxy group(s) with suitable acyl halide, suitable acid anhydride, suitable sulfonyl chloride, suitable sulfonyl anhydride and mixed anhydride, or with a condensing agent. Examples include $CH_3COO$—, $C_2H_5COO$—, tert-BuCOO—, $C_{15}H_{31}COO$—, PhCOO—, (m-NaOOCPh)COO—, $NaOOCCH_2CH_2COO$—, $CH_3CH(NH_2)COO$—, $CH_2N$ $(CH_3)_2COO$—, $CH_3SO_3$—, $CH_3CH_2SO_3$—, $CF_3SO_3$—, $CH_2FSO_3$—, $CF_3CH_2SO_3$—, p-$CH_3O$-$PhSO_3$—, $PhSO_3$—, and p-$CH_3PhSO_3$—.

Since the compound according to the present invention has coronavirus 3CL protease inhibitory activity, the compound is useful as a therapeutic and/or prophylactic agent for a disease associated with coronavirus 3CL proteases. When the term "therapeutic agent and/or prophylactic agent" is used in the present invention, this also includes a symptom ameliorating agent. The disease associated with coronavirus 3CL proteases may be viral infections, and preferably coronavirus infections.

According to an aspect, the coronavirus may be a coronavirus that infects human beings. The coronavirus that infects human beings may be HCoV-229E, HCoV-NL63, HCoV-HKU1, HCoV-OC43, SARS-CoV, MERS-CoV, and/or SARS-CoV-2.

As an embodiment, as the coronavirus, alphacoronavirus and/or betacoronavirus, more preferably betacoronavirus, and further preferably sarbecovirus are exemplified.

According to an aspect, the alphacoronavirus may be HCoV-229E and HCoV-NL63. The alphacoronavirus may be particularly preferably HCoV-229E.

According to an aspect, the betacoronavirus may be HCoV-HKU1, HCoV-OC43, SARS-CoV, MERS-CoV, and/or SARS-CoV-2. The betacoronavirus may be HCoV-OC43 or SARS-CoV-2, and particularly preferably SARS-CoV-2.

According to an aspect, the betacoronavirus may be betacoronavirus lineage A (ß-coronavirus lineage A), betacoronavirus lineage B (ß-coronavirus lineage B), and betacoronavirus lineage C (ß-coronavirus lineage C). The betacoronavirus may be more preferably betacoronavirus lineage A (ß-coronavirus lineage A) and betacoronavirus lineage B (ß-coronavirus lineage B) and particularly preferably betacoronavirus lineage B (ß-coronavirus lineage B).

Examples of the betacoronavirus lineage A (ß-coronavirus lineage A) include HCoV-HKU1 and HCoV-OC43, and preferably HCoV-OC43. Examples of the betacoronavirus lineage B (ß-coronavirus lineage B) include SARS-CoV and SARS-CoV-2, and preferably SARS-CoV-2. The betacoronavirus lineage C (ß-coronavirus lineage C) may be MERS-CoV.

According to an aspect, the coronavirus may be HCoV-229E, HCoV-OC43, and/or SARS-CoV-2, and particularly preferably SARS-CoV-2.

The coronavirus infections may be infections caused by HCoV-229E, HCoV-NL63, HCoV-OC43, HCoV-HKU1, SARS-CoV, MERS-CoV, and/or SARS-CoV-2. Preferably, the coronavirus infections may be infections caused by HCoV-229E, HCoV-OC43, and/or SARS-CoV-2, and particularly preferably infection caused by SARS-CoV-2.

The coronavirus infections may be particularly preferably novel coronavirus infections (COVID-19).

Method for Producing Compound of Present Invention

For example, the compound represented by Formula (I) according to the present invention can be prepared by the general procedure described below. Regarding extraction, purification, and the like, the treatments carried out in ordinary experiments of organic chemistry may be carried out.

The compounds of the present invention can be produced with reference to techniques known in the art. The compound can be produced, for example, with reference to WO 2012/020742 A, WO 2013/118855 A, and the like.

(Method A) When Ring A in the formula is a ring represented by Formula:

[Chemical Formula 76]

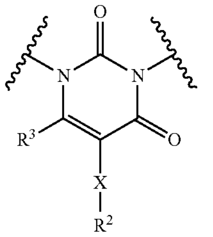

wherein the reference symbols have the same meanings as described above, X is a single bond, —$CR^{4a}R^{4b}$— or —O—, and $R^3$ is non-aromatic heterocyclyl, aromatic carbocyclyloxy, non-aromatic carbocyclyloxy, aromatic heterocyclyloxy, non-aromatic heterocyclyloxy, amino or alkyloxy.

[Chemical Formula 77]

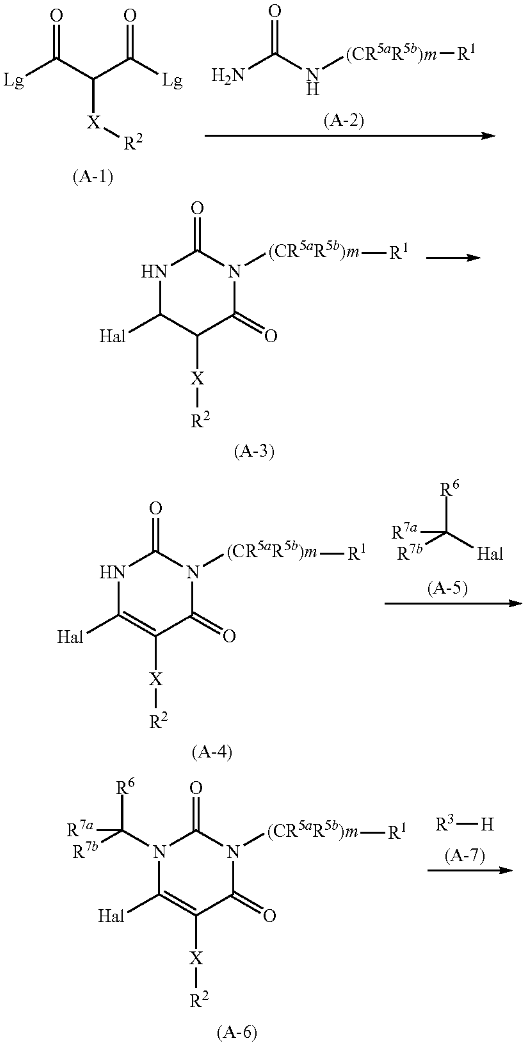

-continued

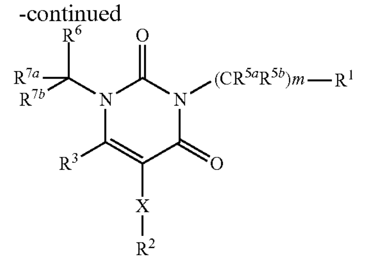

(I-A)

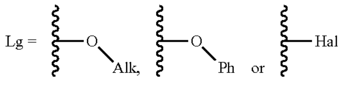

wherein Hal is halogen (a chlorine atom, a bromine atom, an iodine atom, or the like), Alk is C1-C3 alkyl, Lg is a leaving group, and other reference symbols have the same meanings as described above.

(First Step)

Compound (A-3) can be produced by reacting Compound (A-1) with Compound (A-2) in the presence of methanol, ethanol, toluene, tetrahydrofuran, 1,4-dioxane, DMF, or the like, or in a mixed solvent thereof, in the presence or absence of a base such as sodium methoxide or sodium ethoxide, at 0° C. to 140° C., preferably at 60° C. to 100° C., for 0.1 hours to 48 hours, and preferably for 0.5 hours to 18 hours.

(Second Step)

A compound represented by Compound (A-4) can be produced by reacting Compound (A-3) with phosphorus oxychloride or phosphorous oxybromide at 60° C. to 150° C., and preferably at 80° C. to 120° C. in the presence of water.

(Third Step)

Compound (A-6) can be produced by adding Compound (A-5) to Compound (A-4), in a solvent such as acetonitrile, acetone, DMF, DMSO, NMP, tetrahydrofuran, or 1,4-dioxane, in the presence of a base such as potassium carbonate, sodium carbonate, cesium carbonate, DBU, triethylamine, N,N-diisopropylethylamine, or pyridine, at 0° C. to 100° C., and preferably at 20° C. to 60° C., for 0.1 hours to 24 hours, and preferably 0.5 hours to 12 hours.

(Fourth Step)

Compound (I-A) can be produced by adding Compound (A-7) to Compound (A-6), in acetonitrile, acetone, DMF, DMSO, NMP, tetrahydrofuran, 1,4-dioxane, or the like, or in a mixed solvent thereof, in the presence of a base such as triethylamine, N,N-diisopropylethylamine, pyridine, or DBU, at 0° C. to 100° C., and preferably at 20° C. to 60° C., for 0.1 hours to 24 hours, and preferably 0.5 hours to 12 hours.

(Method B) When Ring A in the formula is a ring represented by Formula:

[Chemical Formula 78]

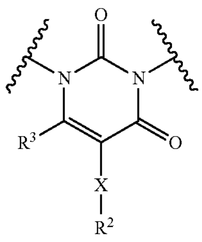

wherein the reference symbols have the same meanings as described above,

X is a single bond, and m=0.

[Chemical Formula 79]

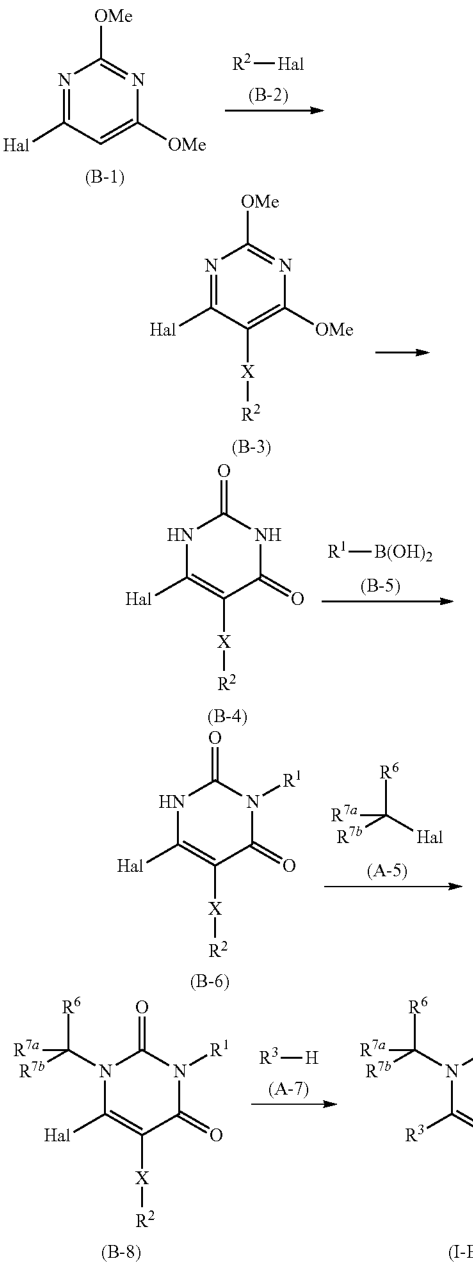

wherein the reference symbols have the same meanings as described above.

(First Step)

Compound (B-3) can be produced by organic zincation of Compound (B-1), followed by the Negishi Reaction using Compound (B-2).

To Compound (B-1), n-butyllithium solution is added, in an organic solvent such as tetrahydrofuran or diethyl ether or a mixed solvent thereof, and the mixture is reacted at −78° C. to −30° C., and preferably at −78° C. to −60° C., for 0.1 hours to 6 hours, and preferably 0.5 hours to 1 hour. Next, zinc chloride is added, and the mixture is reacted at −78° C. to 25° C., and preferably at −20° C. to 25° C., for 0.1 hours to 6 hours, and preferably 0.5 hours to 1 hour. Subsequently, a palladium catalyst, a phosphine ligand, and Compound (B-2) are reacted at 25° C. to 100° C., and preferably at 45° C. to 60° C., for 0.1 hours to 24 hours, and preferably 10 hours to 16 hours, whereby Compound (B-3) can be produced.

As the palladium catalyst, $Pd_2(dba)_3$, $PdCl_2(dppf)$, $PdCl_2(PPh_3)_2$, $Pd(OAc)_2$, $Pd(PPh_3)_4$, Pd/C, $PdCl_2$, Pd-PEPPSI-IPr, Bis[cinnamyl palladium Cl], $PdCl_2(Xantphos)$, or $Pd(OH)_2$ can be used.

As the phosphine ligand, Xantphos, $P(2\text{-furyl})_3$, $PPh_3$, $P(o\text{-tol})_3$, $P(OPh)_3$, $P(OMe)_3$, dppp, dppb, dppf, BINAP, X-Phos, $P(t\text{-Bu})_3$, $P(Oi\text{-Pr})_3$, $P(p\text{-MeOPh})_3$, DPEPhos, or the like can be used.

(Second Step)

Compound (B-4) can be produced by heat-treating compound (B-3) with a strong acid such as hydrochloric acid in an organic solvent such as tetrahydrofuran, 1,4-dioxane, acetonitrile, acetone, DMF, DMSO or NMP, or a mixed solvent thereof.

(Third Step)

Compound (B-6) can be produced by the Chan-Lam coupling reaction using Compound (B-4) and Compound (B-5).

Regarding the solvent, acetonitrile, DMF, NMP, dioxane, DMSO, or the like can be used.

Regarding the copper catalyst, for example, commercially available copper catalysts such as copper acetate, copper iodide, copper cyanide, or copper bromide, can be used.

As the base, triethylamine, N,N-diisopropylethylamine, pyridine, and DBU can be used.

Regarding the reaction temperature, the reaction may be carried out at from room temperature to a temperature at which the solvent refluxes, and preferably, the reaction may be carried out at room temperature to 50° C.

(Fourth Step)

Compound (B-8) can be produced by reacting Compound (B-6) with Compound (A-5) in the same manner as in the third step of the above-described method A.

(Fifth Step)

Compound (I-B) can be produced by reacting Compound (B-8) with Compound (B-9) in the same manner as in the fourth step of the above-described method A.

(Method C) When Ring A in the formula is represented by Formula:

[Chemical Formula 80]

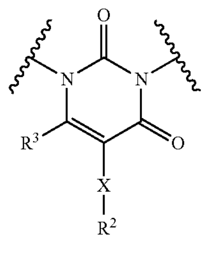

wherein the reference symbols have the same meanings as described above, and X is a single bond.

[Chemical Formula 81]

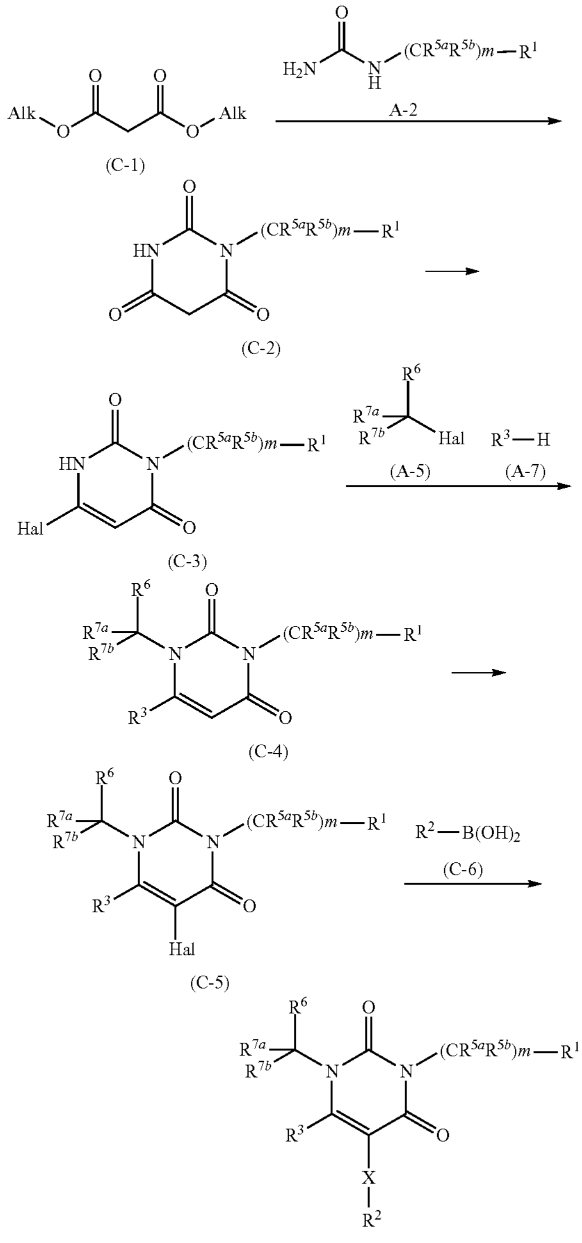

wherein the reference symbols have the same meanings as described above.

(First Step)

Compound (C-2) can be produced by reacting Compound (C-1) with Compound (A-2) in the same manner as in the first step of the above-described method A.

(Second Step)

Compound (C-3) can be produced by reacting Compound (C-2) in the same manner as in the second step of the above-described method A.

(Third Step)

Compound (C-4) can be produced by performing the third step and the fourth step of the above-described Method A in one pot.

(Fourth Step)

Compound (C-5) can be produced by halogenating Compound (C-4).

Regarding the solvent, acetonitrile, DMF, NMP, dioxane, DMSO, or the like can be used.

As the halogenation reagent, for example, commercially available halogenation reagents such as NIS, NBS, and NIS can be used.

Regarding the reaction temperature, the reaction may be carried out at from room temperature to a temperature at which the solvent refluxes, and preferably, the reaction may be carried out at room temperature to 50° C.

(Fifth Step)

Compound (I-C) can be produced by the Suzuki-Miyaura reaction using Compound (C-5) and Compound (C-6).

As the palladium catalyst, $Pd_2(dba)_3$, $PdCl_2(dppf)$, $PdCl_2(PPh_3)_2$, $Pd(OAc)_2$, $Pd(PPh_3)_4$, Pd/C, $PdCl_2$, Pd-PEPPSI-IPr, Bis[cinnamyl palladium Cl], $PdCl_2$(Xantphos), or $Pd(OH)_2$ can be used.

As the phosphine ligand, Xantphos, $P(2\text{-furyl})_3$, $PPh_3$, $P(o\text{-tol})_3$, $P(OPh)_3$, $P(OMe)_3$, dppp, dppb, dppf, BINAP, X-Phos, $P(t\text{-Bu})_3$, $P(Oi\text{-Pr})_3$, $P(p\text{-MeOPh})_3$, DPEPhos, or the like can be used.

As the solvent, 1,4-dioxane, tetrahydrofuran, water, or the like can be used.

Regarding the reaction temperature, the reaction may be carried out at from room temperature to a temperature at which the solvent refluxes, and preferably, the reaction may be carried out by heating under reflux.

(Method D) When Ring A in the formula is represented by Formula:

[Chemical Formula 82]

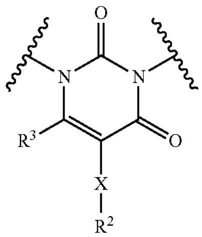

wherein the reference symbols have the same meanings as described above, and X is —S—.

[Chemical Formula 83]

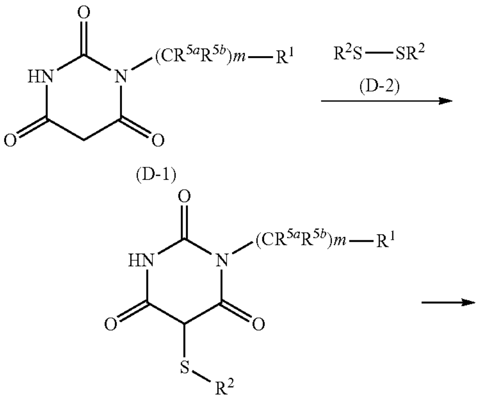

(D-1)

(D-3)

-continued

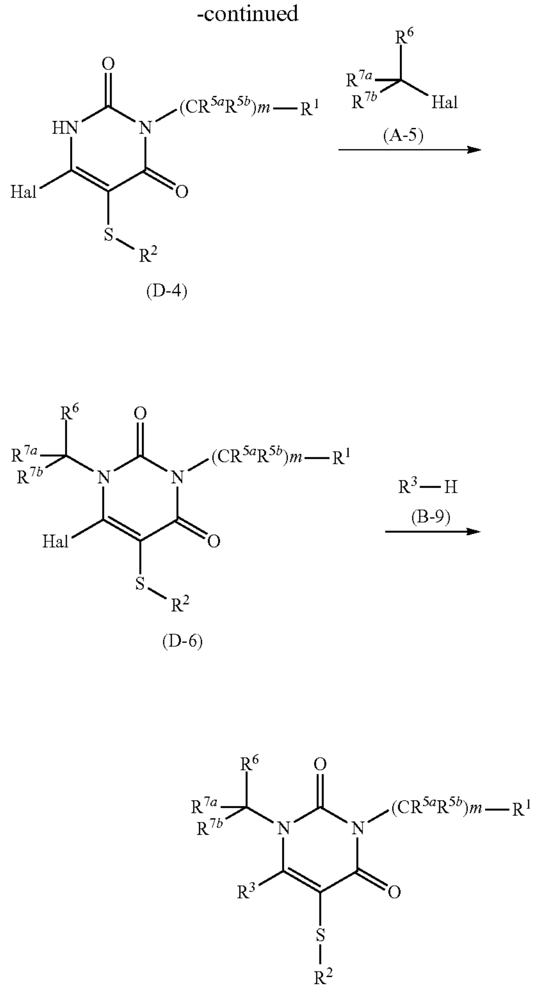

(D-4)

(D-6)

(I-D)

wherein the reference symbols have the same meanings as described above.

(First Step)

Compound (D-3) can be produced by adding Compound (D-2) and iodine to Compound (D-1), in an organic solvent such as acetonitrile, acetone, DMF, DMSO, NMP, tetrahydrofuran, 1,4-dioxane, or the like, or in a mixed solvent thereof, in the presence of a base such as potassium hydroxide or sodium hydroxide, and reacting the same at 25° C. to 100° C., and preferably at 50° C. to 70° C., for 0.1 hours to 6 hours, and preferably 1 hour to 3 hours.

(Second Step)

Compound (D-4) can be produced by reacting phosphorous oxychloride or phosphorous oxybromide in the same manner as in the second step of the above-described method A.

(Third Step)

Compound (D-6) can be produced by reacting Compound (D-4) with Compound (A-5) in the same manner as in the third step of the above-described method A.

(Fourth Step)

Compound (I-D) can be produced by reacting Compound (D-6) with Compound (B-9) in the same manner as in the fourth step of the above-described method A.

(Method E) When Ring A in the formula is represented by Formula:

[Chemical Formula 84]

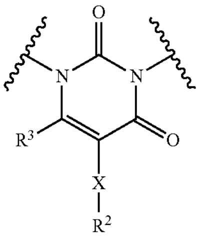

wherein the reference symbols have the same meanings as described above, X is a single bond, $CR^{4a}R^{4b}$—, —O—, or —S—, and $R^3$ is aromatic carbocyclyl or aromatic heterocyclyl.

[Chemical Formula 85]

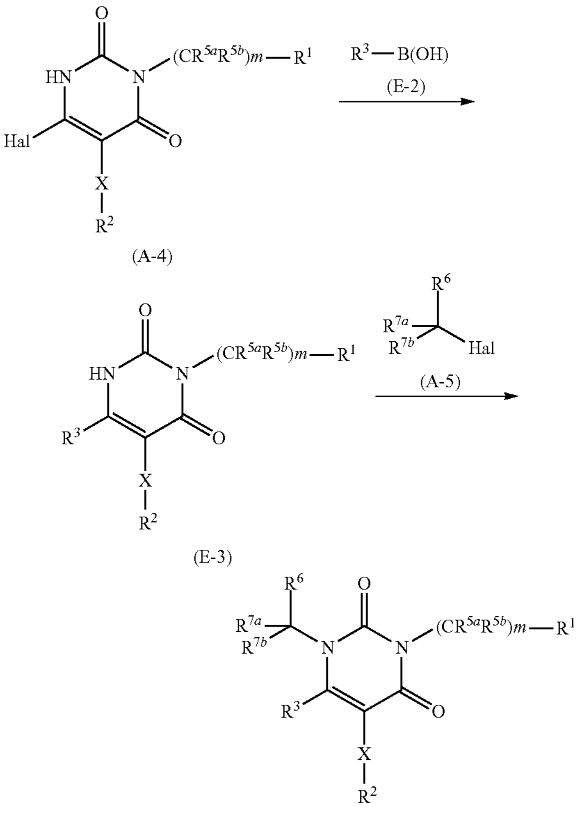

wherein the reference symbols have the same meanings as described above.

(First Step)

Compound (E-3) can be produced by the Suzuki-Miyaura reaction using Compound (A-4) and Compound (E-2).

As the palladium catalyst, $Pd_2(dba)_3$, $PdCl_2(dppf)$, $PdCl_2(PPh_3)_2$, $Pd(OAc)_2$, $Pd(PPh_3)_4$, Pd/C, $PdCl_2$, Pd-PEPPSI (trademark)-IPr, Bis[cinnamyl palladium Cl], $PdCl_2$ (Xantphos), $Pd(OH)_2$, or the like can be used.

As the phosphine ligand, Xantphos, $P(2\text{-furyl})_3$, $PPh_3$, $P(o\text{-tol})_3$, $P(OPh)_3$, $P(OMe)_3$, dppp, dppb, dppf, dtbpf, BINAP, X-Phos, $P(t\text{-Bu})_3$, $P(Oi\text{-Pr})_3$, $P(p\text{-MeOPh})_3$, DPEPhos, or the like can be used.

As the solvent, 1,4-dioxane, tetrahydrofuran, water, or the like can be used.

Regarding the reaction temperature, the reaction may be carried out at from room temperature to a temperature at which the solvent refluxes, and preferably, the reaction may be carried out by heating under reflux.

(Second Step)

Compound (I-E) can be produced by reacting Compound (E-3) with Compound (A-5) in the same manner as in the third step of the above-described method A.

(Method F) When Ring A in the formula is represented by Formula:

[Chemical Formula 86]

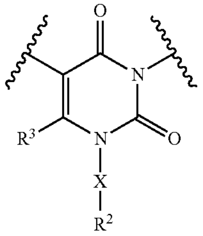

wherein the reference symbols have the same meanings as described above, and X is $—CR^{4a}R^{4b}—$.

[Chemical Formula 87]

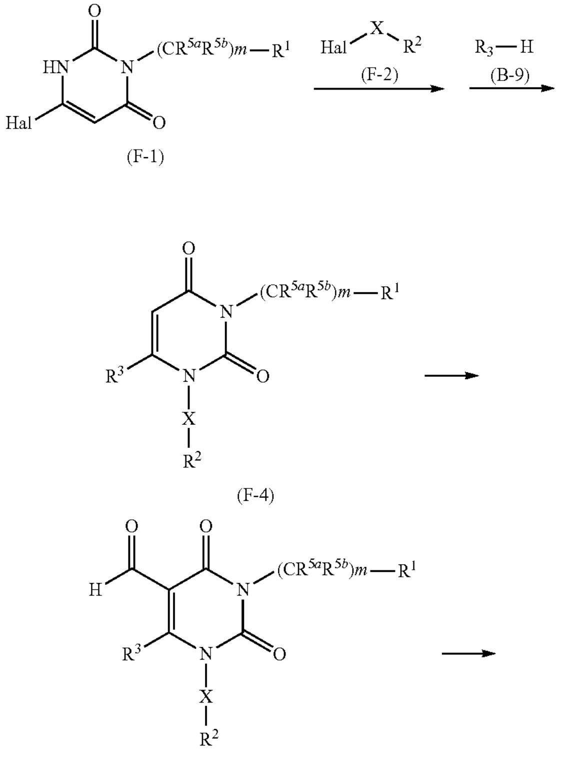

-continued

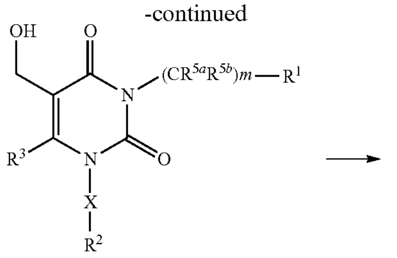

(F-6)

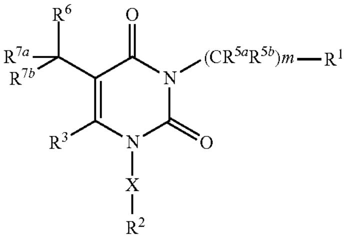

(I-F)

wherein the reference symbols have the same meanings as described above.

(First Step)

Compound (F-4) can be produced by reacting Compound (F-1) with Compound (F-2) in a solvent such as acetonitrile, acetone, DMF, DMSO, or the like, in the presence of a base such as potassium carbonate, sodium carbonate, N,N-diisopropylethylamine, or the like, at 50° C. to a condition of heating under reflux, and preferably under a condition of heating under reflux, and then, reacting the same with Compound (B-9).

(Second Step)

Compound (F-5) can be produced by the Vilsmeier-Haack reaction using Compound (F-4).

As the acid chloride, phosphorus oxychloride, oxalyl chloride, thionyl chloride, benzenesulfonyl chloride, or the like can be used.

As the formylation reagent, N, N-dimethylformamide, N, N-dimethylacetamide, or the like can be used.

As the solvent, dichloromethane, chloroform, tetrahydrofuran, toluene, or the like can be used.

Regarding the reaction temperature, the reaction may be carried out at from 0° C. to 50° C., and preferably, the reaction may be carried out at 25° C.

(Third Step)

Compound (F-6) can be produced by a reduction reaction using Compound (F-5).

As the reducing agent, sodium borohydride, lithium borohydride, sodium cyanoborohydride, or the like can be used.

As the reaction solvent, ethanol, acetonitrile, 1,4-dioxane, tetrahydrofuran, water, or the like can be used.

Regarding the reaction temperature, the reaction may be carried out at from 0° C. to room temperature, and preferably, the reaction may be carried out at room temperature.

(Fourth Step)

Compound (I-F) can be produced by a methanesulfonylation reaction of Compound (F-6) followed by cyanation.

As the methanesulfonylating agent, methanesulfonic anhydride, methanesulfonyl chloride, or the like can be used.

As the cyanating agent, tetrabutylammonium cyanide, sodium cyanide, potassium cyanide, or the like can be used.

As the reaction solvent, dichloromethane, acetonitrile, 1,4-dioxane, tetrahydrofuran, DMF, DMA, or the like can be used.

Regarding the reaction temperature, the reaction may be carried out at from 0° C. to room temperature, and preferably, the reaction may be carried out at room temperature.

(Method G) When Ring A is represented by Formula:

[Chemical Formula 88]

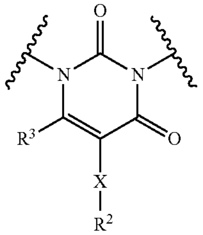

wherein the reference symbols have the same meanings as described above, and X is —C(=O)—.

[Chemical Formula 89]

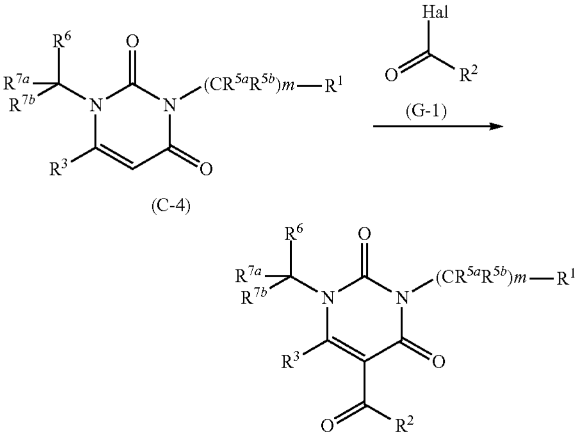

(C-4)

(G-1)

(I-G)

wherein the reference symbols have the same meanings as described above.

(First Step)

Compound (I-G) can be produced by reacting Compound (C-4) with Compound (G-1) in a solvent such as dichloromethane, tetrahydrofuran, or the like or without a solvent, in the presence of a base such as pyridine, triethylamine, or N,N-diisopropylethylamine, at 25° C. to 100° C., and preferably at 90° C.

(Method H) When Ring A in the formula is represented by Formula:

[Chemical Formula 90]

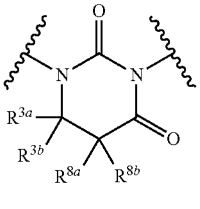

wherein the reference symbols have the same meanings as described above.

[Chemical Formula 91]

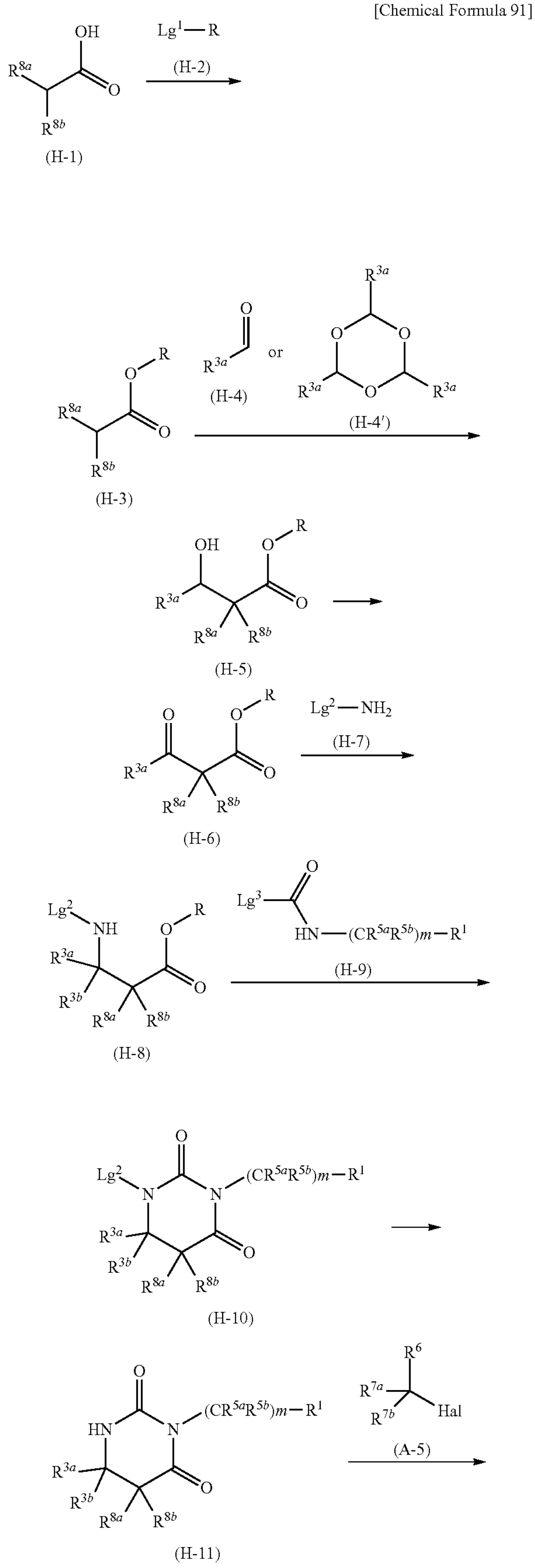

-continued

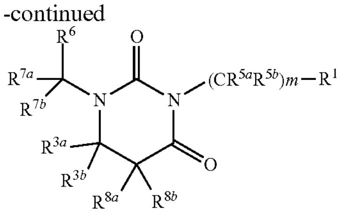

(I-H)

wherein $Lg^1$, $Lg^2$, and $Lg^3$ are leaving groups, respectively; and other reference symbols have the same meanings as described above.

(First Step)

Compound (H-3) can be produced by adding Compound (H-2) to Compound (H-1), in the presence of acetonitrile, acetone, DMF, DMSO, NMP, or the like or in a mixed solvent thereof, in the presence of a base such as potassium carbonate, sodium carbonate, or cesium carbonate, or the like, and reacting the same at 0° C. to 100° C., and preferably at 0° C. to 60° C., for 0.1 hours to 24 hours, and preferably 0.5 hours to 12 hours.

Examples of the leaving group $Lg^1$ include halogen and $—OSO_2(C_tF_{2t+1})$, wherein t is an integer of 1 to 4. The halogen is preferably chlorine, iodine, or bromine, and the $—OSO_2(C_tF_{2t+1})$ group is preferably an —OTf group (trifluoromethanesulfonate).

(Second Step)

Compound (H-5) can be produced by reacting Compound (H-3) with a base such as LDA, LHMDS, sodium methoxide, or the like in the presence of a solvent such as tetrahydrofuran, diethyl ether, toluene, DMF, DMSO, NMP, or the like, or in a mixed solvent thereof, at −100° C. to 0° C., and preferably at −78° C. to 0° C., for 0.1 hours to 24 hours, and preferably 0.5 hours to 1 hour, and then, adding Compound (H-4) or Compound (H-4') and reacting the same at 0° C. to 100° C., and preferably at 0° C. to 25° C., for 0.1 hours to 24 hours, and preferably 0.5 hours to 3 hours.

(Third Step)

Compound (H-6) can be produced by reacting Compound (H-5) with an oxidizing agent such as Dess-Martin reagent, 2-iodoxybenzoic acid, manganese dioxide, or the like, in the presence of a solvent such as dichloromethane, chloroform, acetonitrile, DMSO, or the like or in a mixed solvent thereof, at 0° C. to 60° C., and preferably at 0° C. to 25° C., for 0.1 hours to 24 hours, and preferably 0.5 hours to 12 hours.

(Fourth Step)

Compound (H-8) can be produced by reacting Compound (H-6) and Compound (H-7) with a reducing agent such as sodium cyanoborohydride, sodium triacetoxyborohydride, or the like, in the presence of a solvent such as methanol, ethanol, tetrahydrofuran, or the like or a mixed solvent thereof, at 0° C. to 60° C., and preferably at room temperature, for 0.1 hours to 24 hours, and preferably 0.5 hours to 1 hour. Examples of the leaving group $Lg^2$ include benzyl group, 4-methoxybenzyl group, and 2,4-dimethoxybenzyl group.

(Fifth Step)

Compound (H-10) can be produced by reacting Compound (H-8) and Compound (H-9) with a base such as triethylamine, DIEA, DBU, sodium hydride, cesium carbonate, or the like, in the presence of a solvent such as toluene, tetrahydrofuran, acetonitrile, DMF, or the like or in a mixed solvent thereof, at 0° C. to 100° C., and preferably at 60° C. to 80° C., for 0.1 hours to 24 hours, and preferably 2 hours to 4 hours. Examples of the leaving group $Lg^3$ include phenyloxy group, 1-imidazolyl group, and N-hydroxyphthalimide group.

(Sixth Step)

Compound (H-11) can be produced by reacting Compound (H-10) with an acid such as trifluoroacetic acid, trifluoromethanesulfonic acid, or the like, at 0° C. to 120° C., and preferably at 80° C. to 120° C., for 0.1 hours to 24 hours, and preferably 4 hours to 6 hours. Anisole or the like may be added as an additive.

(Seventh Step)

Compound (I-H) can be produced by adding Compound (A-5) to Compound (H-11), in a solvent such as acetonitrile, acetone, DMF, DMSO, NMP, or the like or in a mixed solvent thereof, in the presence of a base such as potassium carbonate, sodium carbonate, cesium carbonate, or the like, and reacting the same at 0° C. to 100° C., and preferably at 20° C. to 60° C., for 0.1 hours to 24 hours, and preferably 2 hours to 12 hours.

Since the compound of the present invention has coronavirus 3CL protease inhibitory activity, the compound is useful as a therapeutic and/or prophylactic agent for coronavirus infections.

Furthermore, the compound of the present invention has utility as a medicine, and preferably, the compound of the present invention has any one or a plurality of the following excellent features.

a) Inhibitory activity against CYP enzymes (for example, CYP1A2, CYP2C9, CYP2C19, CYP2D6, and CYP3A4) is weak.
b) Satisfactory pharmacokinetics such as high bioavailability or adequate clearance are exhibited.
c) Metabolic stability is high.
d) Irreversible inhibitory activity is not exhibited against CYP enzymes (for example, CYP3A4) within the concentration range of the measurement conditions described in the present specification.
e) Mutagenicity is not exhibited.
f) The cardiovascular risk is low.
g) High solubility is exhibited.
h) The protein unbinding rate (fu value) is high.
i) High coronavirus 3CL protease selectivity is exhibited.
j) High coronavirus replication inhibitory activity is exhibited. For example, high coronavirus replication inhibitory activity is exhibited when human blood serum (HS) or human serum albumin (HSA) is added.
k) High proliferation inhibitory activity is exhibited against 3CL protease inhibitor-resistant viruses.

Regarding the coronavirus replication inhibitor, for example, an aspect in which in the CPE effect (SARS-CoV-2) that will be described below, for example, $EC_{50}$ is 10 μM or less, preferably 1 μM or less, and more preferably 100 nM or less, may be mentioned.

The pharmaceutical composition of the present invention can be administered by either an oral method or a parenteral method. Examples of a parenteral administration method include percutaneous, subcutaneous, intravenous, intra-arterial, intramuscular, intraperitoneal, transmucosal, inhalation, transnasal, ocular instillation, ear instillation, and intravaginal administration.

In the case of oral administration, the pharmaceutical composition may be prepared into any dosage form that is commonly used, such as a solid preparation for internal use (for example, a tablet, a powder preparation, a granular preparation, a capsule, a pill, or a film preparation), or a liquid preparation for internal use (for example, a suspension, an emulsion, an elixir, a syrup, a limonade, a spirit preparation, an aromatic water preparation, an extraction, a decoction, or a tincture) and administered. The tablet may be a dragee, a film-coated tablet, an enteric-coated tablet, a sustained release tablet, a troche, a sublingual tablet, a buccal tablet, a chewable tablet, or an orally disintegrating tablet; the powder preparation and granular preparation may be dry syrups; and the capsule may be a soft capsule, a microcapsule, or a sustained release capsule.

In the case of parenteral administration, the pharmaceutical composition can be suitably administered in any dosage form that is commonly used, such as an injectable preparation, an infusion, or a preparation for external use (for example, an eye drop, a nasal drop, an ear drop, an aerosol, an inhalant, a lotion, an impregnating agent, a liniment, a gargling agent, an enema, an ointment, a plaster, a jelly, a cream, a patch, a poultice, a powder preparation for external use, or a suppository). The injectable preparation may be an O/W, W/O, O/W/O, or W/O/W type emulsion, or the like.

A pharmaceutical composition can be obtained by mixing an effective amount of the compound of the present invention with various pharmaceutical additives appropriate for the dosage form, such as an excipient, a binder, a disintegrating agent, and a lubricating agent, as necessary. Furthermore, the pharmaceutical composition can be prepared into a pharmaceutical composition for use for a child, an elderly, a patient with a serious case, or a surgical operation, by appropriately changing the effective amount of the compound of the present invention, the dosage form, and/or various pharmaceutical additives. For example, pediatric pharmaceutical compositions may be administered to patients who are neonates (younger than 4 weeks old after the birth), infants (4 weeks old to younger than 1 year old after the birth), infant children (1 year old or older and younger than 7 years old), children (7 years old or older and younger than 15 years old), or 15 to 18 years old. For example, a pharmaceutical composition for an elderly may be administered to a patient 65 years of age or older.

It is desirable to set the amount of administration of the pharmaceutical composition of the present invention, after considering the age and body weight of the patient, the type and degree of the disease, the route of administration, and the like; however, in the case of oral administration, the amount of administration is usually 0.01 to 100 mg/kg/day and is preferably in the range of 0.05 to 50 mg/kg/day. In the case of parenteral administration, the amount of administration may vary greatly depending on the route of administration; however, the amount of administration is usually 0.005 to 200 mg/kg/day and is preferably in the range of 0.01 to 100 mg/kg/day. This may be administered once a day or several times a day.

The compound of the present invention may be used in combination with, for example, another therapeutic agent for novel coronavirus infections (COVID-19) (the therapeutic agent includes an approved drug and a drug that is under development or to be developed in the future) (hereinafter, referred to as concomitant drug), for the purpose of enhancing the action of the compound, reducing the amount of administration of the compound, or the like. At this time, the timing of administration for the compound of the present invention and the concomitant drug is not limited, and these may be administered simultaneously to the target of administration or may be administered with a time difference. Furthermore, the compound of the present invention and the concomitant drug may be administered as two or more kinds of preparations each including active ingredients, or may be administered as a single preparation including those active ingredients.

The amount of administration of the concomitant drug can be appropriately selected based on the clinically used dosage. Furthermore, the blending ratio of the compound of the present invention and the concomitant drug can be appropriately selected according to the target of administration, the route of administration, the target disease, symptoms, combination, and the like. For example, when the target of administration is a human being, 0.01 to 100 parts by weight of the concomitant drug may be used with respect to 1 part by weight of the compound of the present invention.

EXAMPLES

Hereinafter, the present invention will be described in more detail by way of Examples, Reference Examples, and Test Examples; however, the present invention is not intended to be limited by these.

Furthermore, abbreviations used in the present specification denote the following meanings.

DBU: 1,8-Diazabicyclo[5.4.0]-7-undecene
DMA: N,N-dimethylacetamide
DMF: N,N-dimethylformamide
DMSO: Dimethyl sulfoxide
DPEphos: bis[2-(diphenylphosphino)phenyl]ether
ESI: Electrospray ionization
FBS: Fetal bovine serum
LDA: Lithium diisopropylamide
LHMDS: Lithium hexamethyldisilazide
NBS: N-bromosuccinimide
NCS: N-chlorosuccinimide
NIS: N-iodosuccinimide
NMP: N-methylpyrrolidone
$P(2\text{-furyl})_3$: Tri(2-furyl)phosphine
$P(o\text{-tol})_3$: Tris(2-methylphenyl)phosphine
$Pd(OAc)_2$: Palladium acetate
$Pd(PPh_3)_4$: Tetrakis(triphenylphosphine)palladium
$Pd_2(dba)_3$: Tris(dibenzylideneacetone)bispalladium
$PdCl_2(PPh_3)_2$: Bis(triphenylphosphine)palladium (II) dichloride
$PdCl_2(dppf)$: [1,1'-bis(diphenylphosphino)ferrocene]palladium (II) dichloride dichloromethane adduct
$PdCl_2(dtbpf)$: [1,1'-bis(di-tert-butylphosphino)ferrocene] palladium (II) dichloride
Ph: Phenyl
X-Phos: 2,4,6-triisopropyl-2'-(dicyclohexylphosphino)biphenyl
Xantphos: 4,5'-Bis(diphenylphosphine)-9,9'-dimethylxanthene
dppb: 1,4-bis(diphenylphosphino)butane
dppf: 1,1'-bis(diphenylphosphino)ferrocene
dppp: 1,3-bis(diphenylphosphino)propane
i-Pr: Isopropyl
t-Bu: tert-butyl
mM: mmol/L
nM: nmol/L
μM: μmol/L (Method for Identifying Compound)

The NMR analysis obtained in each Example was performed at 400 MHz, and measurement was made using DMSO-$d_6$ or $CDCl_3$. Furthermore, when NMR data are shown, there are occasions in which all the measured peaks are not described.

The term RT in the specification indicates retention time in an LC/MS: liquid chromatography/mass analysis, and the retention time was measured under the following conditions.

(Measurement Conditions A)

Column: ACQUITY UPLC (registered trademark) BEH C18 (1.7 μm i.d. 2.1×50 mm) (Waters)
Flow rate: 0.8 mL/min
UV detection wavelength: 254 nm
Mobile phase: [A] was 0.1% formic acid-containing aqueous solution, and [B] was 0.1% formic acid-containing acetonitrile solution.
Gradient: A linear gradient of 5% to 100% solvent [B] was carried out for 3.5 minutes, and then 100% solvent [B] was maintained for 0.5 minutes.

(Measurement Conditions B)

Column: ACQUITY UPLC (registered trademark) BEH C18 (1.7 μm i.d. 2.1×50 mm) (Waters)
Flow rate: 0.8 mL/min
UV detection wavelength: 254 nm
Mobile phase: [A] is 10 mM ammonium carbonate in aqueous solution, and [B] is acetonitrile.
Gradient: A linear gradient of 5% to 100% solvent [B] was carried out for 3.5 minutes, and then 100% solvent [B] was maintained for 0.5 minutes.

(Measurement Conditions D)

Column: Shim-pack XR-ODS (2.2 μm, i.d. 3.0×50 mm) (Shimadzu)
Flow rate: 1.6 mL/min
UV detection wavelength: 254 nm
Mobile phase: [A] was 0.1% formic acid-containing aqueous solution, and [B] was 0.1% formic acid-containing acetonitrile solution.
Gradient: A linear gradient of 10% to 100% solvent [B] was carried out for 3 minutes, and then 100% solvent [B] was maintained for 0.5 minutes.

Incidentally, in the specification, the description of MS (m/z) indicates a value observed by mass analysis.

Example 1

Synthesis of Compound (I-205)

[Chemical Formula 92]

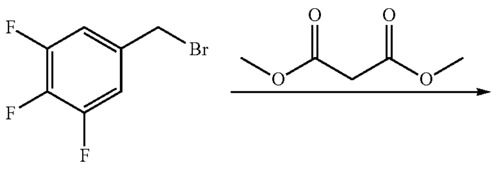

1

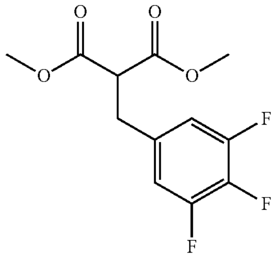

2

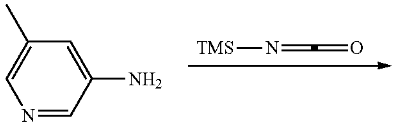

3

-continued

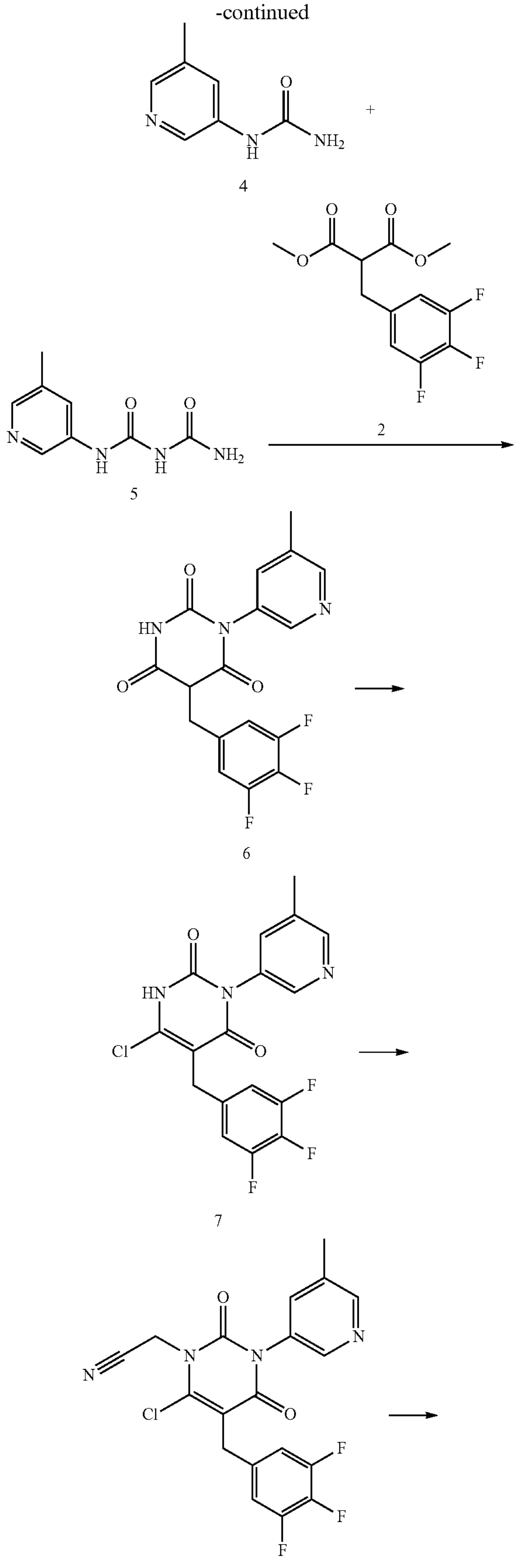

4

5

6

7

8

-continued

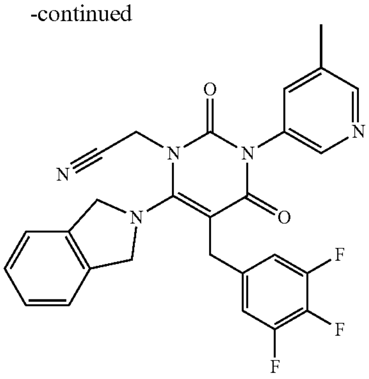

I-205

Step 1 Synthesis of Compound 2

Compound 1 (5.9 mL, 44.4 mmol), acetone (40 mL), potassium carbonate (9.2 g, 66.7 mmol), and dimethyl malonate (8.4 mL, 66.7 mmol) were mixed, and the solution thus obtained was stirred at 45° C. for 1 hour and 30 minutes, and then, it was allowed to stand at room temperature for 15 hours 30 minutes. The precipitate was filtered off and washed with acetone. The filtrate was concentrated, the residue thus obtained was purified by silica gel column chromatography (hexane:ethyl acetate=10:0 to 9:1), the solvent was distilled off under reduced pressure, and Compound 2 (6.0 g, 21.5 mmol, yield 49%) was obtained.

LC/MS (ESI): m/z=277, RT=2.20 min, LC/MS measurement conditions A

Step 2 Synthesis of Compound 4

A solution obtained by mixing dichloromethane (42 mL) to Compound 3 (11.3 g, 104 mmol) was ice-cooled, trimethylsilyl isocyanate (6.9 mL, 52.1 mmol) was added thereto, and the mixture was stirred at room temperature for 30 minutes. The reaction solution was allowed to stand at room temperature for 66 hours, then methanol (12 mL) was added thereto, and the mixture was stirred for 5 minutes. The solution was concentrated, dichloromethane (15 mL) and diisopropyl ether (45 mL) were added thereto, and the obtained precipitate was collected by filtration and washed with a mixed solution of dichloromethane and diisopropyl ether (1:3). The residue thus obtained was dried under reduced pressure, and a mixture of Compounds 4 and 5 (6.8 g, 5:1) was obtained. Compound 4 (purity 80%, 36.2 mmol, yield 70%)

LC/MS (ESI): m/z=152, RT=0.58 min, LC/MS measurement conditions B

Step 3 Synthesis of Compound 6

Compound 2 (2.4 g, 8.73 mmol), a 5:1 mixture of Compounds 4 and 5 (1.2 g, Compound 4: 6.35 mmol), and a 20% sodium ethoxide solution (9.2 mL) were mixed, and the obtained solution was stirred at 90° C. for 4 hours. The reaction solution was cooled in an ice bath, and was neutralized with 2 mol/L hydrochloric acid (7.9 mL). A saturated aqueous sodium bicarbonate solution (1 mL) was added, then water (14 mL) was added, and the obtained precipitate was collected by filtration and washed with water and diisopropyl ether. The residue thus obtained was dried under reduced pressure, and Compound 6 (1.2 g, 3.30 mmol, yield 52%) was obtained.

LC/MS (ESI): m/z=364, RT=1.28 min, LC/MS measurement conditions B

Step 4 Synthesis of Compound 7

Phosphorus oxychloride (6.6 mL, 70.5 mmol) was slowly added dropwise to Compound 6 (1.3 g, 3.52 mmol), and water (0.3 mL, 17.6 mmol) was slowly added thereto dropwise. The obtained solution was stirred at room temperature for 5 minutes, and then stirred at 100° C. for 6 hours. The reaction solution was slowly added dropwise to water (10 mL) cooled in an ice bath, and then a 4 mol/L aqueous lithium hydroxide solution (53 mL) was added little by little. The obtained precipitate was collected by filtration and washed with water. The residue thus obtained was dried under reduced pressure, and Compound 7 (1.2 g, 3.14 mmol, yield 89%) was obtained.

LC/MS (ESI): m/z=382, RT=1.80 min, LC/MS measurement conditions A

Step 5 Synthesis of Compound 8

To a solution obtained by mixing Compound 7 (700 mg, 1.83 mmol), potassium carbonate (760 mg, 5.50 mmol), and DMF (7.0 mL), 2-bromoacetonitrile (367 μL, 5.50 mmol) was added. The obtained solution was stirred at room temperature for 3 hours, then the reaction solution was cooled in an ice bath, water (14 mL) was added thereto, and the mixture was extracted with ethyl acetate. The organic layer was washed with water and brine, dried over sodium sulfate, and filtered. The filtrate was concentrated, and ethyl acetate (3.5 mL) and hexane (7.0 mL) were added thereto. The obtained precipitate was collected by filtration and washed with a mixed solution of hexane and ethyl acetate (1:2). The residue thus obtained was dried under reduced pressure, and Compound 8 (469 mg, 1.12 mmol, yield 61%) was obtained.

LC/MS (ESI): m/z=421, RT=2.11 min, LC/MS measurement conditions A

Step 6 Synthesis of Compound (I-205)

A solution obtained by mixing Compound 8 (51.5 mg, 0.122 mmol), isoindoline (41.3 μL, 0.367 mmol), and ethanol (1.0 mL) was stirred at 100° C. for 2 hours. The reaction solution was cooled to room temperature, water (2 mL) was added thereto, and the mixture was extracted with ethyl acetate. The organic layer was dried over sodium sulfate, and filtered. The filtrate was concentrated, the residue thus obtained was purified by silica gel column chromatography (chloroform:methanol=10:0 to 9.5:0.5), the solvent was distilled off under reduced pressure, and Compound (I-205) (6.1 mg, 0.012 mmol, yield 10%) was obtained.

$^1$H-NMR ($CDCl_3$) δ: 2.42 (s, 3H), 3.57 (s, 2H), 4.64 (s, 4H), 4.95 (s, 2H), 6.64 (dd, J=6.7, 8.0 Hz, 2H), 7.30 (dd, J=3.2, 5.6 Hz, 2H), 7.40 (dd, J=3.2, 5.6 Hz, 2H), 7.45 (dd, J=1.3, 2.3 Hz, 1H), 8.35 (d, J=2.3 Hz, 1H), 8.51 (d, J=1.3 Hz, 1H)

LC/MS (ESI): m/z=504, RT=2.41 min, LC/MS measurement conditions A

Example 2

[Chemical Formula 93]

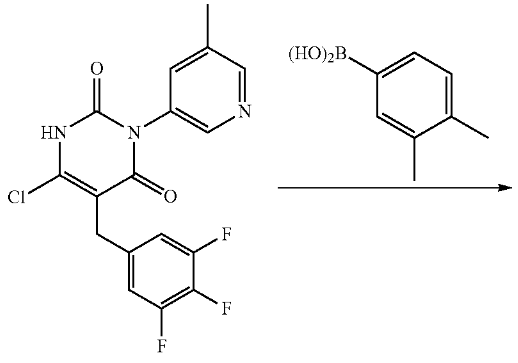

7

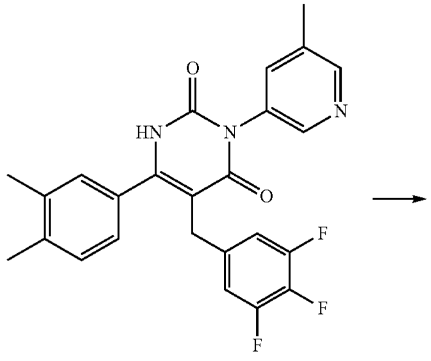

9

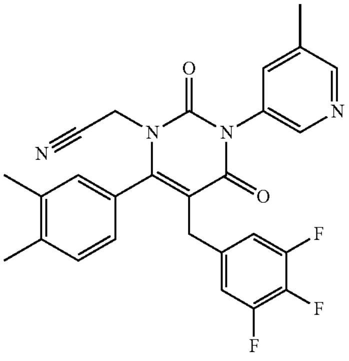

I-060

Step 1 Synthesis of Compound 9

A solution obtained by mixing Compound 7 (20.0 mg, 0.052 mmol), (3,4-dimethylphenyl)boronic acid (9.4 mg, 0.063 mmol), sodium carbonate (16.7 mg, 0.157 mmol), $PdCl_2$ (dtbpf) (3.4 mg, 5.2 μmol), 1,4-dioxane (0.2 mL), and water (40 μL) was stirred at 120° C. for 1 hour and 30 minutes, and then the reaction solution was concentrated. The residue thus obtained was purified by silicagel column chromatography (chloroform:methanol=10:0 to 9.7:0.3), and the solvent was distilled off under reduced pressure.

Ethyl acetate (0.2 mL) and hexane (0.4 mL) were added to the obtained residue, and the obtained precipitate was collected by filtration and washed with a mixed solution of hexane and ethyl acetate (1:2). The residue thus obtained was dried under reduced pressure, and Compound 9 (8.3 mg, 0.018 mmol, yield 35%) was obtained.

LC/MS (ESI): m/z=452, RT=2.35 min, LC/MS measurement conditions A

Step 8 Synthesis of Compound (I-060)

To a solution obtained by mixing Compound 9 (59 mg, 0.131 mmol), potassium carbonate (21.7 mg, 0.157 mmol), and DMF (0.6 mL), 2-bromoacetonitrile (9.6 μL, 0.144 mmol) was added. The obtained solution was stirred at room temperature for 30 minutes, then water (2 mL) was added to the reaction solution, and the mixture was extracted with ethyl acetate. The organic layer was washed with water, dried over sodium sulfate, and filtered. The filtrate was concentrated, and ethyl acetate (0.6 mL) and hexane (0.6 mL) were added thereto. The obtained precipitate was collected by filtration and washed with a mixed solution of hexane and ethyl acetate (1:1). The residue thus obtained was dried under reduced pressure, and Compound (I-060) (29.6 mg, 0.060 mmol, yield 46%) was obtained.

$^1$H-NMR ($CDCl_3$) δ: 2.36 (s, 3H), 2.41 (s, 3H), 2.43 (s, 3H), 3.39 (d, J=14.8 Hz, 1H), 3.49 (d, J=14.7 Hz, 1H), 4.43 (s, 2H), 6.56 (dd, J=6.8, 8.5 Hz, 2H), 7.06 (d, J=1.6 Hz, 1H), 7.07 (dd, J=1.6, 7.8 Hz, 1H), 7.40 (d, J=7.7 Hz, 1H), 7.48 (dd, J=1.1, 2.3 Hz, 1H), 8.38 (d, J=2.3 Hz, 1H), 8.53 (d, J=1.1 Hz, 1H)

LC/MS (ESI): m/z=491, RT=2.58 min, LC/MS measurement conditions A

Example 31

Synthesis of Compound (I-042)

[Chemical Formula 94]

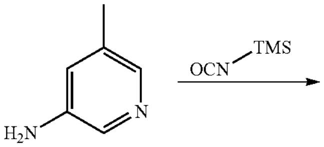

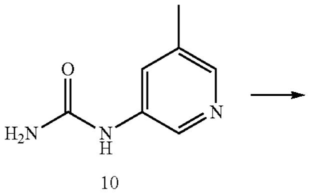

10

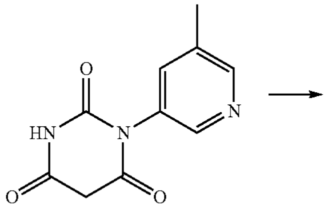

11

-continued

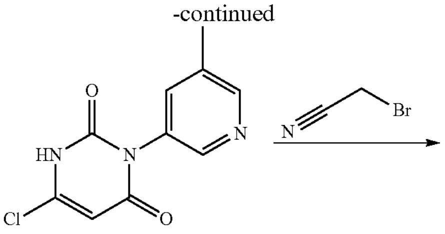

12

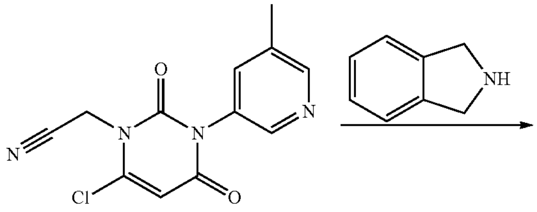

13

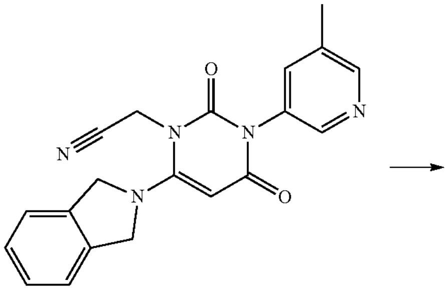

14

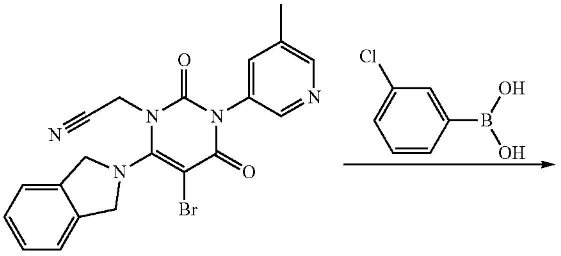

15

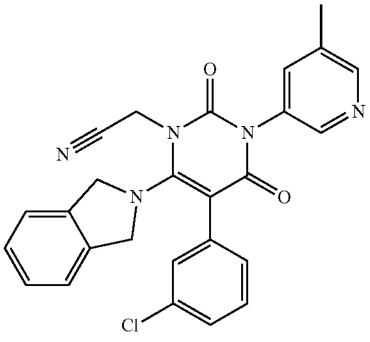

I-042

Step 1 Synthesis of Compound 10

In dichloromethane (75 mL), 2-amino-4-methylpyridine (20.1 g, 186 mmol) was dissolved under ice cooling, and trimethylsilyl isocyanate (12.6 mL, 93 mmol) was added dropwise thereto. The reaction solution was heated to room temperature and stirred for 17 hours. Methanol (18.8 mL) and diisopropyl ether (240 mL) were added into the reaction solution, and the obtained solid was separated by filtration, washed with a mixed solution (60 mL) of dichloromethane: diisopropyl ether=1:3, and dried under reduced pressure to obtain Compound 10 (7.05 g, 44.6 mmol, yield 50%). The obtained Compound 10 was used in the next step without further purification.

$^1$H-NMR (DMSO-$d_6$) δ: 8.66 (1H, s), 8.30 (1H, d, J=2.3 Hz), 7.95 (1H, d, J=1.1 Hz), 7, 75 (1H, s), 5.99 (2H, s), 2.24 (31H, s).

Step 2 Synthesis of Compound 11

Compound 10 (3 g, 19.9 mmol) was dissolved in ethanol (21 mL), and diethyl malonate (3.33 mL, 21.8 mmol) and a sodium ethoxide ethanol solution (20 wt %, 9.21 mL, 23.8 mmol) were sequentially added thereto, then the mixture was refluxed for 20 hours. The reaction solution was air-cooled, then 2 mol/l hydrochloric acid (11.9 mL, 23.8 mmol) was added thereto, and the mixture was concentrated and dried. The obtained solid was purified by silicagel column chromatography (chloroform/methanol=99:1 to 95:5) to give Compound 11 (4.4 g, 20.07 mmol, yield 101%).

LC/MS (ESI): m/z=220 [M+H]$^+$, RT=0.75 min, LC/MS measurement conditions A

Step 3 Synthesis of Compound 12

Phosphorus oxychloride (4.24 mL, 45.6 mmol) and water (205 μL, 11.4 mmol) were sequentially added to Compound 11 (1 g, 4.56 mmol) at room temperature, and the mixture was stirred for 10 minutes, then stirred at 100° C. for 1 hour. The reaction solution was cooled with ice, and water (2.46 mL, 137 mmol) and an aqueous potassium carbonate solution (9.1 mol/l, 15 mL, 137 mmol) were gradually added dropwise thereto. A 2 mol/l aqueous sodium hydroxide solution was added so that the pH of the reaction solution was 5 to 6, and the obtained solid was separated by filtration and washed with water. The obtained solid was suspended in water (5 mL) and finely crushed, then separated by filtration and washed with water to obtain compound 12 (523 mg, 2.20 mmol, yield 48%). The obtained Compound 12 was used in the next step without further purification.

LC/MS (ESI): m/z=238 [M+H]$^+$, RT=0.85 min, LC/MS measurement conditions A $^1$H-NMR (DMSO-$d_6$) δ: 8.43 (1H, d, J=1.3 Hz), 8.28 (1H, d, J=2.1 Hz), 7.58 (1H, s), 6.05 (1H, s), 2.34 (3H, s).

Step 4 Synthesis of Compound 13

Compound 12 (523 mg, 2.20 mmol) was suspended in DMF (5.2 mL), and potassium carbonate (912 mg, 6.60 mmol) and 2-bromoacetonitrile (440 μL, 6.60 mmol) were added, then the mixture was stirred at room temperature for 20 hours. The reaction solution was diluted with ethyl acetate, the organic layer was washed with water, and then dried over sodium sulfate. The solid was separated by filtration and dried under reduced pressure, then purified by silicagel column chromatography (ethyl acetate 100%) to give Compound 13 (89 mg, 0.321 mmol, yield 14.6%).

LC/MS (ESI): m/z=277 [M+H]$^+$, RT=1.05 min, LC/MS measurement conditions A $^1$H-NMR ($CDCl_3$) δ: 8.47 (1H, s), 8.25 (1H, d, J=2.3 Hz), 7.34 (1H, s), 6.13 (1H, s), 4.96 (2H, s), 2.35 (3H, s).

Step 5 Synthesis of Compound 14

Compound 13 (89 mg, 0.322 mmol) was dissolved in ethanol (1.8 mL), isoindoline (73 μL, 0.643 mmol) was added thereto, and the mixture was stirred at 100° C. for 30 minutes. The reaction solution was air-cooled, diluted with ethyl acetate, and washed with water. After the solid thus obtained was separated by filtration and washed with ethyl acetate, the solid together with an organic layer were dried under reduced pressure, and then purified by silicagel column chromatography (ethyl acetate 100%) to give Compound 14 (63 mg, 175 mmol, yield 54%).

LC/MS (ESI): m/z=360 [M+H]$^+$, RT=1.57 min, LC/MS measurement conditions A $^1$H-NMR (DMSO-$d_6$) δ: 8.44 (1H, d, J=1.3 Hz), 8.26 (1H, d, J=2.1 Hz), 7.55 (1H, s), 7.42-7.34 (4H, m), 5.50 (1H, s), 4.95 (2H, s), 4.78 (4H, s), 2.36 (3H, s).

Step 6 Synthesis of Compound 15

Compound 14 (63 mg, 0.175 mmol) and N-bromosuccinimide (34.3 mg, 0.193 mmol) were dissolved in chloroform (1.3 mL), and the mixture was stirred at room temperature for 2.5 hours. The reaction solution was purified by silicagel column chromatography (hexane:ethyl acetate=50:50 to 30:70), and Compound 15 (59 mg, 0.135 mmol, yield 77%) was obtained.

LC/MS (ESI): m/z=438 [M+H]$^+$, RT=1.98 min, LC/MS measurement conditions A $^1$H-NMR (DMSO-$d_6$) δ: 8.39 (1H, s) 8, 24 (1H, d, J=2.3 Hz), 7.54 (1H, s), 7.33 (2H, dd, J=5.4, 3.4 Hz), 7.25 (2H, dd, J=5.4, 3.1 Hz), 5.00 (2H, s), 4.66 (4H, s), 2.28 (3H, s).

Step 7 Synthesis of Compound (I-042)

Compound 15 (59 mg, 0.135 mmol) was dissolved in 1,4 dioxane (1.2 mL), and (3-chlorophenyl) boronic acid (31.6 mg, 0.202 mmol), an aqueous potassium carbonate solution (2 mmol/l, 135 μL, 0.269 mmol) and $PdCl_2$ (dppf) $CH_2Cl_2$ (11 mg, 0.013 mmol) were sequentially added. Nitrogen purge was carried out, and then, the mixture was stirred at 100° C. for 1 hour and allowed to stand for 16 hours. The reaction solution was diluted with ethyl acetate, and washed sequentially with water and brine. The organic layer was dried under reduced pressure and purified by HPLC (acetonitrile:water=30:70 to 80:20) to give Compound (I-042) (23.4 mg, 0.05 mmol, yield 37%).

LCMS (ESI): m/z=470 [M+H]$^+$, RT=2.23 min, LC/MS measurement conditions A $^1$H-NMR (DMSO-$d_6$) δ: 8.47 (1H, s), 8.32 (1H, s), 7.60 (1H, s), 7.25-7.11 (8H, m), 5.08 (2H, s), 4.44 (4H, s), 2.36 (3H, s).

Example 4

Synthesis of Compound (I-088)

[Chemical Formula 95]

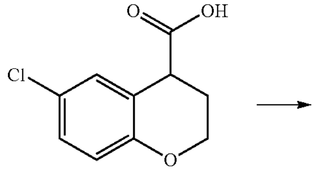

16

-continued

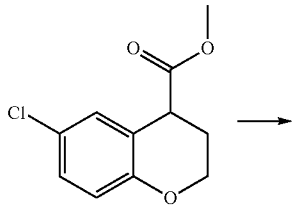

17

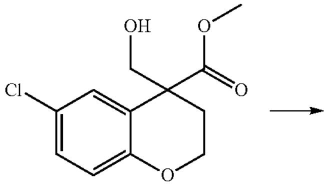

18

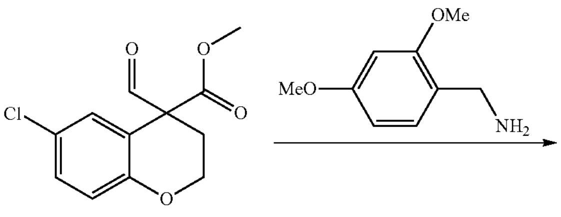

19

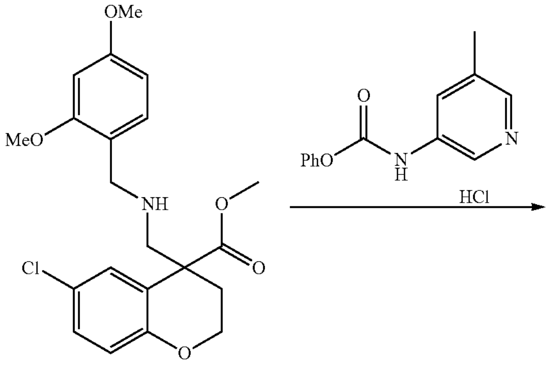

20

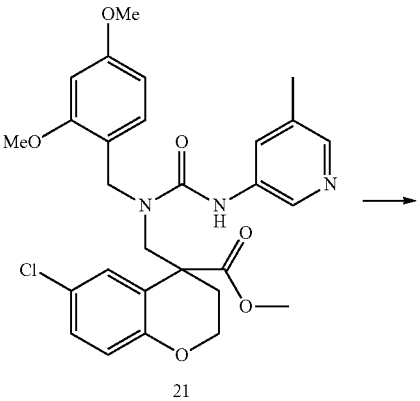

21

-continued

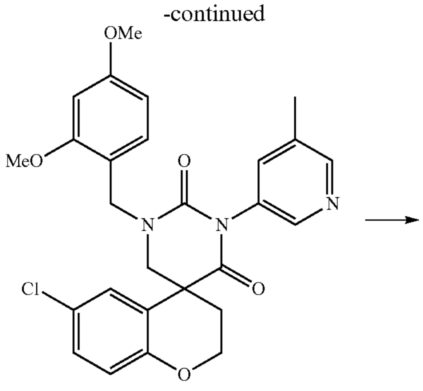

22

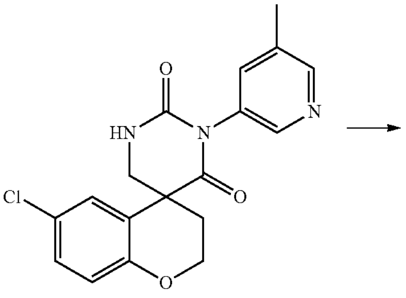

23

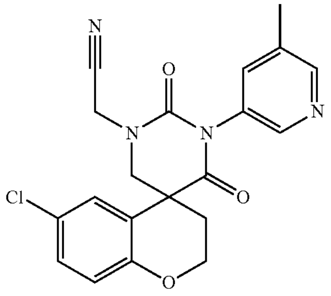

I-088

Step 1 Synthesis of Compound 17

Compound 16 (300 mg, 1.41 mmol) and potassium carbonate (299 mg, 2.12 mmol) were suspended in dimethylformamide (3 mL), and methyl iodide (0.14 mL, 2.1 mmol) was added under ice cooling. The reaction solution was heated to room temperature and stirred for 1 hour. A 10% aqueous citric acid solution was added to the reaction solution, followed by the extraction with ethyl acetate. The obtained organic layer was washed with water and dried under reduced pressure to obtain Compound 17 (298 mg, 1.32 mmol, yield 94%). The obtained Compound 17 was used in the next step without further purification.

$^{1}$H-NMR ($CDCl_3$) δ: 7.23 (1H, dd, J=2.5, 0.6 Hz), 7.11 (1H, dd, J=8.8, 2.5 Hz), 6.77 (1H, d, J=8.8 Hz), 4.29-4.21 (2H, m), 3.76 (3H, s), 3.75 (1H, dd, J=9.6, 5.6 Hz), 2.32 (1H, dq, J=14.1, 3.7 Hz), 2.14-2.03 (1H, m).

Step 2 Synthesis of Compound 18

N, N-diisopropylamine (0.41 mL, 2.9 mmol) was dissolved in tetrahydrofuran (3.8 mL), and a n-butyllithium hexane solution (1.6 M, 1.8 mL, 2.9 mmol) was added dropwise thereto at −78° C. The reaction solution was heated to the level of ice cooling and stirred for 20 minutes, and then a tetrahydrofuran solution (4 mL) of the compound 17 (279 mg, 1.23 mmol) was added thereto at −78° C. The reaction solution was stirred at −78° C. for 1 hour, and paraformaldehyde (343 mg, 11.4 mmol) was added thereto. The reaction solution was heated to the level of ice cooling and stirred for 1 hour. A 10% aqueous citric acid solution was added to the reaction solution, followed by the extraction with ethyl acetate. The obtained organic layer was washed with a 10% citric acid aqueous solution and water, and dried under reduced pressure. The residue thus obtained was purified by silica gel column chromatography (hexane: ethyl acetate=90:10 to 60:40), and Compound 18 (251 mg, 0.978 mmol, yield 79%) was obtained.

$^1$H-NMR ($CDCl_3$) δ: 7.15 (1H, d, J=2.5 Hz), 7.13 (1H, dd, J=8.7, 2.5 Hz), 6.81 (1H, d, J=8.8 Hz), 4.28 (1H, ddd, J=11.4, 7.0, 3.5 Hz), 4.22-4.15 (2H, m), 3.75 (3H, s), 3.68 (1H, dd, J=11.6, 8.6 Hz), 2.48-2.39 (2H, m), 2.28 (1H, ddd, J=14.3, 7.0, 3.3 Hz).

Step 3 Synthesis of Compound 19

Compound 18 (91 wt %, 1.49 g, 5.25 mmol) was dissolved in dichloromethane (22 mL), and Dess-Martin periodinane (2.67 g, 6.86 mmol) was added thereto. The reaction solution was stirred at room temperature for 1.5 hours, and an aqueous sodium carbonate solution and an aqueous sodium thiosulfate solution were sequentially added thereto under ice cooling. The mixture was extracted with hexane: ethyl acetate=2:1, and the organic layer was washed with an aqueous sodium carbonate solution and water and dried under reduced pressure to obtain Compound 19 (1.46 g, 5.54 mmol, yield 106%). The obtained Compound 19 was used in the next step without further purification.

$^1$H-NMR ($CDCl_3$) δ: 9.67 (1H, d, J=10.9 Hz), 7.29 (1H, d, J=2.6 Hz), 7.21 (1H, dd, J=8.8, 2.6 Hz), 6.86 (1H, d, J=8.6 Hz), 4.21 (1H, ddd, J=11.4, 7.0, 3.5 Hz), 4.09 (1H, ddd, J=11.4, 7.6, 3.1 Hz), 4.06 (1H, d, J=3.1 Hz), 3.83 (3H, s), 2.51 (1H, ddd, J=14.1, 7.6, 3.4 Hz), 2.42 (1H, ddd, J=14.1, 7.3, 3.5 Hz).

Step 4 Synthesis of Compound 20

Compound 19 (102 mg, 0.401 mmol) was dissolved in methanol (1.5 mL), and acetic acid (0.12 mL, 2.0 mmol), 2,4-dimethoxyphenylmethylamine (0.30 mL, 2.0 mmol), and sodium cyanoborohydride (76 mg, 1.2 mmol) were sequentially added. The reaction solution was stirred at room temperature for 1 hour, and an aqueous sodium carbonate solution was added thereto. The mixture was extracted with ethyl acetate, and the organic layer was washed with water and dried under reduced pressure. The residue thus obtained was purified by silica gel column chromatography (hexane: ethyl acetate=60:40 to 20:80), and Compound 20 (94.1 mg, 0.232 mmol, yield 58%) was obtained.

LC/MS (ESI): m/z=406 [M+H]$^+$, RT=1.83 min, LC/MS measurement conditions A $^1$H-NMR ($CDCl_3$) δ: 7.26 (1H, d, J=2.4 Hz), 7.08 (1H, d, J=8.8 Hz), 7.08 (1H, dd, J=8.4, 2.4 Hz), 6.75 (1H, d, J=8.8 Hz), 6.45 (1H, d, J=2.3 Hz), 6.42 (1H, dd, J=8.4, 2.3 Hz), 4.21-4.12 (2H, m), 3.80 (3H, s), 3.77 (3H, s), 3.76 (2H, d, J=13.6 Hz), 3.69 (3H, s), 3.64 (1H, d, J=13.6 Hz), 3.16 (1H, d, J=12.0 Hz), 2.78 (1H, d, J=12.0 Hz), 2.45 (1H, ddd, J=14.1, 5.2, 3.2 Hz), 2.22 (1H, ddd, J=14.1, 8.9, 4.7 Hz).

Step 5 Synthesis of Compound 21

Compound 20 (94.1 mg, 0.232 mmol) was dissolved in toluene (1.8 mL), phenyl(5-methylpyridin-3-yl)carbonate (123 mg, 0.464 mmol) and triethylamine (0.16 mL, 1.2 mmol) were added, and the mixture was stirred at 70° C. for 4 hours. The reaction solution was purified by silicagel column chromatography (hexane/ethyl acetate=60:40 to 0:100), and Compound 21 (110 mg, 0.204 mmol, yield 88%) was obtained.

LC/MS (ESI): m/z=540 [M+H]$^+$, RT=2.06 min, LC/MS measurement conditions A $^1$H-NMR ($CDCl_3$) δ: 8.08-8.05 (2H, m), 7.80-7.77 (1H, m), 7.42 (1H, d, J=2.5 Hz), 7.37 (1H, brs), 7.14 (1H, d, J=8.3 Hz), 7.11 (1H, dd, J=8.7, 2.6 Hz), 6.78 (1H, d, J=8.8 Hz), 6.51 (1H, dd, J=8.3, 2.4 Hz), 6.48 (1H, d, J=2.4 Hz), 4.43-4.30 (3H, m), 4.27-4.16 (2H, m), 3.99 (1H, d, J=14.7 Hz), 3.87 (3H, s), 3.81 (4H, s), 3.80 (1H, d, J=14.2 Hz), 3.71 (3H, s), 2.57 (1H, ddd, J=14.2, 6.6, 2.7 Hz), 2.30 (3H, s), 2.17 (1H, ddd, J=14.2, 8.5, 3.1 Hz).

Step 6 Synthesis of Compound 22

Compound 21 (110 mg, 0.204 mmol) and diazabicycloundecene (0.092 mL, 0.61 mmol) were dissolved in toluene (1.7 mL) and stirred at 60° C. for 1 hour. The reaction solution was concentrated under reduced pressure and purified by silica gel column chromatography (hexane:ethyl acetate=50:50 to 0:100), and Compound 22 (81.5 mg, 0.160 mmol, yield 79%) was obtained.

LC/MS (ESI): m/z=508 [M+H]$^+$, RT=2.28 min, LC/MS measurement conditions A $^1$H-NMR ($CDCl_3$) δ: 8.44 (1H, d, J=1.3 Hz), 8.27 (1H, d, J=2.3 Hz), 7.38-7.36 (1H, m), 7.12 (1H, dd, J=8.8, 2.3 Hz), 6.98 (1H, d, J=2.3 Hz), 6.78 (1H, d, J=8.8 Hz), 6.48 (2H, dd, J=8.3, 2.3 Hz), 6.44 (2H, d, J=2.3 Hz), 4.86 (1H, d, J=14.0 Hz), 4.40 (1H, d, J=14.0 Hz), 4.13 (1H, dd, J=15.2, 5.6 Hz), 3.84 (1H, d, J=13.5 Hz), 3.82-3.74 (2H, m), 3.82 (3H, s), 3.78 (3H, s), 3.48 (1H, d, J=13.5 Hz), 2.39 (3H, s), 2.24 (1H, ddd, J=13.9, 9.6, 3.6 Hz), 1.96 (1H, ddd, J=14.0, 5.7, 2.6 Hz).

Step 7 Synthesis of Compound 23

Compound 22 (76 mg, 0.15 mmol) was dissolved in anisole (1.1 mL) and trifluoroacetic acid (1.6 mL), and the mixture was sealed and stirred at 115° C. for 5 hours. The reaction solution was dried under reduced pressure, and was purified by silicagel column chromatography (chloroform/methanol=100:0 to 85:15) to give Compound 23 (50 mg, 0.134 mmol, yield 89%).

LC/MS (ESI): m/z=358 [M+H]$^+$, RT=1.58 min, LC/MS measurement conditions A $^1$H-NMR (DMSO-$d_6$) δ: 8.38 (1H, d, J=1.3 Hz), 8.30 (1H, d, J=4.1 Hz), 8.26 (1H, d, J=2.1 Hz), 7.55 (1H, brs), 7.42 (1H, d, J=2.3 Hz), 7.23 (1H, dd, J=8.8, 2.6 Hz), 6.87 (1H, d, J=8.6 Hz), 4.25-4.15 (2H, m), 3.97 (1H, d, J=12.7 Hz), 3.33 (1H, d, J=12.7 Hz), 2.34 (3H, s), 2.31-2.26 (2H, m).

Step 8 Synthesis of Compound (I-088)

Compound 23 (42.6 mg, 0.119 mmol) and potassium carbonate (49 mg, 0.36 mmol) was suspended in DMF (0.6 mL), and 2-bromoacetonitrile (24 μL, 0.36 mmol) were added, then the mixture was stirred at room temperature for 3 hours. Potassium carbonate (49 mg, 0.36 mmol) and 2-bromoacetonitrile (24 μl, 0.36 mmol) were added, then the mixture was stirred at room temperature for 3 hours, and at 40° C. for 1 hour. Water was added to the mixture under ice cooling, the thus obtained mixture was extracted with ethyl acetate, and the organic layer was dried over sodium sulfate. The obtained solid was separated by filtration, dried under reduced pressure, and purified by silicagel column chromatography (chloroform/methanol=100:0 to 93:7) to give Compound (I-088) (22.9 mg, 0.055 mmol, yield 47%).

LC/MS (ESI): m/z=397 $[M+H]^+$, RT=1.85 min, LC/MS measurement conditions A $^1$H-NMR ($CDCl_3$) δ: 8.47 (1H, brs), 8.24 (1H, d, J=2.1 Hz), 7.34 (1H, brs), 7.20 (1H, dd, J=8.8, 2.3 Hz), 7.05 (1H, d, J=2.3 Hz), 6.87 (1H, d, J=8.8 Hz), 4.77 (1H, d, J=17.6 Hz), 4.36 (1H, ddd, J=11.8, 6.5, 3.4 Hz), 4.29-4.23 (1H, m), 4.24 (1H, d, J=17.6 Hz), 4.04 (1H, d, J=12.7 Hz), 3.62 (1H, d, J=12.7 Hz), 2.47 (1H, ddd, J=14.1, 8.6, 3.6 Hz), 2.39 (3H, s), 2.30 (1H, ddd, J=14.3, 6.7, 3.2 Hz).

Example 5

Synthesis of Compound (I-055)

[Chemical Formula 96]

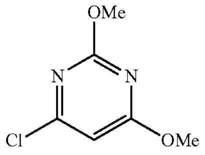

24

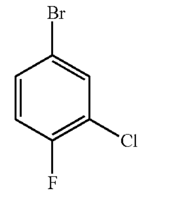

25

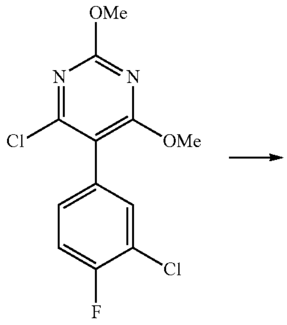

26

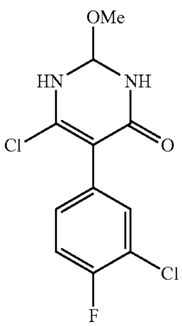

27

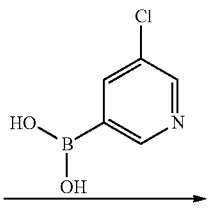

-continued

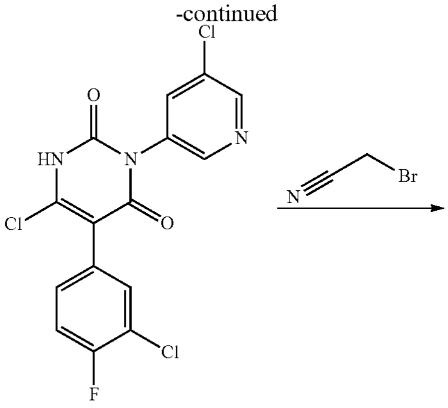

28

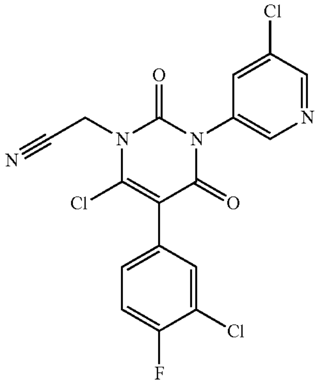

I-055

Step 1 Synthesis of Compound 26

To a mixed solution of a 2.64 mol/L n-butyllithium solution in hexane (31 mL, 82.4 mmol) and tetrahydrofuran (20 mL), a tetrahydrofuran (70 mL) solution of Compound 24 (12 g, 68.7 mmol) was added dropwise at −78° C. over 15 minutes. The mixture was stirred at −78° C. for 1 hour. A 1.9 mol/L zinc chloride 2-methyltetrahydrofuran solution (43 mL, 82.4 mmol) was added dropwise over 5 minutes. The mixture was stirred at room temperature for 2 hours. Compound 25 (9.1 mL, 75.6 mmol) and tetrakis(triphenylphosphine)palladium (4.0 g, 3.44 mmol) were added, and the mixture was stirred at 80° C. for 1.5 hours. The reaction solution was cooled to room temperature, water (80 mL) and 2 mol/L hydrochloric acid (40 mL) were added thereto, and the mixture was extracted with ethyl acetate. The organic layer was concentrated under reduced pressure, and isopropanol (40 mL) was added to the obtained residue. The precipitate was collected by filtration and washed with isopropanol. The mixture was air-dried to obtain Compound 26 (14.8 g, 49 mmol).

$^1$H-NMR ($CDCl_3$) δ: 3.95 (s, 3H), 4.05 (s, 3H), 7.18-7.23 (m, 2H), 7.35 (d, J=6.8 Hz, 1H)

LC/MS (ESI): m/z=303, RT=2.70 min, LC/MS measurement conditions A

Step 2 Synthesis of Compound 27

Acetic acid (40 mL) and concentrated hydrochloric acid (41 mL) were added to Compound 26 (14.8 g, 48.8 mmol), and the mixture was stirred at 110° C. for 5 hours. The reaction solution was cooled to room temperature, and then water (80 ml) was added thereto. The precipitate was collected by filtration and washed with water. The mixture was air-dried to obtain Compound 27 (11.6 g, 42.2 mmol).

$^1$H-NMR (DMSO-$d_6$) δ: 7.31 (ddd, J=8.8, 4.9, 2.1 Hz, 1H), 7.45 (t, J=8.8 Hz, 1H), 7.53 (dd, J=7.3, 2.1 Hz, 1H), 11.57 (s, 1H), 12.24 (brs, 1H)

LC/MS (ESI): m/z=275, RT=1.81 min, LC/MS measurement condition A

Step 3 Synthesis of Compound 28

Compound 27 (1.00 g, 3.64 mmol), 5-chloropyridine-3-boronic acid (1.14 g, 7.27 mmol), copper (II) acetate (0.99 g, 5.45 mmol), acetonitrile (10 mL), triethylamine (5.04 mL, 36.4 mmol) and pyridine (7.34 mL, 91.0 mmol) were mixed, and the solution was stirred at room temperature overnight. The saturated aqueous sodium hydrogen carbonate solution (5 mL) was added to the reaction mixture. The mixture was extracted with ethyl acetate. The organic layer was washed with water, dried over sodium sulfate, and filtered. The filtrate was concentrated, the obtained residue was purified by silica gel column chromatography (chloroform:methanol=100:0 to 90:10), and the solvent was distilled off under reduced pressure. The residue thus obtained was dried under reduced pressure, and Compound 28 (1.15 g, 2.97 mmol, yield 82%) was obtained.

$^1$H-NMR (DMSO-$d_6$) δ: 7.35-7.37 (1H, m), 7.49 (1H, t, J=9.0 Hz), 7.54-7.56 (1H, m), 8.07 (1H, t, J=2.1 Hz), 8.54 (1H, d, J=2.0 Hz), 8.70 (1H, d, J=2.3 Hz).

LC/MS (ESI): m/z=386, RT=1.98 min, LC/MS measurement condition A

Step 4 Synthesis of Compound (I-055)

To a solution obtained by mixing compound 28 (520 mg, 1.345 mmol), N,N'-diisopropylethylamine (0.705 mL, 4.04 mmol), and DMF (5.2 mL), 2-bromoacetonitrile (269 μL, 4.04 mmol) was added, and the solution was stirred at room temperature overnight. A 2 mol/L hydrochloric acid solution (2 mL) was added to the reaction solution under ice cooling, and the mixture was extracted with ethyl acetate. The organic layer was washed with water, dried over sodium sulfate, and filtered. The filtrate was concentrated, the obtained residue was purified by silica gel column chromatography (chloroform:methanol=100:0 to 99:1), and the solvent was distilled off under reduced pressure. The residue thus obtained was dried under reduced pressure, and Compound (I-055) (291 mg, 0.684 mmol, yield 51%) was obtained.

$^1$H-NMR ($CDCl_3$) δ: 5.13 (2H, s), 7.23-7.24 (2H, m), 7.42 (1H, d, J=7.3 Hz), 7.67 (1H, t, J=2.1 Hz), 8.45 (1H, d, J=2.3 Hz), 8.67 (1H, d, J=2.3 Hz).

LC/MS (ESI): m/z=425, RT=2.17 min, LC/MS measurement condition A

Example 6

Synthesis of Compound (I-077)

[Chemical Formula 97]

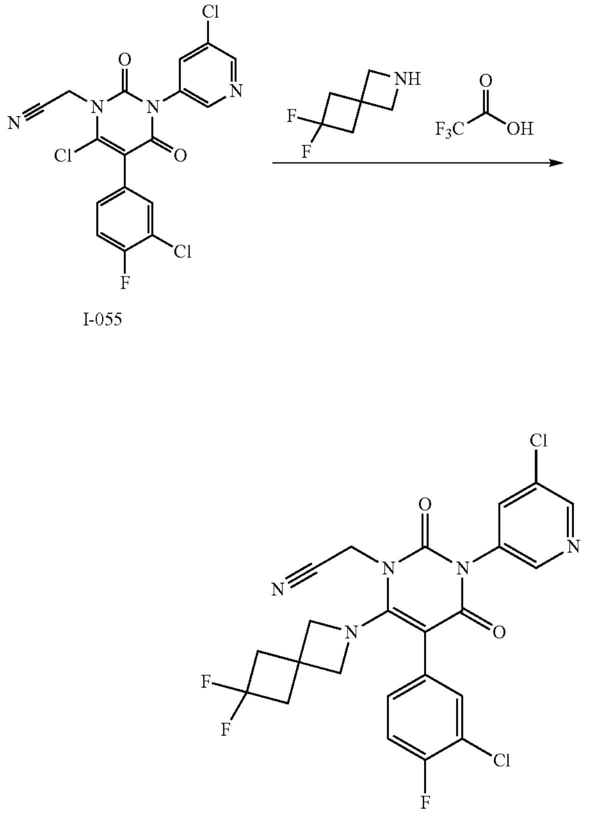

I-055

I-077

Step 1 Synthesis of Compound (I-077)

Compound (I-055) (25.0 mg, 0.059 mmol), 6,6-difluoro-2-azaspiro[3.3]heptane trifluoroacetic acid salt (17.4 mg, 0.070 mmol), N, N-diisopropylethylamine (20.5 μL, 0.117 mmol), and DMF (0.5 mL) were mixed, and the solution was stirred at 60° C. for 2 hours. Water (2 mL) was added to the reaction solution, and the mixture was extracted with ethyl acetate. The organic layer was washed with water, dried over sodium sulfate, and filtered. The filtrate was concentrated, and ethyl acetate (0.05 mL), hexane (0.125 mL), and diisopropyl ether (0.125 mL) were added. The obtained precipitate was collected by filtration and washed with diisopropyl ether. The obtained solid was dried under reduced pressure to obtain Compound (I-077) (22.0 mg, 0.042 mmol, yield 72%).

$^1$H-NMR ($CDCl_3$) δ: 2.75 (4H, t, J=12.0 Hz), 4.02 (4H, s), 4.74 (2H, s), 7.16-7.18 (2H, m), 7.32-7.35 (1H, m), 7.65 (1H, t, J=2.1 Hz), 8.43 (1H, d, J=2.3 Hz), 8.61 (1H, d, J=2.3 Hz).

LC/MS (ESI): m/z=522, RT=2.27 min, LC/MS measurement condition A

Example 7

Synthesis of Compound (I-306)

[Chemical Formula 98]

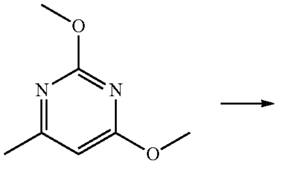

29

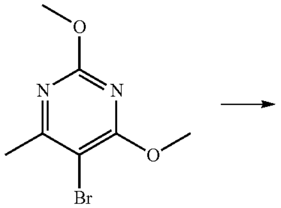

30

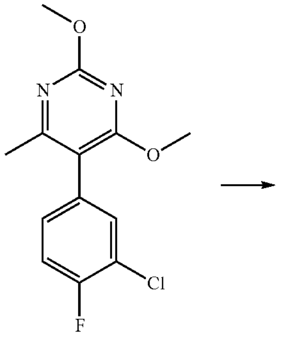

31

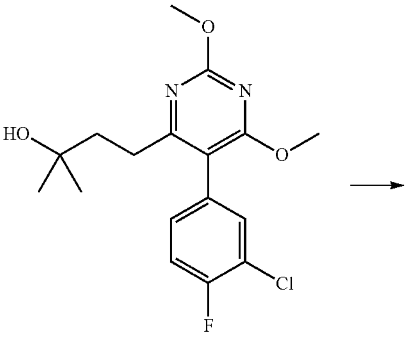

32

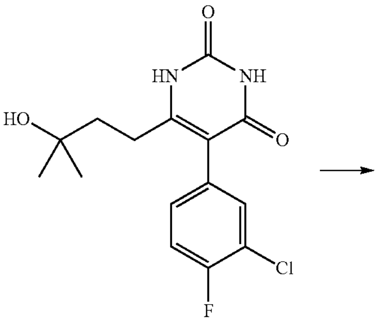

33

-continued

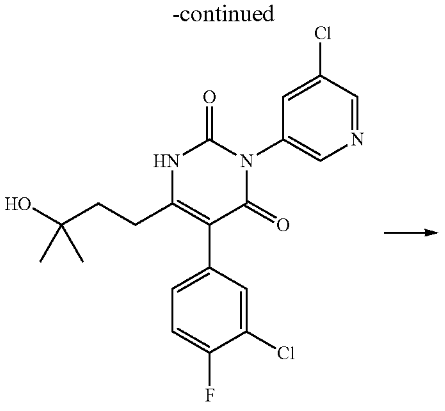

34

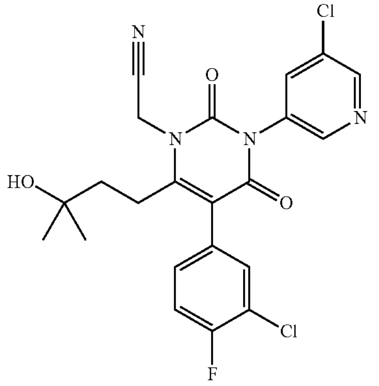

I-306

Step 1 Synthesis of Compound 30

N-bromosuccinimide (6.93 g, 38.9 mmol) was added to a mixed solution of Compound 29 (5 g, 32.4 mmol) and acetic acid (50 mL) at room temperature, and then the mixture was stirred at 120° C. for 3 hours. After completion of the reaction, the mixture was concentrated, an aqueous saturated sodium bicarbonate solution and an aqueous sodium thiosulfate solution were added to the reaction solution, and the mixture was extracted with chloroform. The organic layer was washed with brine, dried over sodium sulfate and filtered. The filtrate was concentrated, the obtained residue was purified by silica gel column chromatography, and the solvent was distilled off under reduced pressure. The residue thus obtained was dried under reduced pressure, and Compound 30 (3.11 g, 13.4 mmol, yield 41%) was obtained.

$^1$H-NMR ($CDCl_3$) δ: 2.52 (s, 3H), 3.97 (s, 3H), 4.03 (s, 3H).

LC/MS (ESI): m/z=234 $[M+H]^+$, RT=2.16 min, LC/MS measurement condition A

Step 2 Synthesis of Compound 31

To a dioxane (30 mL) solution of Compound 30 (3 g, 12.9 mmol), (3-chloro-4-fluorophenyl)boronic acid (3.37 g, 19.3 mmol), [1,1'-bis(diphenylphosphino)ferrocene]dichloropalladium (II) (0.942 g, 1.29 mmol), and a 2 mol/l aqueous potassium carbonate solution (12.87 mL, 25.7 mmol) were added, and the mixture was stirred at 110° C. for 4 hours. After completion of the reaction, a 10% aqueous citric acid solution was added, and the mixture was extracted with ethyl acetate. The organic layer was washed with brine, dried over sodium sulfate and filtered. The filtrate was concentrated, the obtained residue was purified by silica gel column chromatography, and the solvent was distilled off under reduced pressure. The residue thus obtained was dried under reduced pressure, and Compound 31 (3.23 g, 11.4 mmol, yield 89%) was obtained.

$^1$H-NMR ($CDCl_3$) δ: 2.23 (s, 3H), 3.91 (s, 3H), 4.02 (s, 3H), 7.06-7.10 (m, 1H), 7.19 (t, J=6.6 Hz, 1H), 7.25-7.28 (m, 1H).

LC/MS (ESI): m/z=283 $[M+H]^+$, RT=2.52 min, LC/MS measurement condition A

Step 3 Synthesis of Compound 32

A tetrahydrofuran (5 mL) solution of Compound 31 (400 mg, 1.42 mmol) was adjusted to −78° C., 2 mol/L of lithium diisopropylamide (1.42 mL, 2.83 mmol) was added thereto, and the mixture was stirred for 30 minutes. Then, 2,2-dimethyloxirane (0.26 mL, 2.83 mmol) was added, and the mixture was heated to 0° C. and stirred for 1 hour. After completion of the reaction, a 10% aqueous citric acid solution was added thereto, and the mixture was extracted with ethyl acetate. The organic layer was washed with brine, dried over sodium sulfate and filtered. The filtrate was concentrated, the obtained residue was purified by silica gel column chromatography, and the solvent was distilled off under reduced pressure. The residue thus obtained was dried under reduced pressure, and Compound 32 (258 mg, 0.73 mmol, yield 52%) was obtained.

$^1$H-NMR ($CDCl_3$) δ: 1.18 (s, 6H), 1.81 (t, J=5.4 Hz, 2H), 2.60 (t, J=5.4 Hz, 2H), 3.91 (s, 3H), 4.02 (s, 3H), 7.05-7.09 (m, 1H), 7.20 (t, J=6.6 Hz, 1H), 7.25-7.27 (m, 1H).

LC/MS (ESI): m/z=355 $[M+H]^+$, RT=2.41 min, LC/MS measurement conditions A

Step 4 Synthesis of Compound 33

Acetic acid (0.497 mL) and concentrated hydrochloric acid (0.424 mL) were added to Compound 32 (180 mg, 0.509 mmol), and the mixture was stirred at 110° C. for 1 hour. Then, a 2 mol/L aqueous sodium hydroxide solution was added, and the mixture was stirred for 1 hour and extracted with ethyl acetate. The organic layer was washed with brine, dried over sodium sulfate and filtered. The filtrate was concentrated, the obtained residue was purified by silica gel column chromatography, and the solvent was distilled off under reduced pressure. The residue thus obtained was dried under reduced pressure, and Compound 33 (71.5 mg, 0.219 mmol, yield 43%) was obtained.

$^1$H-NMR ($CDCl_3$) δ: 1.21 (s, 6H), 1.75 (t, J=5.1 Hz, 2H), 2.49 (t, J=5.1 Hz, 2H), 7.08-7.11 (m, 1H), 7.18 (t, J=6.6 Hz, 1H), 7.26-7.29 (m, 1H), 9.18 (s, 1H), 10.53 (s, 1H).

LC/MS (ESI): m/z=327 $[M+H]^+$, RT=1.74 min, LC/MS measurement conditions A

Step 5 Synthesis of Compound 34

A solution obtained by mixing 5-chloropyridine-3-boronic acid (107 mg, 0.680 mmol), copper (II) acetate (74.1 mg, 0.408 mmol), pyridine (0.55 mL, 6.8 mmol), and triethylamine (0.377 mL, 2.72 mmol) in an acetonitrile (1 mL) solution of Compound 33 (88.9 mg, 0.272 mmol) was stirred at room temperature overnight. A saturated aqueous ammonium chloride solution (5 mL) was added to the reaction solution, and the mixture was extracted with ethyl acetate. The organic layer was washed with brine, dried over sodium sulfate and filtered. The filtrate was concentrated, the obtained residue was purified by silica gel column chromatography, and the solvent was distilled off under reduced pressure. The residue thus obtained was dried under reduced pressure, and Compound 34 (76.3 mg, 0.174 mmol, yield 64%) was obtained.

$^1$H-NMR ($CDCl_3$) δ: 1.26 (s, 6H), 1.81 (t, J=4.8 Hz, 2H), 2.57 (t, J=4.8 Hz, 2H), 7.10-7.14 (m, 1H), 7.18 (t, J=6.6 Hz, 1H), 7.31 (dd, J=1, 5, 6.6 Hz, 1H), 7.68 (t, J=1.5 Hz, 1H), 8.46 (d, J=1.5 Hz, 1H), 8.60 (d, J=1.5 Hz, 1H).

LC/MS (ESI): m/z=438 $[M+H]^+$, RT=2.13 min, LC/MS measurement conditions A

Step 6 Synthesis of Compound I-306

Potassium carbonate (33.3 mg, 0.241 mmol) and 2-bromoacetonitrile (14.8 μL, 0.223 mmol) were added to a DMF (1 mL) solution of Compound 34 (81.3 mg, 0.185 mmol), and the mixture was stirred at room temperature overnight. After completion of the reaction, a 10% aqueous citric acid solution was added, and the mixture was extracted with ethyl acetate. The organic layer was washed with brine, dried over sodium sulfate and filtered. The filtrate was concentrated, the obtained residue was purified by silica gel column chromatography, and the solvent was distilled off under reduced pressure. The residue thus obtained was dried under reduced pressure, and Compound I-306 (54.4 mg, 0.114 mmol, yield 61%) was obtained.

$^1$H-NMR ($CDCl_3$) δ: 1.20 (s, 6H), 1.69 (t, J=6.0 Hz, 2H), 2.69 (t, J=6.0 Hz, 2H), 5.10 (s, 2H), 7.12-7.15 (m, 1H), 7.21-7.26 (m, 1H), 7.32-7.33 (m, 1H), 7.68 (t, J=1.5 Hz, 1H), 8.45 (d, J=1.5 Hz, 1H), 8.63 (d, J=1.5 Hz, 1H).

LC/MS (ESI): m/z=477 $[M+H]^+$, RT=2.23 min, LC/MS measurement conditions A

Example 8

Synthesis of Compound (I-072)

Compound (I-072) (15 mg, 0.030 mmol, yield 63%) was obtained from Compound (I-055) (20 mg, 0.047 mmol) according to the synthesis method of Compound (I-077).

$^1$H-NMR ($CDCl_3$) δ: 1.12 (6H, s), 2.48-2.55 (1H, m), 3.89-3.97 (4H, m), 4.77 (2H, s), 7.12-7.18 (2H, m), 7.37 (1H, dd, J=7.0, 2.0 Hz), 7.67 (1H, t, J=2.1 Hz), 8.44 (1H, d, J=2.3 Hz), 8.60 (1H, d, J=2.3 Hz).

LC/MS (ESI): m/z=504 $[M+H]^+$, RT=1.94 min, LC/MS measurement conditions A

Example 9

Synthesis of Compound (I-086)

Compound (I-086) (14 mg, 0.027 mmol, yield 58%) was obtained from Compound (I-055) (20 mg, 0.047 mmol) according to the synthesis method of Compound (I-077).

$^1$H-NMR ($CDCl_3$) δ: 3.20-3.22 (1H, m), 3.91-4.19 (4H, m), 4.76 (2H, s), 7.16-7.21 (2H, m), 7.37 (1H, dd, J=6.9, 2.0 Hz), 7.66 (1H, t, J=2.1 Hz), 8.44 (1H, d, J=2.1 Hz), 8.62 (1H, d, J=2.1 Hz).

LC/MS (ESI): m/z=514 $[M+H]^+$, RT=2.25 min, LC/MS measurement conditions A

Example 10

Synthesis of Compound (I-142)

Compound (I-142) (15 mg, 0.028 mmol, yield 60%) was obtained from Compound (I-055) (20 mg, 0.047 mmol) according to the synthesis method of Compound (I-077).

NMR ($CDCl_3$) δ: 3.57 (1H, brs), 3.88-3.98 (2H, m), 4.12-4.21 (2H, m), 4.76 (2H, s), 7.14-7.24 (2H, m), 7.37 (1H, dd, J=6.8, 2.0 Hz), 7.68 (1H, t, J=2.0 Hz), 8.43 (1H, d, J=2.0 Hz), 8.61 (1H, d, J=2.0 Hz).

LC/MS (ESI): m/z=530 $[M+H]^+$, RT=1.89 min, LC/MS measurement conditions D

Example 11

Synthesis of Compound (I-181)

Compound (I-181) (91 mg, 0.181 mmol, yield 77%) was obtained from Compound (I-055) (100 mg, 0.235 mmol) according to the synthesis method of Compound (I-077).

$^1H$-NMR ($CDCl_3$) δ: 2.11 (2H, t, J=7.2 Hz), 3.78-3.84 (4H, m), 3.92 (4H, s), 4.75 (2H, brs), 7.17 (2H, d, J=7.8 Hz), 7.35 (1H, d, J=7.0 Hz), 7.66 (1H, t, J=2.0 Hz), 8.44 (1H, d, J=2.0 Hz), 8.61 (1H, d, J=2.0 Hz).

LC/MS (ESI): m/z=502 $[M+H]^+$, RT=2.04 min, LC/MS measurement conditions A

Example 12

Synthesis of Compound (I-230)

Compound (I-230) (40 mg, 0.078 mmol, yield 74%) was obtained from Compound (I-055) (45 mg, 0.106 mmol) according to the synthesis method of Compound (I-077).

$^1H$-NMR (DMSO-$d_6$) δ: 3.73-3.84 (2H, m), 3.97-4.11 (2H, m), 4.85 (2H, s), 6.08 (1H, t, J=55.3 Hz), 6.68 (1H, s), 7.21-7.26 (1H, m), 7.40-7.47 (1H, m), 8.01 (1H, t, J=2.1 Hz), 8.48 (1H, d, J=1.9 Hz), 8.69 (1H, d, J=2.3 Hz).

LC/MS (ESI): m/z=512 $[M+H]^+$, RT=1.75 min, LC/MS measurement conditions D

Example 13

Synthesis of Compound (I-232)

Compound (I-232) (17 mg, 0.031 mmol, yield 54%) was obtained from Compound (I-055) (25 mg, 0.059 mmol) according to the synthesis method of Compound (I-077).

$^1H$-NMR ($CDCl_3$) δ: 4.15-4.29 (2H, m), 4.34-4.48 (2H, m), 4.88 (2H, s), 5.39 (1H, s), 7.13 (1H, t, J=8.6 Hz), 7.20-7.28 (1H, m), 7.38 (1H, t, J=4.9 Hz), 7.44 (1H, dd, J=7.0, 2.1 Hz), 7.70 (1H, t, J=2.1 Hz), 8.48 (1H, d, J=2.0 Hz), 8.61 (1H, d, J=2.1 Hz), 8.83 (2H, d, J=4.9 Hz).

LC/MS (ESI): m/z=540 $[M+H]^+$, RT=1.67 min, LC/MS measurement conditions D

Example 14

Synthesis of Compound (I-234)

Compound (I-234) (48 mg, 0.086 mmol, 39% yield) was obtained from Compound (I-055) (94 mg, 0.221 mmol) according to the synthesis method of Compound (I-077).

$^1H$-NMR ($CDCl_3$) δ: 4.13-4.30 (2H, m), 4.30-4.50 (2H, m), 4.86 (2H, s), 5.07 (1H, s), 7.14 (1H, t, J=8.6 Hz), 7.19-7.28 (1H, m), 7.43 (1H, dd, J=6.8, 1.9 Hz), 7.67-7.72 (1H, m), 8.48 (1H, d, J=1.9 Hz), 8.69 (1H, d, J=2.0 Hz), 8.69 (2H, s).

LC/MS (ESI): m/z=558 $[M+H]^+$, RT=1.93 min, LC/MS measurement conditions A

Example 15

Synthesis of Compound (I-250)

Compound (I-250) (23 mg, 0.047 mmol, 40% yield) was obtained from Compound (I-055) (50 mg, 0.117 mmol) according to the synthesis method of Compound (I-077).

$^1H$-NMR ($CDCl_3$) δ: 2.91-3.07 (1H, m), 3.91-4.09 (4H, m), 4.76 (2H, s), 5.93 (1H, td, J=55.7, 3.0 Hz), 7.18 (2H, dd, J=6.1, 1.4 Hz), 7.35-7.38 (1H, m) 7.67 (1H, t, J=2.1 Hz), 8.44 (1H, d, J=2.1 Hz), 8.61 (1H, d, J=2.1 Hz).

LC/MS (ESI): m/z=496 $[M+H]^+$, RT=2.20 min, LC/MS measurement conditions A

Example 16

Synthesis of Compound (I-257)

Compound (I-257) (25 mg, 0.047 mmol, yield 67%) was obtained from Compound (I-055) (30 mg, 0.070 mmol) according to the synthesis method of Compound (I-077).

$^1H$-NMR ($CDCl_3$) δ: 3.97-4.10 (2H, m), 4.19-4.32 (2H, m), 4.77 (2H, s), 4.81-4.90 (1H, m), 7.17-7.22 (2H, m), 7.37 (1H, d, J=6.9, 1.8 Hz), 7.66 (1H, t, J=2.1 Hz), 8.44 (1H, d, J=2.0 Hz), 8.62 (1H, d, J=2.0 Hz).

LC/MS (ESI): m/z=530 $[M+H]^+$, RT=2.33 min, LC/MS measurement conditions A

Example 17

Synthesis of Compound (I-298)

Compound (I-298) (20 mg, 0.039 mmol, yield 42%) was obtained from Compound (I-055) (40 mg, 0.094 mmol) according to the synthesis method of Compound (I-077).

$^1H$-NMR ($CDCl_3$) δ: 3.94-4.01 (2H, m), 4.19-4.27 (2H, m), 4.76 (2H, s), 4.85-4.93 (1H, m), 6.23 (1H, t, J=71.8 Hz), 7.16-7.21 (2H, m), 7.34-7.38 (1H, m), 7.66 (1H, t, J=2.3 Hz), 8.44 (1H, d, J=2.0 Hz), 8.61 (1H, d, J=2.0 Hz).

LC/MS (ESI): m/z=512 $[M+H]^+$, RT=2.17 min, LC/MS measurement conditions A

Example 18

Synthesis of Compound (I-308)

[Chemical Formula 99]

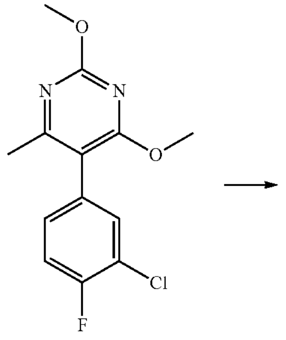

31

-continued

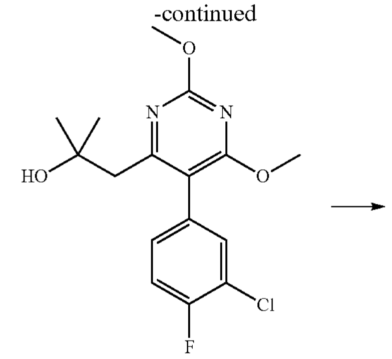

35

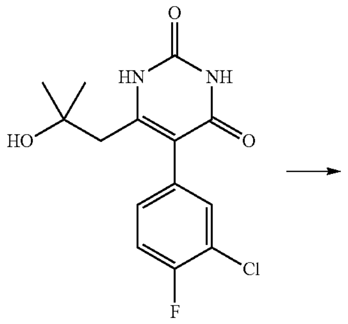

36

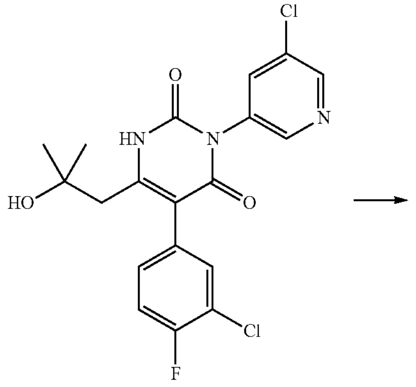

37

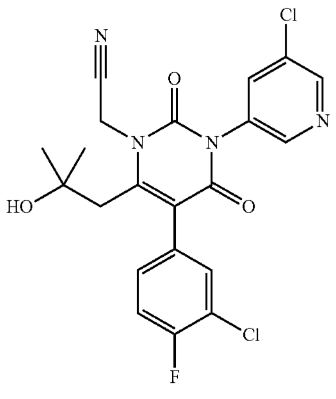

I-308

Step 1 Synthesis of Compound 35

LDA (2 mol/L, 0.796 mL, 1.59 mmol) was added to a THF (2 mL) solution of Compound 31 (300 mg, 1.06 mmol) at −78° C., and the mixture was stirred for 35 minutes at the same temperature. Acetone (0.094 mL, 1.27 mmol) was added to the reaction solution, and the mixture was stirred at −78° C. for 1 hour. After completion of the reaction, a 10% aqueous citric acid solution was added, and the mixture was extracted with ethyl acetate. The organic layer was washed with brine, dried over sodium sulfate and filtered. The filtrate was concentrated, and the obtained residue was purified by silica gel column chromatography to obtain Compound 35 (362 mg, 1.06 mmol, yield 100%).

LC/MS (ESI): m/z=341 $[M+H]^+$, RT=2.56 min, LC/MS measurement conditions A

Step 2 Synthesis of Compound 36

Concentrated hydrochloric acid (0.885 μL, 10.6 mmol) was added to an acetic acid (1.0 mL) solution of Compound 35 (362 mg, 1.06 mmol), and the mixture was stirred at 110° C. After completion of the reaction, the mixture was allowed to cool, water was added thereto, and the mixture was stirred at room temperature for 1 hour. The reaction solution was filtered to obtain Compound 36 (265 mg, 0.847 mmol, yield 80%).

LC/MS (ESI): m/z=313 $[M+H]^+$, RT=1.87 min, LC/MS measurement conditions A

Step 3 Synthesis of Compound 37

(5-Chloropyridin-3 yl)boronic acid (333 mg, 2.12 mmol), copper (II) acetate (231 mg, 1.27 mmol), pyridine (1.71 mL, 21.2 mmol) and triethylamine (1.17 mL, 8.47 mmol) were added to an acetonitrile (2.5 mL) solution of Compound 36 (265 mg, 0.847 mmol), and the mixture was stirred at room temperature overnight. After completion of the reaction, a saturated aqueous ammonium chloride solution was added, and the mixture was extracted with ethyl acetate. The organic layer was washed with brine, dried over sodium sulfate and filtered. The filtrate was concentrated, and the obtained residue was purified by silica gel column chromatography to obtain Compound 37 (276 mg, 0.649 mmol, yield 77%).

LC/MS (ESI): m/z=424 $[M+H]^+$, RT=2.21 min, LC/MS measurement conditions A

Step 4 Synthesis of Compound (I-308)

Potassium carbonate (42.3 mg, 0.306 mmol) and 2-bromoacetonitrile (19 μL, 0.283 mmol) were added to a DMF (1 mL) solution of Compound 37 (100 mg, 0.236 mmol), and the mixture was stirred at room temperature for 1.5 hours. To the reaction solution, 2-bromoacetonitrile (19 μL, 0.283 mmol) was added, and the mixture was stirred at room temperature overnight. Furthermore, 2-bromoacetonitrile (38 μL, 0.566 mmol) was added, and the mixture was stirred at room temperature for 2 hours. After completion of the reaction, a 10% aqueous citric acid solution was added, and the mixture was extracted with ethyl acetate. The organic layer was washed with brine, dried over sodium sulfate and filtered. The filtrate was concentrated, and the obtained residue was purified by silica gel column chromatography to obtain Compound (I-308) (81 mg, 0.175 mmol, yield 74%).

$^1$H-NMR ($CDCl_3$) δ: 1.04-1.38 (6H, m), 3.04 (2H, brs), 5.41 (2H, brs), 7.10-7.40 (3H, m), 7.70 (1H, t, J=2.1 Hz), 8.47 (1H, d, J=2.0 Hz), 8.63 (1H, d, J=2.0 Hz).

LC/MS (ESI): m/z=463 $[M+H]^+$, RT=2.26 min, LC/MS measurement conditions A

Example 19

Synthesis of Compound (I-307)

[Chemical Formula 100]

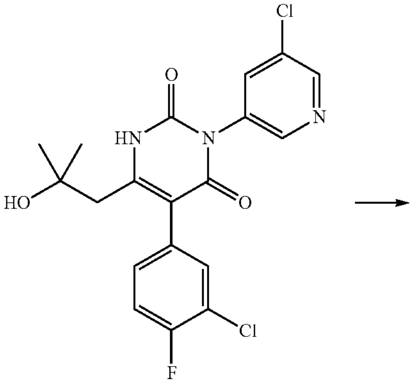

37

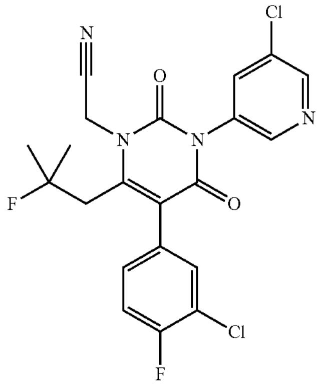

I-307

Step 1 Synthesis of Compound (I-307)

DAST (3.1 μL, 0.024 mmol) was added to a $CH_2Cl_2$ (0.5 mL) solution of Compound 37 (10 mg, 0.024 mmol), and the mixture was stirred at room temperature for 15 minutes.

After completion of the reaction, a saturated aqueous sodium bicarbonate solution was added. DAST (6.2 μL, 0.047 mmol) was added to a $CH_2Cl_2$ (0.5 mL) solution of Compound 37 (20 mg, 0.047 mmol) prepared in another flask, and the mixture was stirred at room temperature for 15 minutes. After completion of the reaction, a saturated aqueous sodium bicarbonate solution was added. The reaction mixtures were mixed, and the mixture was extracted with ethyl acetate. The organic layer was washed with brine, dried over sodium sulfate and filtered. The filtrate was concentrated to obtain a crude product. Potassium carbonate (12.7 mg, 0.091 mmol) and 2-bromoacetonitrile (5.6 μL, 0.084 mmol) were added to a DMF (0.5 mL) solution of the obtained crude product, and the mixture was stirred at room temperature overnight. After completion of the reaction, a 10% aqueous citric acid solution was added, and the mixture was extracted with ethyl acetate. The organic layer was washed with brine, dried over sodium sulfate and filtered. The filtrate was concentrated, and the obtained residue was purified by silica gel column chromatography to obtain Compound (I-307) (8.5 mg, 0.018 mmol, yield 26%).

$^1$H-NMR ($CDCl_3$) δ: 1.23-1.44 (6H, m), 3.15 (2H, brs), 5.12 (2H, brs), 7.08-7.39 (3H, m), 7.70 (11H, t, J=1.9 Hz), 8.47 (11H, d, J=1.9 Hz), 8.65 (11H, d, J=1.9 Hz).

LC/MS (ESI): m/z=465 $[M+H]^+$, RT=2.42 min, LC/MS measurement conditions A

The following compounds were synthesized according to the above general synthesis method and the method described in Examples. The structure and physical properties (LC/MS data, NMR spectrum) are shown in the tables below.

Incidentally, in the structural formula, "wedged line" and "dashed line" indicate the configuration.

Particularly, with regard to compounds whose configurations are described, a compound described as "a" in the item of "Configuration" is a racemic compound whose relative configuration has been specified. A compound described as "b" in the item of "Configuration" is a single enantiomer whose absolute configuration is unknown. A compound described as "c" in the item of "Configuration" indicates that the configuration is determined as shown in the chemical structure.

In addition, with regard to compounds in which the bonds forming an asymmetric carbon are described by solid lines, a compound described as "d" in the item of "Configuration" is a racemic compound. A compound described as "e" in the item of "Configuration" is a stereoisomeric mixture.

TABLE 1

| Structure | Compound No. | LC/MS measurement condition | Retention time (min) | m/z | Configuration |
|---|---|---|---|---|---|
| 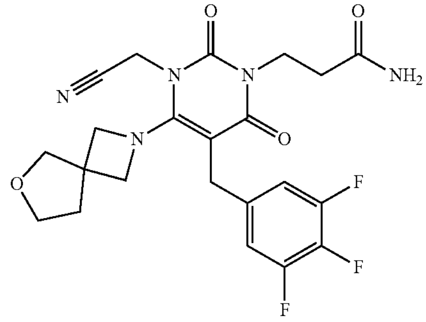 [SMILES: N#CCn1c(N2CC3(CCOC3)C2)c(Cc2cc(F)c(F)c(F)c2)c(=O)n(CCC(N)=O)c1=O] | I-001 | A | 1.67 | 478 | |

TABLE 1-continued
| Structure | Compound No. | LC/MS measurement condition | Retention time (min) | m/z | Configuration |
|---|---|---|---|---|---|
| 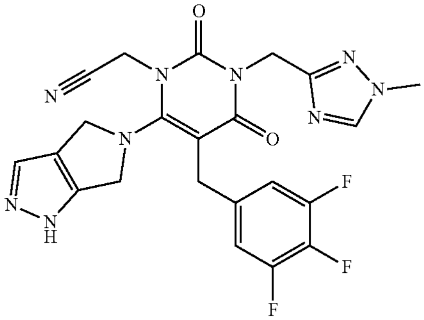 [SMILES: Cn1cnc(Cn2c(=O)c(Cc3cc(F)c(F)c(F)c3)c(N3Cc4cn[nH]c4C3)n(CC#N)c2=O)n1] | I-002 | A | 1.60 | 498 | |
| 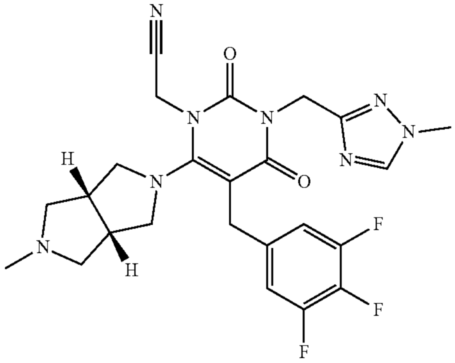 | I-003 | A | 1.35 | 515 | c |
| 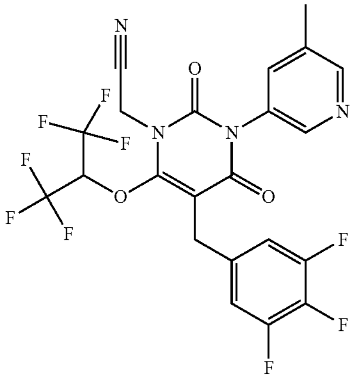 [SMILES: Cc1cncc(-n2c(=O)c(Cc3cc(F)c(F)c(F)c3)c(OC(C(F)(F)F)C(F)(F)F)n(CC#N)c2=O)c1] | I-004 | A | 2.48 | 553 | |
| 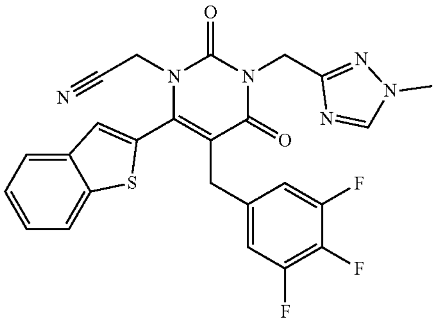 [SMILES: Cn1cnc(Cn2c(=O)c(Cc3cc(F)c(F)c(F)c3)c(-c3cc4ccccc4s3)n(CC#N)c2=O)n1] | I-005 | A | 2.34 | 523 | |

TABLE 1-continued
| Structure | Compound No. | LC/MS measurement condition | Retention time (min) | m/z | Configuration |
|---|---|---|---|---|---|
| 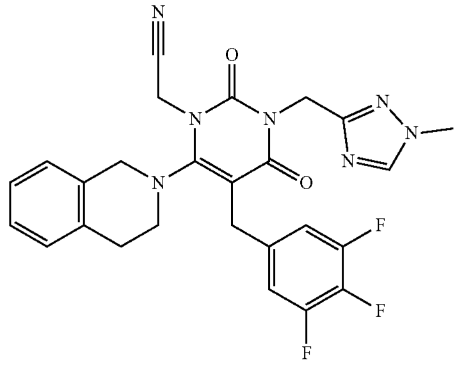 [SMILES: Cn1cnc(Cn2c(=O)c(Cc3cc(F)c(F)c(F)c3)c(N3CCc4ccccc4C3)n(CC#N)c2=O)n1] | I-006 | A | 2.33 | 522 | |
TABLE 2
| Structure | Compound No. | LC/MS measurement condition | Retention time (min) | m/z | Configuration |
|---|---|---|---|---|---|
| 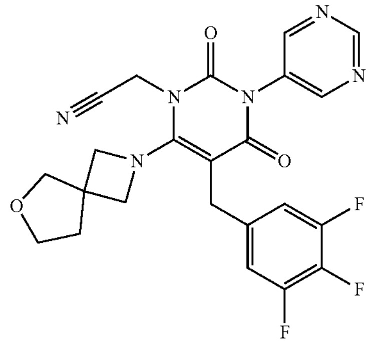 [SMILES: N#CCn1c(N2CC3(CCOC3)C2)c(Cc2cc(F)c(F)c(F)c2)c(=O)n(-c2cncnc2)c1=O] | I-007 | A | 1.83 | 485 | |
| 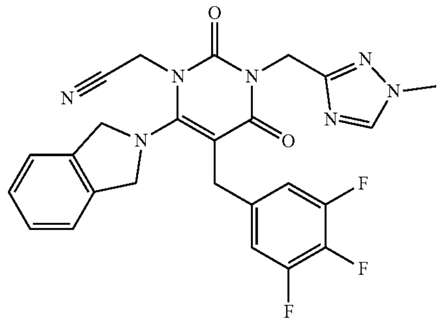 [SMILES: Cn1cnc(Cn2c(=O)c(Cc3cc(F)c(F)c(F)c3)c(N3Cc4ccccc4C3)n(CC#N)c2=O)n1] | I-008 | B | 2.26 | 508 | |

TABLE 2-continued
| Structure | Compound No. | LC/MS measurement condition | Retention time (min) | m/z | Configuration |
|---|---|---|---|---|---|
| 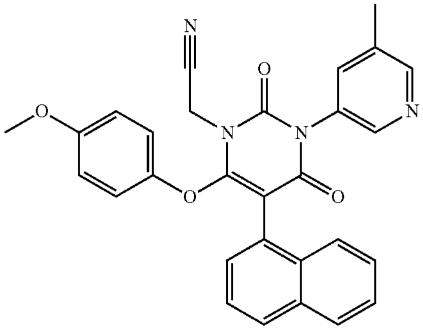 [SMILES: COc1ccc(Oc2c(-c3cccc4ccccc34)c(=O)n(-c3cncc(C)c3)c(=O)n2CC#N)cc1] | I-009 | A | 2.15 | 491 | |
| 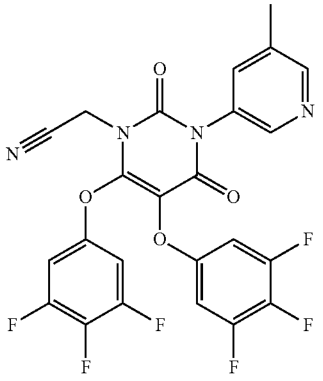 [SMILES: Cc1cncc(-n2c(=O)c(Oc3cc(F)c(F)c(F)c3)c(Oc3cc(F)c(F)c(F)c3)n(CC#N)c2=O)c1] | I-010 | A | 2.43 | 535 | |
| 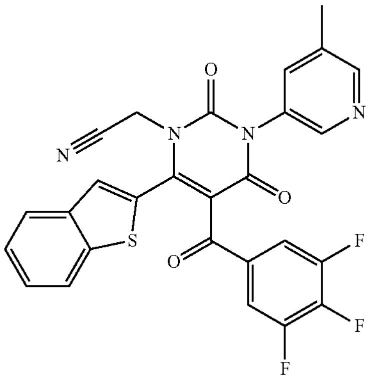 [SMILES: Cc1cncc(-n2c(=O)c(C(=O)c3cc(F)c(F)c(F)c3)c(-c3cc4ccccc4s3)n(CC#N)c2=O)c1] | I-011 | A | 2.44 | 533 | |

TABLE 3
| Structure | Compound No. | LC/MS measurement condition | Retention time (min) | m/z | Configuration |
|---|---|---|---|---|---|
| 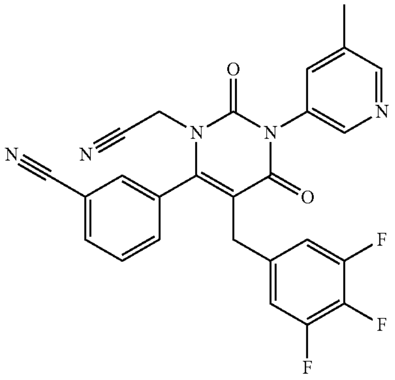 [SMILES: Cc1cncc(-n2c(=O)c(Cc3cc(F)c(F)c(F)c3)c(-c3cccc(C#N)c3)n(CC#N)c2=O)c1] | I-012 | A | 2.17 | 488 | |
| 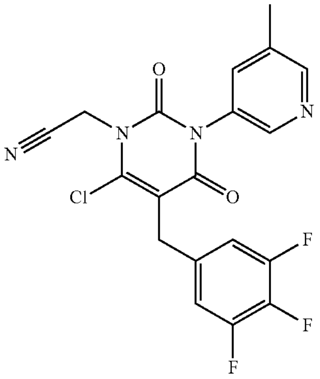 [SMILES: Cc1cncc(-n2c(=O)c(Cc3cc(F)c(F)c(F)c3)c(Cl)n(CC#N)c2=O)c1] | I-013 | A | 2.11 | 421 | |
| 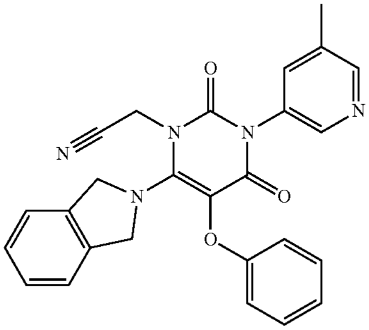 [SMILES: Cc1cncc(-n2c(=O)c(Oc3ccccc3)c(N3Cc4ccccc4C3)n(CC#N)c2=O)c1] | I-014 | A | 2.13 | 452 | |
| 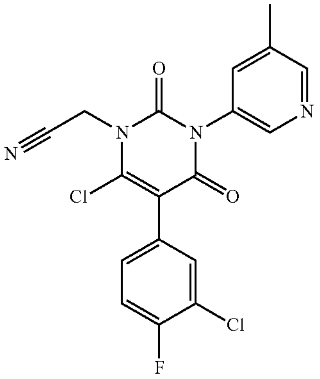 [SMILES: Cc1cncc(-n2c(=O)c(-c3ccc(F)c(Cl)c3)c(Cl)n(CC#N)c2=O)c1] | I-015 | A | 1.99 | 405 | |

TABLE 3-continued
| Structure | Compound No. | LC/MS measurement condition | Retention time (min) | m/z | Configuration |
|---|---|---|---|---|---|
| 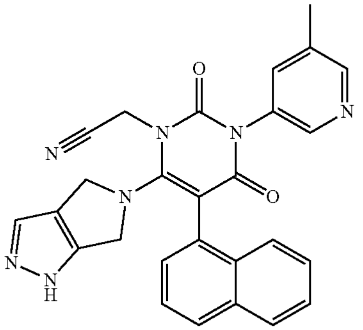 [SMILES: Cc1cncc(-n2c(=O)c(-c3cccc4ccccc34)c(N3Cc4cn[nH]c4C3)n(CC#N)c2=O)c1] | I-016 | A | 1.61 | 476 | |
TABLE 4
| Structure | Compound No. | LC/MS measurement condition | Retention time (min) | m/z | Configuration |
|---|---|---|---|---|---|
| 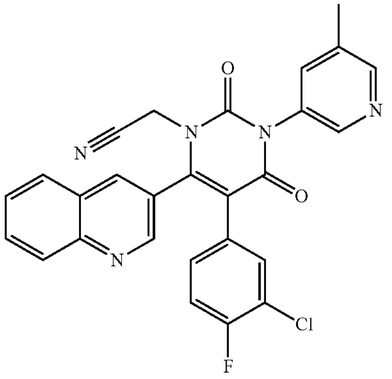 [SMILES: Cc1cncc(-n2c(=O)c(-c3ccc(F)c(Cl)c3)c(-c3cnc4ccccc4c3)n(CC#N)c2=O)c1] | I-017 | A | 2.02 | 498 | |
| 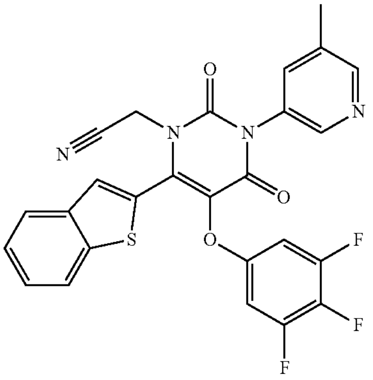 [SMILES: Cc1cncc(-n2c(=O)c(Oc3cc(F)c(F)c(F)c3)c(-c3cc4ccccc4s3)n(CC#N)c2=O)c1] | I-018 | A | 2.49 | 521 | |

TABLE 4-continued
| Structure | Compound No. | LC/MS measurement condition | Retention time (min) | m/z | Configuration |
|---|---|---|---|---|---|
| 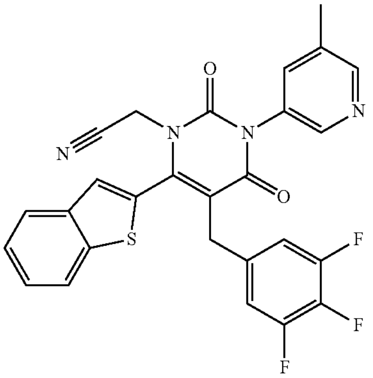 [SMILES: Cc1cncc(-n2c(=O)c(Cc3cc(F)c(F)c(F)c3)c(-c3cc4ccccc4s3)n(CC#N)c2=O)c1] | I-019 | A | 2.51 | 519 | |
| 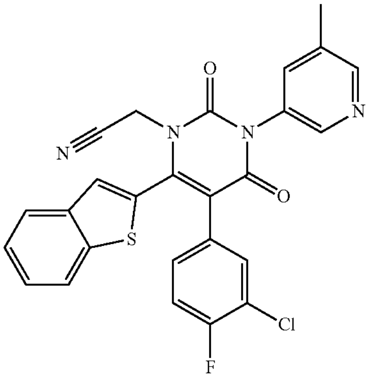 [SMILES: Cc1cncc(-n2c(=O)c(-c3ccc(F)c(Cl)c3)c(-c3cc4ccccc4s3)n(CC#N)c2=O)c1] | I-020 | A | 2.36 | 503 | |
| 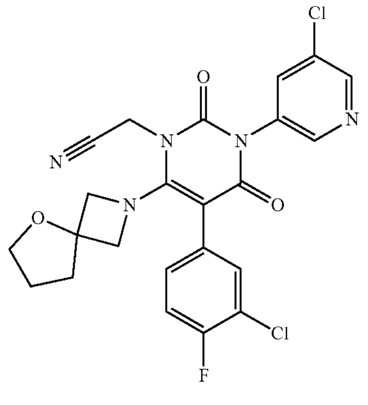 [SMILES: N#CCn1c(N2CC3(CCCO3)C2)c(-c2ccc(F)c(Cl)c2)c(=O)n(-c2cncc(Cl)c2)c1=O] | I-021 | A | 2.19 | 502 | |

TABLE 5
| Structure | Compound No. | LC/MS measurement condition | Retention time (min) | m/z | Configuration |
|---|---|---|---|---|---|
| 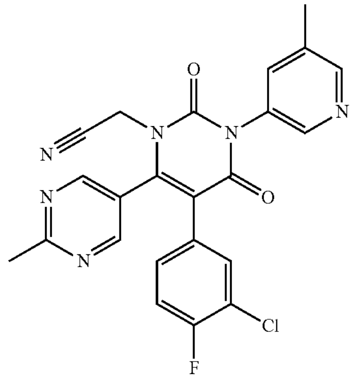 [SMILES: Cc1cncc(-n2c(=O)c(-c3ccc(F)c(Cl)c3)c(-c3cnc(C)nc3)n(CC#N)c2=O)c1] | I-022 | A | 1.77 | 463 | |
| 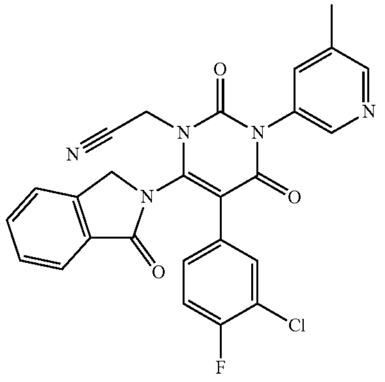 [SMILES: Cc1cncc(-n2c(=O)c(-c3ccc(F)c(Cl)c3)c(N3Cc4ccccc4C3=O)n(CC#N)c2=O)c1] | I-023 | A | 2.06 | 502 | |
| 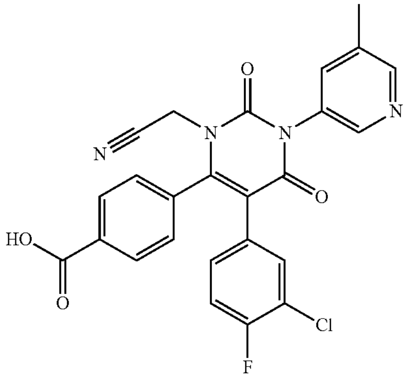 [SMILES: Cc1cncc(-n2c(=O)c(-c3ccc(F)c(Cl)c3)c(-c3ccc(C(=O)O)cc3)n(CC#N)c2=O)c1] | I-024 | A | 1.80 | 491 | |
| 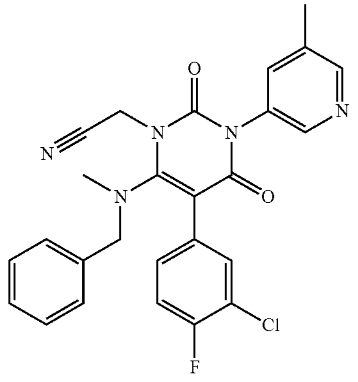 [SMILES: Cc1cncc(-n2c(=O)c(-c3ccc(F)c(Cl)c3)c(N(C)Cc3ccccc3)n(CC#N)c2=O)c1] | I-025 | A | 2.33 | 490 | |

TABLE 5-continued
| Structure | Compound No. | LC/MS measurement condition | Retention time (min) | m/z | Configuration |
|---|---|---|---|---|---|
| 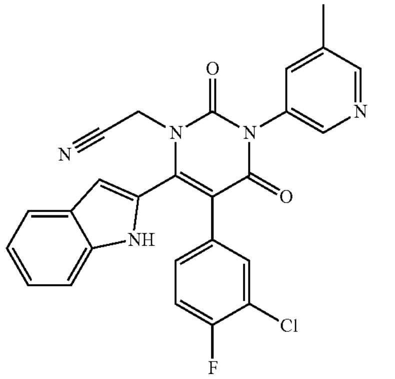 [SMILES: Cc1cncc(-n2c(=O)c(-c3ccc(F)c(Cl)c3)c(-c3cc4ccccc4[nH]3)n(CC#N)c2=O)c1] | I-026 | A | 2.24 | 486 | |
TABLE 6
| Structure | Compound No. | LC/MS measurement condition | Retention time (min) | m/z | Configuration |
|---|---|---|---|---|---|
| 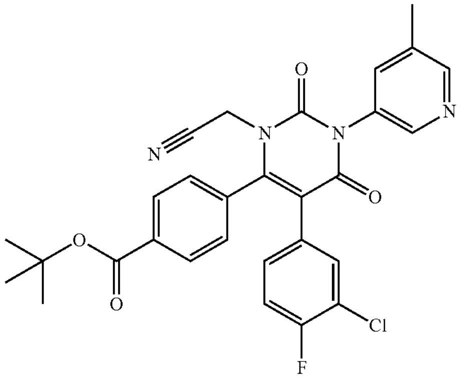 [SMILES: Cc1cncc(-n2c(=O)c(-c3ccc(F)c(Cl)c3)c(-c3ccc(C(=O)OC(C)(C)C)cc3)n(CC#N)c2=O)c1] | I-027 | A | 2.57 | 547 | |
| 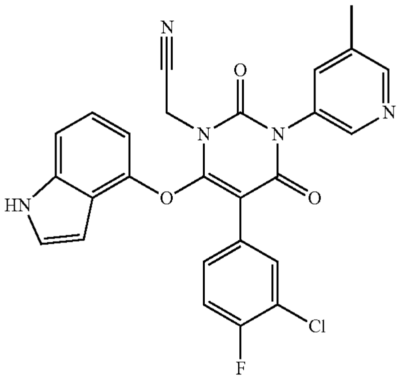 [SMILES: Cc1cncc(-n2c(=O)c(-c3ccc(F)c(Cl)c3)c(Oc3cccc4[nH]ccc34)n(CC#N)c2=O)c1] | I-028 | A | 2.04 | 502 | |

TABLE 6-continued
| Structure | Compound No. | LC/MS measurement condition | Retention time (min) | m/z | Configuration |
|---|---|---|---|---|---|
| 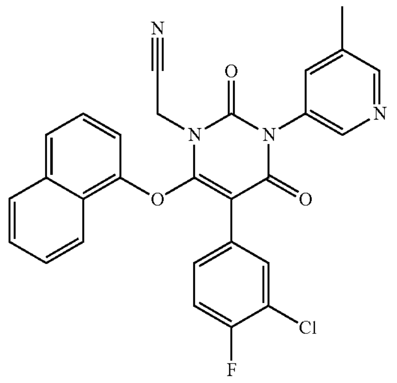 [SMILES: Cc1cncc(-n2c(=O)c(-c3ccc(F)c(Cl)c3)c(Oc3cccc4ccccc34)n(CC#N)c2=O)c1] | I-029 | A | 2.37 | 513 | |
| 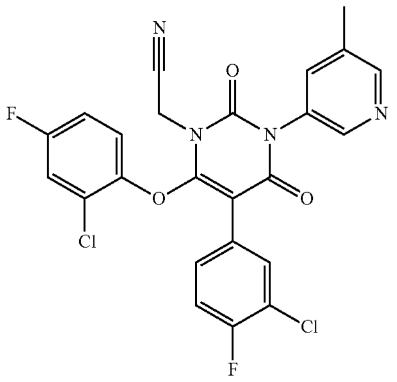 [SMILES: Cc1cncc(-n2c(=O)c(-c3ccc(F)c(Cl)c3)c(Oc3ccc(F)cc3Cl)n(CC#N)c2=O)c1] | I-030 | A | 2.31 | 515 | |
| 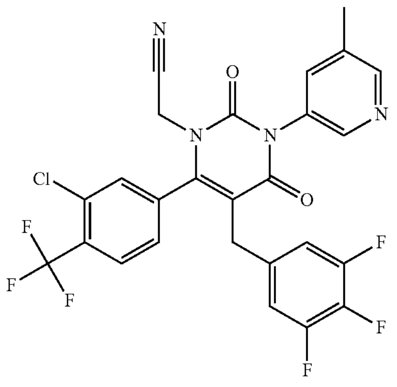 [SMILES: Cc1cncc(-n2c(=O)c(Cc3cc(F)c(F)c(F)c3)c(-c3ccc(C(F)(F)F)c(Cl)c3)n(CC#N)c2=O)c1] | I-031 | A | 2.60 | 565 | |

TABLE 7
| Structure | Compound No. | LC/MS measurement condition | Retention time (min) | m/z | Configuration |
|---|---|---|---|---|---|
| 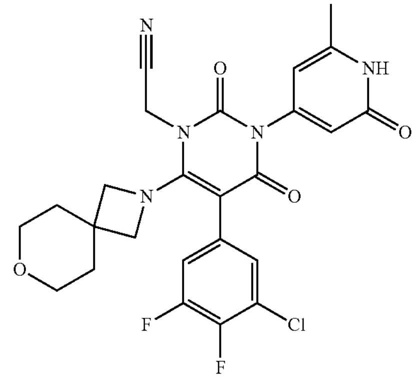 [SMILES: Cc1cc(-n2c(=O)c(-c3cc(F)c(F)c(Cl)c3)c(N3CC4(CCOCC4)C3)n(CC#N)c2=O)cc(=O)[nH]1] | I-032 | A | 1.71 | 530 | |
| 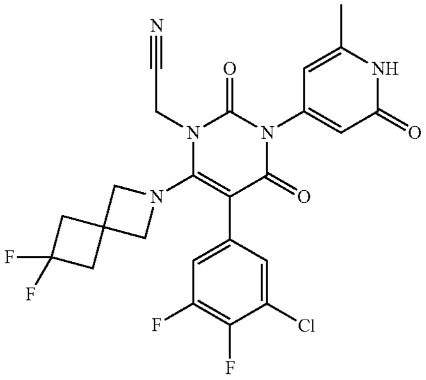 [SMILES: Cc1cc(-n2c(=O)c(-c3cc(F)c(F)c(Cl)c3)c(N3CC4(C3)CC(F)(F)C4)n(CC#N)c2=O)cc(=O)[nH]1] | I-033 | A | 1.99 | 536 | |
| 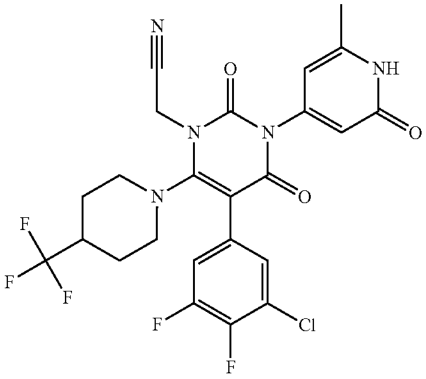 [SMILES: Cc1cc(-n2c(=O)c(-c3cc(F)c(F)c(Cl)c3)c(N3CCC(C(F)(F)F)CC3)n(CC#N)c2=O)cc(=O)[nH]1] | I-034 | A | 2.19 | 556 | |
| 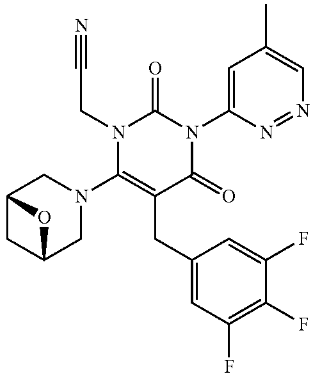 [SMILES: Cc1cnnc(-n2c(=O)c(Cc3cc(F)c(F)c(F)c3)c(N3C[C@H]4C[C@@H](C3)O4)n(CC#N)c2=O)c1] | I-035 | A | 1.90 | 485 | c |

TABLE 7-continued
| Structure | Compound No. | LC/MS measurement condition | Retention time (min) | m/z | Configuration |
|---|---|---|---|---|---|
| 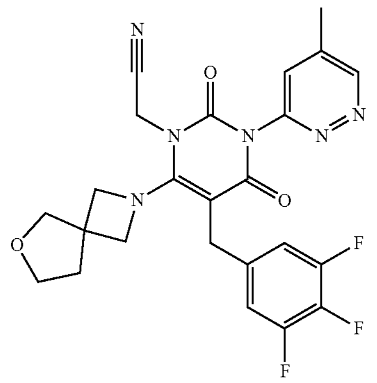 [SMILES: Cc1cnnc(-n2c(=O)c(Cc3cc(F)c(F)c(F)c3)c(N3CC4(CCOC4)C3)n(CC#N)c2=O)c1] | I-036 | A | 1.85 | 499 | |
TABLE 8
| Structure | Compound No. | LC/MS measurement condition | Retention time (min) | m/z | Configuration |
|---|---|---|---|---|---|
| 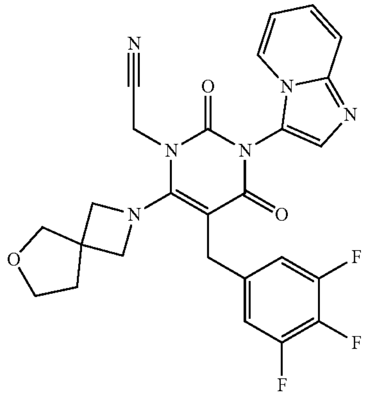 [SMILES: N#CCn1c(N2CC3(CCOC3)C2)c(Cc2cc(F)c(F)c(F)c2)c(=O)n(-c2cnc3ccccn23)c1=O] | I-037 | A | 1.57 | 523 | |
| 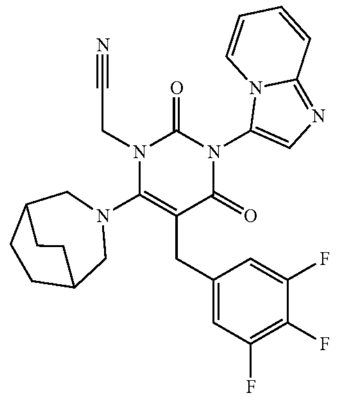 [SMILES: N#CCn1c(N2CC3CCC(CC3)C2)c(Cc2cc(F)c(F)c(F)c2)c(=O)n(-c2cnc3ccccn23)c1=O] | I-038 | A | 2.19 | 535 | |

TABLE 8-continued
| Structure | Compound No. | LC/MS measurement condition | Retention time (min) | m/z | Configuration |
|---|---|---|---|---|---|
| 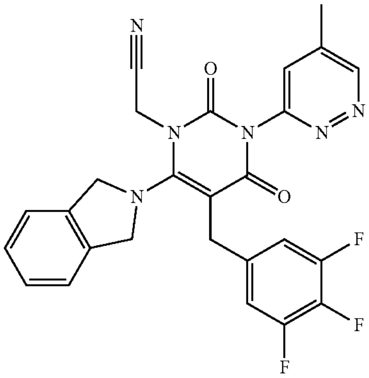 [SMILES: Cc1cnnc(-n2c(=O)c(Cc3cc(F)c(F)c(F)c3)c(N3Cc4ccccc4C3)n(CC#N)c2=O)c1] | I-039 | A | 2.34 | 505 | |
| 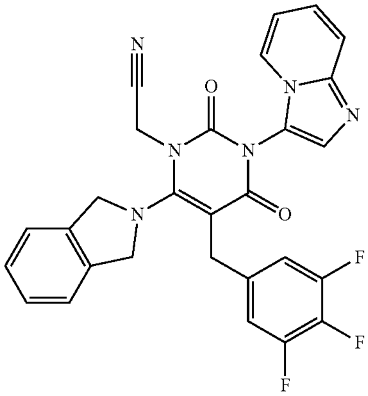 [SMILES: N#CCn1c(N2Cc3ccccc3C2)c(Cc2cc(F)c(F)c(F)c2)c(=O)n(-c2cnc3ccccn23)c1=O] | I-040 | A | 2.17 | 529 | |
| 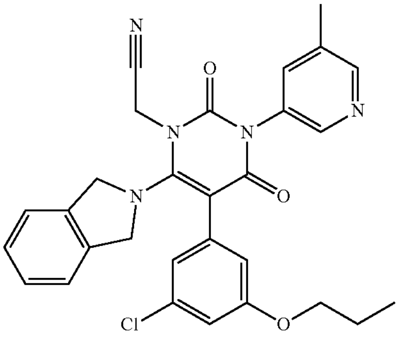 [SMILES: CCCOc1cc(Cl)cc(-c2c(N3Cc4ccccc4C3)n(CC#N)c(=O)n(-c3cncc(C)c3)c2=O)c1] | I-041 | A | 2.53 | 528 | |

TABLE 9
| Structure | Compound No. | LC/MS measurement condition | Retention time (min) | m/z | Configuration |
|---|---|---|---|---|---|
| 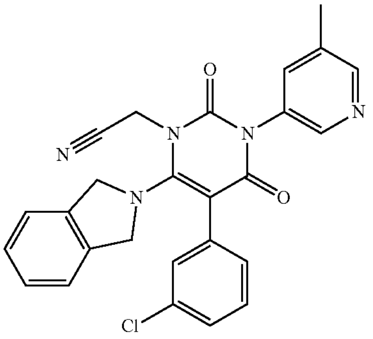 [SMILES: Cc1cncc(-n2c(=O)c(-c3cccc(Cl)c3)c(N3Cc4ccccc4C3)n(CC#N)c2=O)c1] | I-042 | A | 2.23 | 470 | |
| 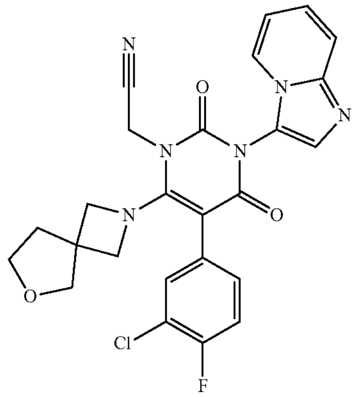 [SMILES: N#CCn1c(N2CC3(CCOC3)C2)c(-c2ccc(F)c(Cl)c2)c(=O)n(-c2cnc3ccccn23)c1=O] | I-043 | A | 1.10 | 507 | |
| 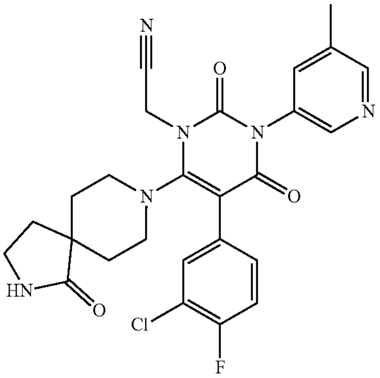 [SMILES: Cc1cncc(-n2c(=O)c(-c3ccc(F)c(Cl)c3)c(N3CCC4(CCNC4=O)CC3)n(CC#N)c2=O)c1] | I-044 | D | 1.46 | 523 | |
| 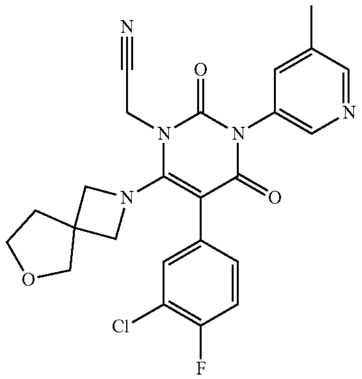 [SMILES: Cc1cncc(-n2c(=O)c(-c3ccc(F)c(Cl)c3)c(N3CC4(CCOC4)C3)n(CC#N)c2=O)c1] | I-045 | A | 1.51 | 482 | |

TABLE 9-continued
| Structure | Compound No. | LC/MS measurement condition | Retention time (min) | m/z | Configuration |
|---|---|---|---|---|---|
| 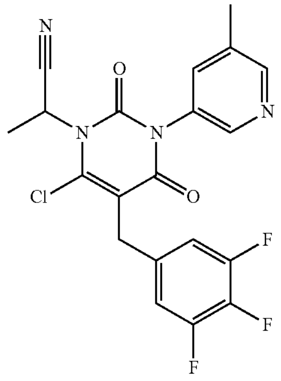 [SMILES: Cc1cncc(-n2c(=O)c(Cc3cc(F)c(F)c(F)c3)c(Cl)n(C(C)C#N)c2=O)c1] | I-046 | A | 2.11 | 435 | d |
TABLE 10
| Structure | Compound No. | LC/MS measurement condition | Retention time (min) | m/z | Configuration |
|---|---|---|---|---|---|
| 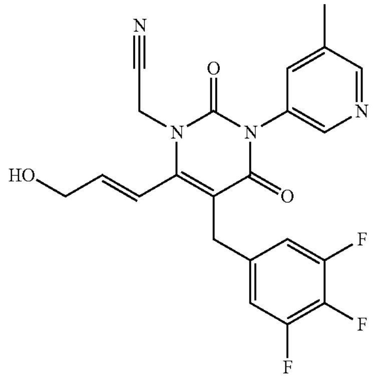 [SMILES: Cc1cncc(-n2c(=O)c(Cc3cc(F)c(F)c(F)c3)c(/C=C/CO)n(CC#N)c2=O)c1] | I-047 | A | 1.71 | 443 | e |
| 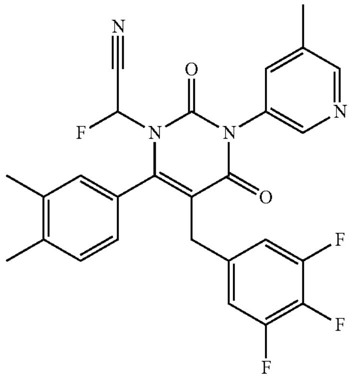 [SMILES: Cc1cncc(-n2c(=O)c(Cc3cc(F)c(F)c(F)c3)c(-c3ccc(C)c(C)c3)n(C(F)C#N)c2=O)c1] | I-048 | A | 2.57 | 509 | d |

TABLE 10-continued
| Structure | Compound No. | LC/MS measurement condition | Retention time (min) | m/z | Configuration |
|---|---|---|---|---|---|
| 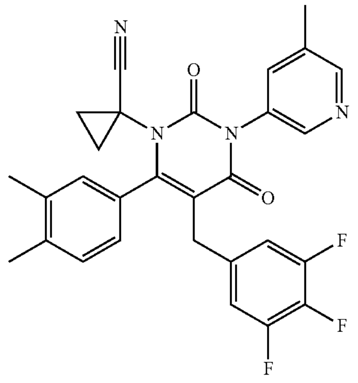 [SMILES: Cc1cncc(-n2c(=O)c(Cc3cc(F)c(F)c(F)c3)c(-c3ccc(C)c(C)c3)n(C3(C#N)CC3)c2=O)c1] | I-049 | A | 2.50 | 517 | |
| 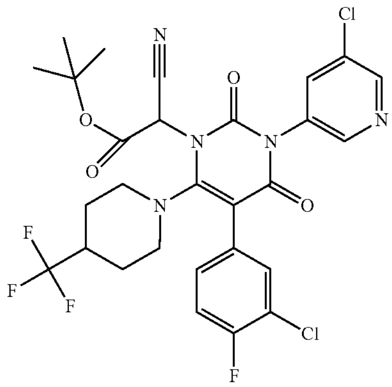 [SMILES: CC(C)(C)OC(=O)C(C#N)n1c(N2CCC(C(F)(F)F)CC2)c(-c2ccc(F)c(Cl)c2)c(=O)n(-c2cncc(Cl)c2)c1=O] | I-050 | A | 2.78 | 642 | d |
| 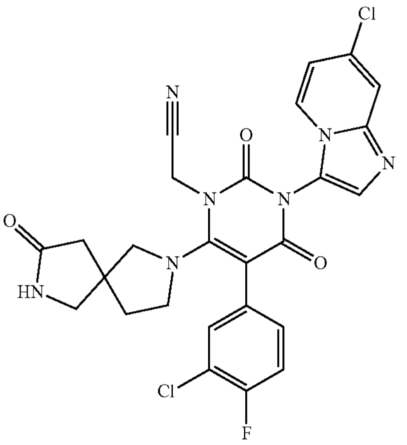 [SMILES: N#CCn1c(N2CCC3(CNC(=O)C3)C2)c(-c2ccc(F)c(Cl)c2)c(=O)n(-c2cnc3cc(Cl)ccn23)c1=O] | I-051 | A | 1.61 | 568 | d |

TABLE 11
| Structure | Compound No. | LC/MS measurement condition | Retention time (min) | m/z | Configuration |
|---|---|---|---|---|---|
| 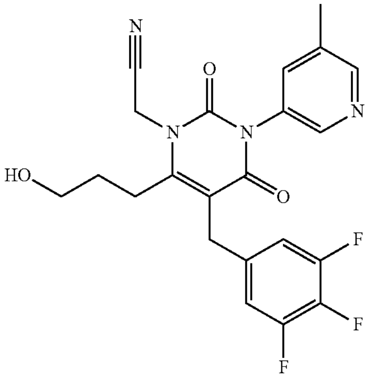 [SMILES: Cc1cncc(-n2c(=O)c(Cc3cc(F)c(F)c(F)c3)c(CCCO)n(CC#N)c2=O)c1] | I-052 | A | 1.70 | 445 | |
| 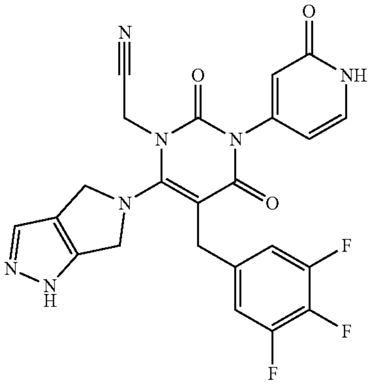 [SMILES: N#CCn1c(N2Cc3cn[nH]c3C2)c(Cc2cc(F)c(F)c(F)c2)c(=O)n(-c2cc[nH]c(=O)c2)c1=O] | I-053 | A | 1.58 | 510 | |
| 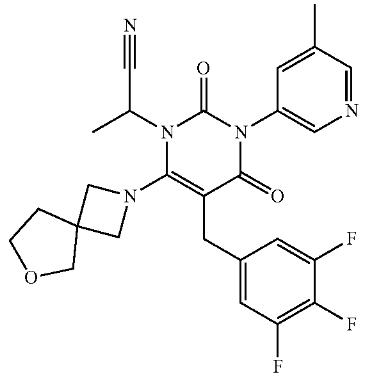 [SMILES: Cc1cncc(-n2c(=O)c(Cc3cc(F)c(F)c(F)c3)c(N3CC4(CCOC4)C3)n(C(C)C#N)c2=O)c1] | I-054 | A | 1.86 | 512 | d |
| 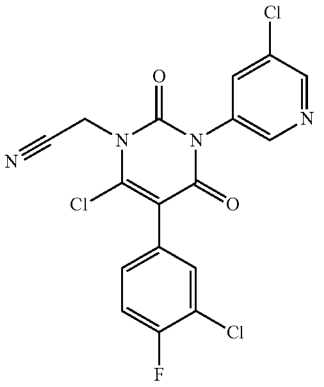 [SMILES: N#CCn1c(Cl)c(-c2ccc(F)c(Cl)c2)c(=O)n(-c2cncc(Cl)c2)c1=O] | I-055 | A | 2.17 | 425 | |

TABLE 11-continued
| Structure | Compound No. | LC/MS measurement condition | Retention time (min) | m/z | Configuration |
|---|---|---|---|---|---|
| 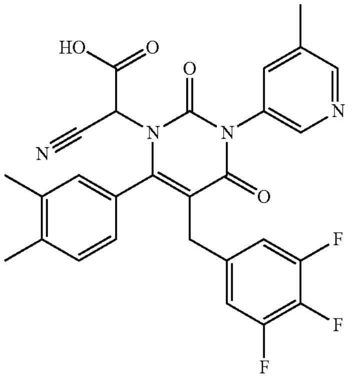 [SMILES: Cc1cncc(-n2c(=O)c(Cc3cc(F)c(F)c(F)c3)c(-c3ccc(C)c(C)c3)n(C(C#N)C(=O)O)c2=O)c1] | I-056 | A | 2.11 | 535 | d |
TABLE 12
| Structure | Compound No. | LC/MS measurement condition | Retention time (min) | m/z | Configuration |
|---|---|---|---|---|---|
| 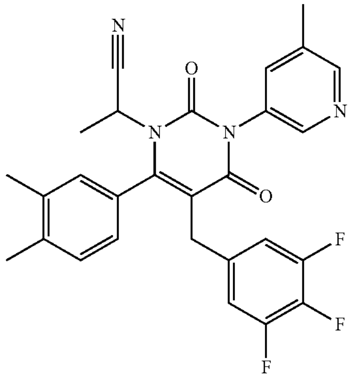 [SMILES: Cc1cncc(-n2c(=O)c(Cc3cc(F)c(F)c(F)c3)c(-c3ccc(C)c(C)c3)n(C(C)C#N)c2=O)c1] | I-057 | A | 2.48 | 505 | d |
| 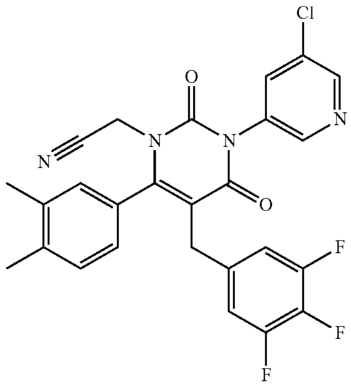 [SMILES: Cc1ccc(-c2c(Cc3cc(F)c(F)c(F)c3)c(=O)n(-c3cncc(Cl)c3)c(=O)n2CC#N)cc1C] | I-058 | A | 2.62 | 511 | |

TABLE 12-continued
| Structure | Compound No. | LC/MS measurement condition | Retention time (min) | m/z | Configuration |
|---|---|---|---|---|---|
| 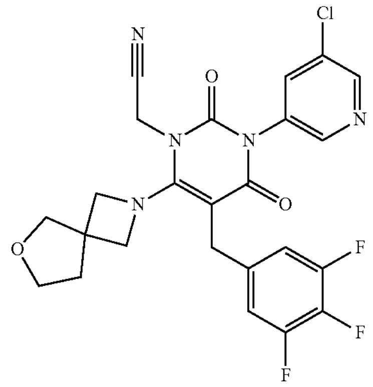 [SMILES: N#CCn1c(N2CC3(CCOC3)C2)c(Cc2cc(F)c(F)c(F)c2)c(=O)n(-c2cncc(Cl)c2)c1=O] | I-059 | A | 2.06 | 518 | |
| 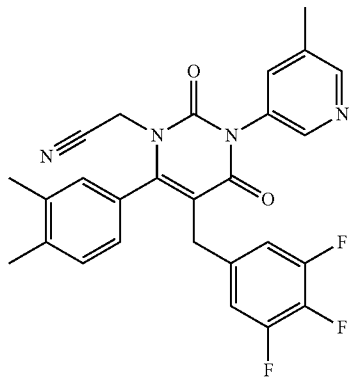 [SMILES: Cc1cncc(-n2c(=O)c(Cc3cc(F)c(F)c(F)c3)c(-c3ccc(C)c(C)c3)n(CC#N)c2=O)c1] | I-060 | A | 2.58 | 491 | |
| 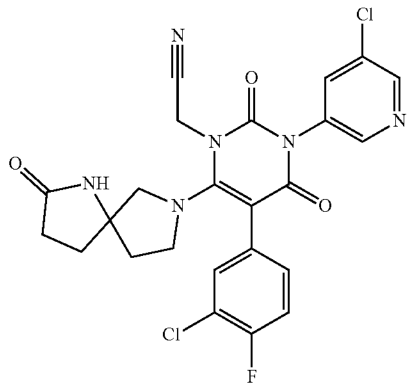 [SMILES: N#CCn1c(N2CCC3(CCC(=O)N3)C2)c(-c2ccc(F)c(Cl)c2)c(=O)n(-c2cncc(Cl)c2)c1=O] | I-061 | A | 1.83 | 529 | d |

TABLE 13
| Structure | Compound No. | LC/MS measurement condition | Retention time (min) | m/z | Configuration |
|---|---|---|---|---|---|
| 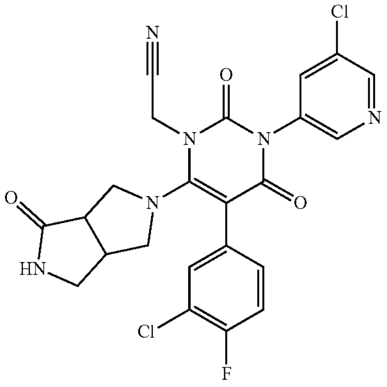 [SMILES: N#CCn1c(N2CC3CNC(=O)C3C2)c(-c2ccc(F)c(Cl)c2)c(=O)n(-c2cncc(Cl)c2)c1=O] | I-062 | A | 1.79 | 515 | d |
| 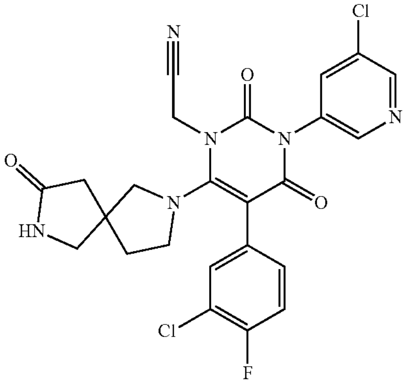 [SMILES: N#CCn1c(N2CCC3(CNC(=O)C3)C2)c(-c2ccc(F)c(Cl)c2)c(=O)n(-c2cncc(Cl)c2)c1=O] | I-063 | A | 1.76 | 529 | d |
| 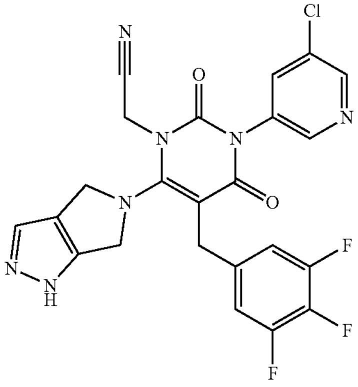 [SMILES: N#CCn1c(N2Cc3cn[nH]c3C2)c(Cc2cc(F)c(F)c(F)c2)c(=O)n(-c2cncc(Cl)c2)c1=O] | I-064 | A | 1.99 | 514 | |

TABLE 13-continued
| Structure | Compound No. | LC/MS measurement condition | Retention time (min) | m/z | Configuration |
|---|---|---|---|---|---|
| 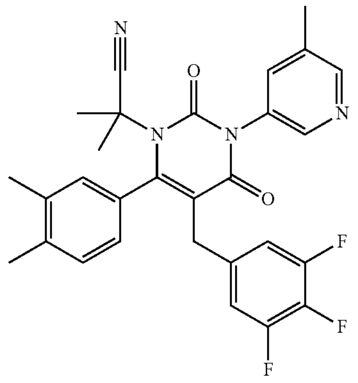 [SMILES: Cc1cncc(-n2c(=O)c(Cc3cc(F)c(F)c(F)c3)c(-c3ccc(C)c(C)c3)n(C(C)(C)C#N)c2=O)c1] | I-065 | A | 2.55 | 519 | |
| 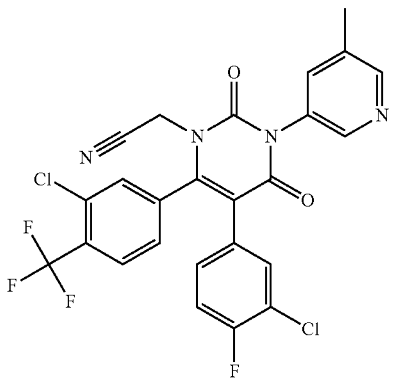 [SMILES: Cc1cncc(-n2c(=O)c(-c3ccc(F)c(Cl)c3)c(-c3ccc(C(F)(F)F)c(Cl)c3)n(CC#N)c2=O)c1] | I-066 | A | 2.46 | 549 | |
TABLE 14
| Structure | Compound No. | LC/MS measurement condition | Retention time (min) | m/z | Configuration |
|---|---|---|---|---|---|
| 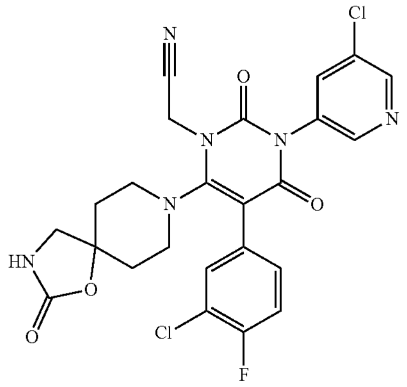 [SMILES: N#CCn1c(N2CCC3(CC2)CNC(=O)O3)c(-c2ccc(F)c(Cl)c2)c(=O)n(-c2cncc(Cl)c2)c1=O] | I-067 | A | 1.85 | 545 | |

TABLE 14-continued
| Structure | Compound No. | LC/MS measurement condition | Retention time (min) | m/z | Configuration |
|---|---|---|---|---|---|
| 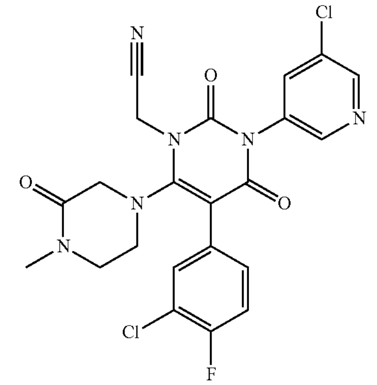 [SMILES: CN1CCN(c2c(-c3ccc(F)c(Cl)c3)c(=O)n(-c3cncc(Cl)c3)c(=O)n2CC#N)CC1=O] | I-068 | A | 1.77 | 503 | |
| 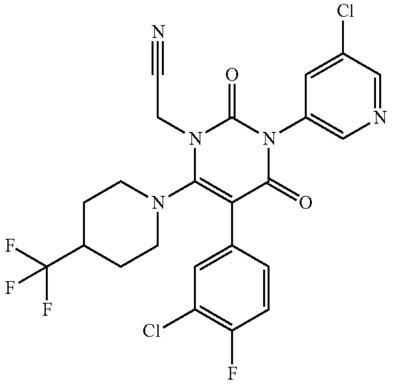 [SMILES: N#CCn1c(N2CCC(C(F)(F)F)CC2)c(-c2ccc(F)c(Cl)c2)c(=O)n(-c2cncc(Cl)c2)c1=O] | I-069 | A | 2.47 | 542 | |
| 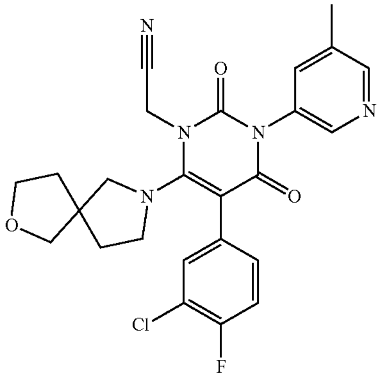 [SMILES: Cc1cncc(-n2c(=O)c(-c3ccc(F)c(Cl)c3)c(N3CCC4(CCOC4)C3)n(CC#N)c2=O)c1] | I-070 | A | 1.85 | 496 | d |
| 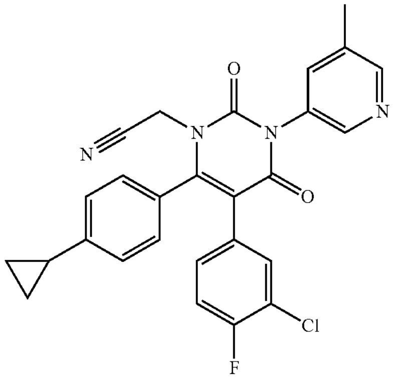 [SMILES: Cc1cncc(-n2c(=O)c(-c3ccc(F)c(Cl)c3)c(-c3ccc(C4CC4)cc3)n(CC#N)c2=O)c1] | I-071 | A | 2.31 | 487 | |

TABLE 15
| Structure | Compound No. | LC/MS measurement condition | Retention time (min) | m/z | Configuration |
|---|---|---|---|---|---|
| 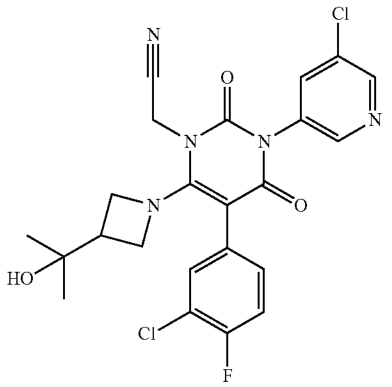 [SMILES: CC(C)(O)C1CN(c2c(-c3ccc(F)c(Cl)c3)c(=O)n(-c3cncc(Cl)c3)c(=O)n2CC#N)C1] | I-072 | A | 1.94 | 504 | |
| 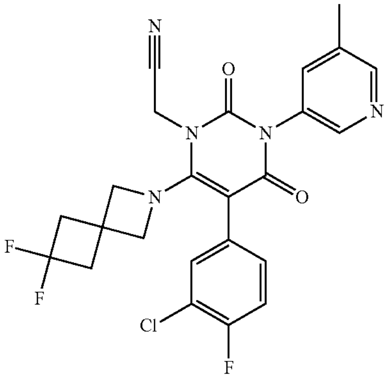 [SMILES: Cc1cncc(-n2c(=O)c(-c3ccc(F)c(Cl)c3)c(N3CC4(C3)CC(F)(F)C4)n(CC#N)c2=O)c1] | I-073 | A | 2.03 | 502 | |
| 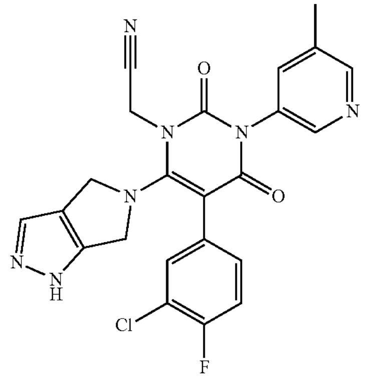 [SMILES: Cc1cncc(-n2c(=O)c(-c3ccc(F)c(Cl)c3)c(N3Cc4cn[nH]c4C3)n(CC#N)c2=O)c1] | I-074 | A | 1.57 | 478 | |
| 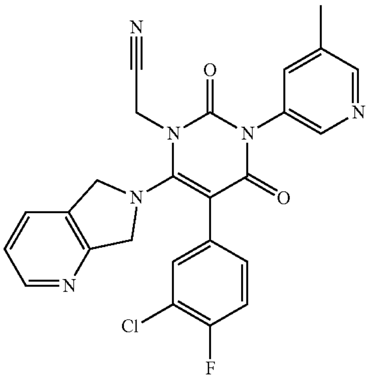 [SMILES: Cc1cncc(-n2c(=O)c(-c3ccc(F)c(Cl)c3)c(N3Cc4cccnc4C3)n(CC#N)c2=O)c1] | I-075 | A | 1.69 | 489 | |

TABLE 15-continued
| Structure | Compound No. | LC/MS measurement condition | Retention time (min) | m/z | Configuration |
|---|---|---|---|---|---|
| 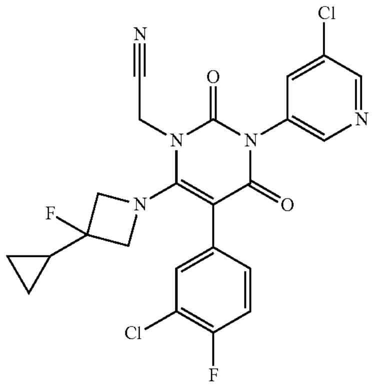 [SMILES: N#CCn1c(N2CC(F)(C3CC3)C2)c(-c2ccc(F)c(Cl)c2)c(=O)n(-c2cncc(Cl)c2)c1=O] | I-076 | A | 2.30 | 504 | |
TABLE 16
| Structure | Compound No. | LC/MS measurement condition | Retention time(min) | m/z | Configu-ration |
|---|---|---|---|---|---|
| 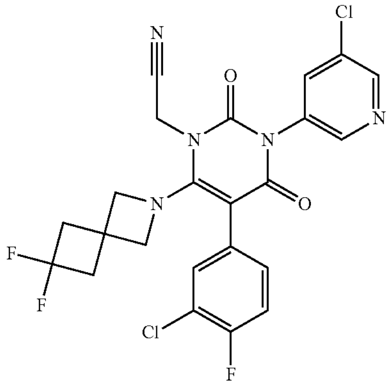 [SMILES: N#CCn1c(N2CC3(C2)CC(F)(F)C3)c(-c2ccc(F)c(Cl)c2)c(=O)n(-c2cncc(Cl)c2)c1=O] | I-077 | A | 2.27 | 522 | |
| 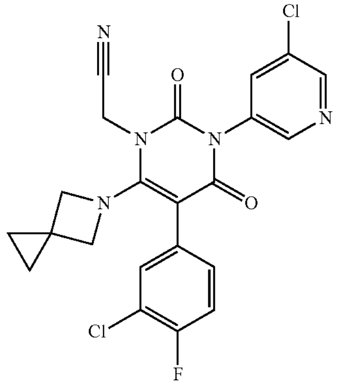 [SMILES: N#CCn1c(N2CC3(CC3)C2)c(-c2ccc(F)c(Cl)c2)c(=O)n(-c2cncc(Cl)c2)c1=O] | I-078 | A | 2.23 | 472 | |

TABLE 16-continued
| Structure | Compound No. | LC/MS measurement condition | Retention time(min) | m/z | Configu-ration |
|---|---|---|---|---|---|
| 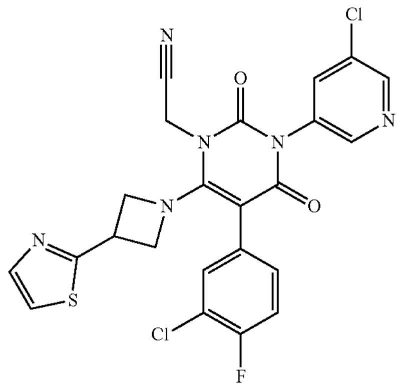 [SMILES: N#CCn1c(N2CC(c3nccs3)C2)c(-c2ccc(F)c(Cl)c2)c(=O)n(-c2cncc(Cl)c2)c1=O] | I-079 | A | 2.06 | 529 | |
| 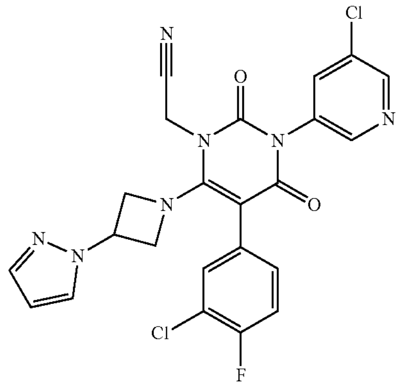 [SMILES: N#CCn1c(N2CC(n3cccn3)C2)c(-c2ccc(F)c(Cl)c2)c(=O)n(-c2cncc(Cl)c2)c1=O] | I-080 | A | 2.01 | 512 | |
| 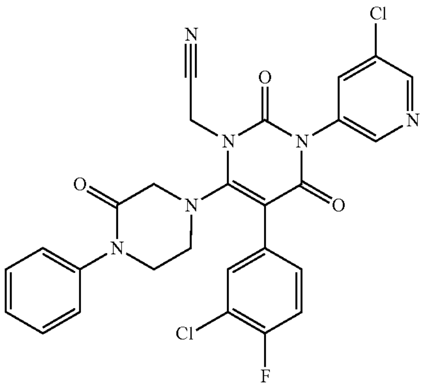 [SMILES: N#CCn1c(N2CCN(c3ccccc3)C(=O)C2)c(-c2ccc(F)c(Cl)c2)c(=O)n(-c2cncc(Cl)c2)c1=O] | I-081 | A | 2.12 | 565 | |

TABLE 17
| Structure | Compound No. | LC/MS measurement condition | Retention time(min) | m/z | Configu-ration |
|---|---|---|---|---|---|
| 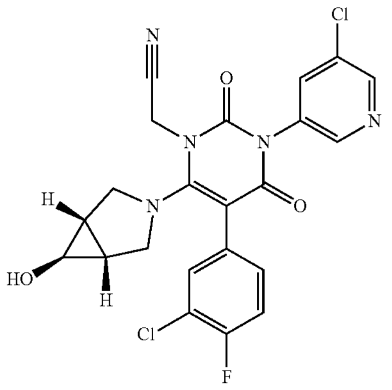 [SMILES: N#CCn1c(N2C[C@@H]3[C@@H](O)[C@@H]3C2)c(-c2ccc(F)c(Cl)c2)c(=O)n(-c2cncc(Cl)c2)c1=O] | I-082 | A | 1.91 | 488 | c |
| 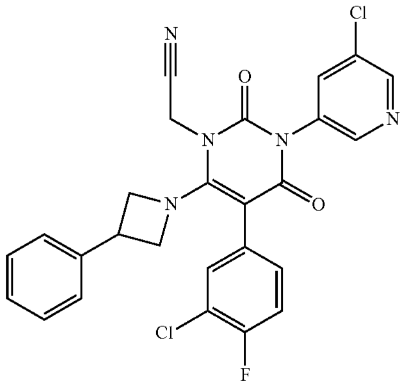 [SMILES: N#CCn1c(N2CC(c3ccccc3)C2)c(-c2ccc(F)c(Cl)c2)c(=O)n(-c2cncc(Cl)c2)c1=O] | I-083 | A | 2.40 | 522 | |
| 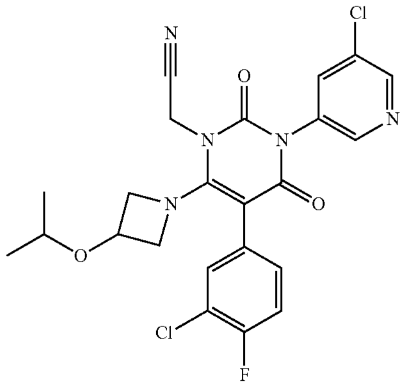 [SMILES: CC(C)OC1CN(c2c(-c3ccc(F)c(Cl)c3)c(=O)n(-c3cncc(Cl)c3)c(=O)n2CC#N)C1] | I-084 | A | 2.27 | 504 | |

TABLE 17-continued
| Structure | Compound No. | LC/MS measurement condition | Retention time(min) | m/z | Configu- ration |
|---|---|---|---|---|---|
| 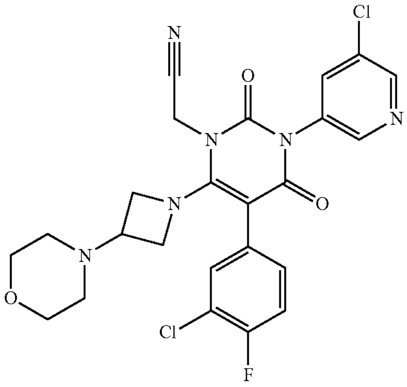 [SMILES: N#CCn1c(N2CC(N3CCOCC3)C2)c(-c2ccc(F)c(Cl)c2)c(=O)n(-c2cncc(Cl)c2)c1=O] | I-085 | A | 1.52 | 531 | |
| 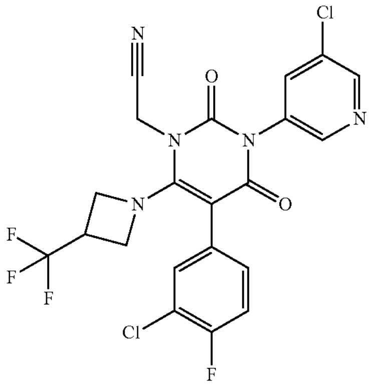 [SMILES: N#CCn1c(N2CC(C(F)(F)F)C2)c(-c2ccc(F)c(Cl)c2)c(=O)n(-c2cncc(Cl)c2)c1=O] | I-086 | A | 2.25 | 514 | |
TABLE 18
| Structure | Compound No. | LC/MS measurement condition | Retention time(min) | m/z | Configu- ration |
|---|---|---|---|---|---|
| 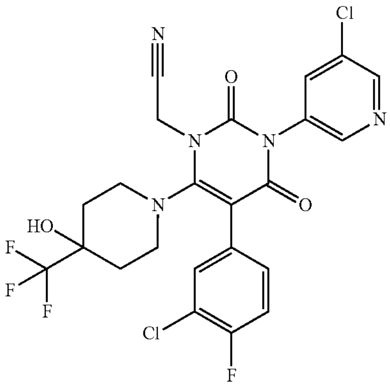 [SMILES: N#CCn1c(N2CCC(O)(C(F)(F)F)CC2)c(-c2ccc(F)c(Cl)c2)c(=O)n(-c2cncc(Cl)c2)c1=O] | I-087 | A | 2.18 | 558 | |

TABLE 18-continued
| Structure | Compound No. | LC/MS measurement condition | Retention time(min) | m/z | Configu-ration |
|---|---|---|---|---|---|
| 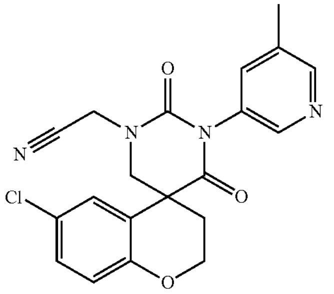 [SMILES: Cc1cncc(N2C(=O)N(CC#N)CC3(CCOc4ccc(Cl)cc43)C2=O)c1] | I-088 | A | 1.85 | 397 | d |
| 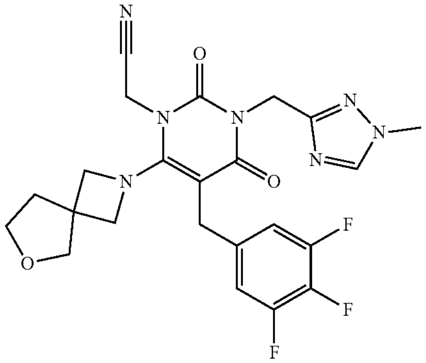 [SMILES: Cn1cnc(Cn2c(=O)c(Cc3cc(F)c(F)c(F)c3)c(N3CC4(CCOC4)C3)n(CC#N)c2=O)n1] | I-089 | A | 1.70 | 502 | |
| 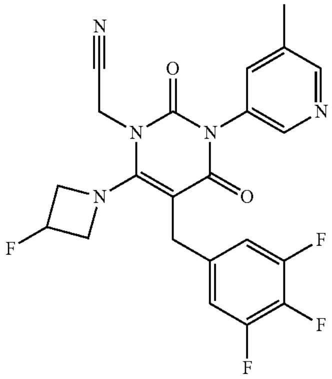 [SMILES: Cc1cncc(-n2c(=O)c(Cc3cc(F)c(F)c(F)c3)c(N3CC(F)C3)n(CC#N)c2=O)c1] | I-090 | A | 1.90 | 460 | |
| 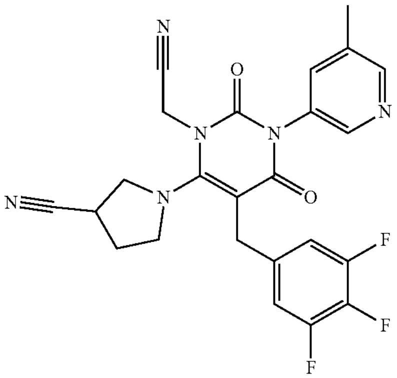 [SMILES: Cc1cncc(-n2c(=O)c(Cc3cc(F)c(F)c(F)c3)c(N3CCC(C#N)C3)n(CC#N)c2=O)c1] | I-092 | A | 1.98 | 481 | d |

TABLE 19
| Structure | Compound No. | LC/MS measurement condition | Retention time(min) | m/z | Configu-ration |
|---|---|---|---|---|---|
| 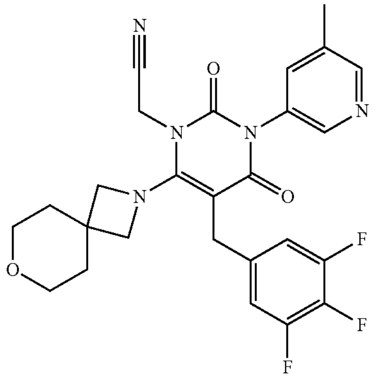 [SMILES: Cc1cncc(-n2c(=O)c(Cc3cc(F)c(F)c(F)c3)c(N3CC4(CCOCC4)C3)n(CC#N)c2=O)c1] | 1-093 | A | 1.86 | 512 | |
| 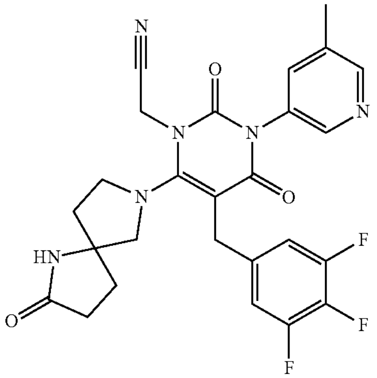 [SMILES: Cc1cncc(-n2c(=O)c(Cc3cc(F)c(F)c(F)c3)c(N3CCC4(CCC(=O)N4)C3)n(CC#N)c2=O)c1] | 1-094 | A | 1.72 | 525 | d |
| 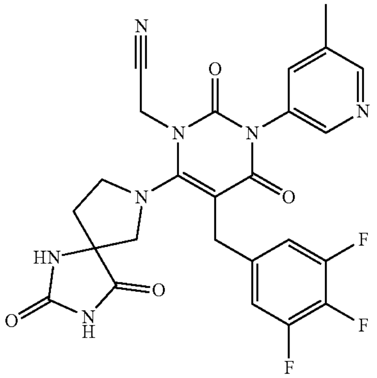 [SMILES: Cc1cncc(-n2c(=O)c(Cc3cc(F)c(F)c(F)c3)c(N3CCC4(C3)NC(=O)NC4=O)n(CC#N)c2=O)c1] | 1-095 | A | 1.68 | 540 | d |
| 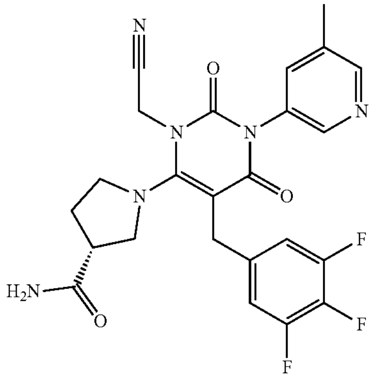 [SMILES: Cc1cncc(-n2c(=O)c(Cc3cc(F)c(F)c(F)c3)c(N3CC[C@@H](C(N)=O)C3)n(CC#N)c2=O)c1] | 1-096 | A | 1.68 | 499 | c |

TABLE 19-continued
| Structure | Compound No. | LC/MS measurement condition | Retention time(min) | m/z | Configu-ration |
|---|---|---|---|---|---|
| 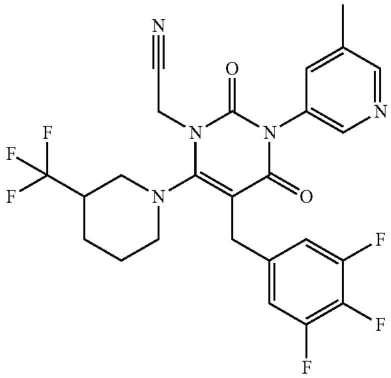 [SMILES: Cc1cncc(-n2c(=O)c(Cc3cc(F)c(F)c(F)c3)c(N3CCCC(C(F)(F)F)C3)n(CC#N)c2=O)c1] | 1-097 | A | 2.42 | 538 | d |
TABLE 20
| Structure | Compound No. | LC/MS measurement condition | Retention time(min) | m/z | Configu-ration |
|---|---|---|---|---|---|
| 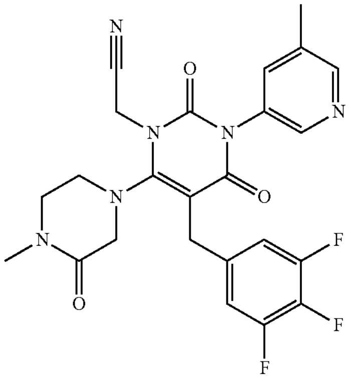 [SMILES: Cc1cncc(-n2c(=O)c(Cc3cc(F)c(F)c(F)c3)c(N3CCN(C)C(=O)C3)n(CC#N)c2=O)c1] | I-098 | A | 1.72 | 1.72 | |
| 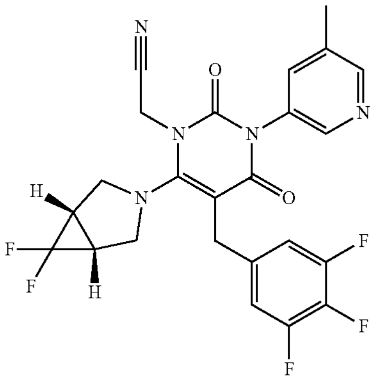 [SMILES: Cc1cncc(-n2c(=O)c(Cc3cc(F)c(F)c(F)c3)c(N3C[C@@H]4[C@H](C3)C4(F)F)n(CC#N)c2=O)c1] | I-099 | A | 2.20 | 2.2 | c |

TABLE 20-continued
| Structure | Compound No. | LC/MS measurement condition | Retention time(min) | m/z | Configu-ration |
|---|---|---|---|---|---|
| 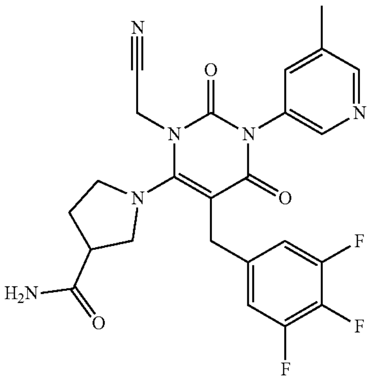 [SMILES: Cc1cncc(-n2c(=O)c(Cc3cc(F)c(F)c(F)c3)c(N3CCC(C(N)=O)C3)n(CC#N)c2=O)c1] | I-100 | A | 1.67 | 499 | d |
| 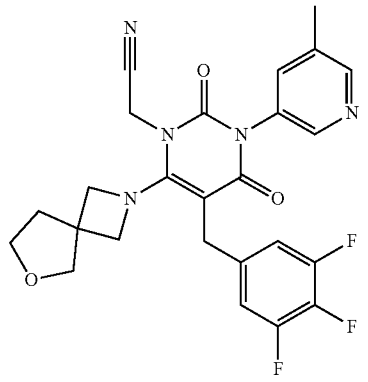 [SMILES: Cc1cncc(-n2c(=O)c(Cc3cc(F)c(F)c(F)c3)c(N3CC4(CCOC4)C3)n(CC#N)c2=O)c1] | I-101 | A | 1.82 | 498 | |
| 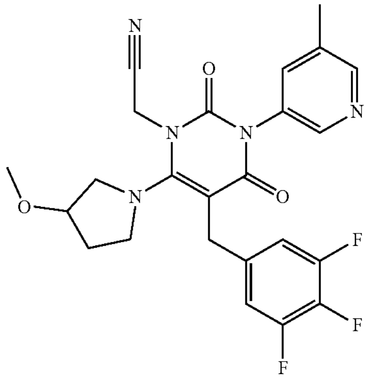 [SMILES: COC1CCN(c2c(Cc3cc(F)c(F)c(F)c3)c(=O)n(-c3cncc(C)c3)c(=O)n2CC#N)C1] | I-102 | A | 2.09 | 486 | d |

TABLE 21
| Structure | Compound No. | LC/MS measurement condition | Retention time(min) | m/z | Configu-ration |
|---|---|---|---|---|---|
| 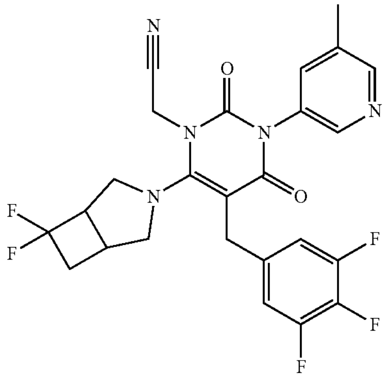 [SMILES: Cc1cncc(-n2c(=O)c(Cc3cc(F)c(F)c(F)c3)c(N3CC4CC(F)(F)C4C3)n(CC#N)c2=O)c1] | I-103 | A | 2.26 | 518 | d |
| 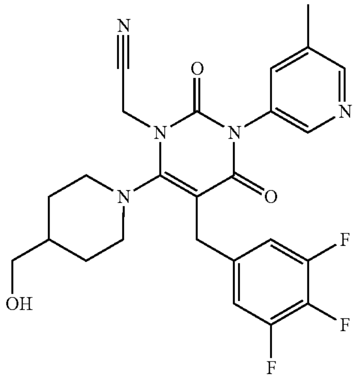 [SMILES: Cc1cncc(-n2c(=O)c(Cc3cc(F)c(F)c(F)c3)c(N3CCC(CO)CC3)n(CC#N)c2=O)c1] | I-104 | A | 1.81 | 500 | |
| 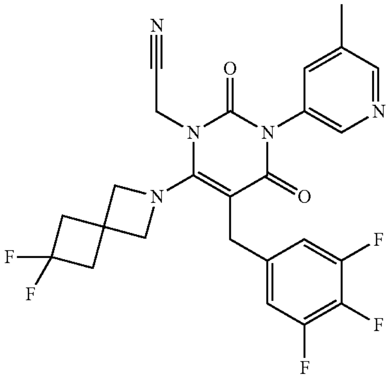 [SMILES: Cc1cncc(-n2c(=O)c(Cc3cc(F)c(F)c(F)c3)c(N3CC4(C3)CC(F)(F)C4)n(CC#N)c2=O)c1] | I-105 | A | 2.14 | 518 | |
| 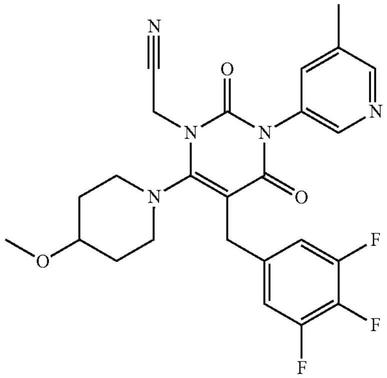 [SMILES: COC1CCN(c2c(Cc3cc(F)c(F)c(F)c3)c(=O)n(-c3cncc(C)c3)c(=O)n2CC#N)CC1] | I-106 | A | 2.08 | 2.08 | |

TABLE 21-continued
| Structure | Compound No. | LC/MS measurement condition | Retention time(min) | m/z | Configu-ration |
|---|---|---|---|---|---|
| 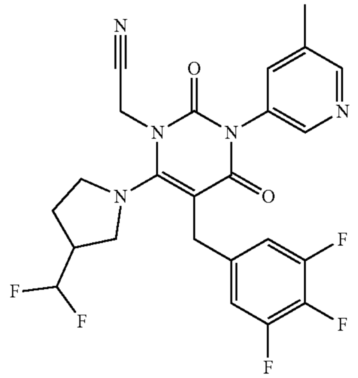 [SMILES: Cc1cncc(-n2c(=O)c(Cc3cc(F)c(F)c(F)c3)c(N3CCC(C(F)F)C3)n(CC#N)c2=O)c1] | I-107 | A | 2.19 | 506 | d |
TABLE 22
| Structure | Compound No. | LC/MS measurement condition | Retention time(min) | m/z | Configu-ration |
|---|---|---|---|---|---|
| 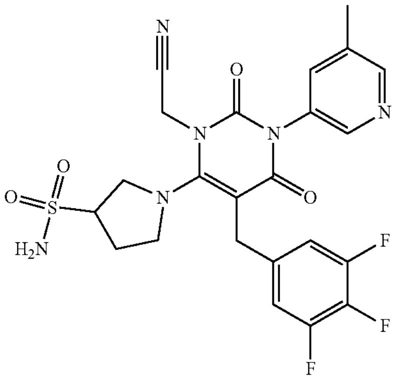 [SMILES: Cc1cncc(-n2c(=O)c(Cc3cc(F)c(F)c(F)c3)c(N3CCC(S(N)(=O)=O)C3)n(CC#N)c2=O)c1] | I-108 | A | 1.76 | 535 | d |
| 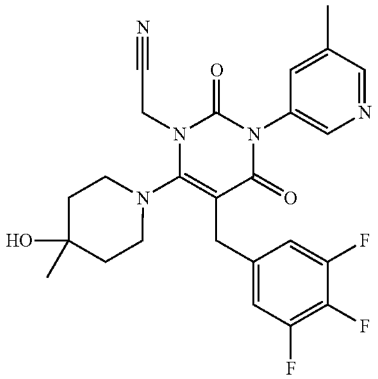 [SMILES: Cc1cncc(-n2c(=O)c(Cc3cc(F)c(F)c(F)c3)c(N3CCC(C)(O)CC3)n(CC#N)c2=O)c1] | I-109 | A | 1.83 | 1.83 | |

TABLE 22-continued
| Structure | Compound No. | LC/MS measurement condition | Retention time(min) | m/z | Configu-ration |
|---|---|---|---|---|---|
| 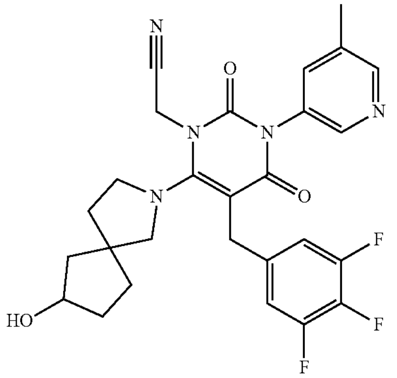 [SMILES: Cc1cncc(-n2c(=O)c(Cc3cc(F)c(F)c(F)c3)c(N3CCC4(CCC(O)C4)C3)n(CC#N)c2=O)c1] | I-110 | A | 1.96 | 526 | d |
| 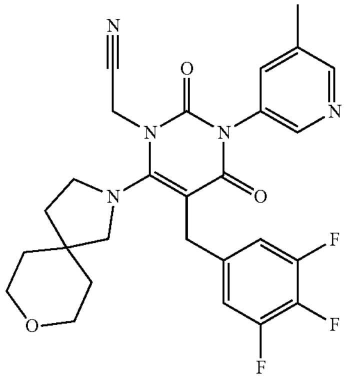 [SMILES: Cc1cncc(-n2c(=O)c(Cc3cc(F)c(F)c(F)c3)c(N3CCC4(CCOCC4)C3)n(CC#N)c2=O)c1] | I-111 | A | 2.06 | 526 | |
| 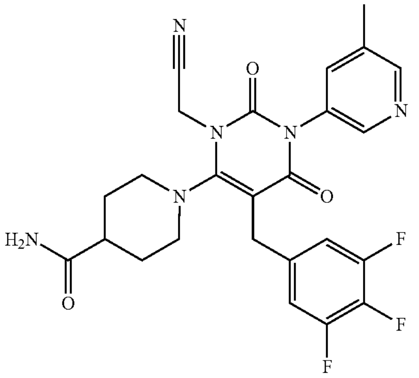 [SMILES: Cc1cncc(-n2c(=O)c(Cc3cc(F)c(F)c(F)c3)c(N3CCC(C(N)=O)CC3)n(CC#N)c2=O)c1] | I-112 | A | 1.67 | 513 | |

TABLE 23
| Structure | Compound No. | LC/MS measurement condition | Retention time(min) | m/z | Configu-ration |
|---|---|---|---|---|---|
| 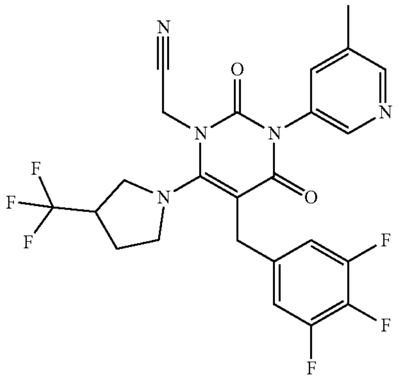 [SMILES: Cc1cncc(-n2c(=O)c(Cc3cc(F)c(F)c(F)c3)c(N3CCC(C(F)(F)F)C3)n(CC#N)c2=O)c1] | I-113 | A | 2.31 | 524 | d |
| 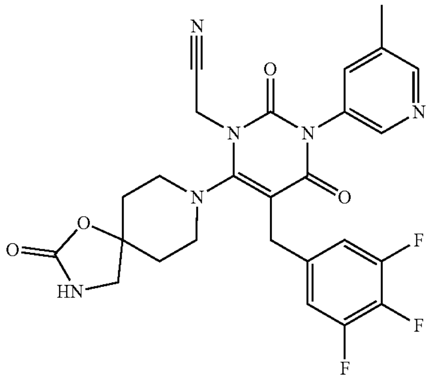 [SMILES: Cc1cncc(-n2c(=O)c(Cc3cc(F)c(F)c(F)c3)c(N3CCC4(CC3)CNC(=O)O4)n(CC#N)c2=O)c1] | I-114 | A | 1.72 | 1.72 | |
| 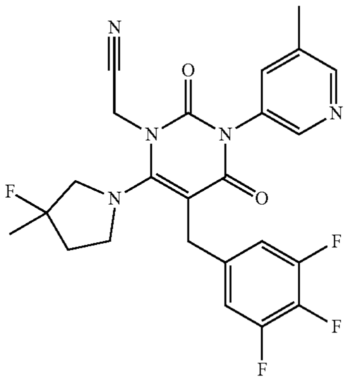 [SMILES: Cc1cncc(-n2c(=O)c(Cc3cc(F)c(F)c(F)c3)c(N3CCC(C)(F)C3)n(CC#N)c2=O)c1] | I-115 | A | 2.21 | 488 | d |
| 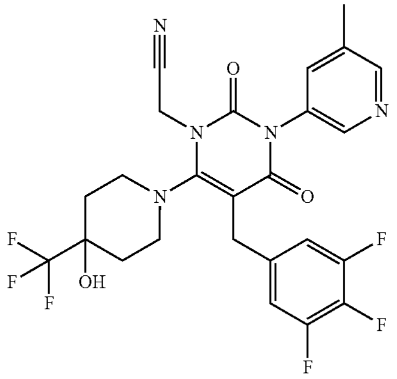 [SMILES: Cc1cncc(-n2c(=O)c(Cc3cc(F)c(F)c(F)c3)c(N3CCC(O)(C(F)(F)F)CC3)n(CC#N)c2=O)c1] | I-116 | A | 2.08 | 554 | |

TABLE 23-continued
| Structure | Compound No. | LC/MS measurement condition | Retention time(min) | m/z | Configu-ration |
|---|---|---|---|---|---|
| 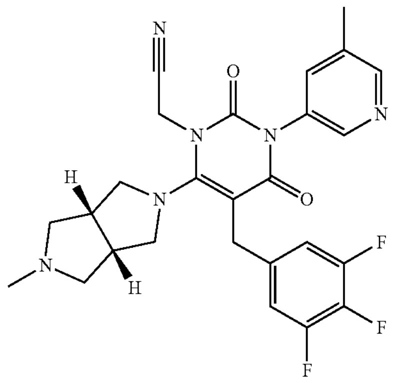 [SMILES: Cc1cncc(-n2c(=O)c(Cc3cc(F)c(F)c(F)c3)c(N3C[C@H]4CN(C)C[C@H]4C3)n(CC#N)c2=O)c1] | I-117 | A | 1.43 | 511 | c |
TABLE 24
| Structure | Compound No. | LC/MS measurement condition | Retention time(min) | m/z | Configu-ration |
|---|---|---|---|---|---|
| 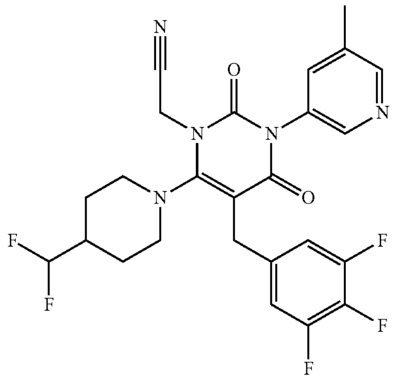 [SMILES: Cc1cncc(-n2c(=O)c(Cc3cc(F)c(F)c(F)c3)c(N3CCC(C(F)F)CC3)n(CC#N)c2=O)c1] | I-118 | A | 2.28 | 2.28 | |
| 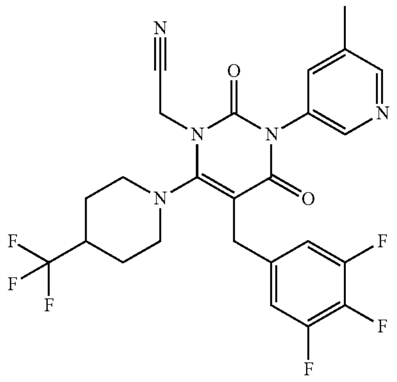 [SMILES: Cc1cncc(-n2c(=O)c(Cc3cc(F)c(F)c(F)c3)c(N3CCC(C(F)(F)F)CC3)n(CC#N)c2=O)c1] | I-119 | A | 2.40 | 538 | |

TABLE 24-continued
| Structure | Compound No. | LC/MS measurement condition | Retention time(min) | m/z | Configu-ration |
|---|---|---|---|---|---|
| 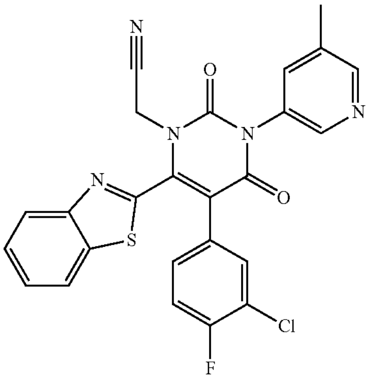 [SMILES: Cc1cncc(-n2c(=O)c(-c3ccc(F)c(Cl)c3)c(-c3nc4ccccc4s3)n(CC#N)c2=O)c1] | I-120 | A | 2.24 | 504 | |
| 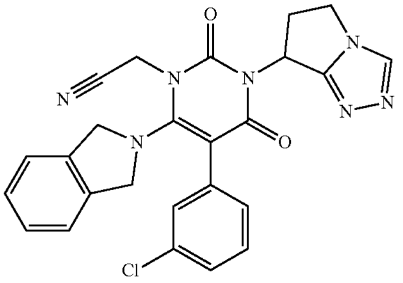 [SMILES: N#CCn1c(N2Cc3ccccc3C2)c(-c2cccc(Cl)c2)c(=O)n(C2CCn3cnnc32)c1=O] | I-121 | D | 2.00 | 486 | d |
| 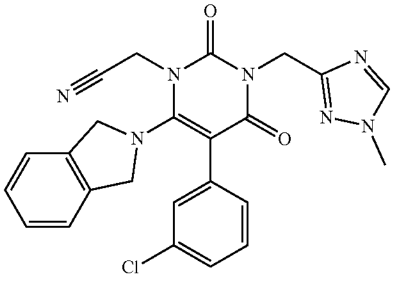 [SMILES: Cn1cnc(Cn2c(=O)c(-c3cccc(Cl)c3)c(N3Cc4ccccc4C3)n(CC#N)c2=O)n1] | I-122 | D | 2.05 | 474 | |
TABLE 25
| Structure | Compound No. | LC/MS measurement condition | Retention time(min) | m/z | Configu-ration |
|---|---|---|---|---|---|
| 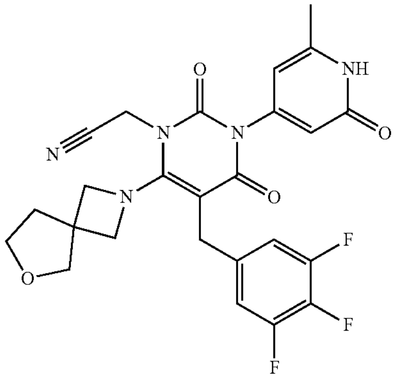 [SMILES: Cc1cc(-n2c(=O)c(Cc3cc(F)c(F)c(F)c3)c(N3CC4(CCOC4)C3)n(CC#N)c2=O)cc(=O)[nH]1] | I-123 | D | 1.70 | 514 | |

TABLE 25-continued
| Structure | Compound No. | LC/MS measurement condition | Retention time(min) | m/z | Configu-ration |
|---|---|---|---|---|---|
| 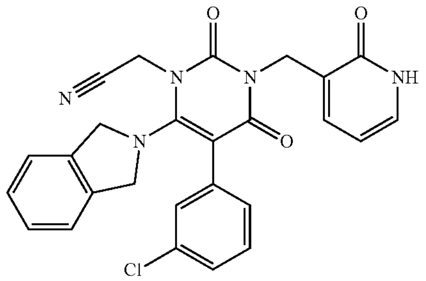 [SMILES: N#CCn1c(N2Cc3ccccc3C2)c(-c2cccc(Cl)c2)c(=O)n(Cc2ccc[nH]c2=O)c1=O] | I-124 | D | 2.07 | 486 | |
| 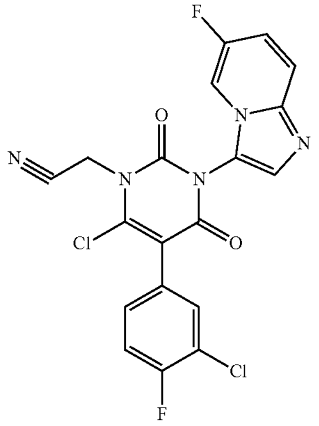 [SMILES: N#CCn1c(Cl)c(-c2ccc(F)c(Cl)c2)c(=O)n(-c2cnc3ccc(F)cn23)c1=O] | I-125 | D | 1.92 | 448 | |
| 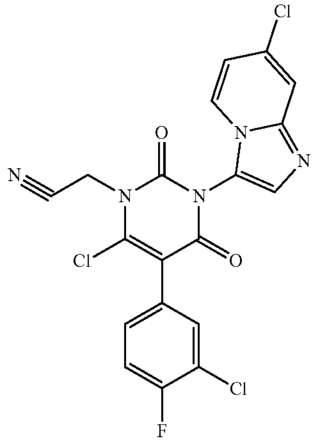 [SMILES: N#CCn1c(Cl)c(-c2ccc(F)c(Cl)c2)c(=O)n(-c2cnc3cc(Cl)ccn23)c1=O] | I-126 | A | 2.02 | 464 | |

TABLE 25-continued
| Structure | Compound No. | LC/MS measurement condition | Retention time(min) | m/z | Configu-ration |
|---|---|---|---|---|---|
| 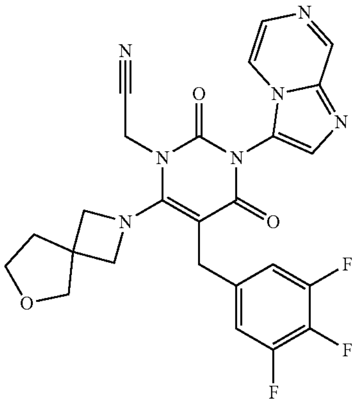 [SMILES: N#CCn1c(N2CC3(CCOC3)C2)c(Cc2cc(F)c(F)c(F)c2)c(=O)n(-c2cnc3cnccn23)c1=O] | I-127 | A | 1.54 | 524 | |
TABLE 26
| Structure | Compound No. | LC/MS measurement condition | Retention time(min) | m/z | Configu-ration |
|---|---|---|---|---|---|
| 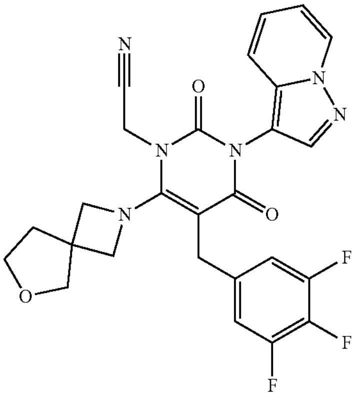 [SMILES: N#CCn1c(N2CC3(CCOC3)C2)c(Cc2cc(F)c(F)c(F)c2)c(=O)n(-c2cnn3ccccc23)c1=O] | I-128 | A | 1.94 | 523 | |
| 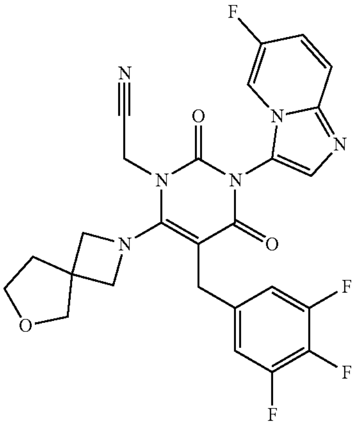 [SMILES: N#CCn1c(N2CC3(CCOC3)C2)c(Cc2cc(F)c(F)c(F)c2)c(=O)n(-c2cnc3ccc(F)cn23)c1=O] | I-129 | D | 1.53 | 541 | |

TABLE 26-continued
| Structure | Compound No. | LC/MS measurement condition | Retention time(min) | m/z | Configu-ration |
|---|---|---|---|---|---|
| 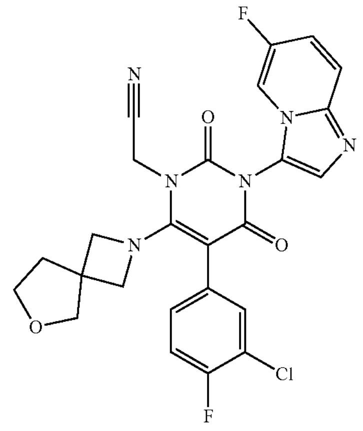 [SMILES: N#CCn1c(N2CC3(CCOC3)C2)c(-c2ccc(F)c(Cl)c2)c(=O)n(-c2cnc3ccc(F)cn23)c1=O] | I-130 | D | 1.61 | 525 | |
| 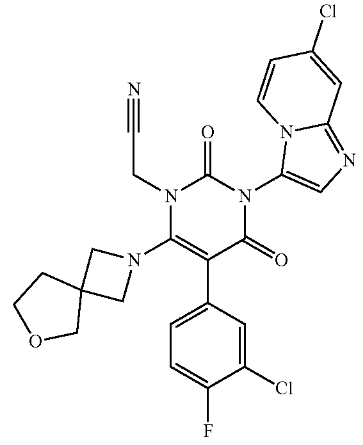 [SMILES: N#CCn1c(N2CC3(CCOC3)C2)c(-c2ccc(F)c(Cl)c2)c(=O)n(-c2cnc3cc(Cl)ccn23)c1=O] | I-131 | A | 1.51 | 543 | |
| 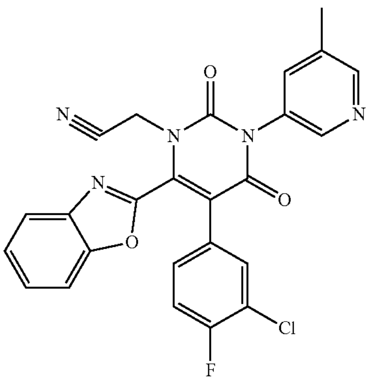 [SMILES: Cc1cncc(-n2c(=O)c(-c3ccc(F)c(Cl)c3)c(-c3nc4ccccc4o3)n(CC#N)c2=O)c1] | I-132 | A | 2.01 | 488 | |

TABLE 27
| Structure | Compound No. | LC/MS measurement condition | Retention time(min) | m/z | Configu-ration |
|---|---|---|---|---|---|
| 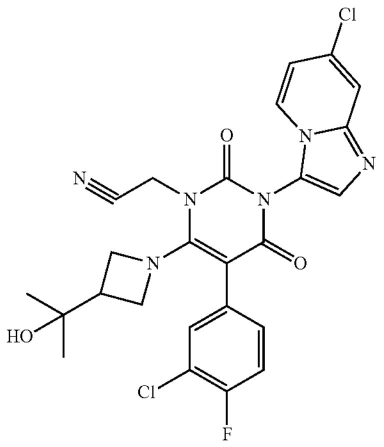 [SMILES: CC(C)(O)C1CN(c2c(-c3ccc(F)c(Cl)c3)c(=O)n(-c3cnc4cc(Cl)ccn34)c(=O)n2CC#N)C1] | I-133 | D | 1.48 | 543 | |
| 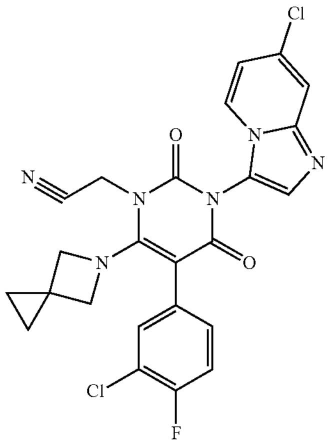 [SMILES: N#CCn1c(N2CC3(CC3)C2)c(-c2ccc(F)c(Cl)c2)c(=O)n(-c2cnc3cc(Cl)ccn23)c1=O] | I-134 | D | 1.74 | 511 | |
| 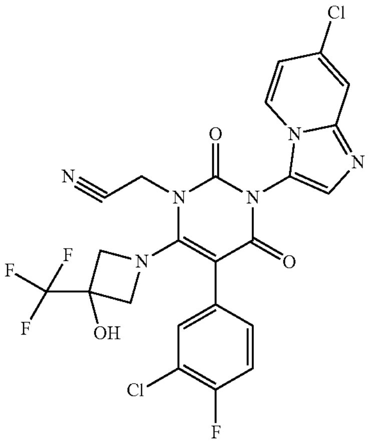 [SMILES: N#CCn1c(N2CC(O)(C(F)(F)F)C2)c(-c2ccc(F)c(Cl)c2)c(=O)n(-c2cnc3cc(Cl)ccn23)c1=O] | I-135 | D | 1.64 | 569 | |

TABLE 27-continued
| Structure | Compound No. | LC/MS measurement condition | Retention time(min) | m/z | Configu-ration |
|---|---|---|---|---|---|
| 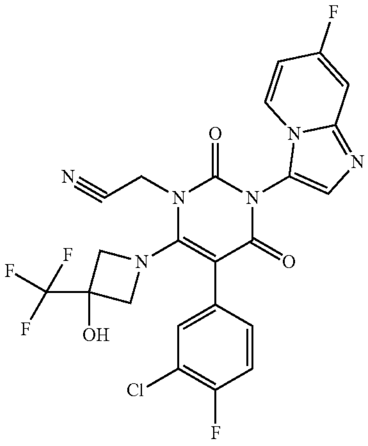 [SMILES: N#CCn1c(N2CC(O)(C(F)(F)F)C2)c(-c2ccc(F)c(Cl)c2)c(=O)n(-c2cnc3cc(F)ccn23)c1=O] | I-136 | D | 1.44 | 553 | |
| 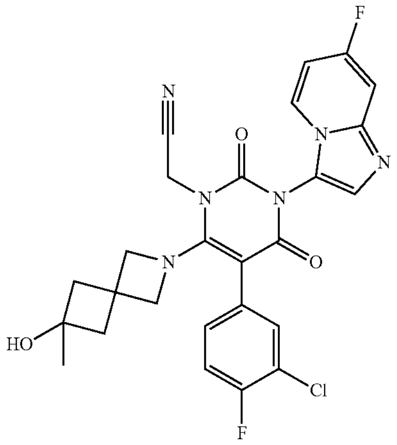 [SMILES: CC1(O)CC2(CN(c3c(-c4ccc(F)c(Cl)c4)c(=O)n(-c4cnc5cc(F)ccn45)c(=O)n3CC#N)C2)C1] | I-137 | D | 1.47 | 539 | |
TABLE 28
| Structure | Compound No. | LC/MS measurement condition | Retention time(min) | m/z | Configu-ration |
|---|---|---|---|---|---|
| 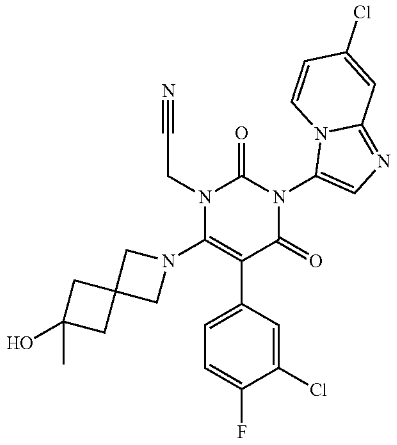 | I-138 | D | 1.41 | 555 | |

TABLE 28-continued
| Structure | Compound No. | LC/MS measurement condition | Retention time(min) | m/z | Configu-ration |
|---|---|---|---|---|---|
| 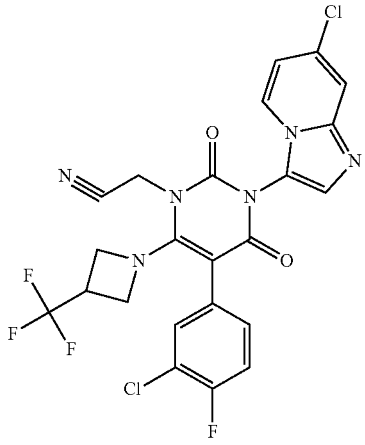 [SMILES: N#CCn1c(N2CC(C(F)(F)F)C2)c(-c2ccc(F)c(Cl)c2)c(=O)n(-c2cnc3cc(Cl)ccn23)c1=O] | I-139 | D | 1.79 | 553 | |
| 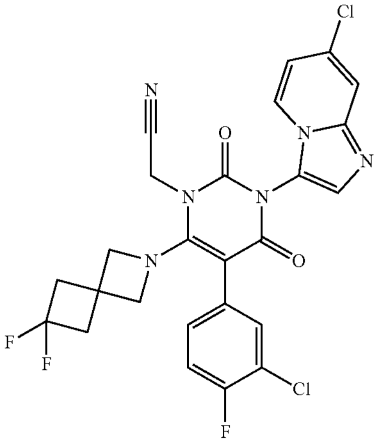 [SMILES: N#CCn1c(N2CC3(C2)CC(F)(F)C3)c(-c2ccc(F)c(Cl)c2)c(=O)n(-c2cnc3cc(Cl)ccn23)c1=O] | I-140 | D | 1.80 | 561 | |
| 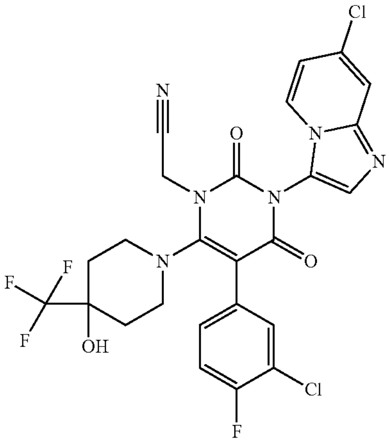 [SMILES: N#CCn1c(N2CCC(O)(C(F)(F)F)CC2)c(-c2ccc(F)c(Cl)c2)c(=O)n(-c2cnc3cc(Cl)ccn23)c1=O] | I-141 | D | 2.00 | 597 | |

TABLE 28-continued
| Structure | Compound No. | LC/MS measurement condition | Retention time(min) | m/z | Configu-ration |
|---|---|---|---|---|---|
| 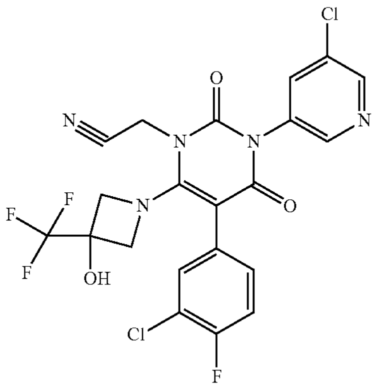 [SMILES: N#CCn1c(N2CC(O)(C(F)(F)F)C2)c(-c2ccc(F)c(Cl)c2)c(=O)n(-c2cncc(Cl)c2)c1=O] | I-142 | D | 1.89 | 530 | |
TABLE 29
| Structure | Compound No. | LC/MS measurement condition | Retention time(min) | m/z | Configu-ration |
|---|---|---|---|---|---|
| 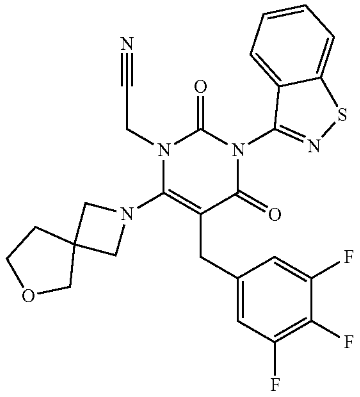 [SMILES: N#CCn1c(N2CC3(CCOC3)C2)c(Cc2cc(F)c(F)c(F)c2)c(=O)n(-c2nsc3ccccc23)c1=O] | I-143 | D | 2.02 | 540 | |
| 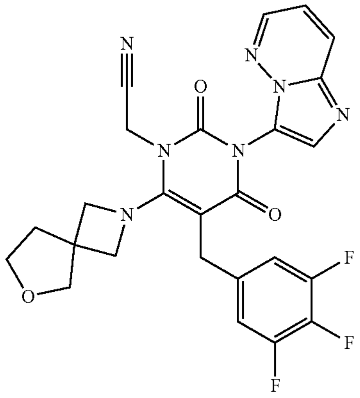 [SMILES: N#CCn1c(N2CC3(CCOC3)C2)c(Cc2cc(F)c(F)c(F)c2)c(=O)n(-c2cnc3cccnn23)c1=O] | I-144 | D | 1.56 | 524 | |

TABLE 29-continued
| Structure | Compound No. | LC/MS measurement condition | Retention time(min) | m/z | Configu-ration |
|---|---|---|---|---|---|
| 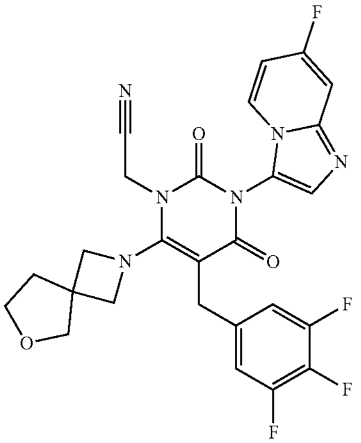 [SMILES: N#CCn1c(N2CC3(CCOC3)C2)c(Cc2cc(F)c(F)c(F)c2)c(=O)n(-c2cnc3cc(F)ccn23)c1=O] | I-145 | D | 1.43 | 541 | |
| 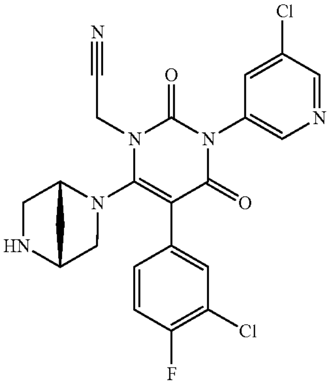 [SMILES: N#CCn1c(N2C[C@H]3C[C@@H]2CN3)c(-c2ccc(F)c(Cl)c2)c(=O)n(-c2cncc(Cl)c2)c1=O] | I-146 | D | 1.03 | 487 | c |
| 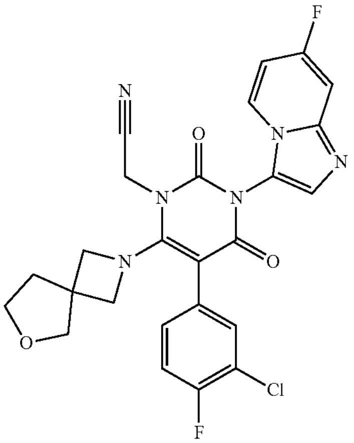 [SMILES: N#CCn1c(N2CC3(CCOC3)C2)c(-c2ccc(F)c(Cl)c2)c(=O)n(-c2cnc3cc(F)ccn23)c1=O] | I-147 | D | 1.29 | 525 | |

TABLE 30
| Structure | Compound No. | LC/MS measurement condition | Retention time(min) | m/z | Configu-ration |
|---|---|---|---|---|---|
| 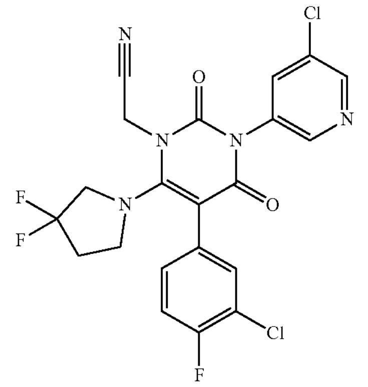 [SMILES: N#CCn1c(N2CCC(F)(F)C2)c(-c2ccc(F)c(Cl)c2)c(=O)n(-c2cncc(Cl)c2)c1=O] | I-148 | D | 2.07 | 496 | |
| 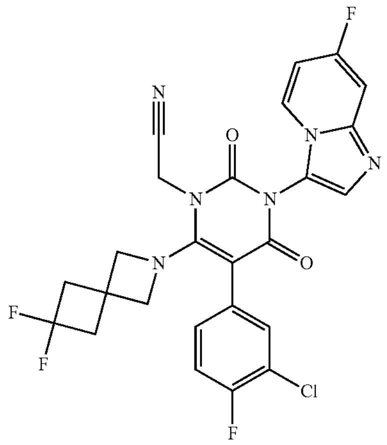 [SMILES: N#CCn1c(N2CC3(C2)CC(F)(F)C3)c(-c2ccc(F)c(Cl)c2)c(=O)n(-c2cnc3cc(F)ccn23)c1=O] | I-149 | D | 1.59 | 545 | |
| 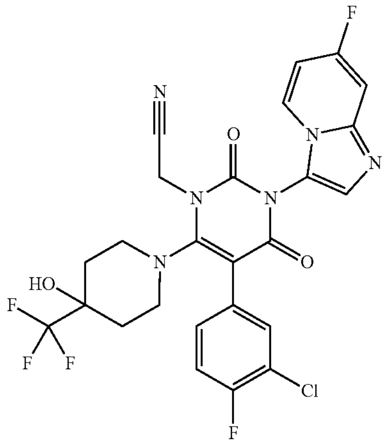 [SMILES: N#CCn1c(N2CCC(O)(C(F)(F)F)CC2)c(-c2ccc(F)c(Cl)c2)c(=O)n(-c2cnc3cc(F)ccn23)c1=O] | I-150 | D | 1.56 | 581 | |

TABLE 30-continued
| Structure | Compound No. | LC/MS measurement condition | Retention time(min) | m/z | Configu-ration |
|---|---|---|---|---|---|
| 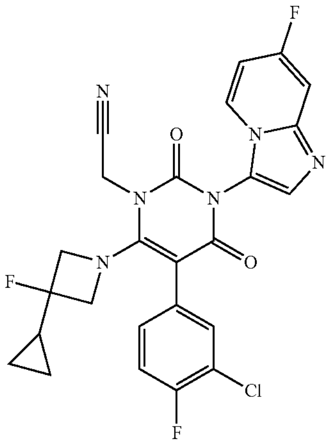 [SMILES: N#CCn1c(N2CC(F)(C3CC3)C2)c(-c2ccc(F)c(Cl)c2)c(=O)n(-c2cnc3cc(F)ccn23)c1=O] | I-151 | D | 1.65 | 527 | |
| 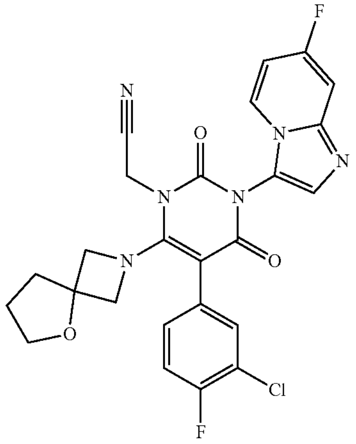 [SMILES: N#CCn1c(N2CC3(CCCO3)C2)c(-c2ccc(F)c(Cl)c2)c(=O)n(-c2cnc3cc(F)ccn23)c1=O] | I-152 | D | 1.44 | 525 | |
TABLE 31
| Structure | Compound No. | LC/MS measurement condition | Retention time(min) | m/z | Configu-ration |
|---|---|---|---|---|---|
| 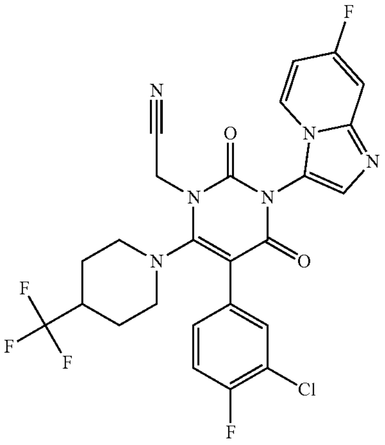 [SMILES: N#CCn1c(N2CCC(C(F)(F)F)CC2)c(-c2ccc(F)c(Cl)c2)c(=O)n(-c2cnc3cc(F)ccn23)c1=O] | I-153 | D | 1.89 | 565 | |

TABLE 31-continued
| Structure | Compound No. | LC/MS measurement condition | Retention time(min) | m/z | Configuration |
|---|---|---|---|---|---|
| 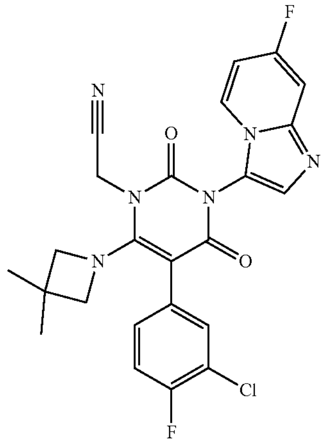 [SMILES: CC1(C)CN(c2c(-c3ccc(F)c(Cl)c3)c(=O)n(-c3cnc4cc(F)ccn34)c(=O)n2CC#N)C1] | I-154 | D | 1.58 | 497 | |
| 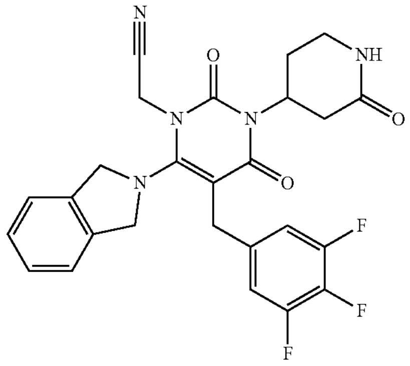 [SMILES: N#CCn1c(N2Cc3ccccc3C2)c(Cc2cc(F)c(F)c(F)c2)c(=O)n(C2CCNC(=O)C2)c1=O] | I-155 | A | 2.23 | 510 | d |
| 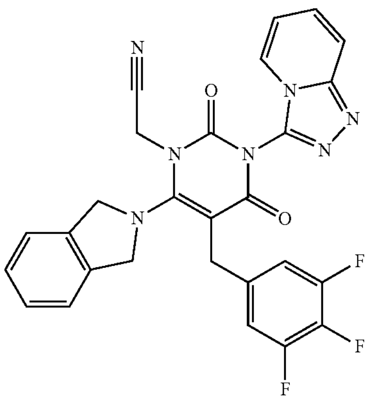 [SMILES: N#CCn1c(N2Cc3ccccc3C2)c(Cc2cc(F)c(F)c(F)c2)c(=O)n(-c2nnc3ccccn23)c1=O] | I-156 | A | 2.30 | 530 | |

TABLE 31-continued
| Structure | Compound No. | LC/MS measurement condition | Retention time(min) | m/z | Configu-ration |
|---|---|---|---|---|---|
| 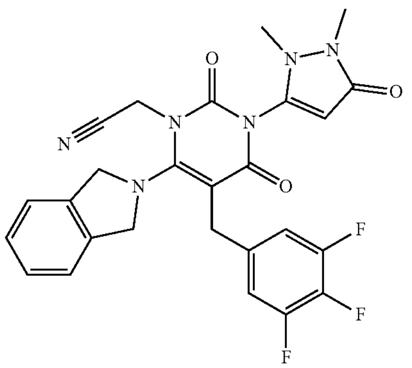 [SMILES: Cn1c(-n2c(=O)c(Cc3cc(F)c(F)c(F)c3)c(N3Cc4ccccc4C3)n(CC#N)c2=O)cc(=O)n1C] | I-157 | A | 2.11 | 523 | |
TABLE 32
| Structure | Compound No. | LC/MS measurement condition | Retention time(min) | m/z | Configu-ration |
|---|---|---|---|---|---|
| 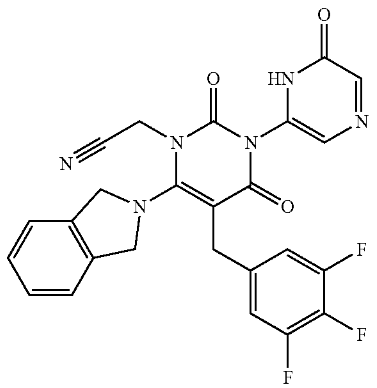 [SMILES: N#CCn1c(N2Cc3ccccc3C2)c(Cc2cc(F)c(F)c(F)c2)c(=O)n(-c2cncc(=O)[nH]2)c1=O] | I-158 | A | 2.30 | 507 | |
| 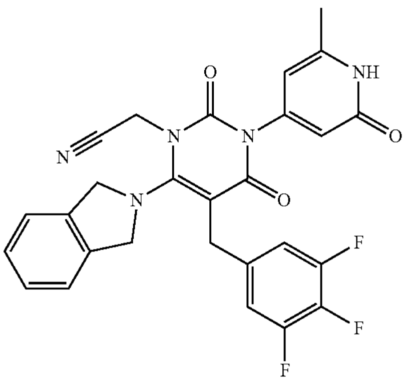 [SMILES: Cc1cc(-n2c(=O)c(Cc3cc(F)c(F)c(F)c3)c(N3Cc4ccccc4C3)n(CC#N)c2=O)cc(=O)[nH]1] | I-159 | D | 2.19 | 520 | |

TABLE 32-continued
| Structure | Compound No. | LC/MS measurement condition | Retention time(min) | m/z | Configu-ration |
|---|---|---|---|---|---|
| 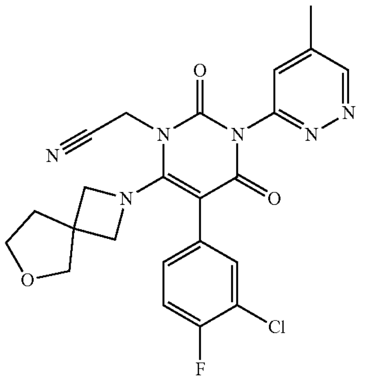 [SMILES: Cc1cnnc(-n2c(=O)c(-c3ccc(F)c(Cl)c3)c(N3CC4(CCOC4)C3)n(CC#N)c2=O)c1] | I-160 | A | 1.72 | 483 | |
| 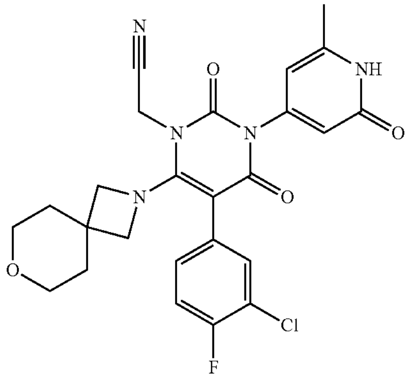 [SMILES: Cc1cc(-n2c(=O)c(-c3ccc(F)c(Cl)c3)c(N3CC4(CCOCC4)C3)n(CC#N)c2=O)cc(=O)[nH]1] | I-161 | A | 1.66 | 512 | |
| 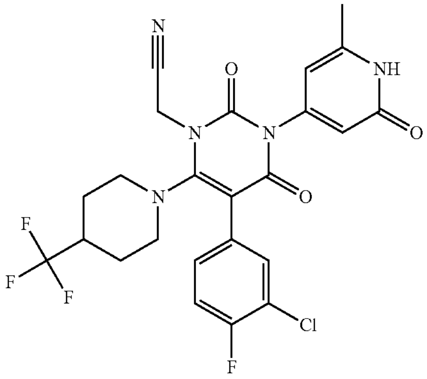 [SMILES: Cc1cc(-n2c(=O)c(-c3ccc(F)c(Cl)c3)c(N3CCC(C(F)(F)F)CC3)n(CC#N)c2=O)cc(=O)[nH]1] | I-162 | A | 2.15 | 538 | |

TABLE 33
| Structure | Compound No. | LC/MS measurement condition | Retention time(min) | m/z | Configu-ration |
|---|---|---|---|---|---|
| 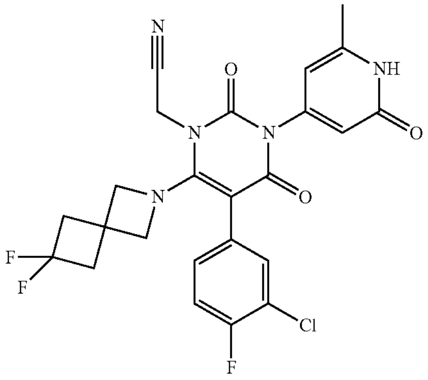 [SMILES: Cc1cc(-n2c(=O)c(-c3ccc(F)c(Cl)c3)c(N3CC4(C3)CC(F)(F)C4)n(CC#N)c2=O)cc(=O)[nH]1] | I-163 | A | 1.93 | 518 | |
| 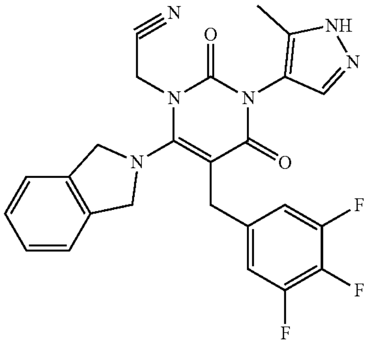 [SMILES: Cc1[nH]ncc1-n1c(=O)c(Cc2cc(F)c(F)c(F)c2)c(N2Cc3ccccc3C2)n(CC#N)c1=O] | I-164 | A | 2.27 | 493 | |
| 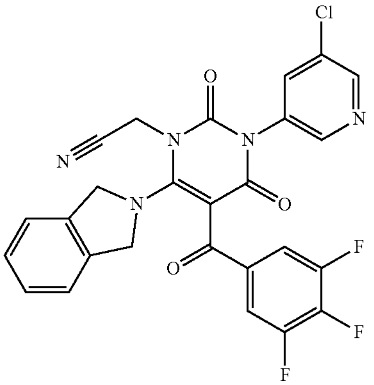 [SMILES: N#CCn1c(N2Cc3ccccc3C2)c(C(=O)c2cc(F)c(F)c(F)c2)c(=O)n(-c2cncc(Cl)c2)c1=O] | I-165 | A | 2.44 | 538 | |
| 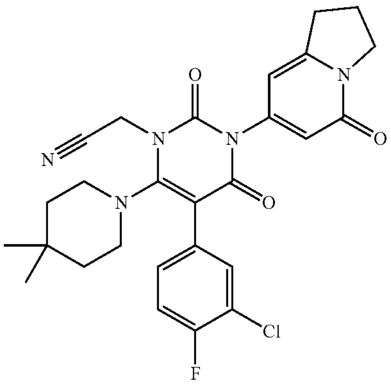 [SMILES: CC1(C)CCN(c2c(-c3ccc(F)c(Cl)c3)c(=O)n(-c3cc4n(c(=O)c3)CCC4)c(=O)n2CC#N)CC1] | I-166 | A | 2.33 | 524 | |

TABLE 33-continued
| Structure | Compound No. | LC/MS measurement condition | Retention time(min) | m/z | Configu-ration |
|---|---|---|---|---|---|
| 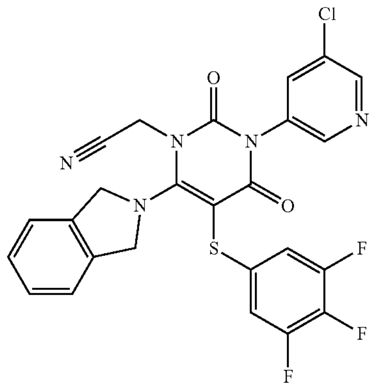 [SMILES: N#CCn1c(N2Cc3ccccc3C2)c(Sc2cc(F)c(F)c(F)c2)c(=O)n(-c2cncc(Cl)c2)c1=O] | I-167 | A | 2.64 | 542 | |
TABLE 34
| Structure | Compound No. | LC/MS measurement condition | Retention time(min) | m/z | Configu-ration |
|---|---|---|---|---|---|
| 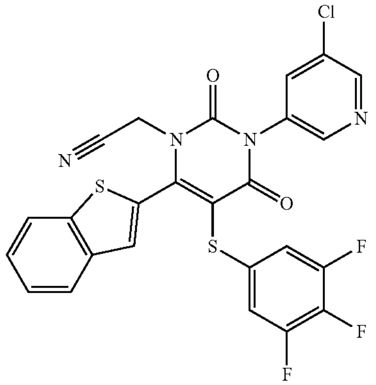 [SMILES: N#CCn1c(-c2cc3ccccc3s2)c(Sc2cc(F)c(F)c(F)c2)c(=O)n(-c2cncc(Cl)c2)c1=O] | I-168 | A | 2.73 | 557 | |
| 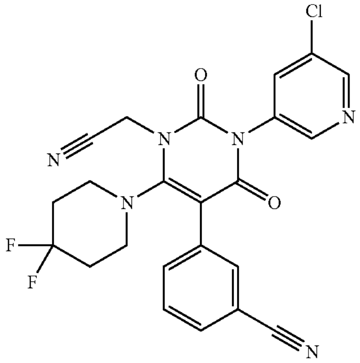 [SMILES: N#CCn1c(N2CCC(F)(F)CC2)c(-c2cccc(C#N)c2)c(=O)n(-c2cncc(Cl)c2)c1=O] | I-169 | A | 2.10 | 483 | |

TABLE 34-continued
| Structure | Compound No. | LC/MS measurement condition | Retention time(min) | m/z | Configu-ration |
|---|---|---|---|---|---|
| 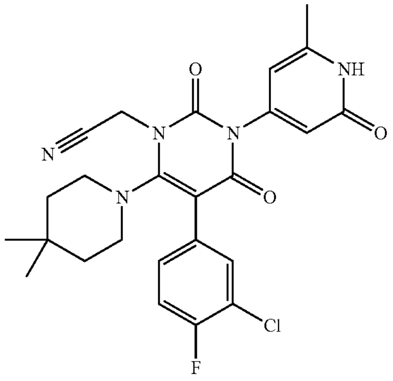 [SMILES: Cc1cc(-n2c(=O)c(-c3ccc(F)c(Cl)c3)c(N3CCC(C)(C)CC3)n(CC#N)c2=O)cc(=O)[nH]1] | I-170 | A | 2.27 | 498 | |
| 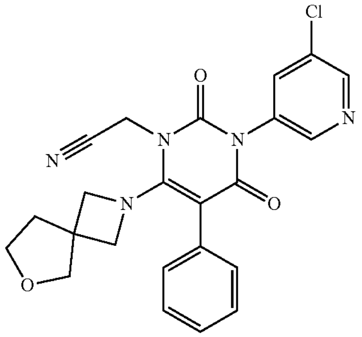 [SMILES: N#CCn1c(N2CC3(CCOC3)C2)c(-c2ccccc2)c(=O)n(-c2cncc(Cl)c2)c1=O] | I-171 | A | 1.79 | 450 | |
| 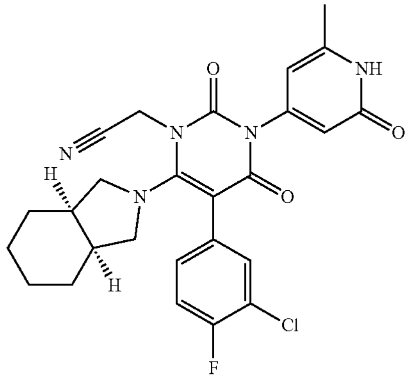 [SMILES: Cc1cc(-n2c(=O)c(-c3ccc(F)c(Cl)c3)c(N3C[C@H]4CCCC[C@H]4C3)n(CC#N)c2=O)cc(=O)[nH]1] | I-172 | A | 2.27 | 510 | c |

TABLE 35
| Structure | Compound No. | LC/MS measurement condition | Retention time(min) | m/z | Configu- ration |
|---|---|---|---|---|---|
| 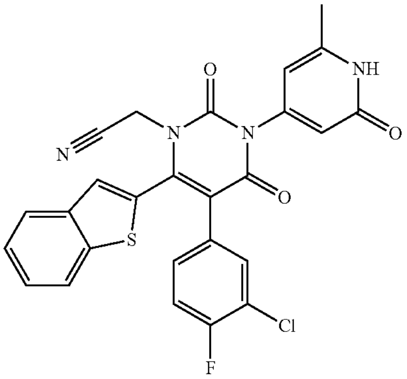 [SMILES: Cc1cc(-n2c(=O)c(-c3ccc(F)c(Cl)c3)c(-c3cc4ccccc4s3)n(CC#N)c2=O)cc(=O)[nH]1] | I-173 | A | 2.14 | 519 | |
| 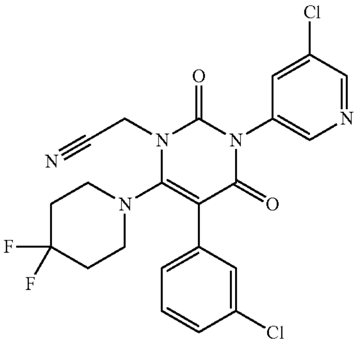 [SMILES: N#CCn1c(N2CCC(F)(F)CC2)c(-c2cccc(Cl)c2)c(=O)n(-c2cncc(Cl)c2)c1=O] | I-174 | A | 2.35 | 492 | |
| 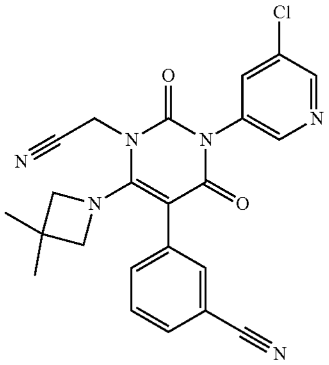 [SMILES: CC1(C)CN(c2c(-c3cccc(C#N)c3)c(=O)n(-c3cncc(Cl)c3)c(=O)n2CC#N)C1] | I-175 | A | 2.26 | 447 | |
| 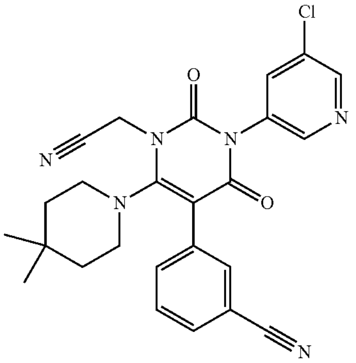 [SMILES: CC1(C)CCN(c2c(-c3cccc(C#N)c3)c(=O)n(-c3cncc(Cl)c3)c(=O)n2CC#N)CC1] | I-176 | A | 2.36 | 475 | |

TABLE 35-continued
| Structure | Compound No. | LC/MS measurement condition | Retention time(min) | m/z | Configu-ration |
|---|---|---|---|---|---|
| 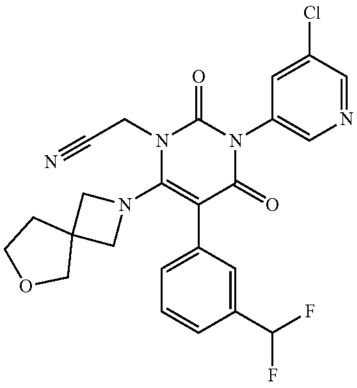 [SMILES: N#CCn1c(N2CC3(CCOC3)C2)c(-c2cccc(C(F)F)c2)c(=O)n(-c2cncc(Cl)c2)c1=O] | I-177 | A | 1.94 | 500 | |
TABLE 36
| Structure | Compound No. | LC/MS measurement condition | Retention time(min) | m/z | Configu-ration |
|---|---|---|---|---|---|
| 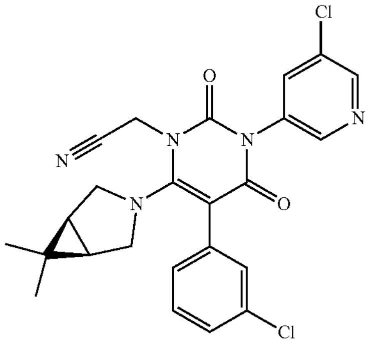 [SMILES: CC1(C)[C@@H]2CN(c3c(-c4cccc(Cl)c4)c(=O)n(-c4cncc(Cl)c4)c(=O)n3CC#N)C[C@@H]21] | I-178 | A | 2.66 | 482 | c |
| 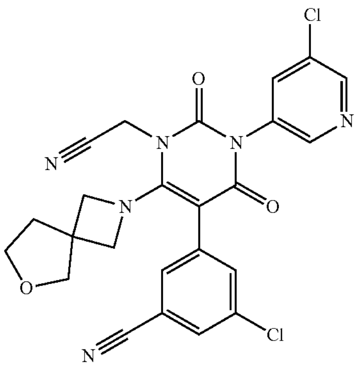 [SMILES: N#CCn1c(N2CC3(CCOC3)C2)c(-c2cc(Cl)cc(C#N)c2)c(=O)n(-c2cncc(Cl)c2)c1=O] | I-179 | A | 1.97 | 509 | |

TABLE 36-continued
| Structure | Compound No. | LC/MS measurement condition | Retention time(min) | m/z | Configu-ration |
|---|---|---|---|---|---|
| 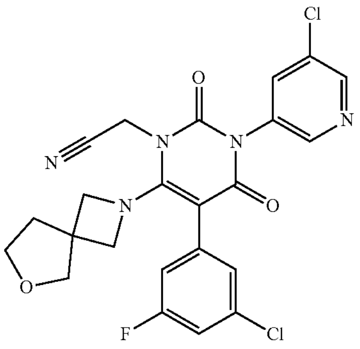 [SMILES: N#CCn1c(N2CC3(CCOC3)C2)c(-c2cc(F)cc(Cl)c2)c(=O)n(-c2cncc(Cl)c2)c1=O] | I-180 | A | 2.05 | 502 | |
| 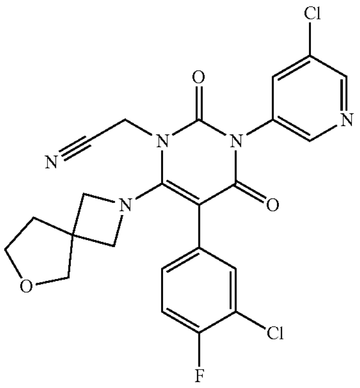 | I-181 | A | 2.04 | 502 | |
| 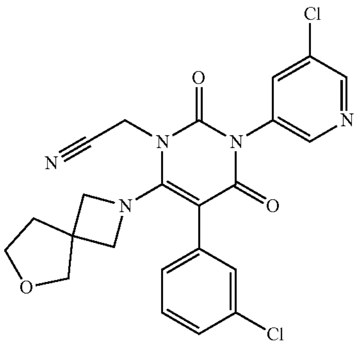 [SMILES: N#CCn1c(N2CC3(CCOC3)C2)c(-c2cccc(Cl)c2)c(=O)n(-c2cncc(Cl)c2)c1=O] | I-182 | A | 1.99 | 484 | |

TABLE 37
| Structure | Compound No. | LC/MS measurement condition | Retention time(min) | m/z | Configu-ration |
|---|---|---|---|---|---|
| 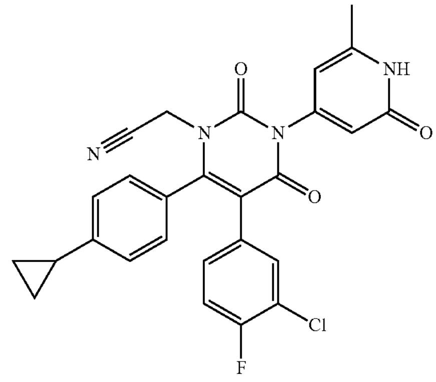 [SMILES: Cc1cc(-n2c(=O)c(-c3ccc(F)c(Cl)c3)c(-c3ccc(C4CC4)cc3)n(CC#N)c2=O)cc(=O)[nH]1] | I-183 | A | 2.19 | 503 | |
| 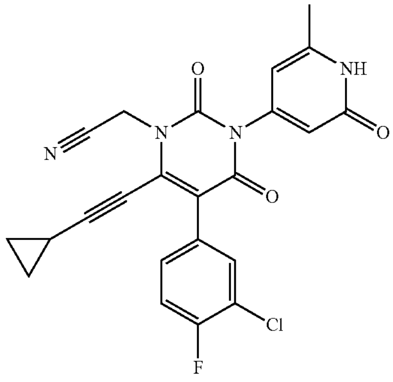 [SMILES: Cc1cc(-n2c(=O)c(-c3ccc(F)c(Cl)c3)c(C#CC3CC3)n(CC#N)c2=O)cc(=O)[nH]1] | I-184 | A | 1.97 | 451 | |
| 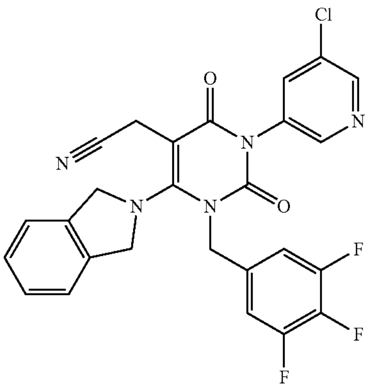 [SMILES: N#CCc1c(N2Cc3ccccc3C2)n(Cc2cc(F)c(F)c(F)c2)c(=O)n(-c2cncc(Cl)c2)c1=O] | I-185 | A | 2.54 | 524 | |

TABLE 37-continued
| Structure | Compound No. | LC/MS measurement condition | Retention time(min) | m/z | Configu-ration |
|---|---|---|---|---|---|
| 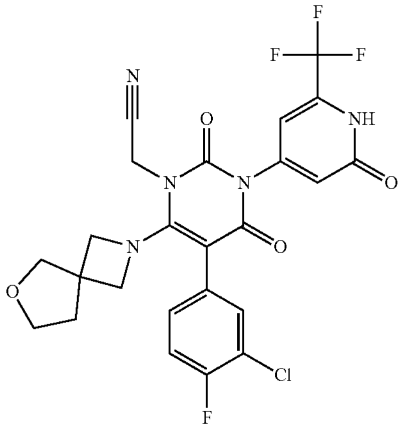 [SMILES: N#CCn1c(N2CC3(CCOC3)C2)c(-c2ccc(F)c(Cl)c2)c(=O)n(-c2cc(C(F)(F)F)[nH]c(=O)c2)c1=O] | I-186 | D | 1.78 | 552 | |
| 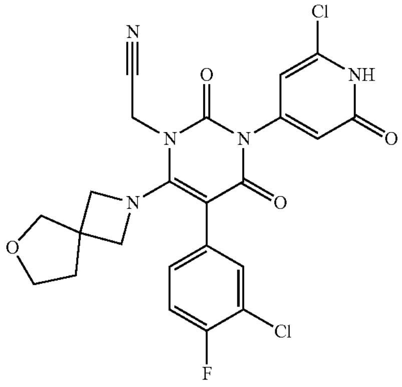 [SMILES: N#CCn1c(N2CC3(CCOC3)C2)c(-c2ccc(F)c(Cl)c2)c(=O)n(-c2cc(Cl)[nH]c(=O)c2)c1=O] | I-187 | D | 1.69 | 518 | |
TABLE 38
| Structure | Compound No. | LC/MS measurement condition | Retention time(min) | m/z | Configu-ration |
|---|---|---|---|---|---|
| 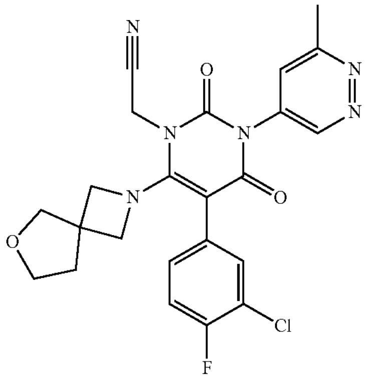 [SMILES: Cc1cc(-n2c(=O)c(-c3ccc(F)c(Cl)c3)c(N3CC4(CCOC4)C3)n(CC#N)c2=O)cnn1] | I-188 | D | 1.49 | 483 | |

TABLE 38-continued
| Structure | Compound No. | LC/MS measurement condition | Retention time(min) | m/z | Configu-ration |
|---|---|---|---|---|---|
| 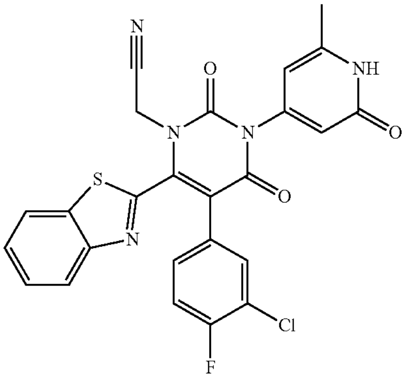 [SMILES: Cc1cc(-n2c(=O)c(-c3ccc(F)c(Cl)c3)c(-c3nc4ccccc4s3)n(CC#N)c2=O)cc(=O)[nH]1] | I-189 | D | 1.81 | 520 | |
| 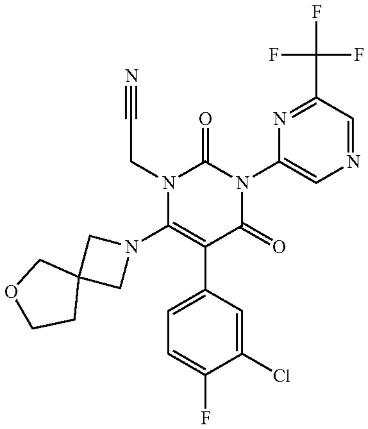 [SMILES: N#CCn1c(N2CC3(CCOC3)C2)c(-c2ccc(F)c(Cl)c2)c(=O)n(-c2cncc(C(F)(F)F)n2)c1=O] | I-190 | D | 2.00 | 537 | |
| 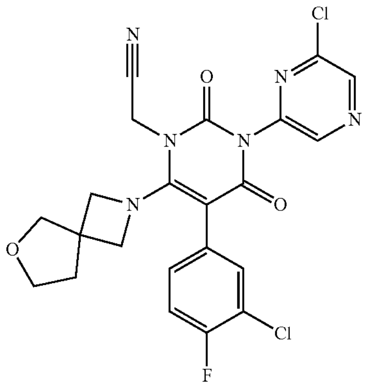 [SMILES: N#CCn1c(N2CC3(CCOC3)C2)c(-c2ccc(F)c(Cl)c2)c(=O)n(-c2cncc(Cl)n2)c1=O] | I-191 | D | 1.85 | 503 | |

TABLE 38-continued
| Structure | Compound No. | LC/MS measurement condition | Retention time(min) | m/z | Configu-ration |
|---|---|---|---|---|---|
| 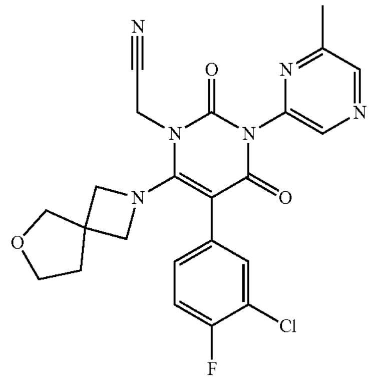 [SMILES: Cc1cncc(-n2c(=O)c(-c3ccc(F)c(Cl)c3)c(N3CC4(CCOC4)C3)n(CC#N)c2=O)n1] | I-192 | D | 1.60 | 483 | |
TABLE 39
| Structure | Compound No. | LC/MS measurement condition | Retention time(min) | m/z | Configu-ration |
|---|---|---|---|---|---|
| 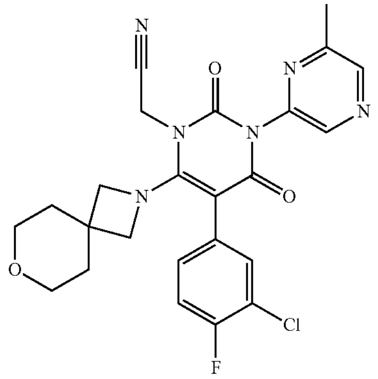 [SMILES: Cc1cncc(-n2c(=O)c(-c3ccc(F)c(Cl)c3)c(N3CC4(CCOCC4)C3)n(CC#N)c2=O)n1] | I-193 | D | 1.66 | 497 | |
| 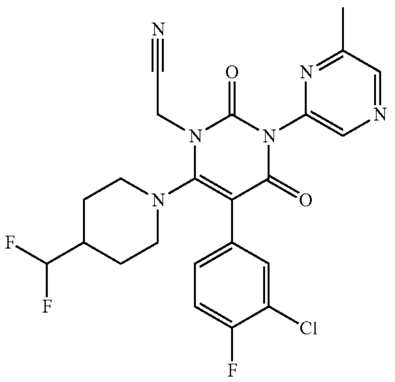 [SMILES: Cc1cncc(-n2c(=O)c(-c3ccc(F)c(Cl)c3)c(N3CCC(C(F)F)CC3)n(CC#N)c2=O)n1] | I-194 | D | 2.04 | 505 | |

TABLE 39-continued
| Structure | Compound No. | LC/MS measurement condition | Retention time(min) | m/z | Configu-ration |
|---|---|---|---|---|---|
| 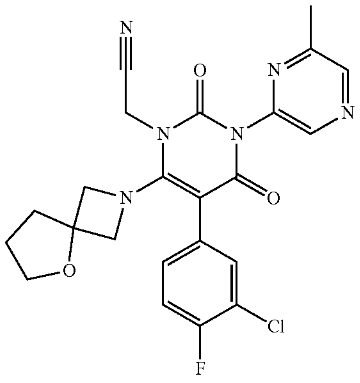 [SMILES: Cc1cncc(-n2c(=O)c(-c3ccc(F)c(Cl)c3)c(N3CC4(CCCO4)C3)n(CC#N)c2=O)n1] | I-195 | D | 1.78 | 483 | |
| 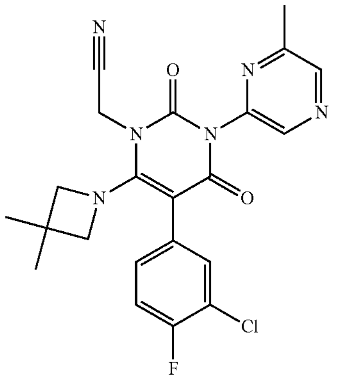 [SMILES: Cc1cncc(-n2c(=O)c(-c3ccc(F)c(Cl)c3)c(N3CC(C)(C)C3)n(CC#N)c2=O)n1] | I-196 | D | 1.97 | 455 | |
| 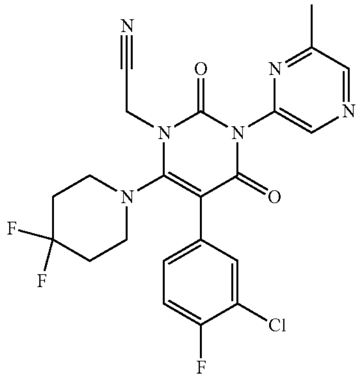 [SMILES: Cc1cncc(-n2c(=O)c(-c3ccc(F)c(Cl)c3)c(N3CCC(F)(F)CC3)n(CC#N)c2=O)n1] | I-197 | D | 1.98 | 491 | |

TABLE 40
| Structure | Compound No. | LC/MS measurement condition | Retention time(min) | m/z | Configu-ration |
|---|---|---|---|---|---|
| 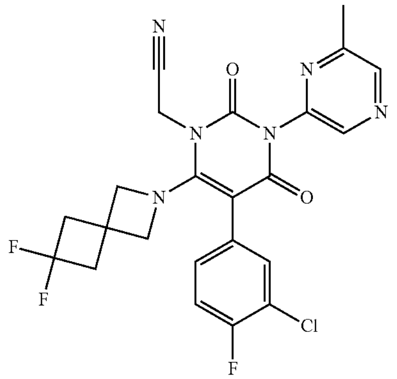 [SMILES: Cc1cncc(-n2c(=O)c(-c3ccc(F)c(Cl)c3)c(N3CC4(C3)CC(F)(F)C4)n(CC#N)c2=O)n1] | I-198 | D | 1.92 | 503 | |
| 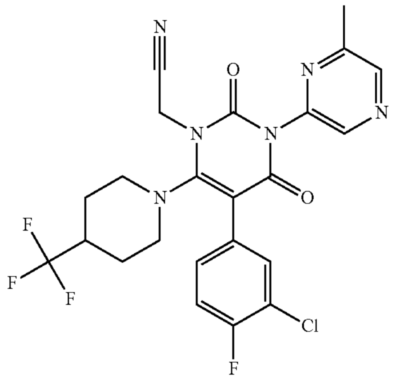 [SMILES: Cc1cncc(-n2c(=O)c(-c3ccc(F)c(Cl)c3)c(N3CCC(C(F)(F)F)CC3)n(CC#N)c2=O)n1] | I-199 | D | 2.16 | 523 | |
| 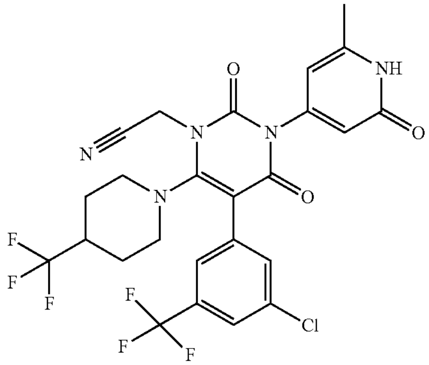 [SMILES: Cc1cc(-n2c(=O)c(-c3cc(Cl)cc(C(F)(F)F)c3)c(N3CCC(C(F)(F)F)CC3)n(CC#N)c2=O)cc(=O)[nH]1] | I-200 | A | 2.33 | 588 | |
| 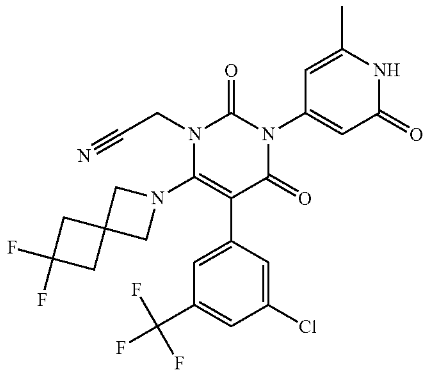 [SMILES: Cc1cc(-n2c(=O)c(-c3cc(Cl)cc(C(F)(F)F)c3)c(N3CC4(C3)CC(F)(F)C4)n(CC#N)c2=O)cc(=O)[nH]1] | I-201 | A | 2.13 | 568 | |

TABLE 40-continued
| Structure | Compound No. | LC/MS measurement condition | Retention time(min) | m/z | Configu-ration |
|---|---|---|---|---|---|
| 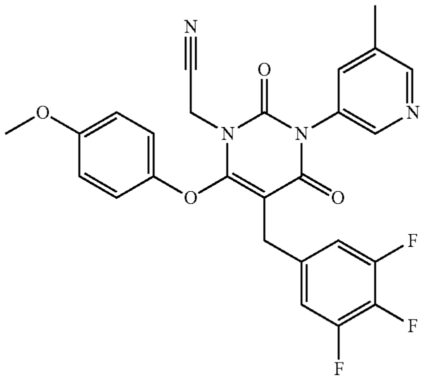 [SMILES: COc1ccc(Oc2c(Cc3cc(F)c(F)c(F)c3)c(=O)n(-c3cncc(C)c3)c(=O)n2CC#N)cc1] | I-202 | A | 2.34 | 509 | |
TABLE 41
| Structure | Compound No. | LC/MS measurement condition | Retention time(min) | m/z | Configu-ration |
|---|---|---|---|---|---|
| 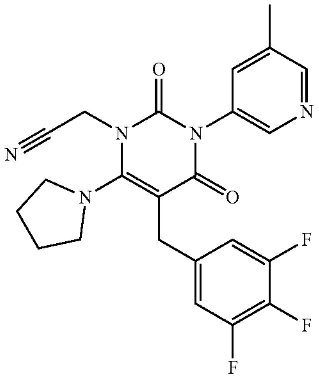 [SMILES: Cc1cncc(-n2c(=O)c(Cc3cc(F)c(F)c(F)c3)c(N3CCCC3)n(CC#N)c2=O)c1] | I-203 | A | 2.13 | 456 | |
| 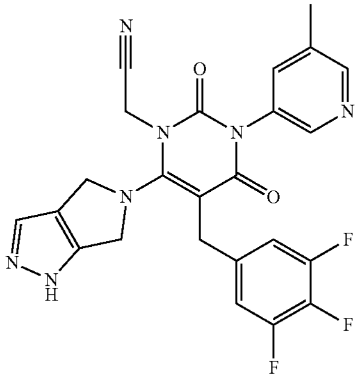 [SMILES: Cc1cncc(-n2c(=O)c(Cc3cc(F)c(F)c(F)c3)c(N3Cc4cn[nH]c4C3)n(CC#N)c2=O)c1] | I-204 | A | 1.72 | 494 | |

TABLE 41-continued
| Structure | Compound No. | LC/MS measurement condition | Retention time(min) | m/z | Configu-ration |
|---|---|---|---|---|---|
| 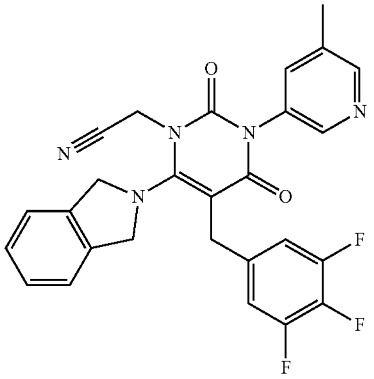 [SMILES: Cc1cncc(-n2c(=O)c(Cc3cc(F)c(F)c(F)c3)c(N3Cc4ccccc4C3)n(CC#N)c2=O)c1] | I-205 | A | 2.41 | 504 | |
TABLE 42
| Structure | Compound No. | LC/MS measurement condition | Retention time(min) | m/z | Configu-ration |
|---|---|---|---|---|---|
| 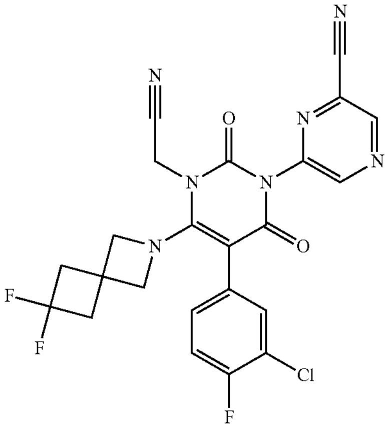 [SMILES: N#CCn1c(N2CC3(C2)CC(F)(F)C3)c(-c2ccc(F)c(Cl)c2)c(=O)n(-c2cncc(C#N)n2)c1=O] | I-206 | D | 2.05 | 514.1 | |
| 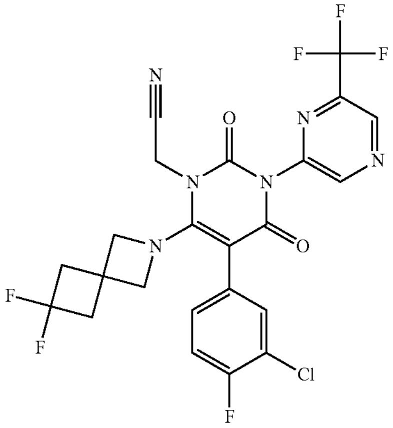 [SMILES: N#CCn1c(N2CC3(C2)CC(F)(F)C3)c(-c2ccc(F)c(Cl)c2)c(=O)n(-c2cncc(C(F)(F)F)n2)c1=O] | I-207 | D | 2.23 | 557 | |

TABLE 42-continued
| Structure | Compound No. | LC/MS measurement condition | Retention time(min) | m/z | Configu-ration |
|---|---|---|---|---|---|
| 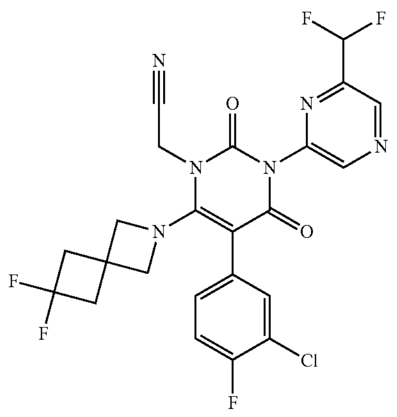 [SMILES: N#CCn1c(N2CC3(C2)CC(F)(F)C3)c(-c2ccc(F)c(Cl)c2)c(=O)n(-c2cncc(C(F)F)n2)c1=O] | I-208 | D | 2.08 | 539.1 | |
| 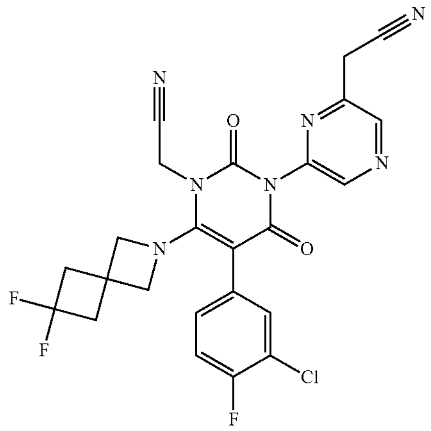 [SMILES: N#CCc1cncc(-n2c(=O)c(-c3ccc(F)c(Cl)c3)c(N3CC4(C3)CC(F)(F)C4)n(CC#N)c2=O)n1] | I-209 | D | 1.91 | 527.9 | |
| 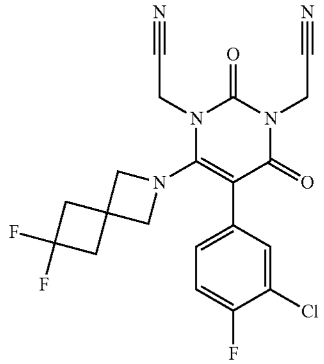 [SMILES: N#CCn1c(N2CC3(C2)CC(F)(F)C3)c(-c2ccc(F)c(Cl)c2)c(=O)n(CC#N)c1=O] | I-210 | D | 2.00 | 449.9 | |

TABLE 43
| Structure | Compound No. | LC/MS measurement condition | Retention time(min) | m/z | Configu-ration |
|---|---|---|---|---|---|
| 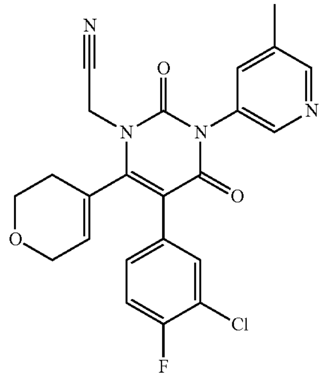 [SMILES: Cc1cncc(-n2c(=O)c(-c3ccc(F)c(Cl)c3)c(C3=CCOCC3)n(CC#N)c2=O)c1] | I-211 | A | 2.10 | 453 | |
| 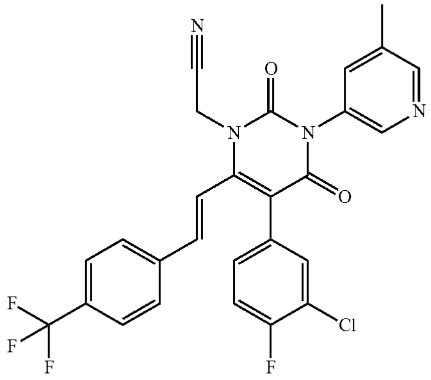 [SMILES: Cc1cncc(-n2c(=O)c(-c3ccc(F)c(Cl)c3)c(/C=C/c3ccc(C(F)(F)F)cc3)n(CC#N)c2=O)c1] | I-212 | A | 2.58 | 541 | |
| 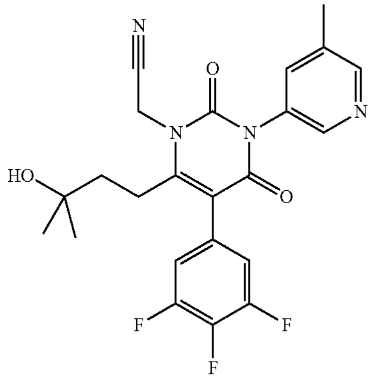 [SMILES: Cc1cncc(-n2c(=O)c(-c3cc(F)c(F)c(F)c3)c(CCC(C)(C)O)n(CC#N)c2=O)c1] | I-213 | A | 2.01 | 459 | |
| 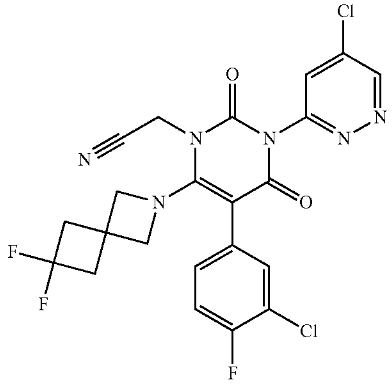 [SMILES: N#CCn1c(N2CC3(C2)CC(F)(F)C3)c(-c2ccc(F)c(Cl)c2)c(=O)n(-c2cc(Cl)cnn2)c1=O] | I-214 | A | 2.22 | 523 | |

TABLE 43-continued
| Structure | Compound No. | LC/MS measurement condition | Retention time(min) | m/z | Configu-ration |
|---|---|---|---|---|---|
| 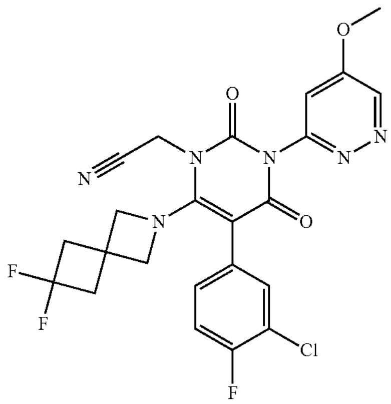 [SMILES: COc1cnnc(-n2c(=O)c(-c3ccc(F)c(Cl)c3)c(N3CC4(C3)CC(F)(F)C4)n(CC#N)c2=O)c1] | I-215 | A | 2.06 | 519 | |
TABLE 44
| Structure | Compound No. | LC/MS measurement condition | Retention time(min) | m/z | Configu-ration |
|---|---|---|---|---|---|
| 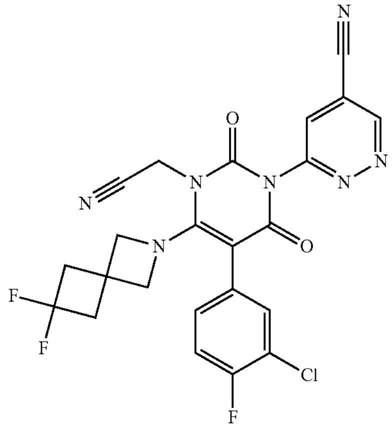 [SMILES: N#CCn1c(N2CC3(C2)CC(F)(F)C3)c(-c2ccc(F)c(Cl)c2)c(=O)n(-c2cc(C#N)cnn2)c1=O] | I-216 | A | 2.23 | 514 | |
| 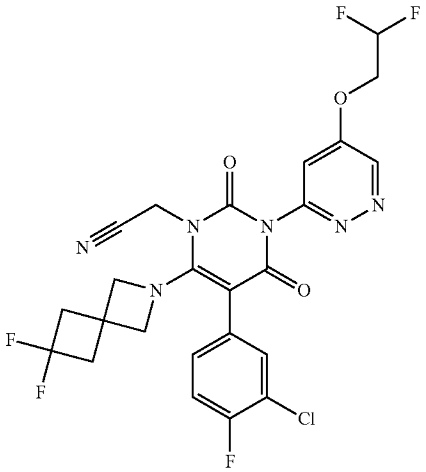 [SMILES: N#CCn1c(N2CC3(C2)CC(F)(F)C3)c(-c2ccc(F)c(Cl)c2)c(=O)n(-c2cc(OCC(F)F)cnn2)c1=O] | I-217 | A | 2.22 | 569 | |

TABLE 44-continued
| Structure | Compound No. | LC/MS measurement condition | Retention time(min) | m/z | Configu-ration |
|---|---|---|---|---|---|
| 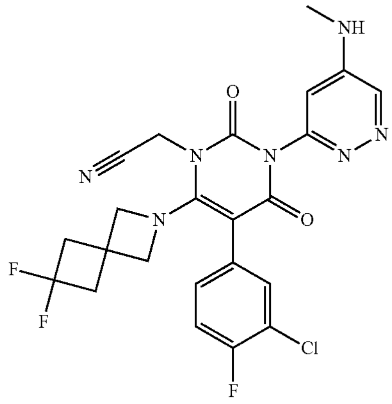 [SMILES: CNc1cnnc(-n2c(=O)c(-c3ccc(F)c(Cl)c3)c(N3CC4(C3)CC(F)(F)C4)n(CC#N)c2=O)c1] | I-218 | A | 1.92 | 518 | |
| 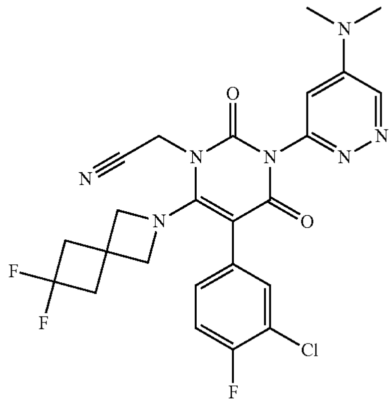 [SMILES: CN(C)c1cnnc(-n2c(=O)c(-c3ccc(F)c(Cl)c3)c(N3CC4(C3)CC(F)(F)C4)n(CC#N)c2=O)c1] | I-219 | A | 1.97 | 532 | |
| 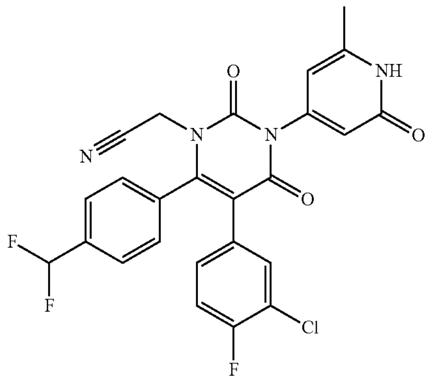 [SMILES: Cc1cc(-n2c(=O)c(-c3ccc(F)c(Cl)c3)c(-c3ccc(C(F)F)cc3)n(CC#N)c2=O)cc(=O)[nH]1] | I-220 | A | 2.03 | 513 | |

TABLE 45
| Structure | Compound No. | LC/MS measurement condition | Retention time(min) | m/z | Configu-ration |
|---|---|---|---|---|---|
| 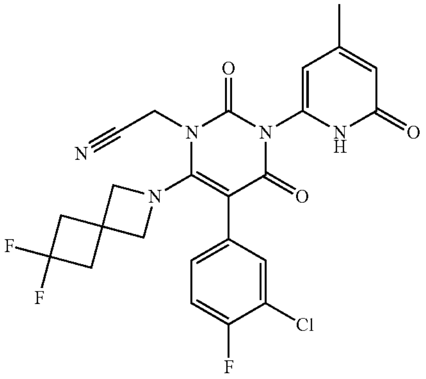 [SMILES: Cc1cc(-n2c(=O)c(-c3ccc(F)c(Cl)c3)c(N3CC4(C3)CC(F)(F)C4)n(CC#N)c2=O)[nH]c(=O)c1] | I-221 | A | 2.03 | 518 | |
| 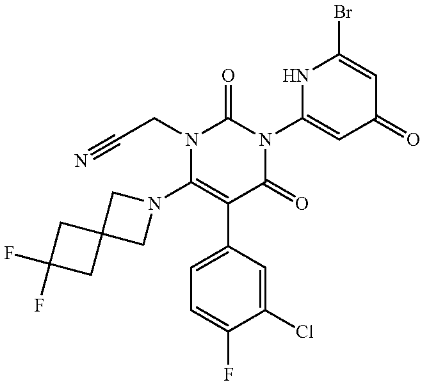 [SMILES: N#CCn1c(N2CC3(C2)CC(F)(F)C3)c(-c2ccc(F)c(Cl)c2)c(=O)n(-c2cc(=O)cc(Br)[nH]2)c1=O] | I-222 | A | 2.29 | 582 | |
| 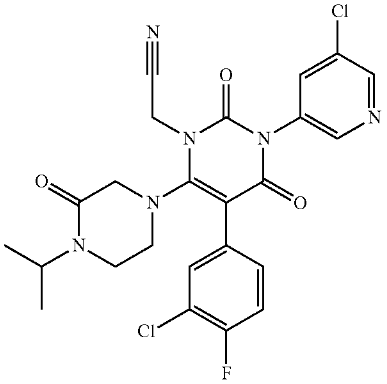 [SMILES: CC(C)N1CCN(c2c(-c3ccc(F)c(Cl)c3)c(=O)n(-c3cncc(Cl)c3)c(=O)n2CC#N)CC1=O] | I-223 | B | 2.05 | 531 | |
| 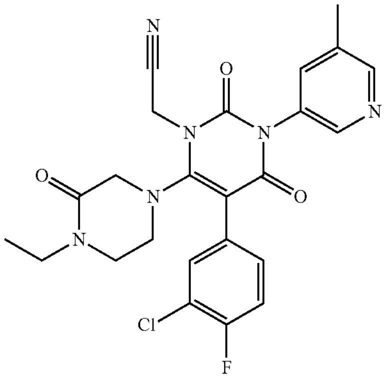 [SMILES: CCN1CCN(c2c(-c3ccc(F)c(Cl)c3)c(=O)n(-c3cncc(C)c3)c(=O)n2CC#N)CC1=O] | I-224 | A | 1.69 | 497 | |

TABLE 45-continued
| Structure | Compound No. | LC/MS measurement condition | Retention time(min) | m/z | Configu-ration |
|---|---|---|---|---|---|
| 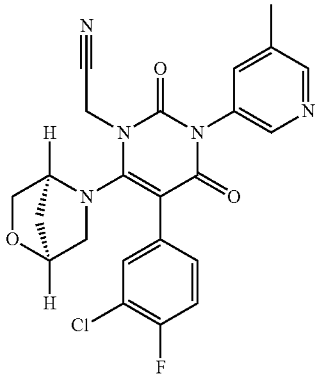 [SMILES: Cc1cncc(-n2c(=O)c(-c3ccc(F)c(Cl)c3)c(N3C[C@@H]4C[C@H]3CO4)n(CC#N)c2=O)c1] | I-225 | A | 1.70 | 468 | c |
TABLE 46
| Structure | Compound No. | LC/MS measurement condition | Retention time(min) | m/z | Configu-ration |
|---|---|---|---|---|---|
| 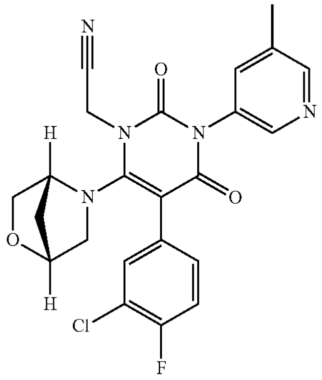 [SMILES: Cc1cncc(-n2c(=O)c(-c3ccc(F)c(Cl)c3)c(N3C[C@H]4C[C@@H]3CO4)n(CC#N)c2=O)c1] | I-226 | A | 1.70 | 468 | c |
| 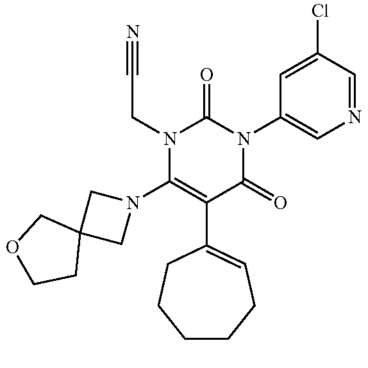 [SMILES: N#CCn1c(N2CC3(CCOC3)C2)c(C2=CCCCCC2)c(=O)n(-c2cncc(Cl)c2)c1=O] | I-227 | A | 2.15 | 468.1 | |

TABLE 46-continued
| Structure | Compound No. | LC/MS measurement condition | Retention time(min) | m/z | Configu-ration |
|---|---|---|---|---|---|
| 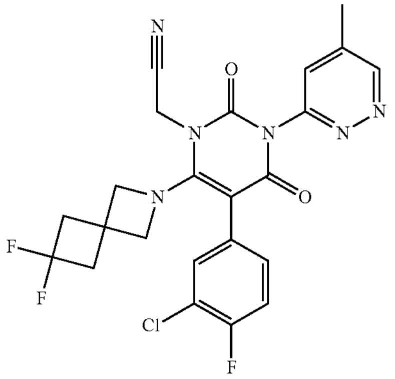 | I-228 | A | 2.97 | 503 | |
| 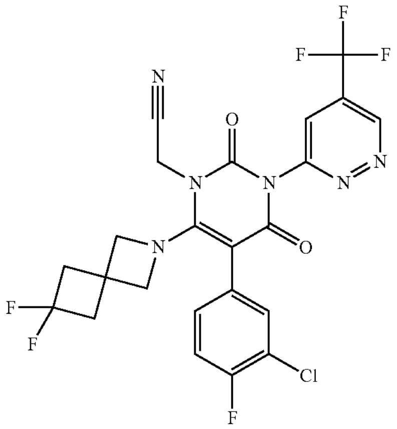 [SMILES: N#CCn1c(N2CC3(C2)CC(F)(F)C3)c(-c2ccc(F)c(Cl)c2)c(=O)n(-c2cc(C(F)(F)F)cnn2)c1=O] | I-229 | D | 2.40 | 557 | |
| 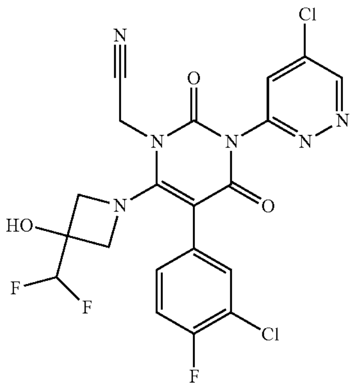 [SMILES: N#CCn1c(N2CC(O)(C(F)F)C2)c(-c2ccc(F)c(Cl)c2)c(=O)n(-c2cc(Cl)cnn2)c1=O] | I-230 | D | 1.75 | 512 | |

TABLE 47
| Structure | Compound No. | LC/MS measurement condition | Retention time(min) | m/z | Configu-ration |
|---|---|---|---|---|---|
| 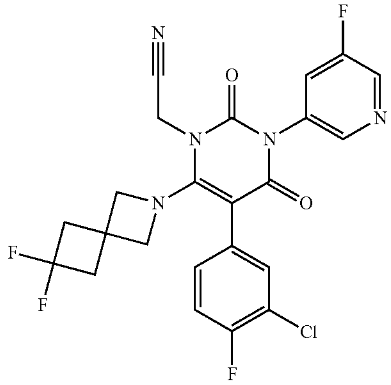 [SMILES: N#CCn1c(N2CC3(C2)CC(F)(F)C3)c(-c2ccc(F)c(Cl)c2)c(=O)n(-c2cncc(F)c2)c1=O] | I-231 | D | 1.96 | 506.1 | |
| 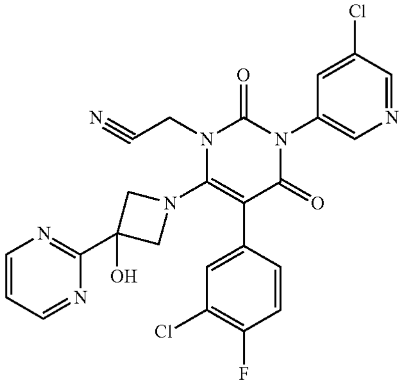 [SMILES: N#CCn1c(N2CC(O)(c3ncccn3)C2)c(-c2ccc(F)c(Cl)c2)c(=O)n(-c2cncc(Cl)c2)c1=O] | I-232 | D | 1.67 | 540 | |
| 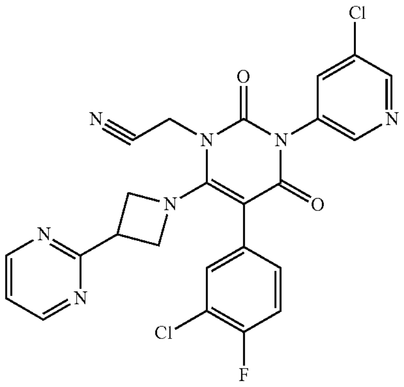 [SMILES: N#CCn1c(N2CC(c3ncccn3)C2)c(-c2ccc(F)c(Cl)c2)c(=O)n(-c2cncc(Cl)c2)c1=O] | I-233 | A | 1.89 | 524 | |

TABLE 47-continued
| Structure | Compound No. | LC/MS measurement condition | Retention time(min) | m/z | Configu-ration |
|---|---|---|---|---|---|
| 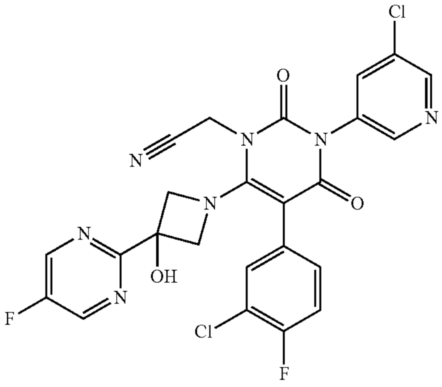 [SMILES: N#CCn1c(N2CC(O)(c3ncc(F)cn3)C2)c(-c2ccc(F)c(Cl)c2)c(=O)n(-c2cncc(Cl)c2)c1=O] | I-234 | A | 1.93 | 558 | |
| 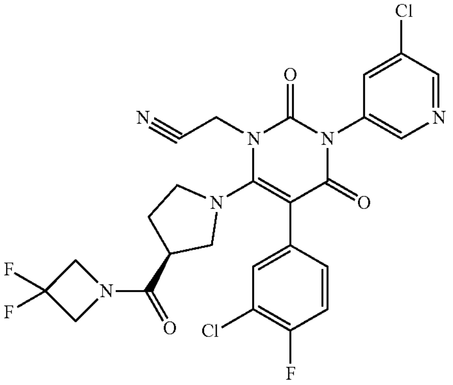 [SMILES: N#CCn1c(N2CC[C@H](C(=O)N3CC(F)(F)C3)C2)c(-c2ccc(F)c(Cl)c2)c(=O)n(-c2cncc(Cl)c2)c1=O] | I-235 | A | 2.15 | 579.1 | c |
TABLE 48
| Structure | Compound No. | LC/MS measurement condition | Retention time(min) | m/z | Configu-ration |
|---|---|---|---|---|---|
| 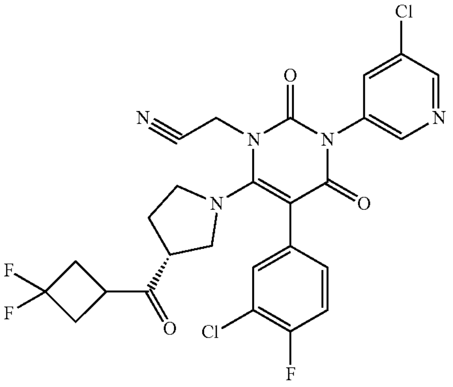 [SMILES: N#CCn1c(N2CC[C@@H](C(=O)C3CC(F)(F)C3)C2)c(-c2ccc(F)c(Cl)c2)c(=O)n(-c2cncc(Cl)c2)c1=O] | I-236 | A | 1.95 | 578.9 | c |

TABLE 48-continued
| Structure | Compound No. | LC/MS measurement condition | Retention time(min) | m/z | Configu-ration |
|---|---|---|---|---|---|
| 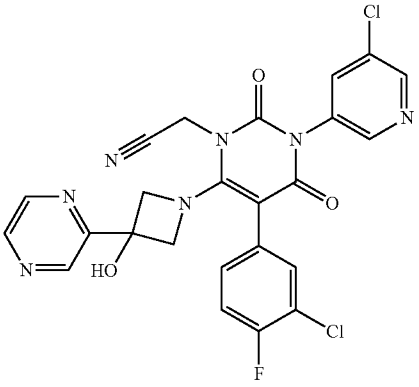 [SMILES: N#CCn1c(N2CC(O)(c3cnccn3)C2)c(-c2ccc(F)c(Cl)c2)c(=O)n(-c2cncc(Cl)c2)c1=O] | I-237 | D | 2.05 | 539.95 | |
| 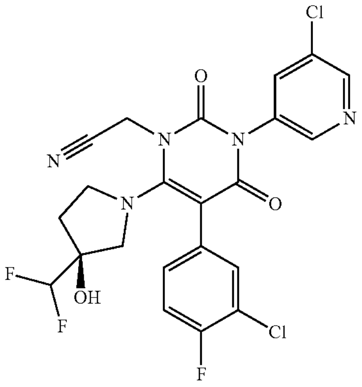 [SMILES: N#CCn1c(N2CC[C@@](O)(C(F)F)C2)c(-c2ccc(F)c(Cl)c2)c(=O)n(-c2cncc(Cl)c2)c1=O] | I-238 | A | 2.26 | 525.95 | b |
| 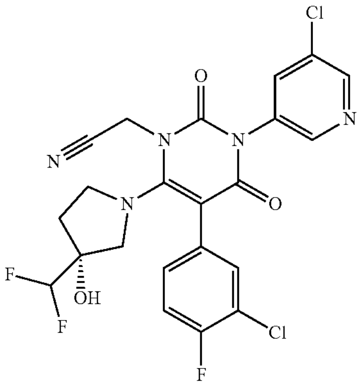 [SMILES: N#CCn1c(N2CC[C@](O)(C(F)F)C2)c(-c2ccc(F)c(Cl)c2)c(=O)n(-c2cncc(Cl)c2)c1=O] | I-239 | A | 2.26 | 525.95 | b |
| 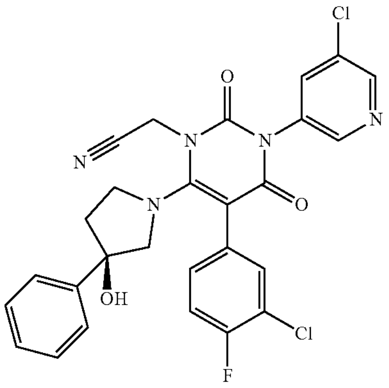 [SMILES: N#CCn1c(N2CC[C@@](O)(c3ccccc3)C2)c(-c2ccc(F)c(Cl)c2)c(=O)n(-c2cncc(Cl)c2)c1=O] | I-240 | A | 2.44 | 552 | b |

TABLE 49
| Structure | Compound No. | LC/MS measurement condition | Retention time(min) | m/z | Configu-ration |
|---|---|---|---|---|---|
| 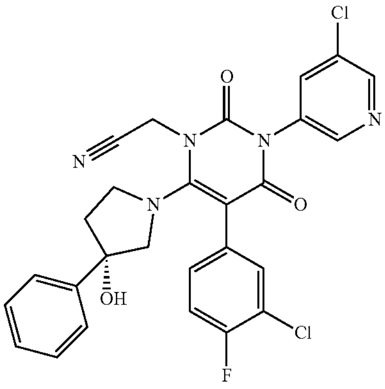 [SMILES: N#CCn1c(N2CC[C@](O)(c3ccccc3)C2)c(-c2ccc(F)c(Cl)c2)c(=O)n(-c2cncc(Cl)c2)c1=O] | I-241 | A | 2.44 | 551.95 | b |
| 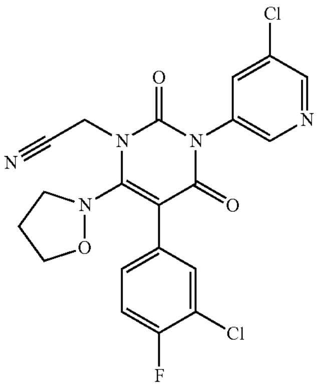 [SMILES: N#CCn1c(N2CCCO2)c(-c2ccc(F)c(Cl)c2)c(=O)n(-c2cncc(Cl)c2)c1=O] | I-242 | A | 2.32 | 461.95 | |
| 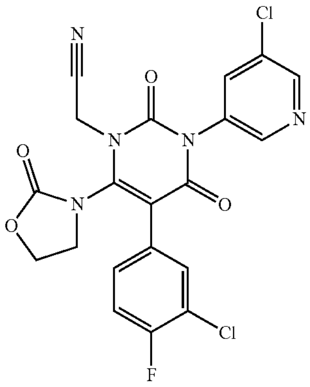 [SMILES: N#CCn1c(N2CCOC2=O)c(-c2ccc(F)c(Cl)c2)c(=O)n(-c2cncc(Cl)c2)c1=O] | I-243 | A | 2.23 | 475.95 | |

TABLE 49-continued
| Structure | Compound No. | LC/MS measurement condition | Retention time(min) | m/z | Configu-ration |
|---|---|---|---|---|---|
| 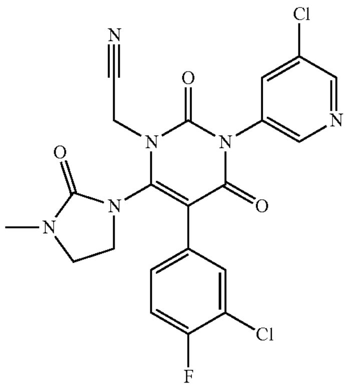 [SMILES: CN1CCN(c2c(-c3ccc(F)c(Cl)c3)c(=O)n(-c3cncc(Cl)c3)c(=O)n2CC#N)C1=O] | I-244 | A | 2.19 | 489 | |
| 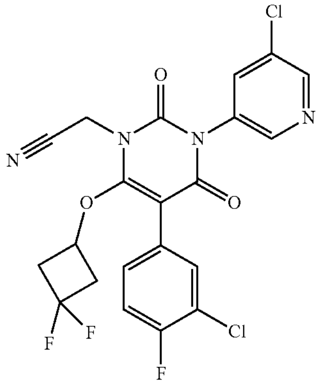 [SMILES: N#CCn1c(OC2CC(F)(F)C2)c(-c2ccc(F)c(Cl)c2)c(=O)n(-c2cncc(Cl)c2)c1=O] | I-245 | A | 2.47 | 496.95 | |
TABLE 50
| Structure | Compound No. | LC/MS measurement condition | Retention time(min) | m/z | Configu-ration |
|---|---|---|---|---|---|
| 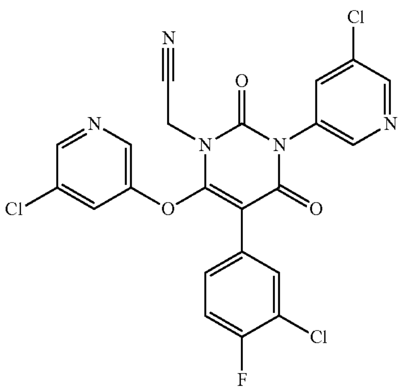 [SMILES: N#CCn1c(Oc2cncc(Cl)c2)c(-c2ccc(F)c(Cl)c2)c(=O)n(-c2cncc(Cl)c2)c1=O] | I-246 | A | 2.27 | 517.95 | |

TABLE 50-continued
| Structure | Compound No. | LC/MS measurement condition | Retention time(min) | m/z | Configu-ration |
|---|---|---|---|---|---|
| 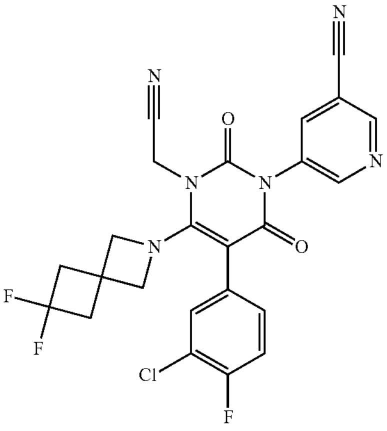 [SMILES: N#CCn1c(N2CC3(C2)CC(F)(F)C3)c(-c2ccc(F)c(Cl)c2)c(=O)n(-c2cncc(C#N)c2)c1=O] | I-247 | A | 1.98 | 513 | |
| 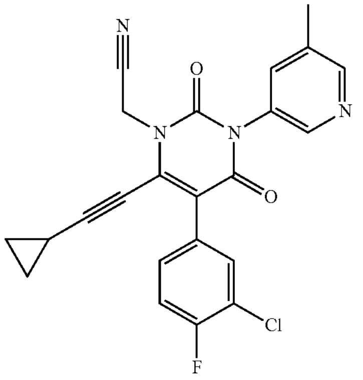 [SMILES: Cc1cncc(-n2c(=O)c(-c3ccc(F)c(Cl)c3)c(C#CC3CC3)n(CC#N)c2=O)c1] | I-248 | A | 1.88 | 435 | |
| 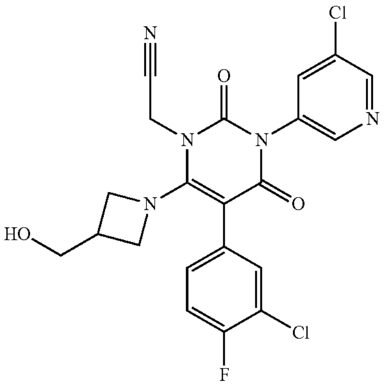 [SMILES: N#CCn1c(N2CC(CO)C2)c(-c2ccc(F)c(Cl)c2)c(=O)n(-c2cncc(Cl)c2)c1=O] | I-249 | A | 1.83 | 476 | |

TABLE 50-continued
| Structure | Compound No. | LC/MS measurement condition | Retention time(min) | m/z | Configu-ration |
|---|---|---|---|---|---|
| 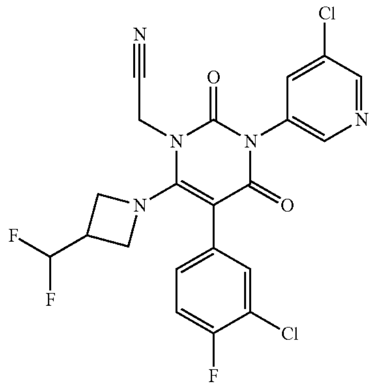 [SMILES: N#CCn1c(N2CC(C(F)F)C2)c(-c2ccc(F)c(Cl)c2)c(=O)n(-c2cncc(Cl)c2)c1=O] | I-250 | A | 2.20 | 496 | |
TABLE 51
| Structure | Compound No. | LC/MS measurement condition | Retention time(min) | m/z | Configu-ration |
|---|---|---|---|---|---|
| 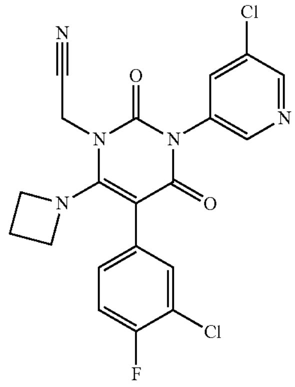 [SMILES: N#CCn1c(N2CCC2)c(-c2ccc(F)c(Cl)c2)c(=O)n(-c2cncc(Cl)c2)c1=O] | I-251 | A | 2.14 | 446 | |
| 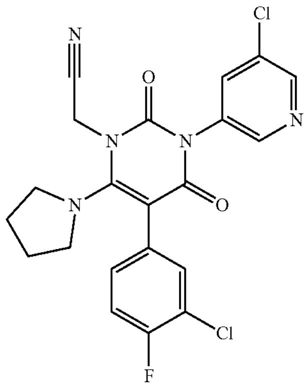 [SMILES: N#CCn1c(N2CCCC2)c(-c2ccc(F)c(Cl)c2)c(=O)n(-c2cncc(Cl)c2)c1=O] | I-252 | A | 2.35 | 460 | |

TABLE 51-continued
| Structure | Compound No. | LC/MS measurement condition | Retention time(min) | m/z | Configu-ration |
|---|---|---|---|---|---|
| 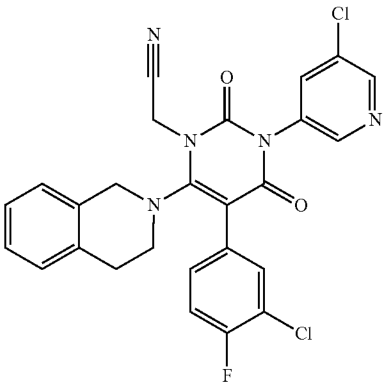 [SMILES: N#CCn1c(N2CCc3ccccc3C2)c(-c2ccc(F)c(Cl)c2)c(=O)n(-c2cncc(Cl)c2)c1=O] | I-253 | A | 2.60 | 522 | |
| 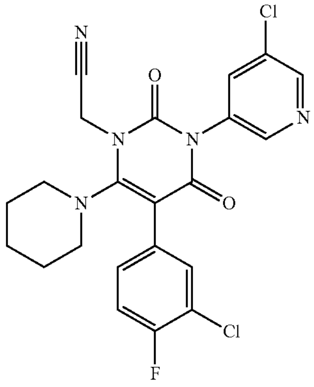 [SMILES: N#CCn1c(N2CCCCC2)c(-c2ccc(F)c(Cl)c2)c(=O)n(-c2cncc(Cl)c2)c1=O] | I-254 | A | 2.48 | 474 | |
| 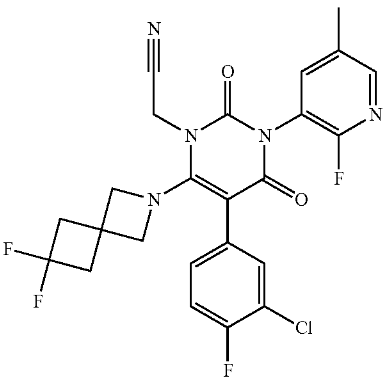 [SMILES: Cc1cnc(F)c(-n2c(=O)c(-c3ccc(F)c(Cl)c3)c(N3CC4(C3)CC(F)(F)C4)n(CC#N)c2=O)c1] | I-255 | A | 2.32 | 520 | |

TABLE 52
| Structure | Compound No. | LC/MS measurement condition | Retention time(min) | m/z | Configu-ration |
|---|---|---|---|---|---|
| 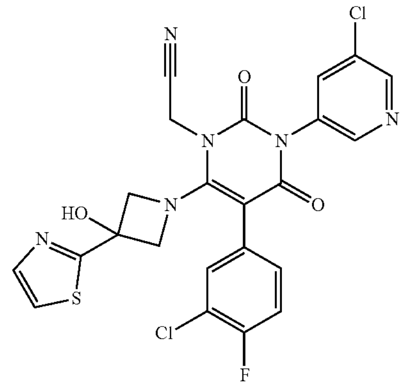 [SMILES: N#CCn1c(N2CC(O)(c3nccs3)C2)c(-c2ccc(F)c(Cl)c2)c(=O)n(-c2cncc(Cl)c2)c1=O] | I-256 | A | 1.97 | 545 | |
| 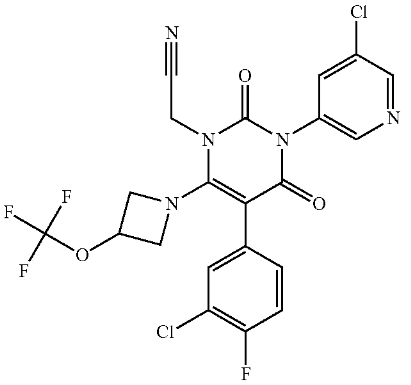 [SMILES: N#CCn1c(N2CC(OC(F)(F)F)C2)c(-c2ccc(F)c(Cl)c2)c(=O)n(-c2cncc(Cl)c2)c1=O] | I-257 | A | 2.33 | 530 | |
| 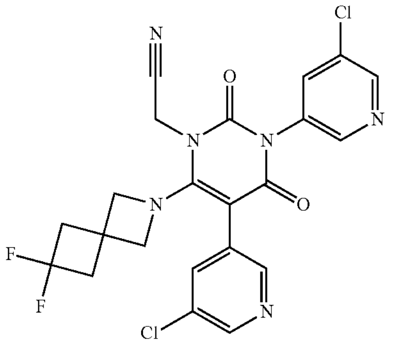 [SMILES: N#CCn1c(N2CC3(C2)CC(F)(F)C3)c(-c2cncc(Cl)c2)c(=O)n(-c2cncc(Cl)c2)c1=O] | I-258 | A | 1.95 | 505 | |
| 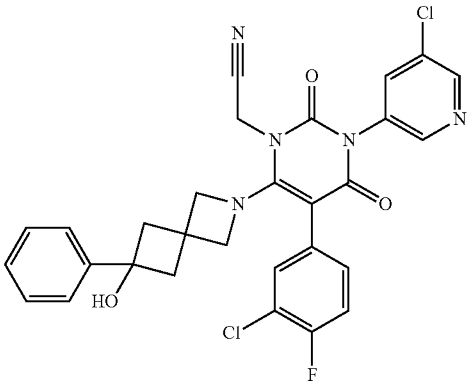 [SMILES: N#CCn1c(N2CC3(C2)CC(O)(c2ccccc2)C3)c(-c2ccc(F)c(Cl)c2)c(=O)n(-c2cncc(Cl)c2)c1=O] | I-259 | A | 1.98 | 537.85 | |

TABLE 52-continued
| Structure | Compound No. | LC/MS measurement condition | Retention time(min) | m/z | Configu-ration |
|---|---|---|---|---|---|
| 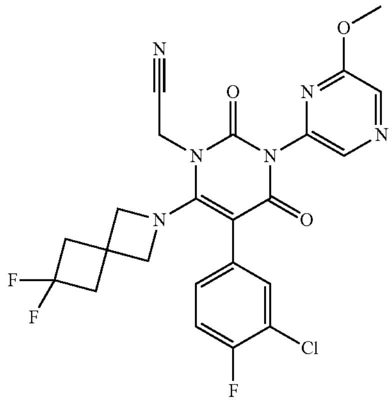 [SMILES: COc1cncc(-n2c(=O)c(-c3ccc(F)c(Cl)c3)c(N3CC4(C3)CC(F)(F)C4)n(CC#N)c2=O)n1] | I-260 | A | 1.99 | 519.2 | |
TABLE 53
| Structure | Compound No. | LC/MS measurement condition | Retention time(min) | m/z | Configu-ration |
|---|---|---|---|---|---|
| 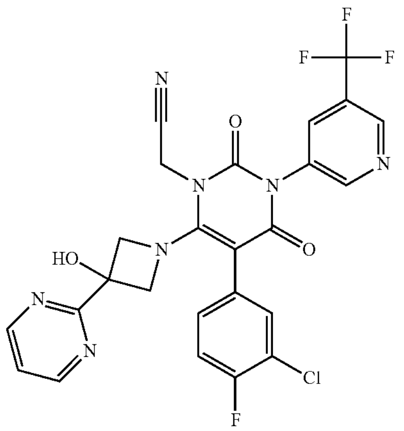 [SMILES: N#CCn1c(N2CC(O)(c3ncccn3)C2)c(-c2ccc(F)c(Cl)c2)c(=O)n(-c2cncc(C(F)(F)F)c2)c1=O] | I-261 | A | 1.86 | 574.85 | |
| 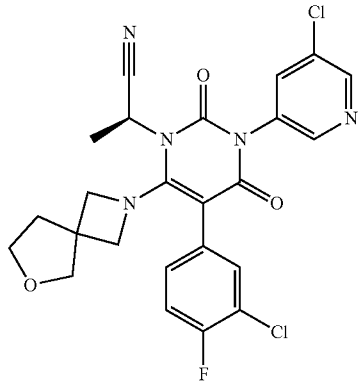 [SMILES: C[C@@H](C#N)n1c(N2CC3(CCOC3)C2)c(-c2ccc(F)c(Cl)c2)c(=O)n(-c2cncc(Cl)c2)c1=O] | I-262 | A | 2.13 | 516 | b |

TABLE 53-continued
| Structure | Compound No. | LC/MS measurement condition | Retention time(min) | m/z | Configu-ration |
|---|---|---|---|---|---|
| 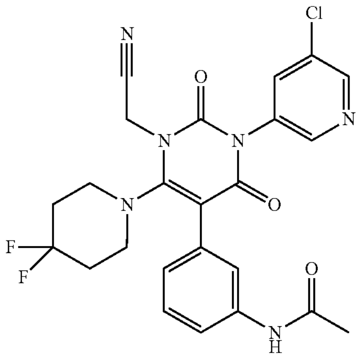 [SMILES: CC(=O)Nc1cccc(-c2c(N3CCC(F)(F)CC3)n(CC#N)c(=O)n(-c3cncc(Cl)c3)c2=O)c1] | I-263 | A | 1.84 | 515 | |
| 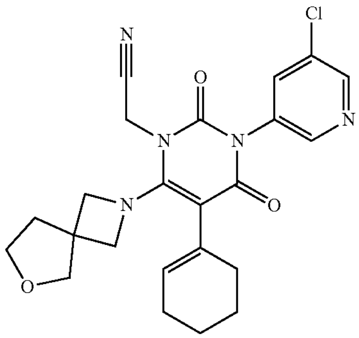 [SMILES: N#CCn1c(N2CC3(CCOC3)C2)c(C2=CCCCC2)c(=O)n(-c2cncc(Cl)c2)c1=O] | I-264 | A | 1.94 | 454.05 | |
| 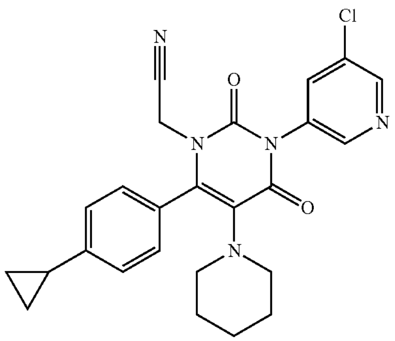 [SMILES: N#CCn1c(-c2ccc(C3CC3)cc2)c(N2CCCCC2)c(=O)n(-c2cncc(Cl)c2)c1=O] | I-265 | A | 2.78 | 462.1 | |

TABLE 54
| Structure | Compound No. | LC/MS measurement condition | Retention time(min) | m/z | Configu-ration |
|---|---|---|---|---|---|
| 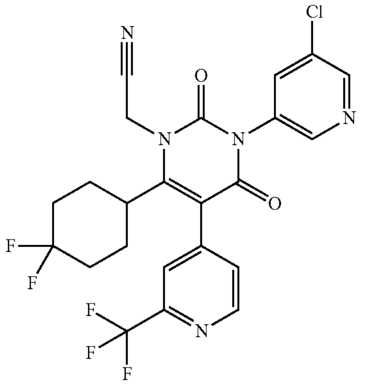 [SMILES: N#CCn1c(C2CCC(F)(F)CC2)c(-c2ccnc(C(F)(F)F)c2)c(=O)n(-c2cncc(Cl)c2)c1=O] | I-266 | A | 2.19 | 527 | |
| 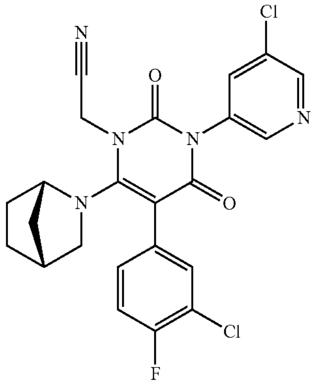 [SMILES: N#CCn1c(N2C[C@@H]3CC[C@H]2C3)c(-c2ccc(F)c(Cl)c2)c(=O)n(-c2cncc(Cl)c2)c1=O] | I-267 | A | 2.38 | 486 | a |
| 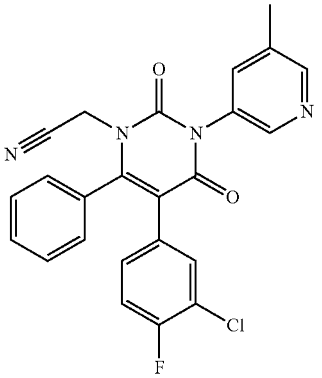 [SMILES: Cc1cncc(-n2c(=O)c(-c3ccc(F)c(Cl)c3)c(-c3ccccc3)n(CC#N)c2=O)c1] | I-268 | B | 2.14 | 447 | |
| 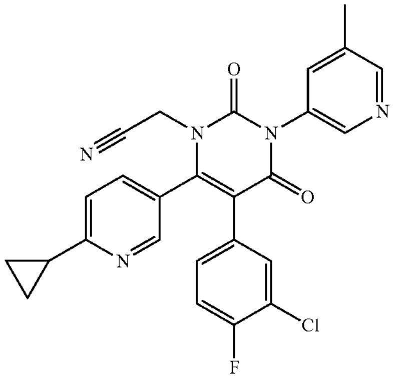 [SMILES: Cc1cncc(-n2c(=O)c(-c3ccc(F)c(Cl)c3)c(-c3ccc(C4CC4)nc3)n(CC#N)c2=O)c1] | I-269 | A | 2.13 | 488 | |

TABLE 54-continued
| Structure | Compound No. | LC/MS measurement condition | Retention time(min) | m/z | Configu-ration |
|---|---|---|---|---|---|
| 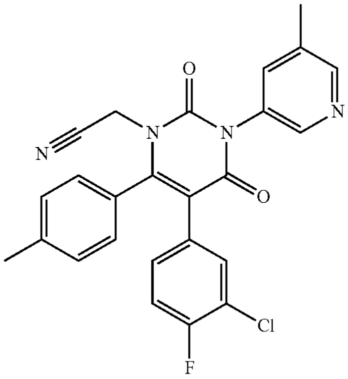 [SMILES: Cc1ccc(-c2c(-c3ccc(F)c(Cl)c3)c(=O)n(-c3cncc(C)c3)c(=O)n2CC#N)cc1] | I-270 | B | 2.28 | 461 | |
TABLE 55
| Structure | Compound No. | LC/MS measurement condition | Retention time(min) | m/z | Configu-ration |
|---|---|---|---|---|---|
| 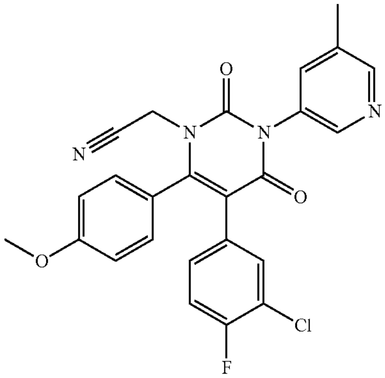 [SMILES: COc1ccc(-c2c(-c3ccc(F)c(Cl)c3)c(=O)n(-c3cncc(C)c3)c(=O)n2CC#N)cc1] | I-271 | B | 2.16 | 477 | |
| 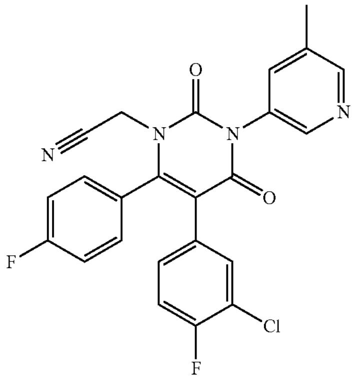 [SMILES: Cc1cncc(-n2c(=O)c(-c3ccc(F)c(Cl)c3)c(-c3ccc(F)cc3)n(CC#N)c2=O)c1] | I-272 | B | 2.20 | 465 | |

TABLE 55-continued
| Structure | Compound No. | LC/MS measurement condition | Retention time(min) | m/z | Configu-ration |
|---|---|---|---|---|---|
| 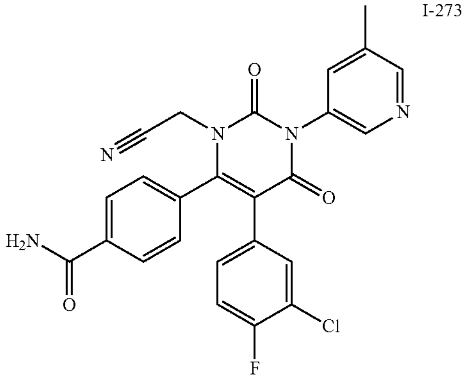 | I-273 | B | 1.63 | 490 | |
| 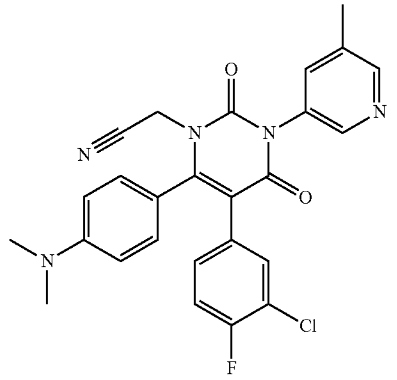 [SMILES: Cc1cncc(-n2c(=O)c(-c3ccc(F)c(Cl)c3)c(-c3ccc(N(C)C)cc3)n(CC#N)c2=O)c1] | I-274 | B | 2.27 | 490 | |
| 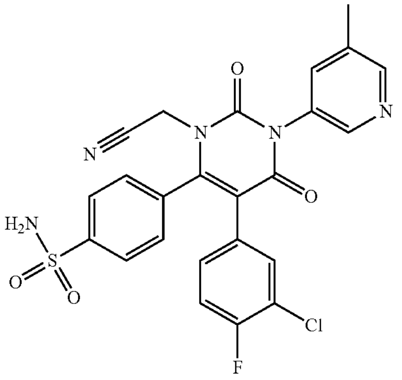 [SMILES: Cc1cncc(-n2c(=O)c(-c3ccc(F)c(Cl)c3)c(-c3ccc(S(N)(=O)=O)cc3)n(CC#N)c2=O)c1] | I-275 | B | 1.77 | 526 | |

TABLE 56
| Structure | Compound No. | LC/MS measurement condition | Retention time(min) | m/z | Configu-ration |
|---|---|---|---|---|---|
| 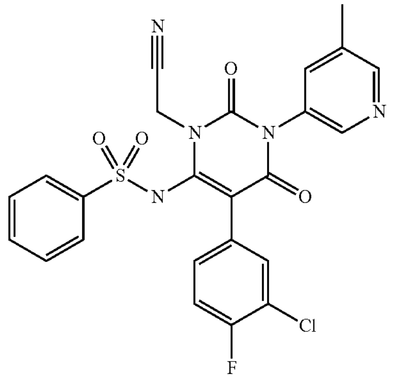 [SMILES: Cc1cncc(-n2c(=O)c(-c3ccc(F)c(Cl)c3)c(NS(=O)(=O)c3ccccc3)n(CC#N)c2=O)c1] | I-276 | A | 2.20 | 540.05 | |
| 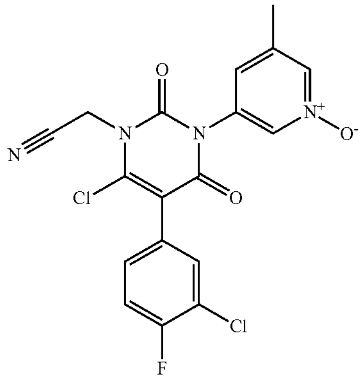 [SMILES: Cc1cc(-n2c(=O)c(-c3ccc(F)c(Cl)c3)c(Cl)n(CC#N)c2=O)c[n+]([O-])c1] | I-277 | A | 1.78 | 420.9 | |
| 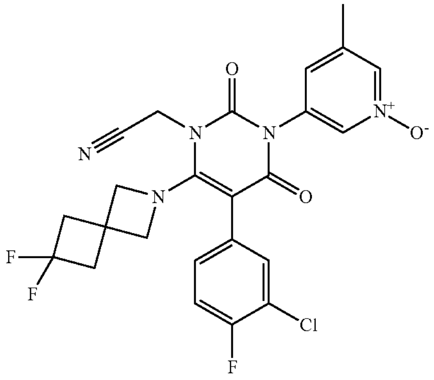 [SMILES: Cc1cc(-n2c(=O)c(-c3ccc(F)c(Cl)c3)c(N3CC4(C3)CC(F)(F)C4)n(CC#N)c2=O)c[n+]([O-])c1] | I-278 | A | 1.92 | 518 | |
| 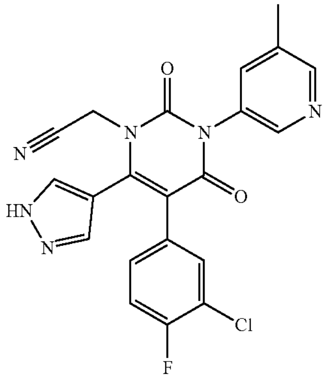 [SMILES: Cc1cncc(-n2c(=O)c(-c3ccc(F)c(Cl)c3)c(-c3cn[nH]c3)n(CC#N)c2=O)c1] | I-279 | A | 1.68 | 436.95 | |

TABLE 56-continued
| Structure | Compound No. | LC/MS measurement condition | Retention time(min) | m/z | Configu-ration |
|---|---|---|---|---|---|
| 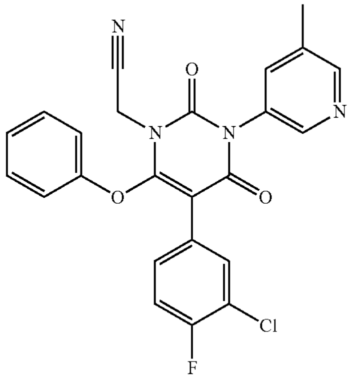 [SMILES: Cc1cncc(-n2c(=O)c(-c3ccc(F)c(Cl)c3)c(Oc3ccccc3)n(CC#N)c2=O)c1] | I-280 | A | 2.24 | 463 | |
TABLE 57
| Structure | Compound No. | LC/MS measurement condition | Retention time(min) | m/z | Configu-ration |
|---|---|---|---|---|---|
| 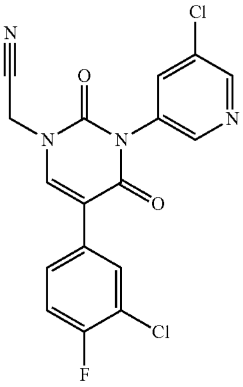 [SMILES: N#CCn1cc(-c2ccc(F)c(Cl)c2)c(=O)n(-c2cncc(Cl)c2)c1=O] | I-281 | A | 2.17 | 390.9 | |
| 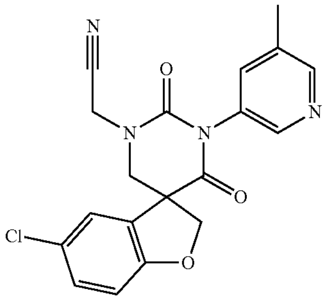 [SMILES: Cc1cncc(N2C(=O)N(CC#N)CC3(COc4ccc(Cl)cc43)C2=O)c1] | I-282 | A | 1.84 | 382.95 | d |

TABLE 58
| Structure | Compound No. | LC/MS measurement condition | Retention time(min) | m/z | Configu-ration |
|---|---|---|---|---|---|
| 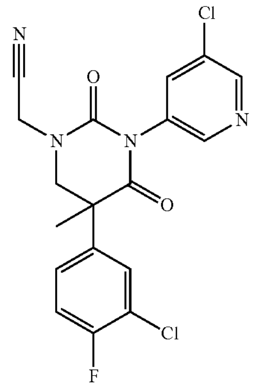 [SMILES: CC1(c2ccc(F)c(Cl)c2)CN(CC#N)C(=O)N(c2cncc(Cl)c2)C1=O] | I-283 | A | 2.23 | 406.9 | d |
| 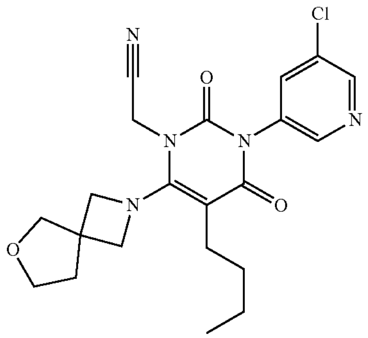 [SMILES: CCCCc1c(N2CC3(CCOC3)C2)n(CC#N)c(=O)n(-c2cncc(Cl)c2)c1=O] | I-284 | A | 1.98 | 430.05 | |
| 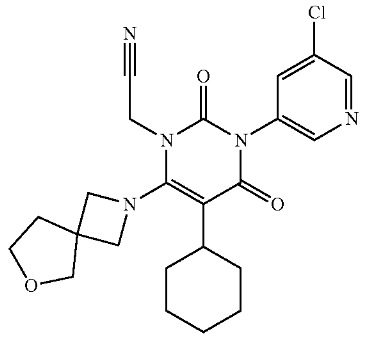 [SMILES: N#CCn1c(N2CC3(CCOC3)C2)c(C2CCCCC2)c(=O)n(-c2cncc(Cl)c2)c1=O] | I-285 | A | 2.24 | 456.1 | |
| 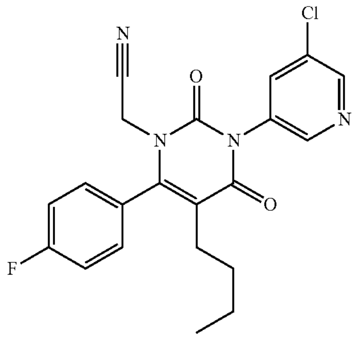 [SMILES: CCCCc1c(-c2ccc(F)cc2)n(CC#N)c(=O)n(-c2cncc(Cl)c2)c1=O] | I-286 | A | 2.45 | 413 | |

TABLE 59
| Structure | Compound No. | LC/MS measurement condition | Retention time (min) | M/Z | Configu-ration |
|---|---|---|---|---|---|
| 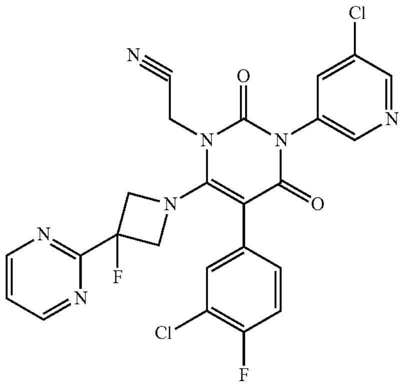 [SMILES: N#CCn1c(N2CC(F)(c3ncccn3)C2)c(-c2ccc(F)c(Cl)c2)c(=O)n(-c2cncc(Cl)c2)c1=O] | I-287 | D | 1.80 | 542 | |
| 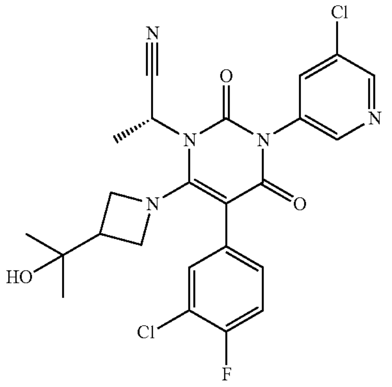 [SMILES: C[C@H](C#N)n1c(N2CC(C(C)(C)O)C2)c(-c2ccc(F)c(Cl)c2)c(=O)n(-c2cncc(Cl)c2)c1=O] | I-288 | A | 2.09 | 518 | b |
| 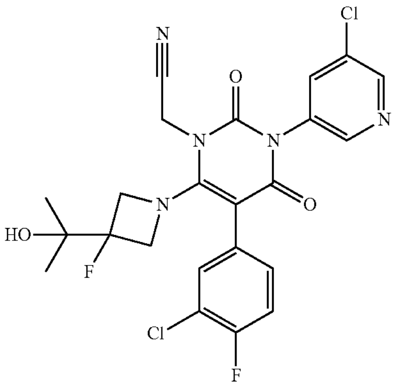 [SMILES: CC(C)(O)C1(F)CN(c2c(-c3ccc(F)c(Cl)c3)c(=O)n(-c3cncc(Cl)c3)c(=O)n2CC#N)C1] | I-289 | A | 1.88 | 522 | |

TABLE 59-continued
| Structure | Compound No. | LC/MS measurement condition | Retention time (min) | M/Z | Configu-ration |
|---|---|---|---|---|---|
| 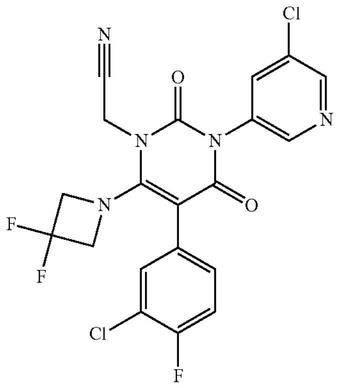 [SMILES: N#CCn1c(N2CC(F)(F)C2)c(-c2ccc(F)c(Cl)c2)c(=O)n(-c2cncc(Cl)c2)c1=O] | I-290 | A | 2.23 | 482 | |
| 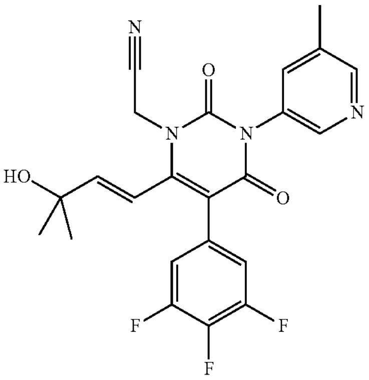 [SMILES: Cc1cncc(-n2c(=O)c(-c3cc(F)c(F)c(F)c3)c(/C=C/C(C)(C)O)n(CC#N)c2=O)c1] | I-291 | A | 2.01 | 457 | |
TABLE 60
| Structure | Compound No. | LC/MS measurement condition | Retention time (min) | M/Z | Configu-ration |
|---|---|---|---|---|---|
| 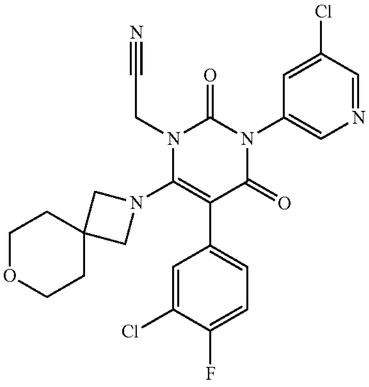 [SMILES: N#CCn1c(N2CC3(CCOCC3)C2)c(-c2ccc(F)c(Cl)c2)c(=O)n(-c2cncc(Cl)c2)c1=O] | I-292 | A | 2.23 | 516 | |

TABLE 60-continued
| Structure | Compound No. | LC/MS measurement condition | Retention time (min) | M/Z | Configu-ration |
|---|---|---|---|---|---|
| 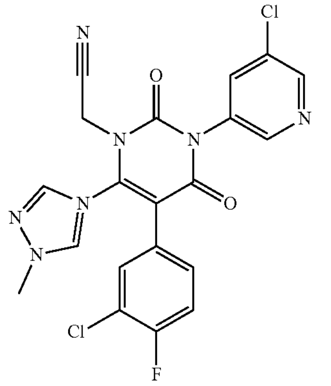 | I-293 | A | 2.18 | 471 | |
| 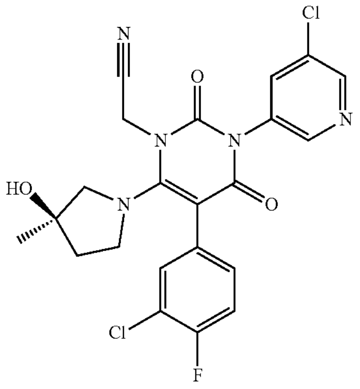 [SMILES: C[C@@]1(O)CCN(c2c(-c3ccc(F)c(Cl)c3)c(=O)n(-c3cncc(Cl)c3)c(=O)n2CC#N)C1] | I-294 | A | 2.18 | 490 | b |
| 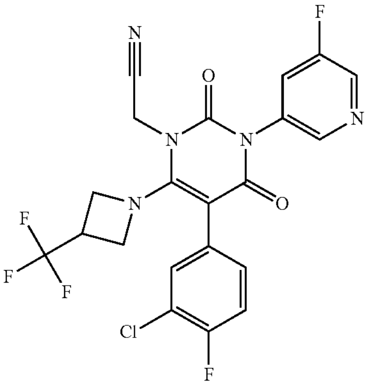 [SMILES: N#CCn1c(N2CC(C(F)(F)F)C2)c(-c2ccc(F)c(Cl)c2)c(=O)n(-c2cncc(F)c2)c1=O] | I-295 | D | 1.94 | 498 | |
| 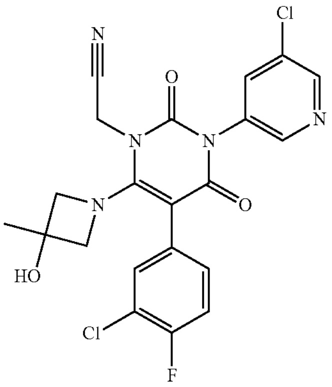 [SMILES: CC1(O)CN(c2c(-c3ccc(F)c(Cl)c3)c(=O)n(-c3cncc(Cl)c3)c(=O)n2CC#N)C1] | I-296 | D | 1.65 | 476 | |

TABLE 61
| Structure | Compound No. | LC/MS measurement condition | Retention time (min) | M/Z | Configu-ration |
|---|---|---|---|---|---|
| 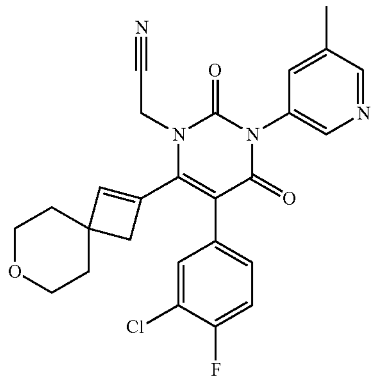 [SMILES: Cc1cncc(-n2c(=O)c(-c3ccc(F)c(Cl)c3)c(C3=CC4(CCOCC4)C3)n(CC#N)c2=O)c1] | I-297 | A | 2.21 | 493 | |
| 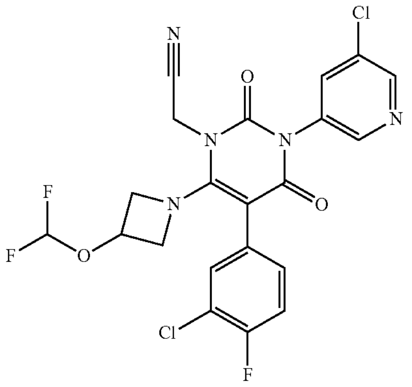 [SMILES: N#CCn1c(N2CC(OC(F)F)C2)c(-c2ccc(F)c(Cl)c2)c(=O)n(-c2cncc(Cl)c2)c1=O] | I-298 | A | 2.17 | 512 | |
| 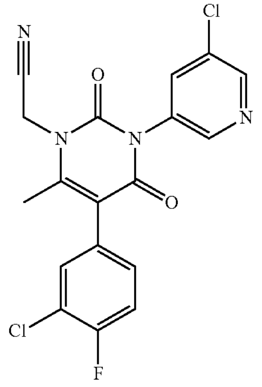 [SMILES: Cc1c(-c2ccc(F)c(Cl)c2)c(=O)n(-c2cncc(Cl)c2)c(=O)n1CC#N] | I-299 | A | 2.26 | 405 | |

TABLE 61-continued
| Structure | Compound No. | LC/MS measurement condition | Retention time (min) | M/Z | Configu-ration |
|---|---|---|---|---|---|
| 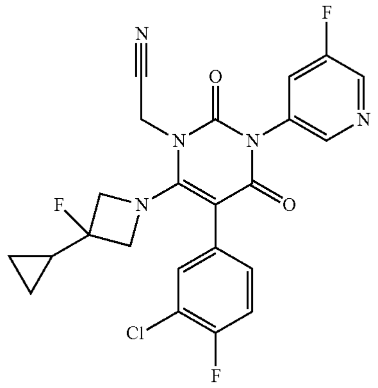 [SMILES: N#CCn1c(N2CC(F)(C3CC3)C2)c(-c2ccc(F)c(Cl)c2)c(=O)n(-c2cncc(F)c2)c1=O] | I-300 | D | 2.01 | 488 | |
| 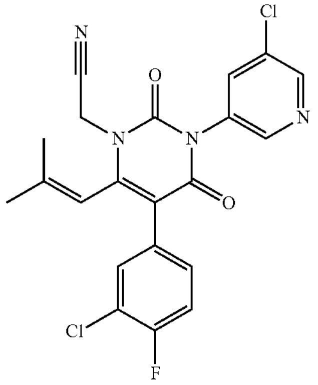 [SMILES: CC(C)=Cc1c(-c2ccc(F)c(Cl)c2)c(=O)n(-c2cncc(Cl)c2)c(=O)n1CC#N] | I-301 | A | 2.49 | 445 | |
TABLE 62
| Structure | Compound No. | LC/MS measurement condition | Retention time (min) | M/Z | Configu-ration |
|---|---|---|---|---|---|
| 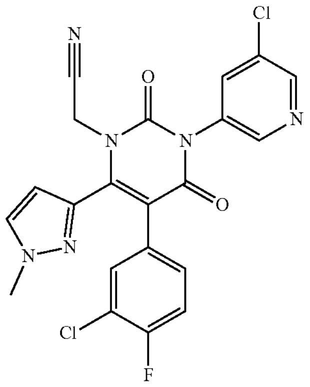 [SMILES: Cn1ccc(-c2c(-c3ccc(F)c(Cl)c3)c(=O)n(-c3cncc(Cl)c3)c(=O)n2CC#N)n1] | I-302 | A | 2.27 | 471 | |

TABLE 62-continued
| Structure | Compound No. | LC/MS measurement condition | Retention time (min) | M/Z | Configu-ration |
|---|---|---|---|---|---|
| 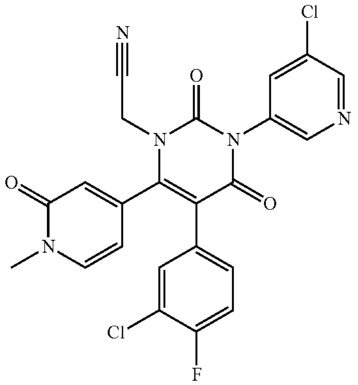 [SMILES: Cn1ccc(-c2c(-c3ccc(F)c(Cl)c3)c(=O)n(-c3cncc(Cl)c3)c(=O)n2CC#N)cc1=O] | I-303 | A | 1.86 | 498 | |
| 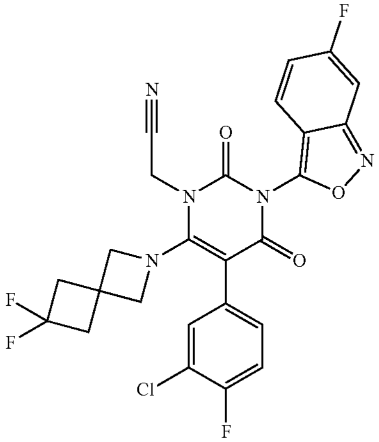 [SMILES: N#CCn1c(N2CC3(C2)CC(F)(F)C3)c(-c2ccc(F)c(Cl)c2)c(=O)n(-c2onc3cc(F)ccc23)c1=O] | I-304 | A | 2.26 | 546 | |
| 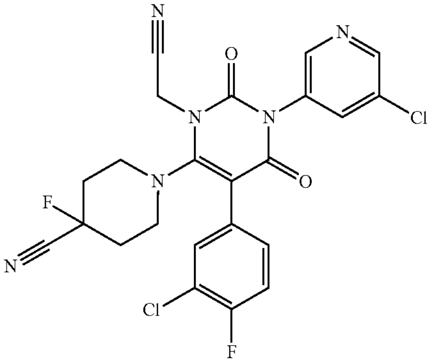 [SMILES: N#CCn1c(N2CCC(F)(C#N)CC2)c(-c2ccc(F)c(Cl)c2)c(=O)n(-c2cncc(Cl)c2)c1=O] | I-305 | A | 2.39 | 517 | |

TABLE 62-continued
| Structure | Compound No. | LC/MS measurement condition | Retention time (min) | M/Z | Configu-ration |
|---|---|---|---|---|---|
| 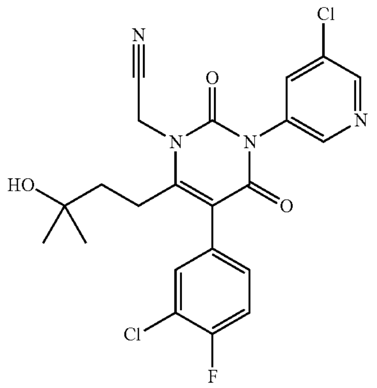 [SMILES: CC(C)(O)CCc1c(-c2ccc(F)c(Cl)c2)c(=O)n(-c2cncc(Cl)c2)c(=O)n1CC#N] | I-306 | A | 2.23 | 477 | |
TABLE 63
| Structure | Compound No. | LC/MS measurement condition | Retention time (min) | M/Z | Configu-ration |
|---|---|---|---|---|---|
| 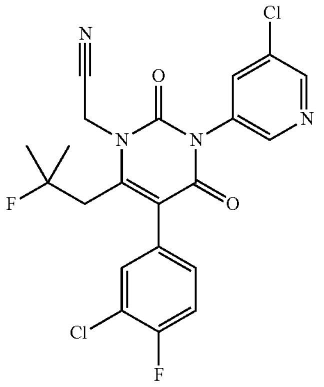 [SMILES: CC(C)(F)Cc1c(-c2ccc(F)c(Cl)c2)c(=O)n(-c2cncc(Cl)c2)c(=O)n1CC#N] | I-307 | A | 2.42 | 465 | |
| 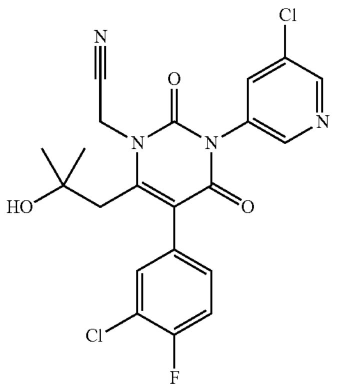 [SMILES: CC(C)(O)Cc1c(-c2ccc(F)c(Cl)c2)c(=O)n(-c2cncc(Cl)c2)c(=O)n1CC#N] | I-308 | A | 2.26 | 463 | |

TABLE 63-continued
| Structure | Compound No. | LC/MS measurement condition | Retention time (min) | M/Z | Configu-ration |
|---|---|---|---|---|---|
| 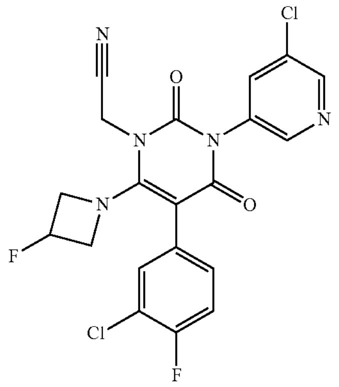 [SMILES: N#CCn1c(N2CC(F)C2)c(-c2ccc(F)c(Cl)c2)c(=O)n(-c2cncc(Cl)c2)c1=O] | I-309 | A | 2.18 | 464 | |
| 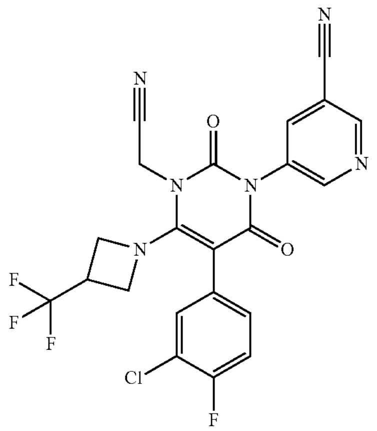 [SMILES: N#CCn1c(N2CC(C(F)(F)F)C2)c(-c2ccc(F)c(Cl)c2)c(=O)n(-c2cncc(C#N)c2)c1=O] | I-310 | A | 2.28 | 505 | |
| 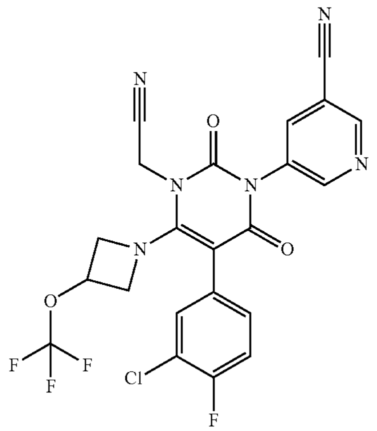 [SMILES: N#CCn1c(N2CC(OC(F)(F)F)C2)c(-c2ccc(F)c(Cl)c2)c(=O)n(-c2cncc(C#N)c2)c1=O] | I-311 | A | 2.37 | 521 | |

TABLE 64
| Structure | Compound No. | LC/MS measurement condition | Retention time (min) | M/Z | Configu-ration |
|---|---|---|---|---|---|
| 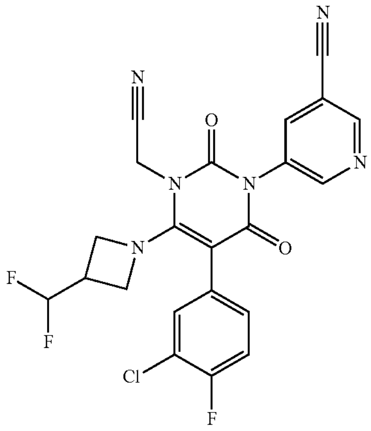 [SMILES: N#CCn1c(N2CC(C(F)F)C2)c(-c2ccc(F)c(Cl)c2)c(=O)n(-c2cncc(C#N)c2)c1=O] | I-312 | A | 2.17 | 487 | |
| 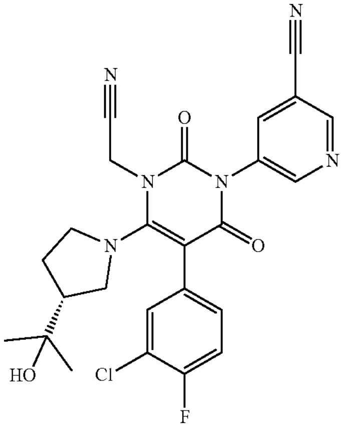 [SMILES: CC(C)(O)[C@@H]1CCN(c2c(-c3ccc(F)c(Cl)c3)c(=O)n(-c3cncc(C#N)c3)c(=O)n2CC#N)C1] | I-313 | A | 2.13 | 509 | c |
| 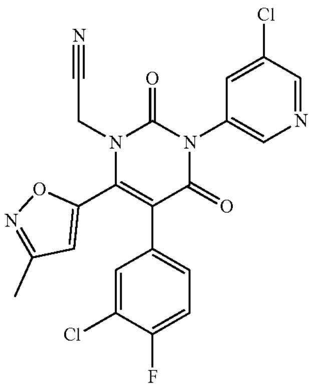 [SMILES: Cc1cc(-c2c(-c3ccc(F)c(Cl)c3)c(=O)n(-c3cncc(Cl)c3)c(=O)n2CC#N)on1] | I-314 | A | 1.81 | 472 | |

TABLE 64-continued
| Structure | Compound No. | LC/MS measurement condition | Retention time (min) | M/Z | Configu-ration |
|---|---|---|---|---|---|
| 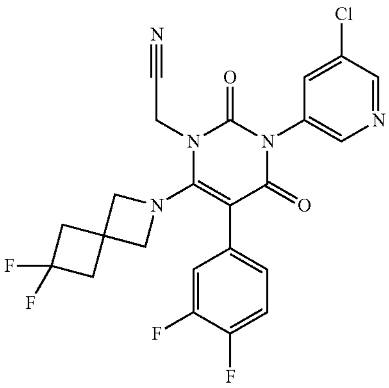 [SMILES: N#CCn1c(N2CC3(C2)CC(F)(F)C3)c(-c2ccc(F)c(F)c2)c(=O)n(-c2cncc(Cl)c2)c1=O] | I-315 | A | 2.24 | 506 | |
| 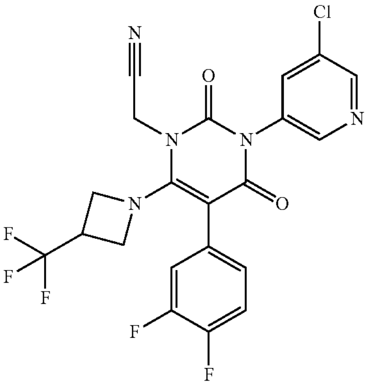 [SMILES: N#CCn1c(N2CC(C(F)(F)F)C2)c(-c2ccc(F)c(F)c2)c(=O)n(-c2cncc(Cl)c2)c1=O] | I-316 | A | 2.20 | 498 | |
TABLE 65
| Structure | Compound No. | LC/MS measurement condition | Retention time (min) | M/Z | Configu-ration |
|---|---|---|---|---|---|
| 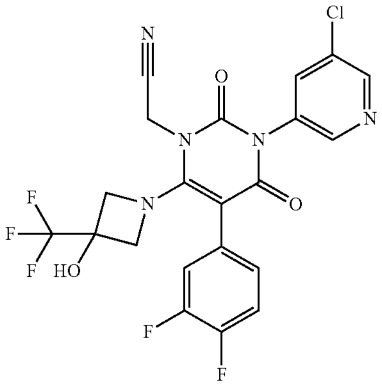 [SMILES: N#CCn1c(N2CC(O)(C(F)(F)F)C2)c(-c2ccc(F)c(F)c2)c(=O)n(-c2cncc(Cl)c2)c1=O] | I-317 | A | 2.04 | 514 | |

TABLE 65-continued
| Structure | Compound No. | LC/MS measurement condition | Retention time (min) | M/Z | Configu-ration |
|---|---|---|---|---|---|
| 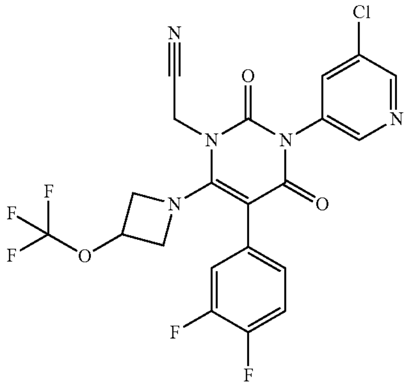 [SMILES: N#CCn1c(N2CC(OC(F)(F)F)C2)c(-c2ccc(F)c(F)c2)c(=O)n(-c2cncc(Cl)c2)c1=O] | I-318 | A | 2.30 | 514 | |
| 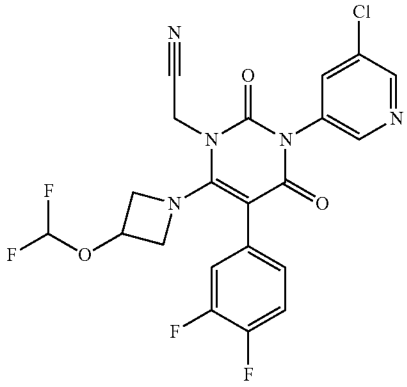 [SMILES: N#CCn1c(N2CC(OC(F)F)C2)c(-c2ccc(F)c(F)c2)c(=O)n(-c2cncc(Cl)c2)c1=O] | I-319 | A | 2.13 | 496 | |
| 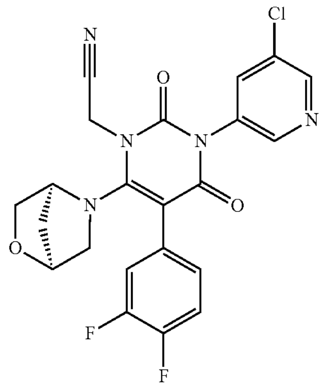 [SMILES: N#CCn1c(N2C[C@@H]3C[C@H]2CO3)c(-c2ccc(F)c(F)c2)c(=O)n(-c2cncc(Cl)c2)c1=O] | I-320 | A | 1.88 | 472 | c |
| 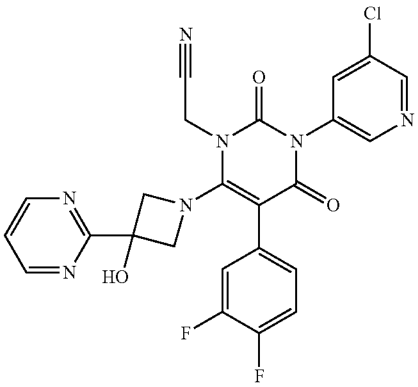 [SMILES: N#CCn1c(N2CC(O)(c3ncccn3)C2)c(-c2ccc(F)c(F)c2)c(=O)n(-c2cncc(Cl)c2)c1=O] | I-321 | A | 1.77 | 524 | |

TABLE 66
| Structure | Compound No. | LC/MS measurement condition | Retention time (min) | M/Z | Configu-ration |
|---|---|---|---|---|---|
| 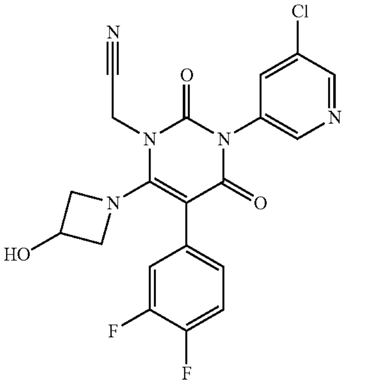 [SMILES: N#CCn1c(N2CC(O)C2)c(-c2ccc(F)c(F)c2)c(=O)n(-c2cncc(Cl)c2)c1=O] | I-322 | A | 1.67 | 446 | |
| 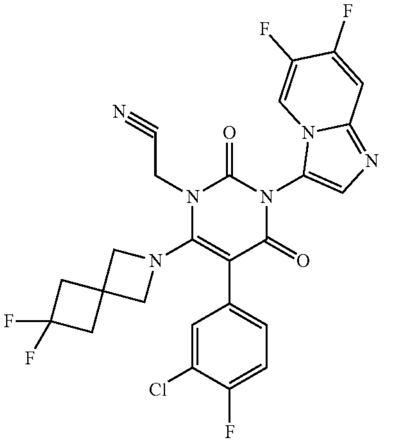 [SMILES: N#CCn1c(N2CC3(C2)CC(F)(F)C3)c(-c2ccc(F)c(Cl)c2)c(=O)n(-c2cnc3cc(F)c(F)cn23)c1=O] | I-323 | A | 2.16 | 563 | |
| 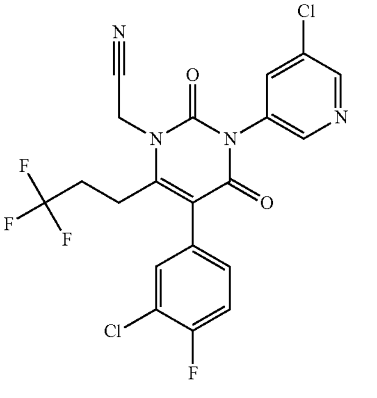 [SMILES: N#CCn1c(CCC(F)(F)F)c(-c2ccc(F)c(Cl)c2)c(=O)n(-c2cncc(Cl)c2)c1=O] | I-324 | A | 2.47 | 487 | |

TABLE 66-continued
| Structure | Compound No. | LC/MS measurement condition | Retention time (min) | M/Z | Configu-ration |
|---|---|---|---|---|---|
| 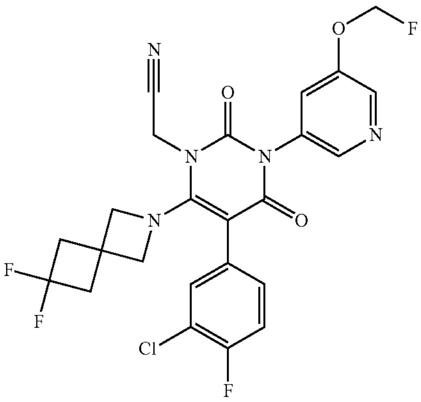 [SMILES: N#CCn1c(N2CC3(C2)CC(F)(F)C3)c(-c2ccc(F)c(Cl)c2)c(=O)n(-c2cncc(OCF)c2)c1=O] | I-325 | D | 1.95 | 536 | |
| 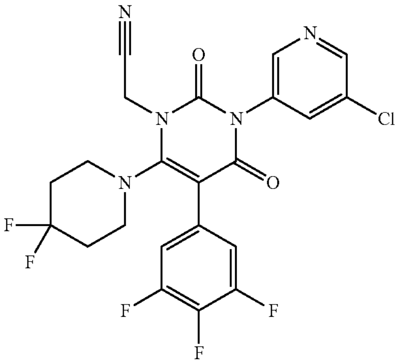 [SMILES: N#CCn1c(N2CCC(F)(F)CC2)c(-c2cc(F)c(F)c(F)c2)c(=O)n(-c2cncc(Cl)c2)c1=O] | I-326 | A | 2.40 | 512 | |
TABLE 67
| Structure | Compound No. | LC/MS measurement condition | Retention time (min) | M/Z | Configu-ration |
|---|---|---|---|---|---|
| 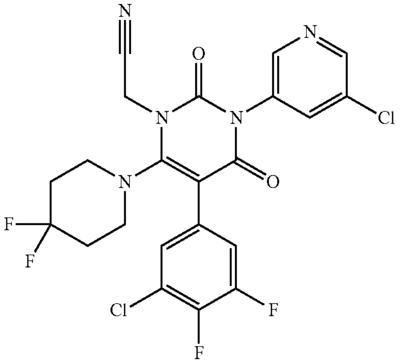 [SMILES: N#CCn1c(N2CCC(F)(F)CC2)c(-c2cc(F)c(F)c(Cl)c2)c(=O)n(-c2cncc(Cl)c2)c1=O] | I-327 | A | 2.49 | 528 | |

TABLE 67-continued
| Structure | Compound No. | LC/MS measurement condition | Retention time (min) | M/Z | Configu-ration |
|---|---|---|---|---|---|
| 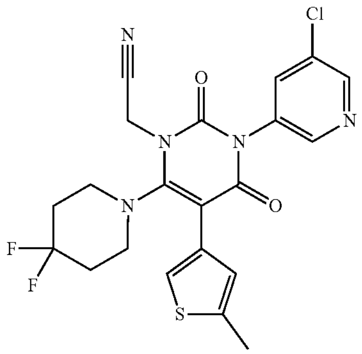 [SMILES: Cc1cc(-c2c(N3CCC(F)(F)CC3)n(CC#N)c(=O)n(-c3cncc(Cl)c3)c2=O)cs1] | I-328 | A | 2.33 | 478 | |
| 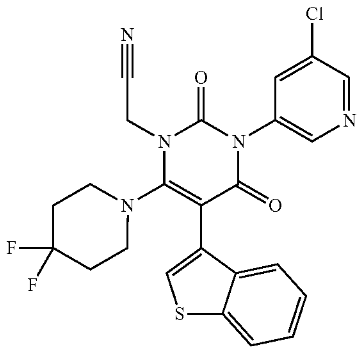 [SMILES: N#CCn1c(N2CCC(F)(F)CC2)c(-c2csc3ccccc23)c(=O)n(-c2cncc(Cl)c2)c1=O] | I-329 | A | 2.41 | 514 | |
| 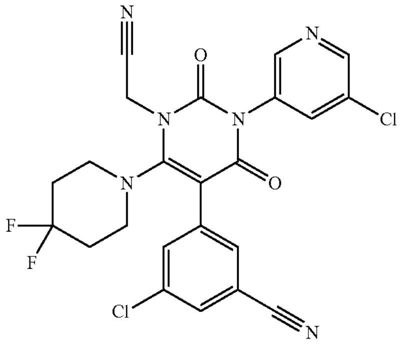 [SMILES: N#CCn1c(N2CCC(F)(F)CC2)c(-c2cc(Cl)cc(C#N)c2)c(=O)n(-c2cncc(Cl)c2)c1=O] | I-330 | A | 2.34 | 517 | |
| 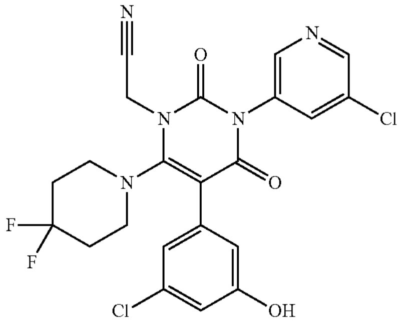 [SMILES: N#CCn1c(N2CCC(F)(F)CC2)c(-c2cc(O)cc(Cl)c2)c(=O)n(-c2cncc(Cl)c2)c1=O] | I-331 | A | 2.17 | 508 | |

TABLE 68
| Structure | Compound No | LC/MS measurement condition | Retention time (min) | M/Z | Configu-ration |
|---|---|---|---|---|---|
| 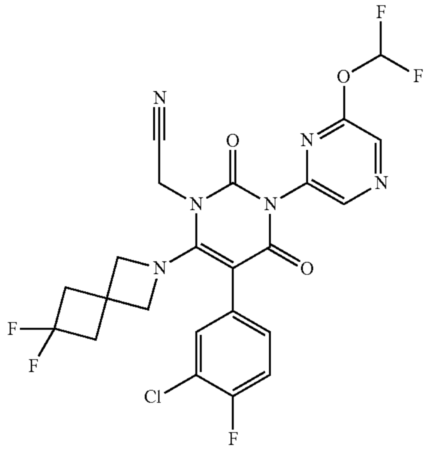 [SMILES: N#CCn1c(N2CC3(C2)CC(F)(F)C3)c(-c2ccc(F)c(Cl)c2)c(=O)n(-c2cncc(OC(F)F)n2)c1=O] | I-332 | A | 2.15 | 555 | |
| 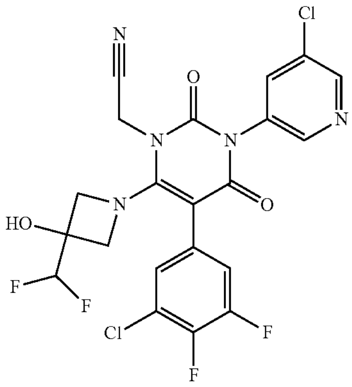 [SMILES: N#CCn1c(N2CC(O)(C(F)F)C2)c(-c2cc(F)c(F)c(Cl)c2)c(=O)n(-c2cncc(Cl)c2)c1=O] | I-333 | D | 1.83 | 530 | |
| 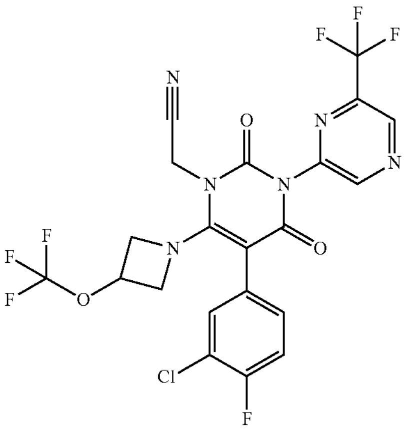 [SMILES: N#CCn1c(N2CC(OC(F)(F)F)C2)c(-c2ccc(F)c(Cl)c2)c(=O)n(-c2cncc(C(F)(F)F)n2)c1=O] | I-334 | A | 2.58 | 565 | |

TABLE 68-continued
| Structure | Compound No | LC/MS measurement condition | Retention time (min) | M/Z | Configu-ration |
|---|---|---|---|---|---|
| 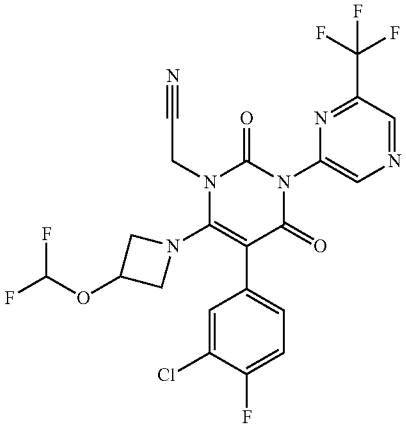 [SMILES: N#CCn1c(N2CC(OC(F)F)C2)c(-c2ccc(F)c(Cl)c2)c(=O)n(-c2cncc(C(F)(F)F)n2)c1=O] | I-335 | A | 2.42 | 547 | |
| 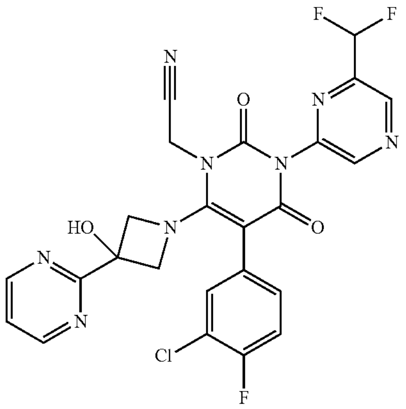 [SMILES: N#CCn1c(N2CC(O)(c3ncccn3)C2)c(-c2ccc(F)c(Cl)c2)c(=O)n(-c2cncc(C(F)F)n2)c1=O] | I-336 | D | 1.68 | 557 | |
TABLE 69
| Structure | Compound No. | LC/MS measurement condition | Retention time (min) | M/Z | Configu-ration |
|---|---|---|---|---|---|
| 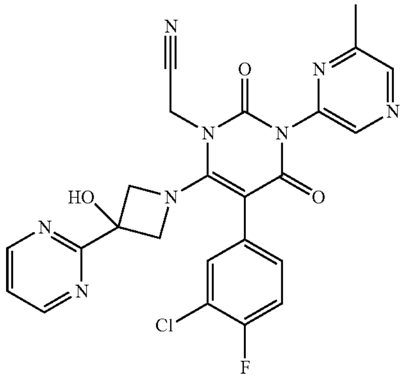 [SMILES: Cc1cncc(-n2c(=O)c(-c3ccc(F)c(Cl)c3)c(N3CC(O)(c4ncccn4)C3)n(CC#N)c2=O)n1] | I-337 | D | 1.46 | 521 | |

TABLE 69-continued
| Structure | Compound No. | LC/MS measurement condition | Retention time (min) | M/Z | Configu-ration |
|---|---|---|---|---|---|
| 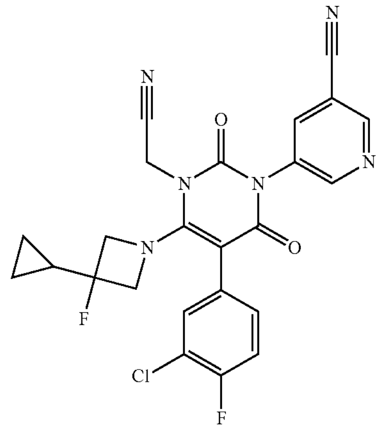 [SMILES: N#CCn1c(N2CC(F)(C3CC3)C2)c(-c2ccc(F)c(Cl)c2)c(=O)n(-c2cncc(C#N)c2)c1=O] | I-338 | A | 2.41 | 495 | |
| 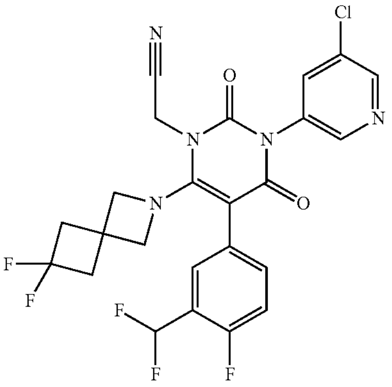 [SMILES: N#CCn1c(N2CC3(C2)CC(F)(F)C3)c(-c2ccc(F)c(C(F)F)c2)c(=O)n(-c2cncc(Cl)c2)c1=O] | I-339 | A | 2.28 | 538 | |
| 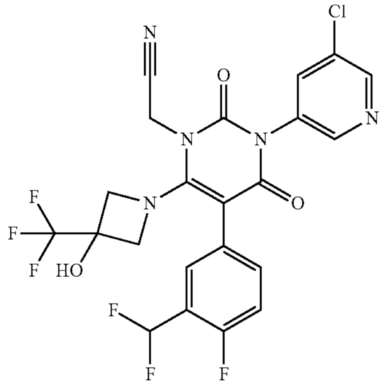 [SMILES: N#CCn1c(N2CC(O)(C(F)(F)F)C2)c(-c2ccc(F)c(C(F)F)c2)c(=O)n(-c2cncc(Cl)c2)c1=O] | I-340 | A | 2.10 | 546 | |

TABLE 69-continued
| Structure | Compound No. | LC/MS measurement condition | Retention time (min) | M/Z | Configu-ration |
|---|---|---|---|---|---|
| 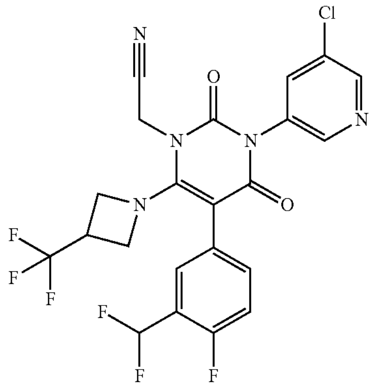 [SMILES: N#CCn1c(N2CC(C(F)(F)F)C2)c(-c2ccc(F)c(C(F)F)c2)c(=O)n(-c2cncc(Cl)c2)c1=O] | I-341 | A | 2.25 | 530 | |
TABLE 70
| Structure | Compound No. | LC/MS measurement condition | Retention time (min) | M/Z | Configu-ration |
|---|---|---|---|---|---|
| 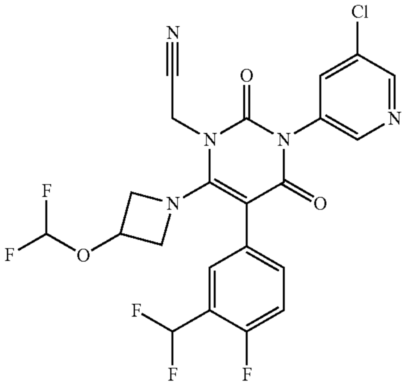 [SMILES: N#CCn1c(N2CC(OC(F)F)C2)c(-c2ccc(F)c(C(F)F)c2)c(=O)n(-c2cncc(Cl)c2)c1=O] | I-342 | A | 2.18 | 528 | |
| 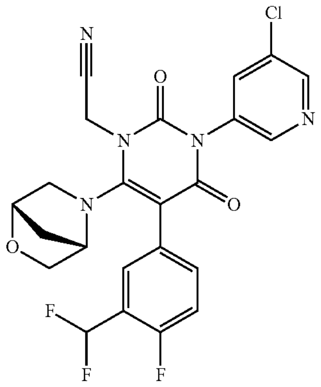 [SMILES: N#CCn1c(N2C[C@@H]3C[C@H]2CO3)c(-c2ccc(F)c(C(F)F)c2)c(=O)n(-c2cncc(Cl)c2)c1=O] | I-343 | A | 1.95 | 504 | c |

TABLE 70-continued
| Structure | Compound No. | LC/MS measurement condition | Retention time (min) | M/Z | Configu-ration |
|---|---|---|---|---|---|
| 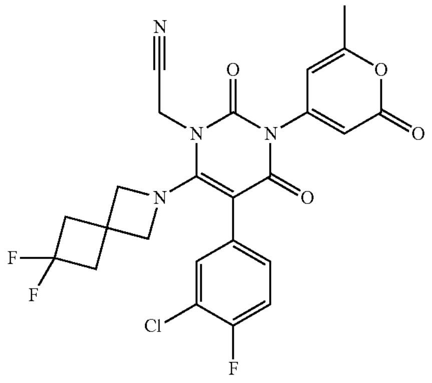 [SMILES: Cc1cc(-n2c(=O)c(-c3ccc(F)c(Cl)c3)c(N3CC4(C3)CC(F)(F)C4)n(CC#N)c2=O)cc(=O)o1] | I-344 | A | 2.27 | 519 | |
| 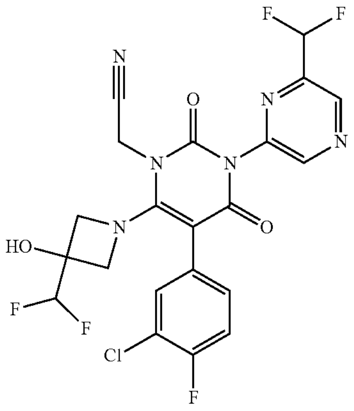 [SMILES: N#CCn1c(N2CC(O)(C(F)F)C2)c(-c2ccc(F)c(Cl)c2)c(=O)n(-c2cncc(C(F)F)n2)c1=O] | I-345 | D | 1.76 | 529 | |
| 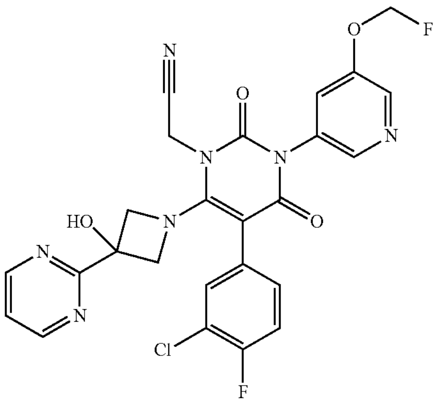 [SMILES: N#CCn1c(N2CC(O)(c3ncccn3)C2)c(-c2ccc(F)c(Cl)c2)c(=O)n(-c2cncc(OCF)c2)c1=O] | I-346 | D | 1.54 | 554 | |

TABLE 71
| Structure | Compound No. | LC/MS measurement condition | Retention time (min) | M/Z | Configu-ration |
|---|---|---|---|---|---|
| 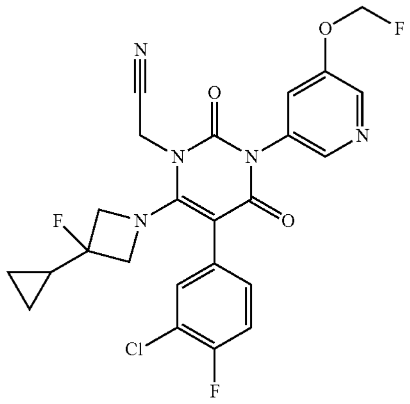 [SMILES: N#CCn1c(N2CC(F)(C3CC3)C2)c(-c2ccc(F)c(Cl)c2)c(=O)n(-c2cncc(OCF)c2)c1=O] | I-347 | D | 2.00 | 518 | |
| 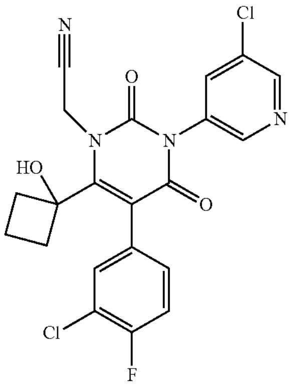 [SMILES: N#CCn1c(C2(O)CCC2)c(-c2ccc(F)c(Cl)c2)c(=O)n(-c2cncc(Cl)c2)c1=O] | I-348 | A | 2.10 | 461 | |
| 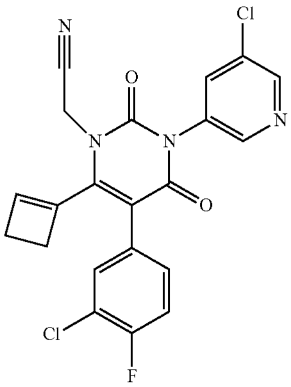 [SMILES: N#CCn1c(C2=CCC2)c(-c2ccc(F)c(Cl)c2)c(=O)n(-c2cncc(Cl)c2)c1=O] | I-349 | A | 2.65 | 443 | |

TABLE 71-continued
| Structure | Compound No. | LC/MS measurement condition | Retention time (min) | M/Z | Configu-ration |
|---|---|---|---|---|---|
| 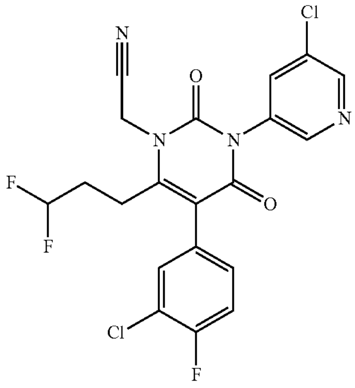 [SMILES: N#CCn1c(CCC(F)F)c(-c2ccc(F)c(Cl)c2)c(=O)n(-c2cncc(Cl)c2)c1=O] | I-350 | A | 2.41 | 469 | |
| 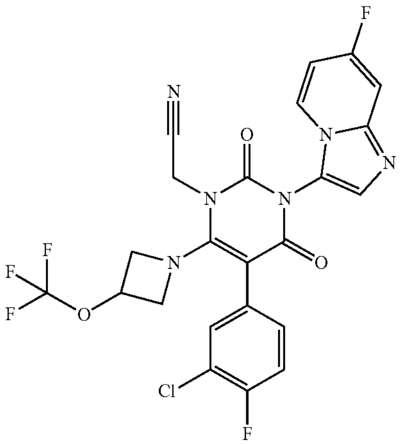 [SMILES: N#CCn1c(N2CC(OC(F)(F)F)C2)c(-c2ccc(F)c(Cl)c2)c(=O)n(-c2cnc3cc(F)ccn23)c1=O] | I-351 | D | 1.68 | 553 | |
TABLE 72
| Structure | Compound No. | LC/MS measurement condition | Retention time (min) | M/Z | Configu-ration |
|---|---|---|---|---|---|
| 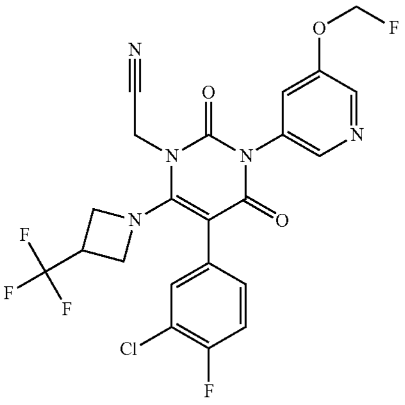 [SMILES: N#CCn1c(N2CC(C(F)(F)F)C2)c(-c2ccc(F)c(Cl)c2)c(=O)n(-c2cncc(OCF)c2)c1=O] | I-352 | D | 1.93 | 528 | |

TABLE 72-continued
| Structure | Compound No. | LC/MS measurement condition | Retention time (min) | M/Z | Configu-ration |
|---|---|---|---|---|---|
| 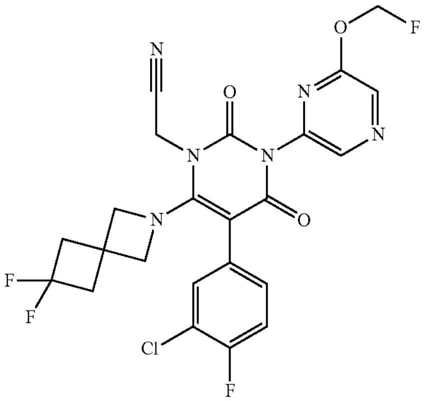 [SMILES: N#CCn1c(N2CC3(C2)CC(F)(F)C3)c(-c2ccc(F)c(Cl)c2)c(=O)n(-c2cncc(OCF)n2)c1=O] | I-353 | D | 2.27 | 537 | |
| 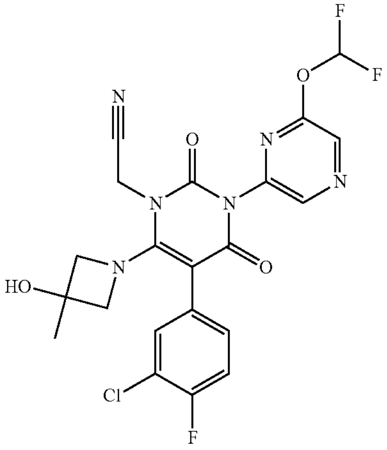 [SMILES: CC1(O)CN(c2c(-c3ccc(F)c(Cl)c3)c(=O)n(-c3cncc(OC(F)F)n3)c(=O)n2CC#N)C1] | I-354 | D | 1.75 | 509 | |
| 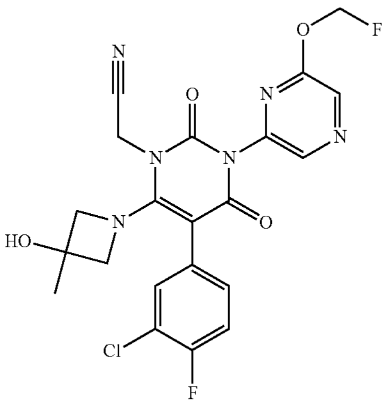 [SMILES: CC1(O)CN(c2c(-c3ccc(F)c(Cl)c3)c(=O)n(-c3cncc(OCF)n3)c(=O)n2CC#N)C1] | I-355 | D | 1.79 | 491 | |

TABLE 72-continued
| Structure | Compound No. | LC/MS measurement condition | Retention time (min) | M/Z | Configu-ration |
|---|---|---|---|---|---|
| 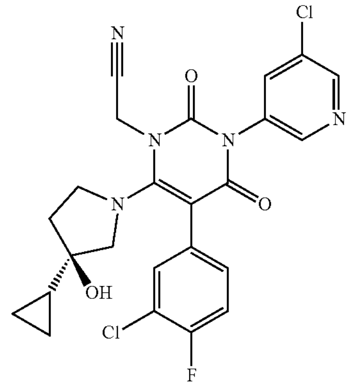 [SMILES: N#CCn1c(N2CC[C@@](O)(C3CC3)C2)c(-c2ccc(F)c(Cl)c2)c(=O)n(-c2cncc(Cl)c2)c1=O] | I-356 | A | 2.34 | 516 | b |
TABLE 73
| Structure | Compound No. | LC/MS measurement condition | Retention time (min) | M/Z | Configu-ration |
|---|---|---|---|---|---|
| 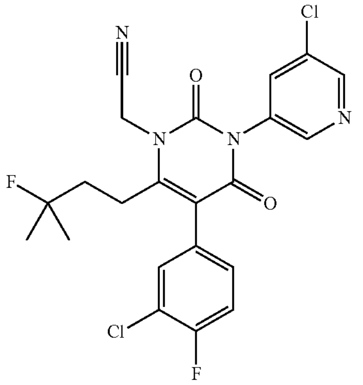 [SMILES: CC(C)(F)CCc1c(-c2ccc(F)c(Cl)c2)c(=O)n(-c2cncc(Cl)c2)c(=O)n1CC#N] | I-357 | A | 2.52 | 479 | |
| 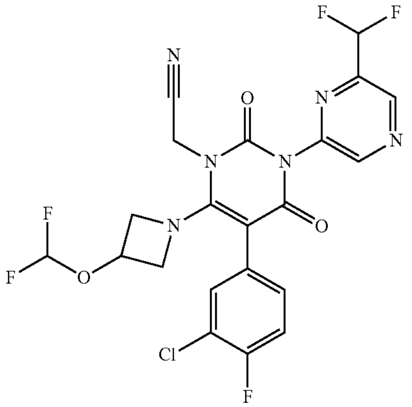 [SMILES: N#CCn1c(N2CC(OC(F)F)C2)c(-c2ccc(F)c(Cl)c2)c(=O)n(-c2cncc(C(F)F)n2)c1=O] | I-358 | D | 1.97 | 529 | |

TABLE 73-continued
| Structure | Compound No. | LC/MS measurement condition | Retention time (min) | M/Z | Configu- ration |
|---|---|---|---|---|---|
| 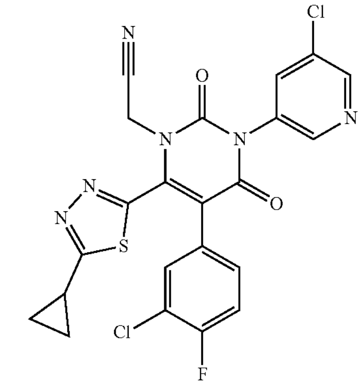 [SMILES: N#CCn1c(-c2nnc(C3CC3)s2)c(-c2ccc(F)c(Cl)c2)c(=O)n(-c2cncc(Cl)c2)c1=O] | I-359 | A | 2.24 | 515 | |
| 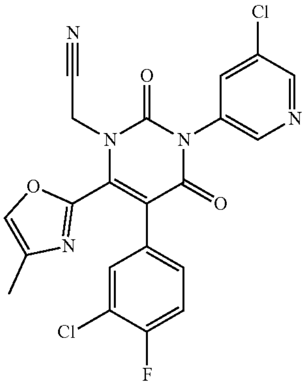 [SMILES: Cc1coc(-c2c(-c3ccc(F)c(Cl)c3)c(=O)n(-c3cncc(Cl)c3)c(=O)n2CC#N)n1] | I-360 | A | 2.44 | 472 | |
| 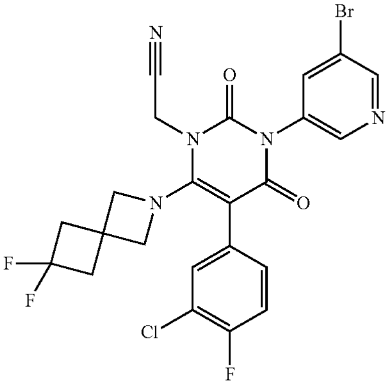 [SMILES: N#CCn1c(N2CC3(C2)CC(F)(F)C3)c(-c2ccc(F)c(Cl)c2)c(=O)n(-c2cncc(Br)c2)c1=O] | I-361 | A | 2.35 | 566 | |

TABLE 74
| Structure | Compound No. | LC/MS measurement condition | Retention time (min) | M/Z | Configu-ration |
|---|---|---|---|---|---|
| 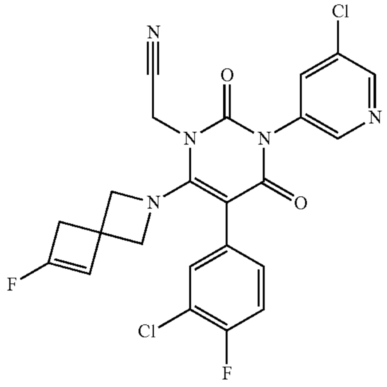 [SMILES: N#CCn1c(N2CC3(C=C(F)C3)C2)c(-c2ccc(F)c(Cl)c2)c(=O)n(-c2cncc(Cl)c2)c1=O] | I-362 | A | 2.37 | 502 | |
| 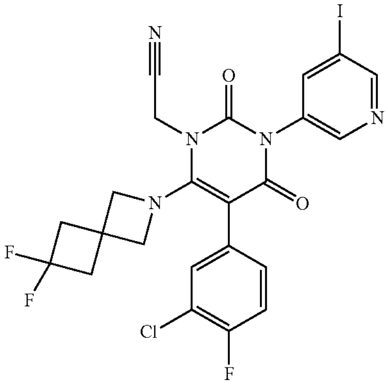 [SMILES: N#CCn1c(N2CC3(C2)CC(F)(F)C3)c(-c2ccc(F)c(Cl)c2)c(=O)n(-c2cncc(I)c2)c1=O] | I-363 | A | 2.38 | 614 | |
| 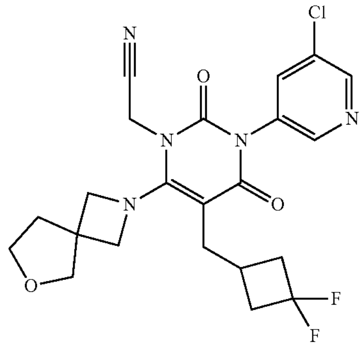 [SMILES: N#CCn1c(N2CC3(CCOC3)C2)c(CC2CC(F)(F)C2)c(=O)n(-c2cncc(Cl)c2)c1=O] | I-364 | A | 1.95 | 478 | |
| 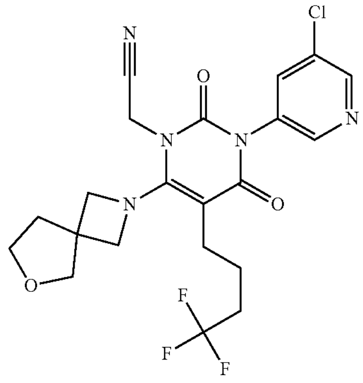 [SMILES: N#CCn1c(N2CC3(CCOC3)C2)c(CCCC(F)(F)F)c(=O)n(-c2cncc(Cl)c2)c1=O] | I-365 | A | 2.01 | 484 | |

TABLE 74-continued
| Structure | Compound No. | LC/MS measurement condition | Retention time (min) | M/Z | Configu-ration |
|---|---|---|---|---|---|
| 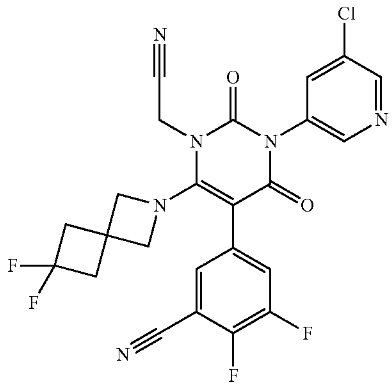 [SMILES: N#CCn1c(N2CC3(C2)CC(F)(F)C3)c(-c2cc(F)c(F)c(C#N)c2)c(=O)n(-c2cncc(Cl)c2)c1=O] | I-366 | A | 2.30 | 531 | |
TABLE 75
| Structure | Compound No. | LC/MS measurement condition | Retention time (min) | M/Z | Configu-ration |
|---|---|---|---|---|---|
| 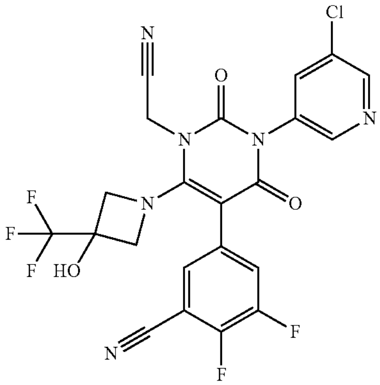 [SMILES: N#CCn1c(N2CC(O)(C(F)(F)F)C2)c(-c2cc(F)c(F)c(C#N)c2)c(=O)n(-c2cncc(Cl)c2)c1=O] | I-367 | A | 2.13 | 539 | |
| 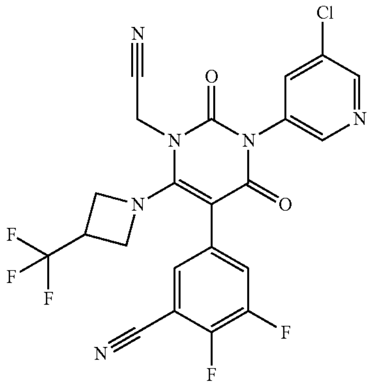 | I-368 | A | 2.26 | 523 | |

TABLE 75-continued
| Structure | Compound No. | LC/MS measurement condition | Retention time (min) | M/Z | Configu-ration |
|---|---|---|---|---|---|
| 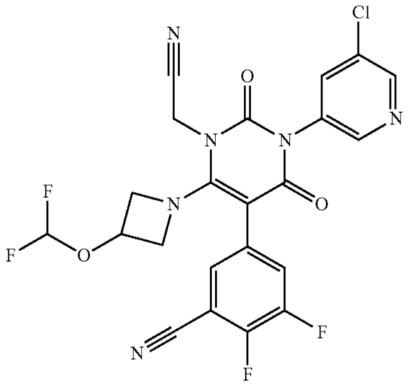 [SMILES: N#CCn1c(N2CC(OC(F)F)C2)c(-c2cc(F)c(F)c(C#N)c2)c(=O)n(-c2cncc(Cl)c2)c1=O] | I-369 | A | 2.21 | 521 | |
| 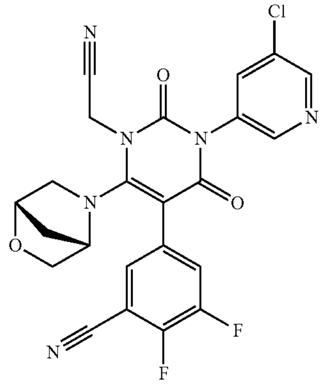 [SMILES: N#CCn1c(N2C[C@@H]3C[C@H]2CO3)c(-c2cc(F)c(F)c(C#N)c2)c(=O)n(-c2cncc(Cl)c2)c1=O] | I-370 | A | 2.00 | 497 | c |
| 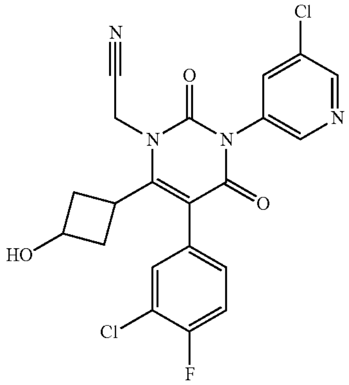 [SMILES: N#CCn1c(C2CC(O)C2)c(-c2ccc(F)c(Cl)c2)c(=O)n(-c2cncc(Cl)c2)c1=O] | I-371 | A | 1.94 | 461 | |

TABLE 76
| Structure | Compound No. | LC/MS measurement condition | Retention time (min) | M/Z | Configu-ration |
|---|---|---|---|---|---|
| 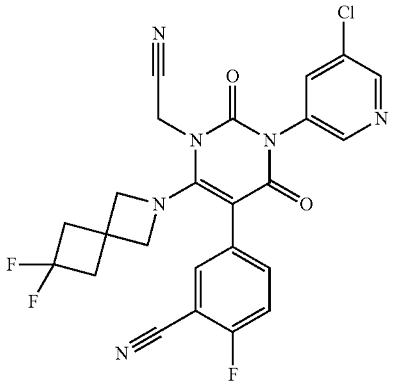 [SMILES: N#CCn1c(N2CC3(C2)CC(F)(F)C3)c(-c2ccc(F)c(C#N)c2)c(=O)n(-c2cncc(Cl)c2)c1=O] | I-372 | A | 2.15 | 513 | |
| 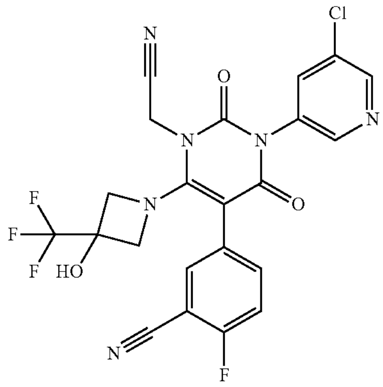 [SMILES: N#CCn1c(N2CC(O)(C(F)(F)F)C2)c(-c2ccc(F)c(C#N)c2)c(=O)n(-c2cncc(Cl)c2)c1=O] | I-373 | A | 1.97 | 521 | |
| 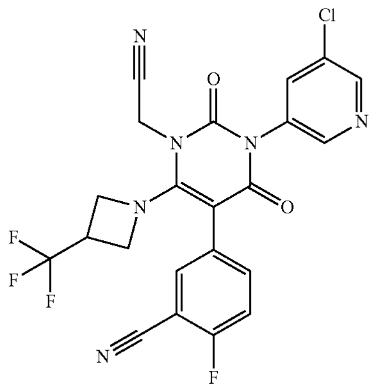 [SMILES: N#CCn1c(N2CC(C(F)(F)F)C2)c(-c2ccc(F)c(C#N)c2)c(=O)n(-c2cncc(Cl)c2)c1=O] | I-374 | A | 2.11 | 505 | |

TABLE 76-continued
| Structure | Compound No. | LC/MS measurement condition | Retention time (min) | M/Z | Configu-ration |
|---|---|---|---|---|---|
| 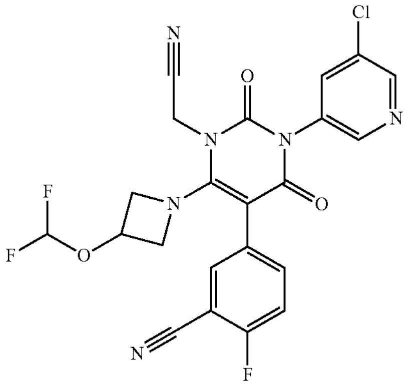 [SMILES: N#CCn1c(N2CC(OC(F)F)C2)c(-c2ccc(F)c(C#N)c2)c(=O)n(-c2cncc(Cl)c2)c1=O] | I-375 | A | 2.05 | 503 | |
| 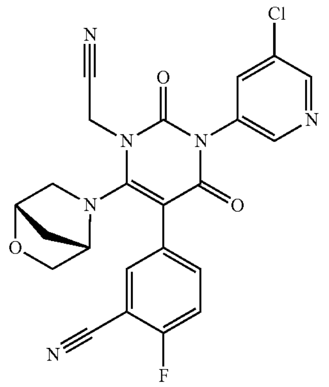 [SMILES: N#CCn1c(N2C[C@@H]3C[C@H]2CO3)c(-c2ccc(F)c(C#N)c2)c(=O)n(-c2cncc(Cl)c2)c1=O] | I-376 | A | 1.81 | 479 | c |
TABLE 77
| Structure | Compound No. | LC/MS measurement condition | Retention time (min) | M/Z | Configu-ration |
|---|---|---|---|---|---|
| 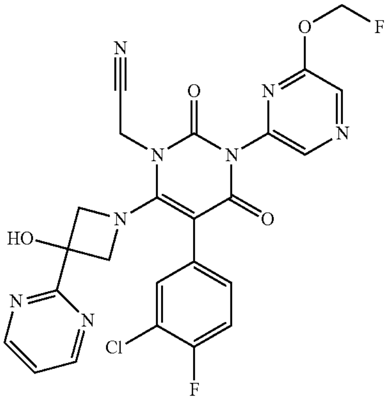 [SMILES: N#CCn1c(N2CC(O)(c3ncccn3)C2)c(-c2ccc(F)c(Cl)c2)c(=O)n(-c2cncc(OCF)n2)c1=O] | I-377 | A | 1.80 | 555 | |

TABLE 77-continued
| Structure | Compound No. | LC/MS measurement condition | Retention time (min) | M/Z | Configu-ration |
|---|---|---|---|---|---|
| 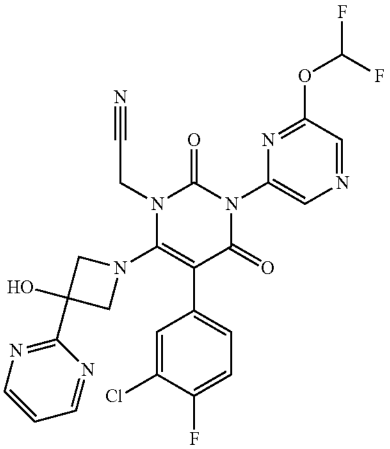 [SMILES: N#CCn1c(N2CC(O)(c3ncccn3)C2)c(-c2ccc(F)c(Cl)c2)c(=O)n(-c2cncc(OC(F)F)n2)c1=O] | I-378 | A | 1.77 | 573 | |
| 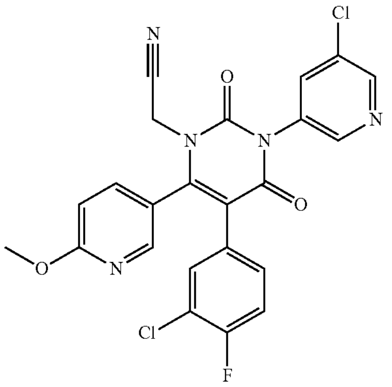 [SMILES: COc1ccc(-c2c(-c3ccc(F)c(Cl)c3)c(=O)n(-c3cncc(Cl)c3)c(=O)n2CC#N)cn1] | I-379 | A | 1.76 | 498 | |
| 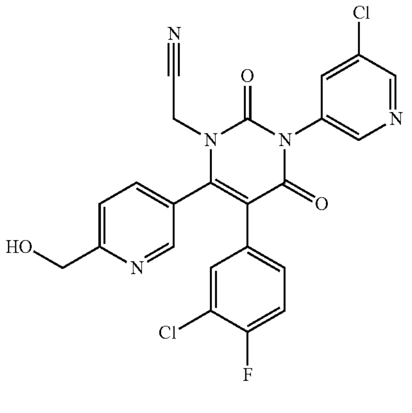 [SMILES: N#CCn1c(-c2ccc(CO)nc2)c(-c2ccc(F)c(Cl)c2)c(=O)n(-c2cncc(Cl)c2)c1=O] | I-380 | A | 1.40 | 498 | |

TABLE 77-continued
| Structure | Compound No. | LC/MS measurement condition | Retention time (min) | M/Z | Configuration |
|---|---|---|---|---|---|
| 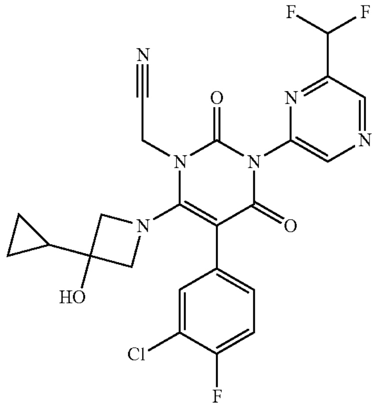 [SMILES: N#CCn1c(N2CC(O)(C3CC3)C2)c(-c2ccc(F)c(Cl)c2)c(=O)n(-c2cncc(C(F)F)n2)c1=O] | I-381 | D | 1.82 | 519 | |
TABLE 78
| Structure | Compound No. | LC/MS measurement condition | Retention time (min) | M/Z | Configuration |
|---|---|---|---|---|---|
| 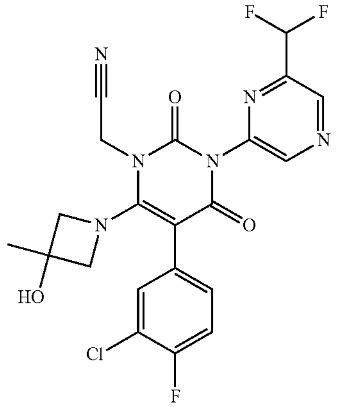 [SMILES: CC1(O)CN(c2c(-c3ccc(F)c(Cl)c3)c(=O)n(-c3cncc(C(F)F)n3)c(=O)n2CC#N)C1] | I-382 | D | 1.66 | 493 | |
| 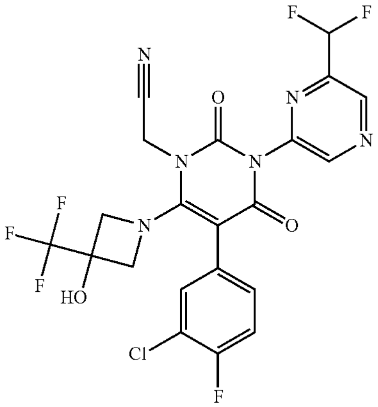 [SMILES: N#CCn1c(N2CC(O)(C(F)(F)F)C2)c(-c2ccc(F)c(Cl)c2)c(=O)n(-c2cncc(C(F)F)n2)c1=O] | I-383 | D | 1.90 | 547 | |

TABLE 78-continued
| Structure | Compound No. | LC/MS measurement condition | Retention time (min) | M/Z | Configu-ration |
|---|---|---|---|---|---|
| 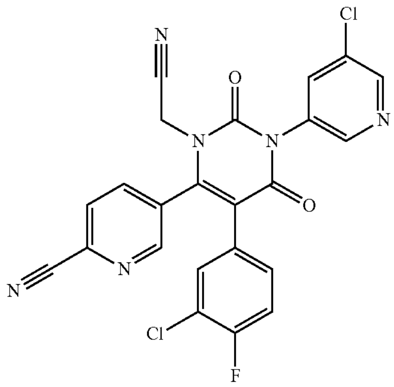 [SMILES: N#CCn1c(-c2ccc(C#N)nc2)c(-c2ccc(F)c(Cl)c2)c(=O)n(-c2cncc(Cl)c2)c1=O] | I-384 | A | 1.69 | 493 | |
| 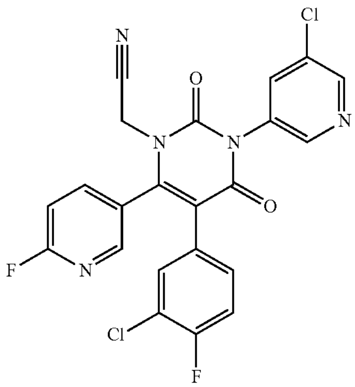 [SMILES: N#CCn1c(-c2ccc(F)nc2)c(-c2ccc(F)c(Cl)c2)c(=O)n(-c2cncc(Cl)c2)c1=O] | I-385 | A | 1.69 | 486 | |
| 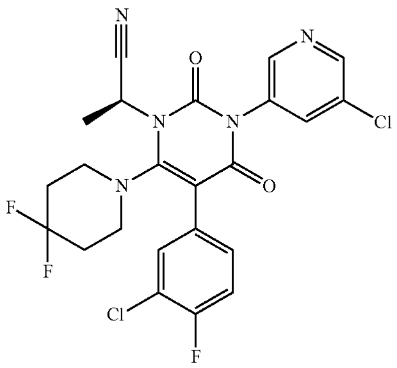 [SMILES: C[C@@H](C#N)n1c(N2CCC(F)(F)CC2)c(-c2ccc(F)c(Cl)c2)c(=O)n(-c2cncc(Cl)c2)c1=O] | I-386 | D | 2.18 | 524 | b |

TABLE 79
| Structure | Compound No. | LC/MS measurement condition | Retention time (min) | M/Z | Configu-ration |
|---|---|---|---|---|---|
| 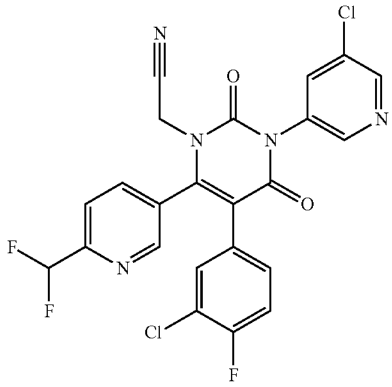 [SMILES: N#CCn1c(-c2ccc(C(F)F)nc2)c(-c2ccc(F)c(Cl)c2)c(=O)n(-c2cncc(Cl)c2)c1=O] | I-387 | A | 1.73 | 518 | |
| 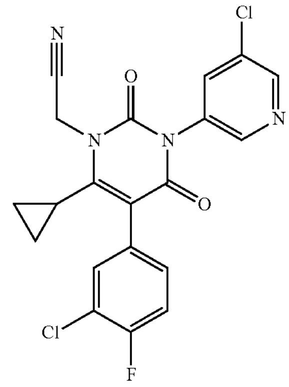 [SMILES: N#CCn1c(C2CC2)c(-c2ccc(F)c(Cl)c2)c(=O)n(-c2cncc(Cl)c2)c1=O] | I-388 | A | 2.49 | 431 | |
| 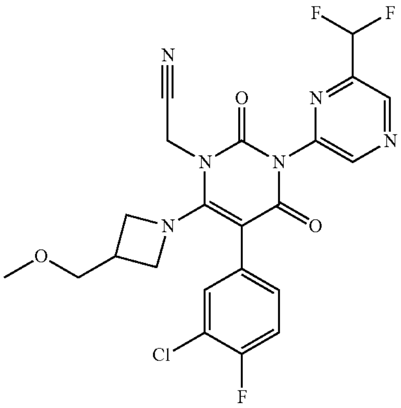 [SMILES: COCC1CN(c2c(-c3ccc(F)c(Cl)c3)c(=O)n(-c3cncc(C(F)F)n3)c(=O)n2CC#N)C1] | I-389 | D | 1.92 | 507 | |

TABLE 79-continued
| Structure | Compound No. | LC/MS measurement condition | Retention time (min) | M/Z | Configu-ration |
|---|---|---|---|---|---|
| 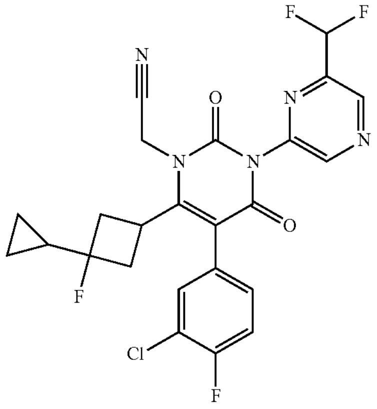 [SMILES: N#CCn1c(C2CC(F)(C3CC3)C2)c(-c2ccc(F)c(Cl)c2)c(=O)n(-c2cncc(C(F)F)n2)c1=O] | I-390 | D | 2.14 | 521 | |
| 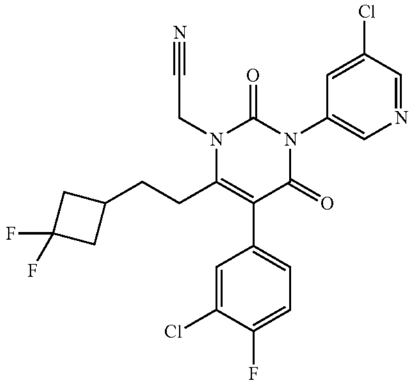 [SMILES: N#CCn1c(CCC2CC(F)(F)C2)c(-c2ccc(F)c(Cl)c2)c(=O)n(-c2cncc(Cl)c2)c1=O] | I-391 | A | 2.65 | 509 | |
TABLE 80
| Structure | Compound No. | LC/MS measurement condition | Retention time (min) | M/Z | Configu-ration |
|---|---|---|---|---|---|
| 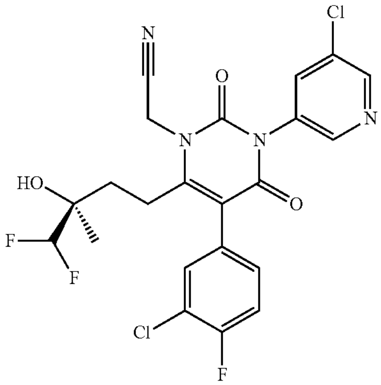 [SMILES: C[C@](O)(CCc1c(-c2ccc(F)c(Cl)c2)c(=O)n(-c2cncc(Cl)c2)c(=O)n1CC#N)C(F)F] | I-392 | A | 2.45 | 513 | b |

TABLE 80-continued
| Structure | Compound No. | LC/MS measurement condition | Retention time (min) | M/Z | Configu-ration |
|---|---|---|---|---|---|
| 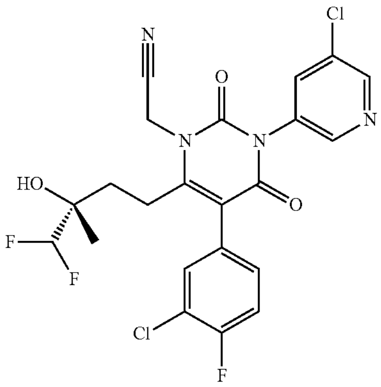 [SMILES: C[C@@](O)(CCc1c(-c2ccc(F)c(Cl)c2)c(=O)n(-c2cncc(Cl)c2)c(=O)n1CC#N)C(F)F] | I-393 | A | 2.45 | 513 | b |
| 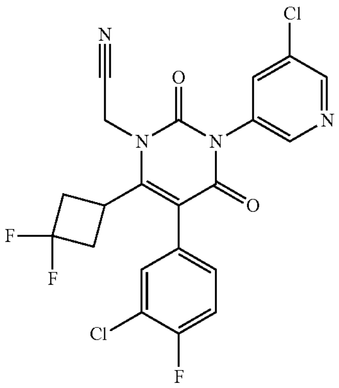 [SMILES: N#CCn1c(C2CC(F)(F)C2)c(-c2ccc(F)c(Cl)c2)c(=O)n(-c2cncc(Cl)c2)c1=O] | I-394 | A | 2.40 | 481 | |
| 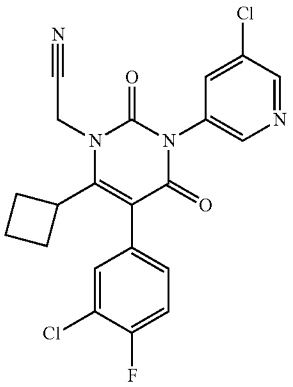 [SMILES: N#CCn1c(C2CCC2)c(-c2ccc(F)c(Cl)c2)c(=O)n(-c2cncc(Cl)c2)c1=O] | I-395 | A | 2.42 | 445 | |

TABLE 80-continued
| Structure | Compound No. | LC/MS measurement condition | Retention time (min) | M/Z | Configu-ration |
|---|---|---|---|---|---|
| 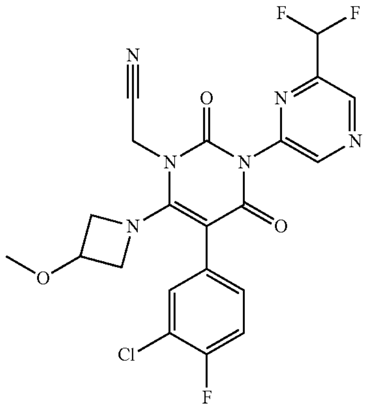 [SMILES: COC1CN(c2c(-c3ccc(F)c(Cl)c3)c(=O)n(-c3cncc(C(F)F)n3)c(=O)n2CC#N)C1] | I-396 | D | 1.87 | 493 | |
TABLE 81
| Structure | Compound No. | LC/MS measurement condition | Retention time (min) | M/Z | Configu-ration |
|---|---|---|---|---|---|
| 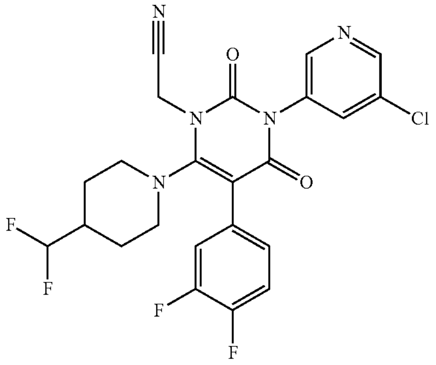 [SMILES: N#CCn1c(N2CCC(C(F)F)CC2)c(-c2ccc(F)c(F)c2)c(=O)n(-c2cncc(Cl)c2)c1=O] | I-397 | A | 2.35 | 508 | |
| 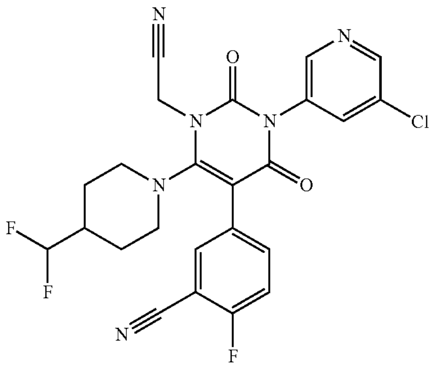 [SMILES: N#CCn1c(N2CCC(C(F)F)CC2)c(-c2ccc(F)c(C#N)c2)c(=O)n(-c2cncc(Cl)c2)c1=O] | I-398 | A | 2.25 | 515 | |

TABLE 81-continued
| Structure | Compound No. | LC/MS measurement condition | Retention time (min) | M/Z | Configu-ration |
|---|---|---|---|---|---|
| 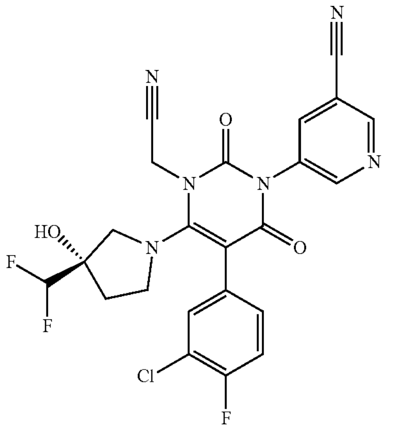 [SMILES: N#CCn1c(N2CC[C@@](O)(C(F)F)C2)c(-c2ccc(F)c(Cl)c2)c(=O)n(-c2cncc(C#N)c2)c1=O] | I-399 | A | 2.33 | 517 | c |
| 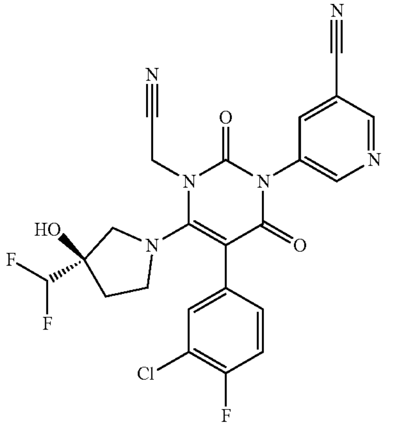 [SMILES: N#CCn1c(N2CC[C@](O)(C(F)F)C2)c(-c2ccc(F)c(Cl)c2)c(=O)n(-c2cncc(C#N)c2)c1=O] | I-400 | A | 2.33 | 517 | c |
| 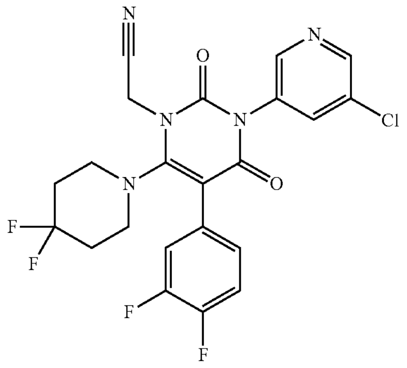 [SMILES: N#CCn1c(N2CCC(F)(F)CC2)c(-c2ccc(F)c(F)c2)c(=O)n(-c2cncc(Cl)c2)c1=O] | I-401 | A | 2.30 | 494 | |

TABLE 82
| Structure | Compound No. | LC/MS measurement condition | Retention time (min) | M/Z | Configu-ration |
|---|---|---|---|---|---|
| 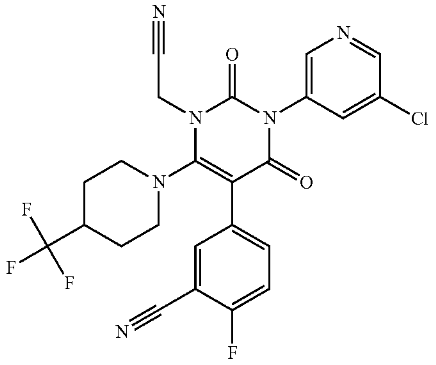 [SMILES: N#CCn1c(N2CCC(C(F)(F)F)CC2)c(-c2ccc(F)c(C#N)c2)c(=O)n(-c2cncc(Cl)c2)c1=O] | I-402 | A | 2.35 | 533 | |
| 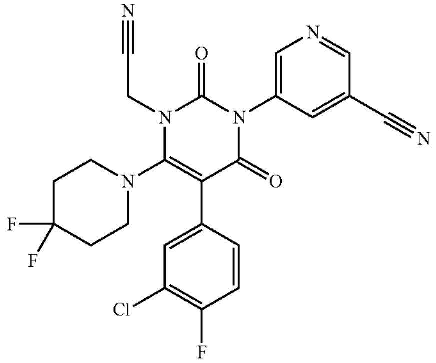 [SMILES: N#CCn1c(N2CCC(F)(F)CC2)c(-c2ccc(F)c(Cl)c2)c(=O)n(-c2cncc(C#N)c2)c1=O] | I-403 | A | 2.55 | 501 | |
| 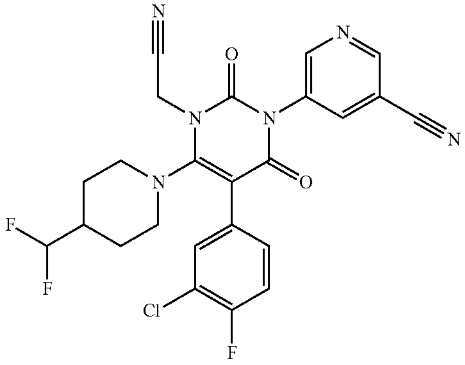 [SMILES: N#CCn1c(N2CCC(C(F)F)CC2)c(-c2ccc(F)c(Cl)c2)c(=O)n(-c2cncc(C#N)c2)c1=O] | I-404 | A | 2.60 | 515 | |
| 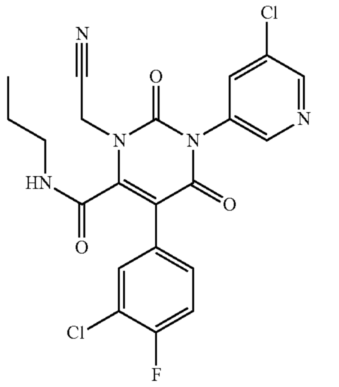 [SMILES: CCCNC(=O)c1c(-c2ccc(F)c(Cl)c2)c(=O)n(-c2cncc(Cl)c2)c(=O)n1CC#N] | I-405 | A | 2.25 | 476 | |

TABLE 82-continued
| Structure | Compound No. | LC/MS measurement condition | Retention time (min) | M/Z | Configu-ration |
|---|---|---|---|---|---|
| 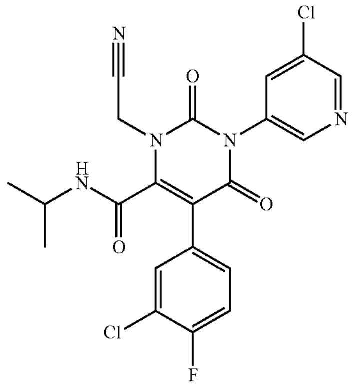 [SMILES: CC(C)NC(=O)c1c(-c2ccc(F)c(Cl)c2)c(=O)n(-c2cncc(Cl)c2)c(=O)n1CC#N] | I-406 | A | 2.23 | 476 | |
TABLE 83
| Structure | Compound No. | LC/MS measurement condition | Retention time (min) | M/Z | Configu-ration |
|---|---|---|---|---|---|
| 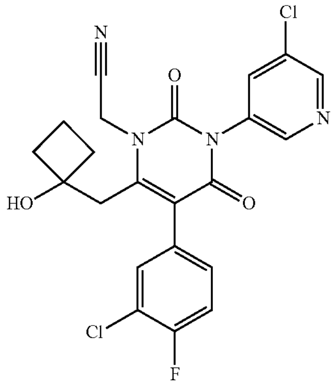 [SMILES: N#CCn1c(CC2(O)CCC2)c(-c2ccc(F)c(Cl)c2)c(=O)n(-c2cncc(Cl)c2)c1=O] | I-407 | D | 2.19 | 475 | |
| 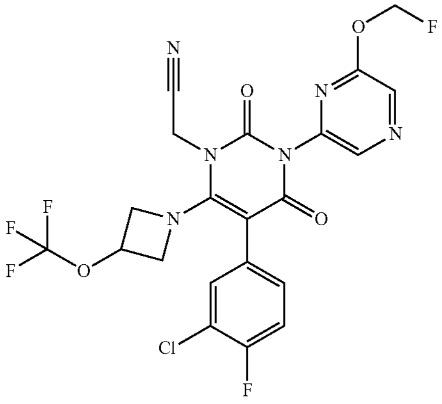 [SMILES: N#CCn1c(N2CC(OC(F)(F)F)C2)c(-c2ccc(F)c(Cl)c2)c(=O)n(-c2cncc(OCF)n2)c1=O] | I-408 | A | 2.10 | 545 | |

TABLE 83-continued
| Structure | Compound No. | LC/MS measurement condition | Retention time (min) | M/Z | Configu-ration |
|---|---|---|---|---|---|
| 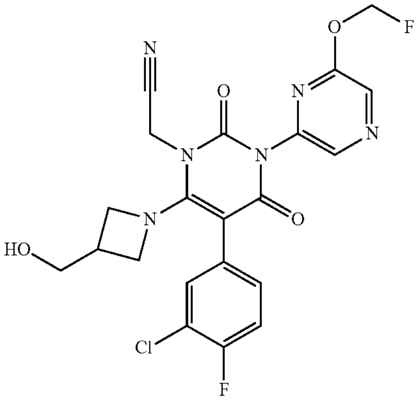 [SMILES: N#CCn1c(N2CC(CO)C2)c(-c2ccc(F)c(Cl)c2)c(=O)n(-c2cncc(OCF)n2)c1=O] | I-409 | A | 1.73 | 491 | |
| 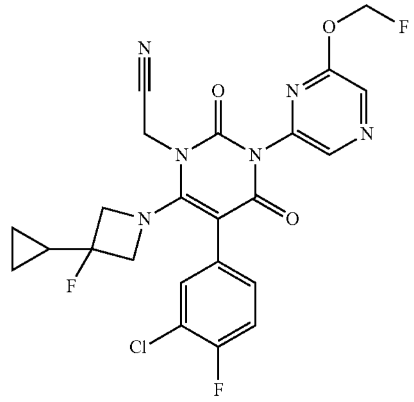 [SMILES: N#CCn1c(N2CC(F)(C3CC3)C2)c(-c2ccc(F)c(Cl)c2)c(=O)n(-c2cncc(OCF)n2)c1=O] | I-410 | A | 2.08 | 519 | |
| 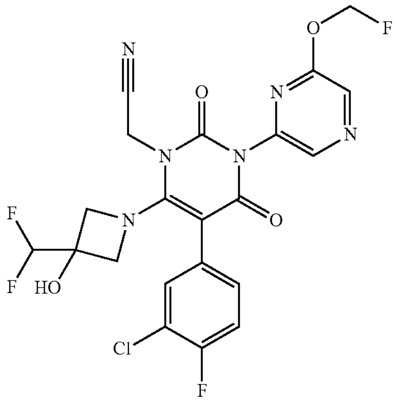 [SMILES: N#CCn1c(N2CC(O)(C(F)F)C2)c(-c2ccc(F)c(Cl)c2)c(=O)n(-c2cncc(OCF)n2)c1=O] | I-411 | A | 1.70 | 527 | |

TABLE 84
| Structure | Compound No. | LC/MS measurement condition | Retention time (min) | M/Z | Configu-ration |
|---|---|---|---|---|---|
| 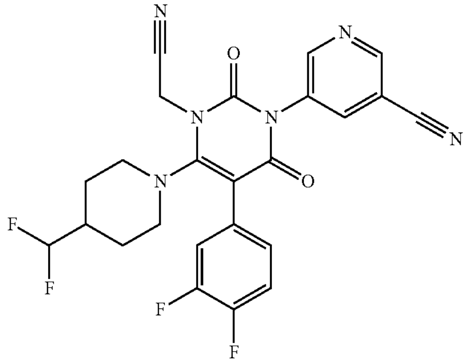 [SMILES: N#CCn1c(N2CCC(C(F)F)CC2)c(-c2ccc(F)c(F)c2)c(=O)n(-c2cncc(C#N)c2)c1=O] | I-412 | A | 2.21 | 499 | |
| 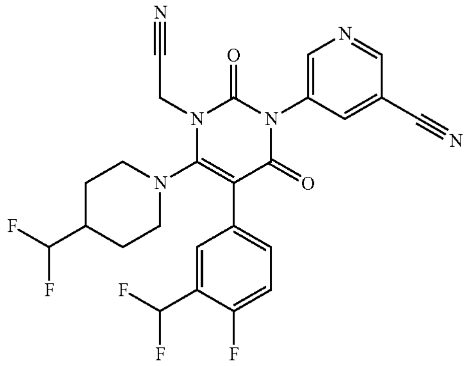 [SMILES: N#CCn1c(N2CCC(C(F)F)CC2)c(-c2ccc(F)c(C(F)F)c2)c(=O)n(-c2cncc(C#N)c2)c1=O] | I-413 | A | 2.34 | 531 | |
| 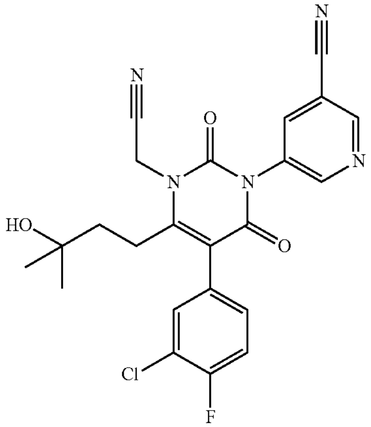 [SMILES: CC(C)(O)CCc1c(-c2ccc(F)c(Cl)c2)c(=O)n(-c2cncc(C#N)c2)c(=O)n1CC#N] | I-414 | A | 1.99 | 468 | |

TABLE 84-continued
| Structure | Compound No. | LC/MS measurement condition | Retention time (min) | M/Z | Configu-ration |
|---|---|---|---|---|---|
| 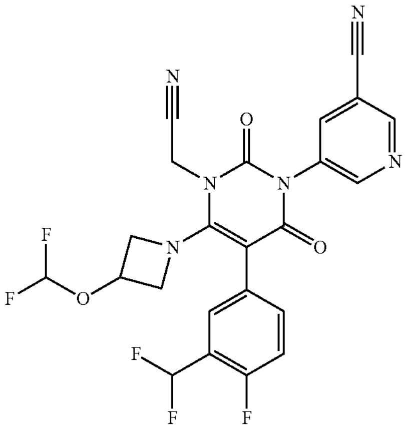 [SMILES: N#CCn1c(N2CC(OC(F)F)C2)c(-c2ccc(F)c(C(F)F)c2)c(=O)n(-c2cncc(C#N)c2)c1=O] | I-415 | D | 2.06 | 519 | |
| 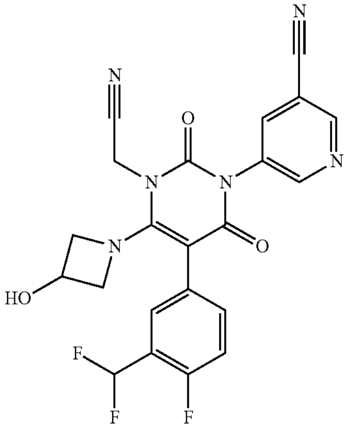 [SMILES: N#CCn1c(N2CC(O)C2)c(-c2ccc(F)c(C(F)F)c2)c(=O)n(-c2cncc(C#N)c2)c1=O] | I-416 | D | 1.63 | 469 | |
TABLE 85
| Structure | Compound No. | LC/MS measurement condition | Retention time (min) | M/Z | Configu-ration |
|---|---|---|---|---|---|
| 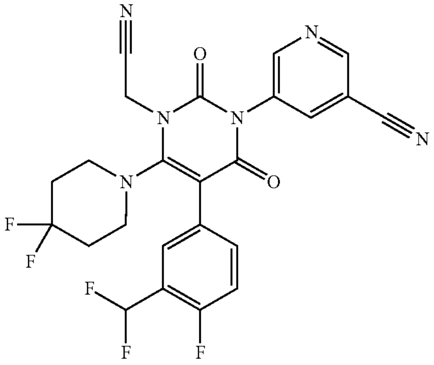 [SMILES: N#CCn1c(N2CCC(F)(F)CC2)c(-c2ccc(F)c(C(F)F)c2)c(=O)n(-c2cncc(C#N)c2)c1=O] | I-417 | D | 2.19 | 517 | |

TABLE 85-continued
| Structure | Compound No. | LC/MS measurement condition | Retention time (min) | M/Z | Configu-ration |
|---|---|---|---|---|---|
| 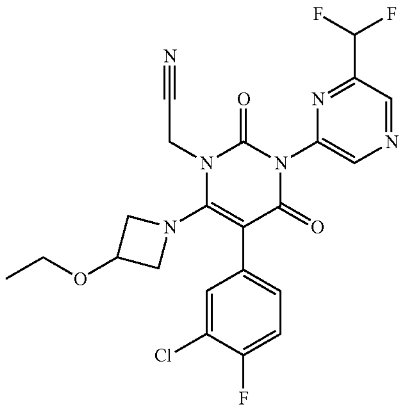 [SMILES: CCOC1CN(c2c(-c3ccc(F)c(Cl)c3)c(=O)n(-c3cncc(C(F)F)n3)c(=O)n2CC#N)C1] | I-418 | D | 2.01 | 507 | |
| 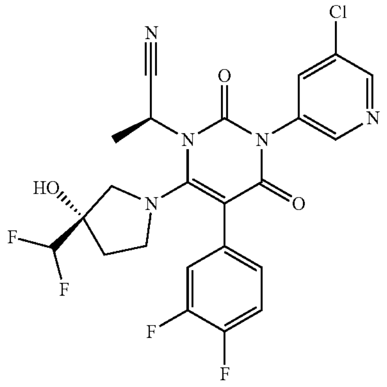 [SMILES: C[C@@H](C#N)n1c(N2CC[C@@](O)(C(F)F)C2)c(-c2ccc(F)c(F)c2)c(=O)n(-c2cncc(Cl)c2)c1=O] | I-419 | A | 2.12 | 524 | b |
| 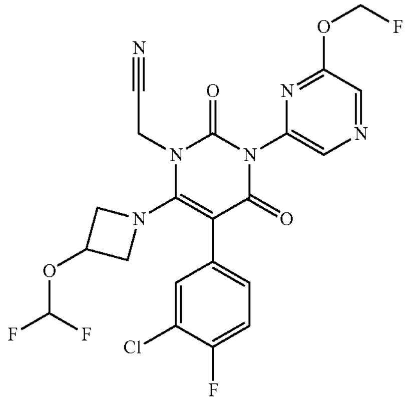 [SMILES: N#CCn1c(N2CC(OC(F)F)C2)c(-c2ccc(F)c(Cl)c2)c(=O)n(-c2cncc(OCF)n2)c1=O] | I-420 | A | 1.92 | 527 | |

TABLE 85-continued
| Structure | Compound No. | LC/MS measurement condition | Retention time (min) | M/Z | Configu-ration |
|---|---|---|---|---|---|
| 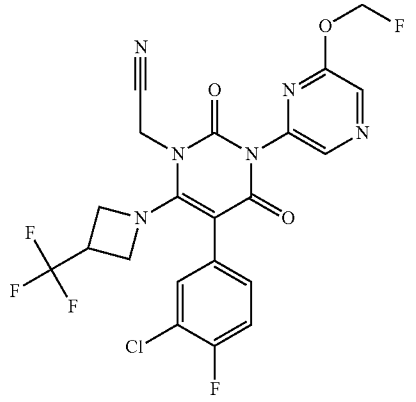 [SMILES: N#CCn1c(N2CC(C(F)(F)F)C2)c(-c2ccc(F)c(Cl)c2)c(=O)n(-c2cncc(OCF)n2)c1=O] | I-421 | A | 2.01 | 529 | |
TABLE 86
| Structure | Compound No. | LC/MS measurement condition | Retention time (min) | M/Z | Configu-ration |
|---|---|---|---|---|---|
| 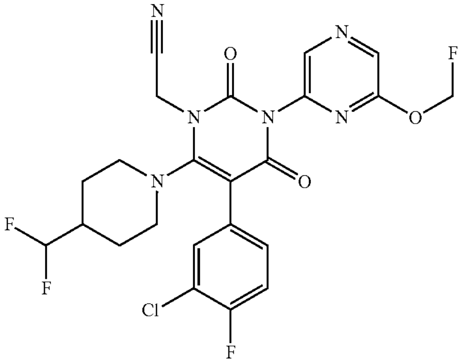 [SMILES: N#CCn1c(N2CCC(C(F)F)CC2)c(-c2ccc(F)c(Cl)c2)c(=O)n(-c2cncc(OCF)n2)c1=O] | I-422 | A | 2.14 | 539 | |
| 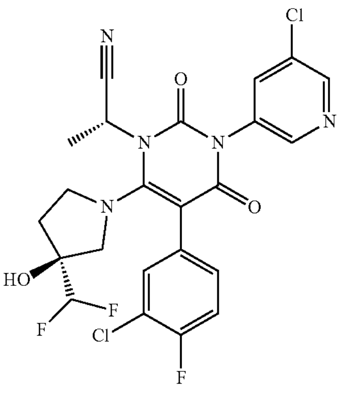 [SMILES: C[C@H](C#N)n1c(N2CC[C@@](O)(C(F)F)C2)c(-c2ccc(F)c(Cl)c2)c(=O)n(-c2cncc(Cl)c2)c1=O] | I-423 | D | 1.92 | 540 | b |

TABLE 86-continued
| Structure | Compound No. | LC/MS measurement condition | Retention time (min) | M/Z | Configu-ration |
|---|---|---|---|---|---|
| 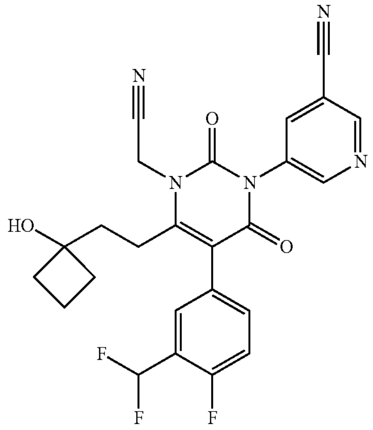 [SMILES: N#CCn1c(CCC2(O)CCC2)c(-c2ccc(F)c(C(F)F)c2)c(=O)n(-c2cncc(C#N)c2)c1=O] | I-424 | A | 1.44 | 496 | |
| 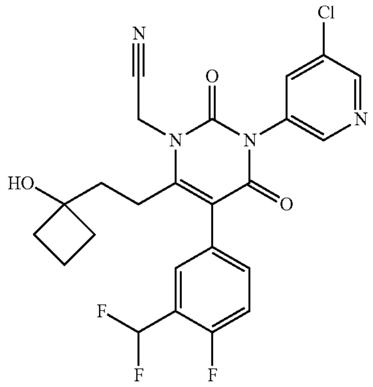 [SMILES: N#CCn1c(CCC2(O)CCC2)c(-c2ccc(F)c(C(F)F)c2)c(=O)n(-c2cncc(Cl)c2)c1=O] | I-425 | A | 1.51 | 505 | |
| 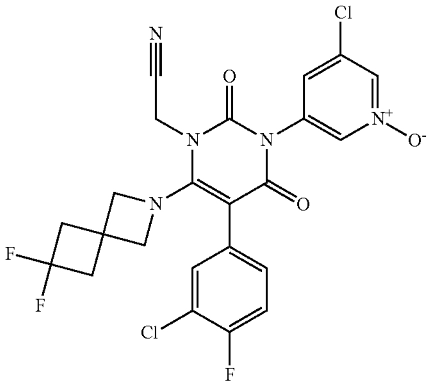 [SMILES: N#CCn1c(N2CC3(C2)CC(F)(F)C3)c(-c2ccc(F)c(Cl)c2)c(=O)n(-c2cc(Cl)c[n+]([O-])c2)c1=O] | I-426 | A | 2.03 | 538 | |

TABLE 87
| Structure | Compound No. | LC/MS measurement condition | Retention time (min) | M/Z | Configu-ration |
|---|---|---|---|---|---|
| 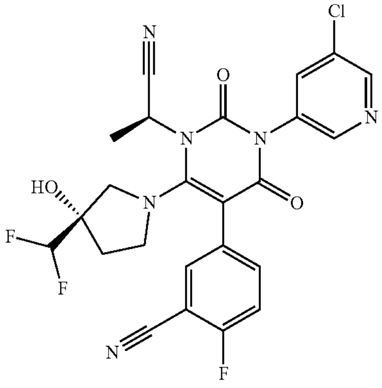 [SMILES: C[C@@H](C#N)n1c(N2CC[C@@](O)(C(F)F)C2)c(-c2ccc(F)c(C#N)c2)c(=O)n(-c2cncc(Cl)c2)c1=O] | I-427 | A | 2.00 | 531 | b |
| 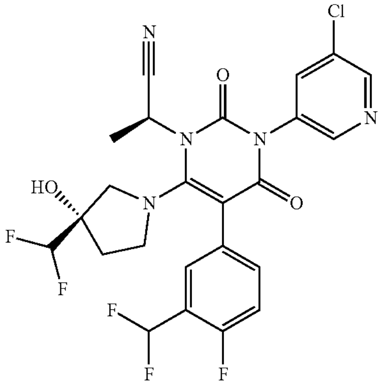 [SMILES: C[C@@H](C#N)n1c(N2CC[C@@](O)(C(F)F)C2)c(-c2ccc(F)c(C(F)F)c2)c(=O)n(-c2cncc(Cl)c2)c1=O] | I-428 | A | 2.16 | 556 | b |
| 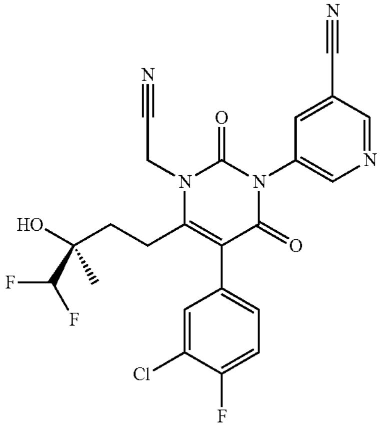 [SMILES: C[C@](O)(CCc1c(-c2ccc(F)c(Cl)c2)c(=O)n(-c2cncc(C#N)c2)c(=O)n1CC#N)C(F)F] | I-429 | A | 2.40 | 504 | b |

TABLE 87-continued
| Structure | Compound No. | LC/MS measurement condition | Retention time (min) | M/Z | Configu-ration |
|---|---|---|---|---|---|
| 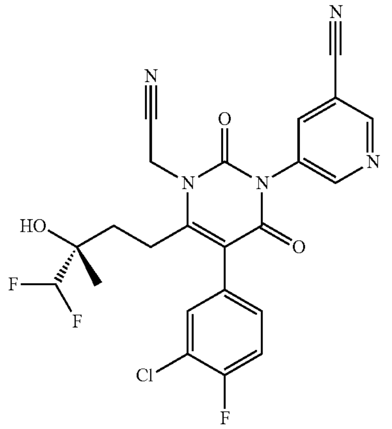 [SMILES: C[C@@](O)(CCc1c(-c2ccc(F)c(Cl)c2)c(=O)n(-c2cncc(C#N)c2)c(=O)n1CC#N)C(F)F] | I-430 | A | 2.40 | 504 | b |
| 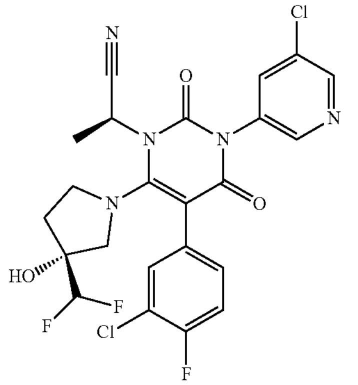 [SMILES: C[C@@H](C#N)n1c(N2CC[C@](O)(C(F)F)C2)c(-c2ccc(F)c(Cl)c2)c(=O)n(-c2cncc(Cl)c2)c1=O] | I-431 | D | 1.93 | 540 | b |
TABLE 88
| Structure | Compound No. | LC/MS measurement condition | Retention time (min) | M/Z | Configu-ration |
|---|---|---|---|---|---|
| 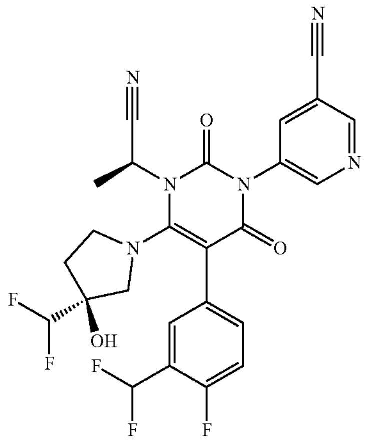 [SMILES: C[C@@H](C#N)n1c(N2CC[C@@](O)(C(F)F)C2)c(-c2ccc(F)c(C(F)F)c2)c(=O)n(-c2cncc(C#N)c2)c1=O] | I-432 | D | 1.76 | 547 | b |

TABLE 88-continued
| Structure | Compound No. | LC/MS measurement condition | Retention time (min) | M/Z | Configu-ration |
|---|---|---|---|---|---|
| 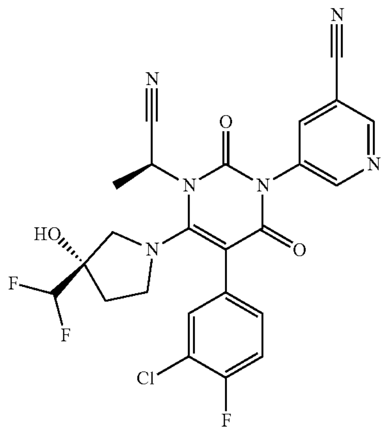 [SMILES: C[C@@H](C#N)n1c(N2CC[C@@](O)(C(F)F)C2)c(-c2ccc(F)c(Cl)c2)c(=O)n(-c2cncc(C#N)c2)c1=O] | I-433 | A | 2.11 | 531 | b |
| 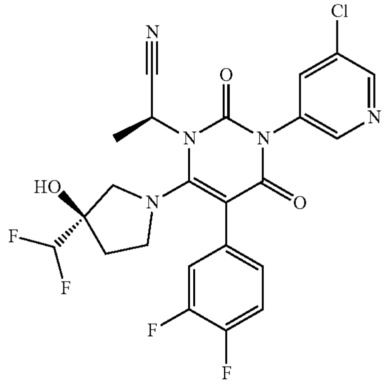 [SMILES: C[C@@H](C#N)n1c(N2CC[C@](O)(C(F)F)C2)c(-c2ccc(F)c(F)c2)c(=O)n(-c2cncc(Cl)c2)c1=O] | I-434 | A | 2.09 | 524 | b |
| 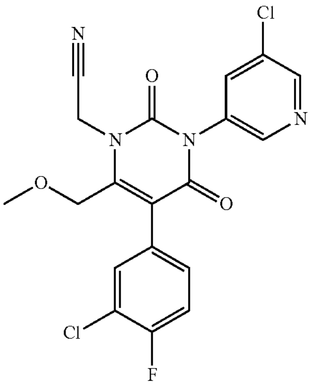 [SMILES: COCc1c(-c2ccc(F)c(Cl)c2)c(=O)n(-c2cncc(Cl)c2)c(=O)n1CC#N] | I-435 | A | 2.51 | 435 | |

TABLE 88-continued
| Structure | Compound No. | LC/MS measurement condition | Retention time (min) | M/Z | Configu-ration |
|---|---|---|---|---|---|
| 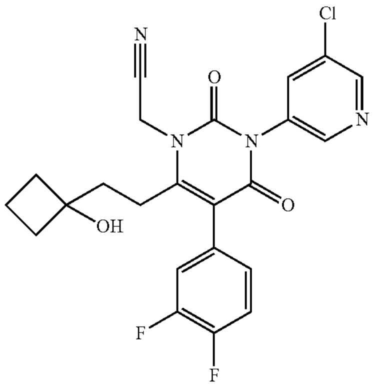 [SMILES: N#CCn1c(CCC2(O)CCC2)c(-c2ccc(F)c(F)c2)c(=O)n(-c2cncc(Cl)c2)c1=O] | I-436 | A | 2.11 | 473 | |
TABLE 89
| Structure | Compound No. | LC/MS measurement condition | Retention time (min) | M/Z | Configu-ration |
|---|---|---|---|---|---|
| 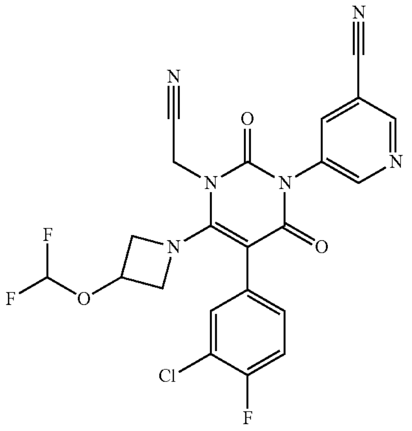 [SMILES: N#CCn1c(N2CC(OC(F)F)C2)c(-c2ccc(F)c(Cl)c2)c(=O)n(-c2cncc(C#N)c2)c1=O] | I-437 | A | 2.19 | 503 | |
| 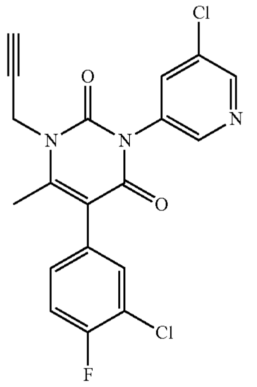 [SMILES: C#CCn1c(C)c(-c2ccc(F)c(Cl)c2)c(=O)n(-c2cncc(Cl)c2)c1=O] | I-438 | A | 2.24 | 404 | |

TABLE 89-continued
| Structure | Compound No. | LC/MS measurement condition | Retention time (min) | M/Z | Configu-ration |
|---|---|---|---|---|---|
| 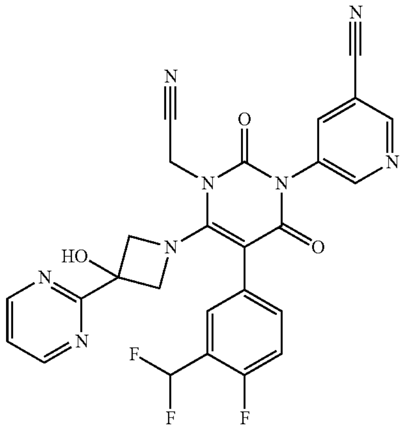 [SMILES: N#CCn1c(N2CC(O)(c3ncccn3)C2)c(-c2ccc(F)c(C(F)F)c2)c(=O)n(-c2cncc(C#N)c2)c1=O] | I-439 | A | 1.76 | 547 | |
| 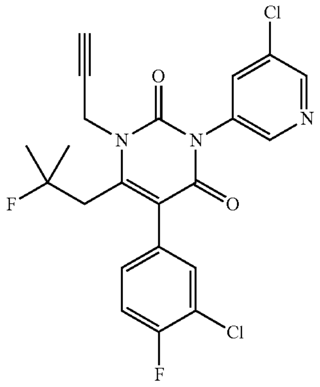 [SMILES: C#CCn1c(CC(C)(C)F)c(-c2ccc(F)c(Cl)c2)c(=O)n(-c2cncc(Cl)c2)c1=O] | I-440 | A | 2.44 | 464 | |
| 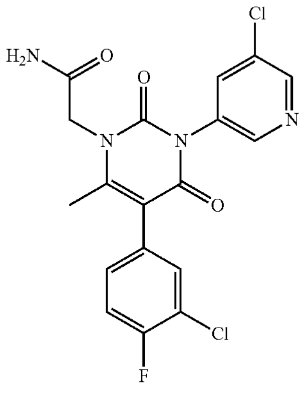 [SMILES: Cc1c(-c2ccc(F)c(Cl)c2)c(=O)n(-c2cncc(Cl)c2)c(=O)n1CC(N)=O] | I-441 | A | 1.81 | 423 | |

TABLE 90
| Structure | Compound No. | LC/MS measurement condition | Retention time (min) | M/Z | Configu-ration |
|---|---|---|---|---|---|
| 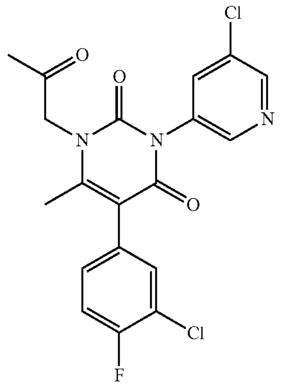 [SMILES: CC(=O)Cn1c(C)c(-c2ccc(F)c(Cl)c2)c(=O)n(-c2cncc(Cl)c2)c1=O] | I-442 | A | 2.04 | 422 | |
| 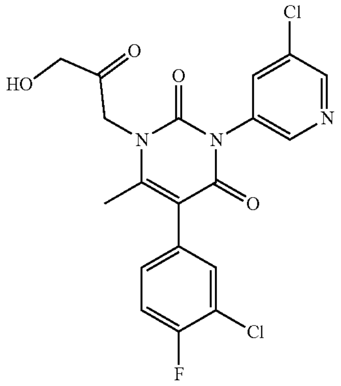 [SMILES: Cc1c(-c2ccc(F)c(Cl)c2)c(=O)n(-c2cncc(Cl)c2)c(=O)n1CC(=O)CO] | I-443 | A | 1.82 | 438 | |
| 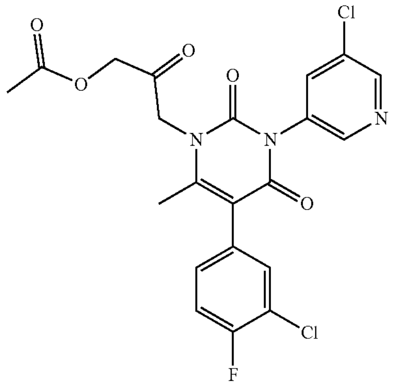 [SMILES: CC(=O)OCC(=O)Cn1c(C)c(-c2ccc(F)c(Cl)c2)c(=O)n(-c2cncc(Cl)c2)c1=O] | I-444 | A | 2.17 | 478 | |
TABLE 91
| | NMR |
|---|---|
| I-018 | 1H-NMR(CDCl3) δ: 2.05 (3H, s), 4.71 (2H, s), 6.58 (2H, dd, J = 8.0, 5.6 Hz), 7.48-7.54 (3H, m), 7.64 (1H, s), 7.90-7.96 (2H, m), 8.41 (1H, d, J = 2.1 Hz), 8.54 (1H, d, J = 1.3 Hz) |
| I-020 | 1H-NMR(CDCl3) δ: 2.44 (3H, s), 4.67 (2H, s), 6.93 (1H, t, J = 8.3 Hz), 7.02-7.07 (1H, m), 7.31 (1H, dd, J = 6.9, 1.8 Hz), 7.44-7.48 (3H, m), 7.52- 7.55 (1H, m), 7.85 (2H, dd, J = 8.7, 5.3 Hz), 8.44 (1H, d. 1.8 Hz), 8.54 (1H, s) |
| I-045 | 1H-NMR (CDCl3) δ: 2.11 (2H, t, J = 7.0 Hz), 2.38 (3H, s), 3.76-3.85 (4H, m), 3.91 (4H, s), 4.76 (2H, brs), 7.14-7.18 (2H, m), 7.34-7.37 (1H, m), 7.44 (1H, s), 8.34 (1H, s), 8.47 (1H, s). |

TABLE 91-continued

| | NMR |
|---|---|
| I-066 | 1H-NMR (CDCl3) δ: 2.44 (3H, s), 4.42 (1H, d, J = 17.6 Hz), 4.61 (1H, d, J = 17.6 Hz), 6.85-6.89 (1H, m), 6.99 (1H, dd, J = 10.2, 7.2 Hz), 7.16 (1H, dd, J = 6.9, 2.1 Hz), 7.41 (1H, d, J = 8.3 Hz), 7.52 (2H, m), 7.83 (1H, d, J = 8.0 Hz), 8.42 (1H, d, J = 2.3 Hz), 8.54-8.56 (1H, br m). |
| I-075 | 1H-NMR (CDCl3) δ: 2.41 (3H, s), 4.52 (4H, brs), 5.02 (2H, s), 6.93-7.04 (2H, m), 7.16 (1H, dd, J = 6.9, 2.1 Hz), 7.22 (1H, dd, J = 7.7, 4.9 Hz), 7.45-7.48 (2H, m), 8.38 (1H, dd, J = 2.0 Hz), 8.47-8.53 (2H, m). |
| I-132 | 1H-NMR (CDCl3) δ: 2.45 (3H, s), 5.14 (2H, s), 6.92-7.03 (2H, m), 7.37 (1H, d, J = 7.3 Hz), 7.45-7.55 (4H, m), 7.87(1H, d, J = 7.3 Hz), 8.39-8.43 (1H, brm), 8.52-8.61 (1H, brm). |
| I-149 | 1H-NMR (DMSO-d6) δ: 2.77-2.83 (4H, m), 4.01-4.12 (4H, m), 4.78 (1H, d, J = 16.8 Hz), 4.85 (1H, d, J = 16.8 Hz), 7.10-7.60 (6H, m), 8.41 (1H, s). |
| I-358 | 1H-NMR (CDCl3) δ: 3.91-4.04 (2H, m), 4.16-4.32 (2H, m), 4.76 (2H, s), 4.82-4.94 (1H, m), 6.23 (1H, t, J = 71.8 Hz), 6.72 (1H, t, J = 54.5 Hz), 7.18 (2H, t, J = 6.8 Hz), 7.37 (1H, d, J = 7.0 Hz), 8.77 (1H, s). 8.99 (1H. s). |
| I-388 | 1H-NMR (CDCl3) δ: 0.58-0.62 (2H, m), 1.05-1.09 (2H, m), 1.87-1.95 (1H, m), 5.18 (2H, s), 7.20 (2H, d, J = 6.5 Hz), 7.39 (1H, d, J= 7.4 Hz), 7.67 (1H, t, J = 2.1 Hz), 8.44 (1H, d, J = 1.9 Hz), 8.64 (1H, d, J = 2.0 Hz). |
| I-437 | 1H-NMR (CDCl3) δ: 3.96-4.03 (2H, m), 4.21-4.28 (2H, m), 4.76 (2H, s), 4.86-4.93 (1H, m), 6.23 (1H, t, J = 71.8 Hz), 7.17-7.21 (2H, m), 7.34-7.38 (1H, m), 7.93 (1H, t, J = 2.1 Hz), 8.75 (1H, d, J = 2.4 Hz), 8.90 (1H, d. J = 1.9 Hz). |

The following compounds can also be synthesized in the same manner as described above.

[Chemical Formula 101]

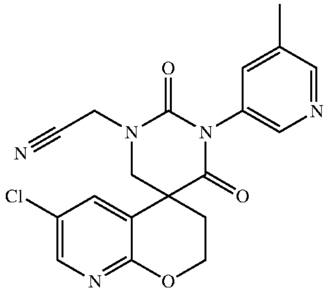

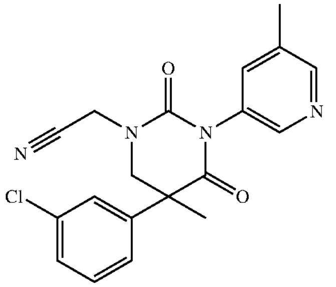

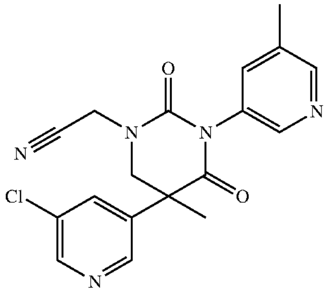

Biological Test Examples for the compounds of the present invention will be described below.

The compound represented by Formula (I) according to the present invention may have coronavirus 3CL protease inhibitory action and may inhibit coronavirus 3CL protease.

Specifically, in the evaluation method described below, the IC50 is preferably 50 μM or less, more preferably 1 μM or less, and even more preferably 100 nM or less. EC50 is preferably 10 μM or less, more preferably 1 μM or less, and even more preferably 100 nM or less.

Test Example 1: Cytopathic Effect (CPE) Suppression Effect Confirmation Test Using HEK293T Cells Expressing Human TMPRSS2, ACE2 (HEK293T/ACE2-TMPRSS2 Cells)

<Operational Procedure>

Dilution and Dispensing of Sample to be Tested

The sample to be tested is diluted in advance to an appropriate concentration with DMSO, and a 2- to 5-fold series of serial dilutions is prepared and then dispensed into a 384-well plate.

Dilution and Dispensing of Cells and SARS-CoV-2

HEK293T/ACE2-TMPRSS2 cells (GCP-SL222, $5\times10^3$ cells/well) and SARS-CoV-2 (200-600 $TCID_{50}$/well) are mixed in a medium (MEM, 2% FBS, penicillin-streptomycin), the mixture is dispensed into the wells in which the sample to be tested has been introduced, and then the cells are cultured for 3 days in a $CO_2$ incubator.

Dispensing of CellTiter-Glo (Registered Trademark) 2.0 and Measurement of Luminescence Signals The plate that has been cultured for 3 days is returned to room temperature, subsequently CellTiter-Glo (registered trademark) 2.0 is dispensed into each well, and the plate is mixed using a plate mixer. The plate is left to stand for a certain time, and then the luminescence signals (Lum) is measured with a plate reader.

<Calculation of Each Measurement Item Value>

Calculation of 50% SARS-CoV-2 Infected Cell Death Inhibitory Concentration ($EC_{50}$)

When x denotes the logarithmic value of the compound concentration and y denotes % Efficacy, the inhibition curve is approximated by the following Logistic regression equation, and the value of x when y=50(%) is inputted is calculated as $EC_{50}$.

$$y = \min + (\max - \min)/\{1 + (X50/x)^\wedge \mathrm{Hill}\}$$

$$\%\ \mathrm{Efficacy} = \{(\mathrm{Sample} - \mathrm{virus\ control})/(\mathrm{cell\ control} - \mathrm{virus\ control})\} * 100\%$$

cell control: the average of Lum of cell control wells virus control: the average of Lum of virus control wells min: lower limit value of y-axis, max: upper limit value of y-axis, X50: x-coordinates of inflection point, Hill: slope of curve at midpoint between min and max The compounds of the present invention were tested essentially as described above. Results are shown below.

The $EC_{50}$ value was determined as "A" for less than 100 nM, "B" for 100 nM or more and less than 1000 nM, and "C" for 1000 nM or more and less than 5000 nM.

Result

TABLE 92

| Compound No. | EC50 [nM] |
|---|---|
| I-014 | 17 |
| I-053 | 2610 |
| I-057 | 29 |
| I-060 | 19 |
| I-072 | 5.21 |
| I-077 | 1.66 |
| I-086 | 3.31 |
| I-088 | 97.2 |
| I-142 | 3.35 |
| I-165 | 228 |
| I-167 | 26.3 |
| I-182 | 1.7 |
| I-185 | 40.5 |
| I-202 | 613 |
| I-205 | 5 |
| I-208 | 7.04 |
| I-230 | 5.36 |
| I-232 | 6.46 |
| I-234 | 6.6 |
| I-238 | 4.62 |
| I-239 | 3.15 |
| I-249 | 7.9 |
| I-250 | 3.31 |
| I-257 | 2.98 |
| I-259 | 5.44 |
| I-261 | 34.5 |

TABLE 93

| Compound No. | EC50 |
|---|---|
| I-003 | C |
| I-005 | B |
| I-006 | B |
| I-007 | B |
| I-008 | B |
| I-009 | B |
| I-010 | C |
| I-011 | A |
| I-012 | A |
| I-015 | B |
| I-016 | A |
| I-017 | A |
| I-018 | A |
| I-019 | A |
| I-020 | A |
| I-021 | A |
| I-022 | A |
| I-023 | A |
| I-025 | A |
| I-026 | A |
| I-027 | B |
| I-028 | A |
| I-029 | A |
| I-030 | A |
| I-031 | A |

TABLE 93-continued

| Compound No. | EC50 |
|---|---|
| I-032 | B |
| I-033 | B |
| I-034 | A |
| I-035 | B |
| I-036 | B |
| I-037 | B |
| I-038 | A |
| I-039 | A |
| I-040 | A |
| I-041 | A |
| I-042 | A |
| I-043 | B |
| I-044 | B |
| I-045 | A |
| I-047 | B |
| I-048 | C |
| I-049 | B |
| I-050 | A |
| I-051 | C |
| I-052 | A |
| I-054 | A |
| I-055 | B |
| I-056 | A |
| I-058 | A |
| I-059 | A |
| I-061 | B |
| I-062 | A |
| I-063 | B |
| I-064 | A |
| I-065 | A |
| I-066 | A |
| I-067 | B |
| I-068 | A |
| I-069 | A |
| I-070 | A |
| I-071 | A |
| I-073 | A |
| I-074 | A |
| I-075 | A |
| I-076 | A |
| I-078 | A |
| I-079 | A |
| I-082 | A |
| I-083 | A |
| I-084 | A |
| I-085 | A |
| I-087 | A |
| I-090 | A |
| I-092 | A |
| I-093 | A |
| I-094 | B |
| I-095 | C |
| I-096 | A |
| I-097 | A |
| I-098 | A |
| I-099 | A |
| I-100 | A |
| I-101 | A |
| I-102 | A |
| I-103 | A |
| I-104 | A |
| I-105 | A |
| I-106 | A |
| I-107 | A |
| I-108 | B |
| I-109 | A |
| I-110 | A |
| I-111 | A |
| I-112 | B |
| I-113 | A |
| I-114 | B |
| I-115 | A |
| I-116 | A |
| I-117 | A |
| I-118 | A |
| I-119 | A |
| I-120 | A |

TABLE 93-continued

| Compound No. | EC50 |
|---|---|
| I-122 | C |
| I-124 | A |
| I-126 | C |
| I-127 | C |
| I-128 | B |
| I-129 | B |
| I-130 | A |
| I-131 | A |
| I-132 | A |
| I-133 | A |
| I-134 | A |
| I-135 | A |
| I-136 | A |
| I-137 | B |
| I-138 | B |
| I-139 | A |
| I-140 | A |
| I-141 | A |
| I-143 | C |
| I-144 | B |
| I-145 | B |
| I-146 | B |
| I-147 | A |
| I-148 | A |
| I-149 | A |
| I-150 | A |
| I-151 | A |
| I-152 | A |
| I-153 | A |
| I-164 | A |
| I-155 | C |
| I-156 | A |
| I-157 | C |
| I-159 | B |
| I-160 | A |
| I-161 | C |
| I-162 | B |
| I-163 | B |
| I-164 | B |
| I-166 | C |
| I-168 | A |
| I-169 | A |
| I-170 | A |
| I-171 | A |
| I-172 | A |
| I-173 | A |
| I-174 | A |
| I-175 | A |
| I-176 | A |
| I-177 | A |
| I-178 | A |
| I-179 | A |
| I-180 | A |
| I-181 | A |
| I-183 | A |
| I-184 | B |
| I-188 | B |
| I-189 | A |
| I-190 | A |
| I-191 | A |
| I-192 | A |
| I-193 | A |
| I-194 | A |
| I-195 | A |
| I-196 | A |
| I-197 | A |
| I-198 | A |
| I-199 | A |
| I-200 | A |
| I-201 | B |
| I-203 | A |
| I-204 | A |

TABLE 94

| Compound No. | EC50 |
|---|---|
| I-206 | A |
| I-207 | A |
| I-209 | A |
| I-210 | B |
| I-211 | A |
| I-212 | B |
| I-213 | A |
| I-214 | A |
| I-215 | A |
| I-216 | A |
| I-217 | A |
| I-218 | C |
| I-219 | B |
| I-220 | B |
| I-221 | C |
| I-223 | A |
| I-224 | A |
| I-225 | A |
| I-226 | A |
| I-227 | A |
| I-228 | A |
| I-229 | A |
| I-231 | A |
| I-233 | A |
| I-235 | A |
| I-236 | A |
| I-237 | A |
| I-240 | A |
| I-241 | A |
| I-242 | A |
| I-243 | B |
| I-244 | A |
| I-245 | A |
| I-246 | B |
| I-247 | A |
| I-248 | B |
| I-251 | A |
| I-282 | A |
| I-253 | A |
| I-264 | A |
| I-255 | A |
| I-256 | A |
| I-258 | A |
| I-260 | A |
| I-262 | A |
| I-263 | C |
| I-284 | A |
| I-265 | B |
| I-266 | B |
| I-267 | A |
| I-268 | A |
| I-269 | A |
| I-270 | A |
| I-271 | A |
| I-272 | A |
| I-273 | A |
| I-274 | A |
| I-275 | B |
| I-276 | A |
| I-278 | B |
| I-279 | A |
| I-280 | A |
| I-281 | A |
| I-286 | B |

TABLE 95

| Compound No. | EC50 |
|---|---|
| I-287 | A |
| I-288 | A |
| I-289 | A |
| I-290 | A |

TABLE 95-continued

| Compound No. | EC50 |
|---|---|
| I-291 | A |
| I-292 | A |
| I-293 | A |
| I-294 | A |
| I-295 | A |
| I-296 | A |
| I-297 | A |
| I-298 | A |
| I-299 | A |
| I-300 | A |
| I-301 | A |
| I-302 | A |
| I-303 | A |
| I-304 | A |
| I-305 | A |
| I-306 | A |
| I-307 | A |
| I-308 | A |
| I-309 | A |
| I-310 | A |
| I-311 | A |
| I-312 | A |
| 1-313 | A |
| I-314 | A |
| I-315 | A |
| I-316 | A |
| I-317 | A |
| I-318 | A |
| I-319 | A |
| I-320 | A |
| I-321 | A |
| I-322 | A |
| I-323 | A |
| I-324 | A |
| I-325 | A |
| I-326 | A |
| I-327 | A |
| I-328 | A |
| I-329 | A |
| I-330 | A |
| I-331 | A |
| I-332 | A |
| I-333 | A |
| I-334 | A |
| I-335 | A |
| I-336 | A |
| I-337 | A |
| I-338 | A |
| I-339 | A |
| I-340 | A |
| I-341 | A |
| I-342 | A |
| I-343 | A |
| I-344 | A |
| I-345 | A |
| I-346 | A |
| I-347 | A |
| I-348 | A |
| I-349 | A |
| I-350 | A |
| I-351 | A |
| I-352 | A |
| I-353 | A |
| I-354 | A |
| I-355 | A |
| I-356 | A |
| I-357 | A |
| I-358 | A |
| I-359 | A |
| I-360 | A |
| I-361 | A |
| I-362 | A |
| I-363 | A |
| I-364 | B |
| I-365 | B |
| I-366 | A |
| I-367 | A |

TABLE 95-continued

| Compound No. | EC50 |
|---|---|
| I-368 | A |
| I-369 | A |
| I-370 | A |
| I-371 | A |
| I-372 | A |
| I-373 | A |
| I-374 | A |
| I-375 | A |
| I-376 | A |
| I-377 | A |
| I-378 | A |
| I-379 | A |
| I-380 | A |
| I-381 | A |
| I-382 | A |
| I-383 | A |
| I-384 | A |
| I-385 | A |
| I-386 | A |
| I-387 | A |
| I-388 | A |
| I-389 | A |
| I-390 | A |
| I-391 | A |
| I-392 | A |
| I-393 | A |
| I-394 | A |
| I-395 | A |
| I-396 | A |
| I-397 | A |
| I-398 | A |
| I-399 | A |
| I-400 | A |
| I-401 | A |
| I-402 | A |
| I-403 | A |
| I-404 | A |
| I-405 | B |
| I-406 | C |
| I-407 | A |
| I-408 | A |
| I-409 | A |
| I-410 | A |
| I-411 | A |
| I-412 | A |
| I-413 | A |
| I-414 | A |
| I-415 | A |
| I-416 | A |
| I-417 | A |
| I-418 | A |
| I-419 | A |
| I-420 | A |
| I-421 | A |
| I-422 | A |
| I-423 | A |
| I-424 | A |
| I-425 | A |
| I-426 | A |
| I-427 | A |
| I-428 | A |
| I-429 | A |
| I-430 | A |
| I-431 | A |
| I-432 | A |
| I-433 | A |
| I-434 | A |
| I-435 | A |
| I-436 | A |
| I-437 | A |
| I-438 | A |
| I-439 | A |
| I-440 | A |
| I-441 | A |

TABLE 95-continued

| Compound No. | EC50 |
|---|---|
| I-442 | A |
| I-443 | B |
| I-444 | B |

Test Example 2: Inhibitory Activity Test Against SARS-CoV-2 3CL Proteases

Materials

Commercially Available Recombinant SARS-CoV-2 3CL Protease
Commercially Available Substrate Peptide Dabcyl-Lys-Thr-Ser-Ala-Val-Leu-Gln-Ser-Gly-Phe-Arg-Lys-Met-Glu(Edans)-$NH_2$ (SEQ ID NO: 1)

Internal Standard Peptide

Dabcyl-Lys-Thr-Ser-Ala-Val-Leu(13C6, 15N)-Gln (SEQ ID NO: 2)

Dabcyl-Lys-Thr-Ser-Ala-Val-Leu(13C6, 15N)-Gln can be synthesized with reference to documents (Atherton, E.; Sheppard, R. C., "In Solid Phase Peptide Synthesis, A Practical Approach", IRL Press at Oxford University Pres, 1989.; Bioorg. Med. Chem., Vol. 5, No. 9, 1997, pp. 1883-1891; and the like). An example will be shown below.

H-Lys-Thr-Ser-Ala-Val-Leu(13C6, 15N)-Glu(resin)-OαOtBu (the Lys-side chain is Boc-protected, the Thr-side chain is protected with a tert-butyl group, the Ser-side chain is protected with a tert-butyl group, the C-terminal OH of Glu is protected with a tert-butyl group, and the carboxylic acid of the Glu-side chain is condensed into the resin) is synthesized by Fmoc solid-phase synthesis using a Rink amide resin. Regarding the modification of the N-terminal Dabcyl group, 4-dimethylaminoazobenzene-4'-carboxylic acid (Dabcyl-OH) is condensed on the resin using EDC/HOBT. Final deprotection and cleavage from the resin are carried out by treatment with TFA/EDT=95:5. Thereafter, purification is performed by reverse phase HPLC.

RapidFire Cartridge C4 Type A

<Operational Procedure>

Preparation of Assay Buffer

In this test, an assay buffer consisting of 20 mM Tris-HCl, 1 mM EDTA, 10 mM DTT, and 0.01% BSA is used.

Dilution and Dispensing of Sample to be Tested

The sample to be tested is diluted in advance to an appropriate concentration with DMSO, and a 2- to 5-fold series of serial dilutions is prepared and then dispensed into a 384-well plate.

Addition of Enzyme and Substrate, and Enzymatic Reaction

To a prepared compound plate, 8 μM substrate, and a 6 or 0.6 nM enzyme solution are added, and incubation is carried out for 3 to 5 hours at room temperature. Thereafter, a reaction stopping solution (0.067 μM Internal Standard, 0.1% formic acid, and 10% or 25% acetonitrile) is added to stop the enzymatic reaction.

Measurement of Reaction Product

The plate in which the reaction has been completed is measured using RapidFire System 360 and a mass analyzer (Agilent, 6550 iFunnel Q-TOF), or RapidFire System 365 and a mass analyzer (Agilent, 6495C Triple Quadrupole). Solution A (75% isopropanol, 15% acetonitrile, 5 mM ammonium formate) and solution B (0.01% trifluoroacetic acid, 0.09% formic acid) are used as a mobile phase at the measurement.

The reaction product detected by the mass analyzer is calculated using RapidFire Integrator or an equivalent program capable of analysis and is taken as Product area value. Furthermore, the Internal Standard that has been detected at the same time is also calculated and is designated as Internal Standard area value.

<Calculation of Each Measurement Item Value>

Calculation of P/IS

The area values obtained in the previous items are calculated by the following formula, and P/IS is calculated.

P/IS=Product Area Value/Internal Standard Area Value

Calculation of 50% SARS-CoV-2 3CL Protease Inhibitory Concentration ($IC_{50}$)

When x denotes the logarithmic value of the compound concentration and y denotes % Inhibition, the inhibition curve is approximated by the following Logistic regression equation, and the value of x obtainable when y=50(%) is inputted is calculated as $IC_{50}$.

$$y = \min + (\max - \min)/\{1 + (X50/x)\hat{}\text{Hill}\}$$

$$\%\ \text{Inhibition} = \{1 - (\text{Sample} - \text{Control}(-))/\text{Control}(+) - \text{Control}(-))\} * 100$$

Control(−): the average of P/IS of enzyme inhibited condition wells

Control(+): the average of P/IS of DMSO control wells min: lower limit value of y-axis, max: upper limit value of y-axis, X50: x-coordinates of inflection point, Hill: slope of curve at midpoint between min and max The compounds of the present invention were tested essentially as described above. Results are shown below.

Incidentally, regarding the $IC_{50}$ value, a value of less than 0.01 μM is denoted by "A", a value of 0.01 μM or more and less than 0.1 μM is denoted by "B", and a value of 0.1 μM or more is denoted by "C".

Result

TABLE 96

| Compound No. | IC50 [μM] |
|---|---|
| I-014 | 0.0051 |
| I-053 | 0.032 |
| I-057 | 0.0098 |
| I-060 | 0.0047 |
| I-072 | 0.00066 |
| I-077 | 0.00036 |
| I-086 | 0.00070 |
| I-088 | 0.071 |
| I-142 | 0.00046 |
| I-165 | 3.8 |
| I-167 | 0.049 |
| I-182 | 0.00040 |
| I-185 | 0.027 |
| I-202 | 0.037 |
| I-205 | 0.00076 |
| I-208 | 0.0018 |
| I-230 | 0.00042 |
| I-232 | 0.00086 |
| I-234 | 0.0012 |
| I-238 | 0.00097 |
| I-239 | 0.00063 |
| I-249 | 0.00054 |
| I-250 | 0.00054 |
| I-257 | 0.00035 |

TABLE 96-continued

| Compound No. | IC50 [μM] |
|---|---|
| I-259 | 0.00045 |
| I-261 | 0.018 |
| I-282 | 2.8 |

TABLE 97

| Compound No. | IC50 |
|---|---|
| I-001 | C |
| I-002 | C |
| I-003 | C |
| I-004 | C |
| I-005 | C |
| I-006 | C |
| I-007 | C |
| I-008 | C |
| I-009 | C |
| I-010 | C |
| I-011 | B |
| I-012 | B |
| I-013 | B |
| I-015 | A |
| I-016 | A |
| I-017 | A |
| I-018 | A |
| I-019 | A |
| I-020 | A |
| I-021 | A |
| I-022 | A |
| I-023 | A |
| I-024 | C |
| I-025 | A |
| I-026 | A |
| I-027 | C |
| I-028 | A |
| I-029 | A |
| I-030 | A |
| I-031 | A |
| I-032 | A |
| I-033 | A |
| I-034 | B |
| I-035 | C |
| I-036 | C |
| I-037 | B |
| I-038 | B |
| I-039 | A |
| I-040 | A |
| I-041 | A |
| I-042 | A |
| I-043 | B |
| I-044 | A |
| I-045 | A |
| I-046 | C |
| I-047 | C |
| I-048 | C |
| I-049 | B |
| I-050 | B |
| I-051 | B |
| I-052 | B |
| I-054 | B |
| I-055 | B |
| I-056 | B |
| I-058 | A |
| I-059 | A |
| I-061 | A |
| I-062 | A |
| I-063 | A |
| I-064 | A |
| I-065 | A |
| I-066 | A |
| I-067 | A |
| I-068 | A |
| I-069 | A |

TABLE 97-continued

| Compound No. | IC50 |
|---|---|
| I-070 | A |
| I-071 | A |
| I-073 | A |
| I-074 | A |
| I-075 | A |
| I-076 | A |
| I-078 | A |
| I-079 | A |
| I-080 | A |
| I-081 | C |
| I-082 | A |
| I-083 | A |
| I-084 | A |
| I-085 | A |
| I-087 | A |
| I-089 | C |
| I-090 | B |
| I-092 | B |
| I-093 | B |
| I-094 | B |
| I-095 | B |
| I-096 | A |
| I-097 | A |
| I-098 | A |
| I-098 | A |
| I-100 | A |
| I-101 | A |
| I-102 | A |
| I-103 | A |
| I-104 | A |
| I-105 | A |
| I-106 | A |
| I-107 | A |
| I-108 | A |
| I-109 | A |
| I-110 | A |
| I-111 | A |
| I-112 | A |
| I-113 | A |
| I-114 | A |
| I-115 | A |
| I-116 | A |
| I-117 | A |
| I-118 | A |
| I-119 | A |
| I-120 | A |
| I-121 | C |
| I-122 | C |
| I-123 | C |
| I-124 | A |
| I-125 | C |
| I-126 | C |
| I-127 | C |
| I-128 | C |
| I-129 | B |
| I-130 | A |
| I-131 | A |
| I-132 | A |
| I-133 | B |
| I-134 | A |
| I-135 | B |
| I-136 | A |
| I-137 | B |
| I-138 | B |
| I-139 | B |
| I-140 | A |
| I-141 | B |
| I-143 | C |
| I-144 | C |
| I-145 | B |
| I-146 | A |
| I-147 | A |
| I-148 | A |
| I-149 | A |
| I-150 | A |
| I-151 | A |
| I-152 | A |

TABLE 97-continued

| Compound No. | IC50 |
|---|---|
| I-153 | A |
| I-154 | A |
| I-155 | C |
| I-156 | B |
| I-157 | C |
| I-158 | B |
| I-159 | B |
| I-160 | A |
| I-161 | A |
| I-162 | B |
| I-163 | A |
| I-164 | C |
| I-166 | C |
| I-168 | B |
| I-169 | B |
| I-170 | B |
| I-171 | A |
| I-172 | A |
| I-173 | A |
| I-174 | A |
| I-175 | A |
| I-176 | A |
| I-177 | A |
| I-178 | A |
| I-179 | A |
| I-180 | A |
| I-181 | A |
| I-183 | B |
| I-184 | C |
| I-186 | B |
| I-187 | B |
| I-188 | B |
| I-189 | A |
| I-190 | A |
| I-191 | A |
| I-192 | A |
| I-183 | A |
| 1.194 | A |
| I-195 | A |
| I-196 | A |
| I-197 | A |
| I-198 | A |
| I-199 | A |
| I-200 | B |
| I-201 | A |
| I-203 | B |
| I-204 | A |

TABLE 98

| Compound No. | IC50 |
|---|---|
| I-206 | A |
| I-207 | A |
| I-209 | A |
| I-210 | C |
| I-211 | A |
| I-212 | B |
| I-213 | A |
| I-214 | A |
| I-215 | A |
| I-216 | A |
| I-217 | A |
| I-218 | A |
| I-219 | B |
| I-220 | A |
| I-221 | C |
| I-222 | C |
| I-223 | A |
| I-224 | A |
| I-225 | A |
| I-226 | A |
| I-227 | A |

TABLE 98-continued

| Compound No. | IC50 |
|---|---|
| I-228 | A |
| I-229 | A |
| I-231 | A |
| I-233 | A |
| I-235 | A |
| I-236 | A |
| I-237 | A |
| I-240 | A |
| I-241 | A |
| I-242 | B |
| I-243 | C |
| I-244 | B |
| I-245 | B |
| I-246 | A |
| I-247 | A |
| I-248 | A |
| I-251 | A |
| I-252 | A |
| I-283 | A |
| I-254 | A |
| I-255 | A |
| I-256 | A |
| I-258 | A |
| I-260 | A |
| I-262 | A |
| I-263 | C |
| I-264 | A |
| I-265 | B |
| I-266 | B |
| I-267 | A |
| I-288 | A |
| I-289 | A |
| I-270 | A |
| I-271 | A |
| I-272 | A |
| I-273 | A |
| I-274 | A |
| I-275 | A |
| I-276 | A |
| I-277 | C |
| I-278 | A |
| I-279 | A |
| I-280 | A |
| I-281 | B |
| I-283 | C |
| I-284 | B |
| I-285 | C |
| I-286 | B |

TABLE 99

| Compound No. | IC50 |
|---|---|
| I-287 | A |
| I-288 | A |
| I-289 | A |
| I-290 | A |
| I-291 | B |
| I-292 | A |
| I-293 | A |
| I-294 | A |
| I-295 | A |
| I-296 | A |
| I-297 | A |
| I-298 | A |
| I-299 | A |
| I-300 | A |
| I-301 | A |
| I-302 | A |
| I-303 | A |
| I-304 | A |
| I-305 | A |
| I-306 | A |

TABLE 99-continued

| Compound No. | IC50 |
|---|---|
| I-307 | A |
| I-308 | A |
| I-309 | A |
| I-310 | A |
| I-311 | A |
| I-312 | A |
| I-313 | A |
| I-314 | A |
| I-315 | A |
| I-316 | A |
| I-317 | A |
| I-318 | A |
| I-319 | A |
| I-320 | A |
| I-321 | A |
| I-322 | A |
| I-323 | A |
| I-324 | A |
| I-325 | A |
| I-326 | A |
| I-327 | A |
| I-328 | B |
| I-329 | A |
| I-330 | A |
| I-331 | A |
| I-332 | A |
| I-333 | A |
| I-334 | A |
| I-335 | A |
| I-336 | A |
| I-337 | A |
| I-338 | A |
| I-339 | A |
| I-340 | A |
| I-341 | A |
| I-342 | A |
| I-343 | A |
| I-344 | B |
| I-345 | A |
| I-346 | A |
| I-347 | A |
| I-348 | B |
| I-349 | B |
| I-350 | A |
| I-351 | A |
| I-352 | A |
| I-353 | A |
| I-354 | A |
| I-355 | A |
| I-356 | A |
| I-357 | A |
| I-358 | A |
| I-359 | A |
| I-360 | A |
| I-361 | A |
| I-362 | A |
| I-363 | A |
| I-364 | C |
| I-365 | B |
| I-366 | A |
| I-367 | A |
| I-368 | A |
| I-369 | A |
| I-370 | A |
| I-371 | A |
| I-372 | A |
| I-373 | A |
| I-374 | A |
| I-375 | A |
| I-376 | A |
| I-377 | A |
| I-378 | A |
| I-379 | A |
| I-380 | A |
| I-381 | A |
| I-382 | A |
| I-383 | A |

TABLE 99-continued

| Compound No. | IC50 |
|---|---|
| I-384 | A |
| I-385 | A |
| I-386 | A |
| I-387 | A |
| I-388 | A |
| I-389 | A |
| I-390 | A |
| I-391 | A |
| I-392 | A |
| I-393 | A |
| I-394 | A |
| I-395 | A |
| I-396 | A |
| I-397 | A |
| I-398 | A |
| I-399 | A |
| I-400 | A |
| I-401 | A |
| I-402 | A |
| I-403 | A |
| I-404 | A |
| I-405 | C |
| I-406 | C |
| I-407 | B |
| I-408 | A |
| I-409 | A |
| I-410 | A |
| I-411 | A |
| I-412 | A |
| I-413 | A |
| I-414 | A |
| I-415 | A |
| I-416 | A |
| I-417 | A |
| I-418 | A |
| I-419 | A |
| I-420 | A |
| I-421 | A |
| I-422 | A |
| I-423 | A |
| I-424 | A |
| I-425 | A |
| I-426 | A |
| I-427 | A |
| I-428 | A |
| I-429 | A |
| I-430 | A |
| I-431 | A |
| I-432 | A |
| I-433 | A |
| I-434 | A |
| I-435 | B |
| I-436 | A |
| I-437 | A |
| I-438 | A |
| I-439 | A |
| I-440 | A |
| I-441 | B |
| I-442 | B |
| I-443 | C |
| I-444 | C |

The preparation examples shown below are only for illustrative purposes and are by no means intended to limit the scope of the invention.

The compound of the present invention can be administered as a pharmaceutical composition by any conventional route, particularly enterally, for example, orally, for example, in the form of a tablet or a capsule; parenterally, for example, in the form of an injectable preparation or a suspension; and topically, for example, in the form of a lotion, a gel, an ointment or a cream, or as a pharmaceutical composition in a transnasal form or a suppository form. A pharmaceutical composition comprising the compound of the present invention in a free form or in the form of a pharmaceutically acceptable salt together with at least one pharmaceutically acceptable carrier or diluent can be produced by a mixing, granulating, or coating method in a conventional manner. For example, the oral composition can be a tablet, a granular preparation, or a capsule, each containing an excipient, a disintegrating agent, a binder, a lubricating agent, and the like, as well as an active ingredient and the like. Furthermore, the composition for injection can be prepared as a solution or a suspension, may be sterilized, and may contain a preservative, a stabilizer, a buffering agent, and the like.

INDUSTRIAL APPLICABILITY

The compound according to the present invention has coronavirus 3CL protease inhibitory activity, and it is considered that the compound is useful as a therapeutic agent and/or a prophylactic agent for a disease or a condition associated with coronavirus 3CL proteases.

SEQUENCE LISTING

```
Sequence total quantity: 2
SEQ ID NO: 1           moltype = AA  length = 14
FEATURE                Location/Qualifiers
REGION                 1..14
                       note = Substrate Peptide
source                 1..14
                       mol_type = protein
                       organism = synthetic construct
SEQUENCE: 1
KTSAVLQSGF RKME                                           14

SEQ ID NO: 2           moltype = AA  length = 7
FEATURE                Location/Qualifiers
REGION                 1..7
                       note = Internal Standard Peptide
source                 1..7
                       mol_type = protein
                       organism = synthetic construct
SEQUENCE: 2
KTSAVLQ                                                   7
```

The invention claimed is:
1. A compound selected from the group consisting of:
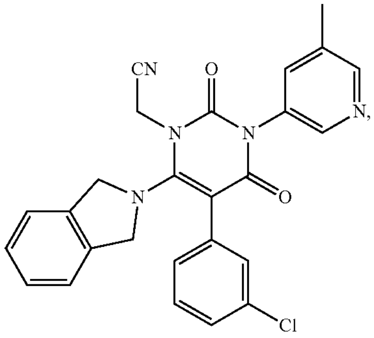
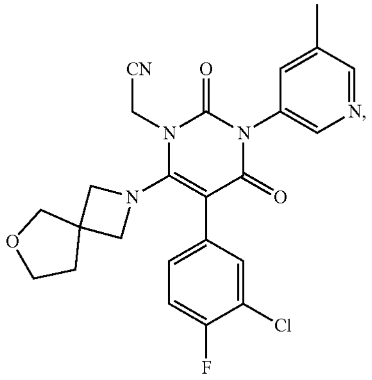
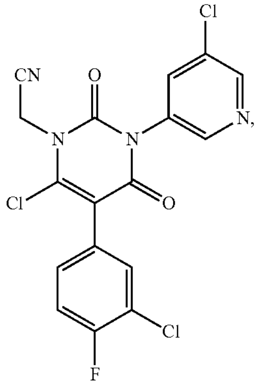
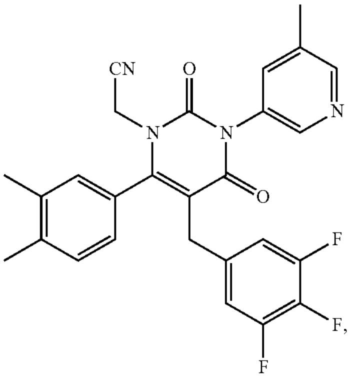
-continued
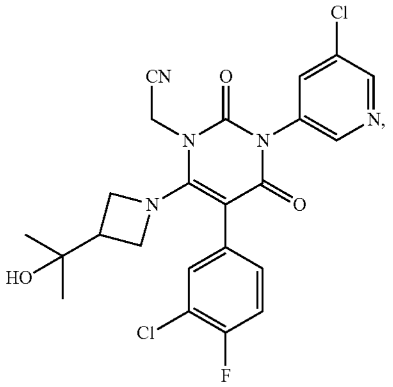
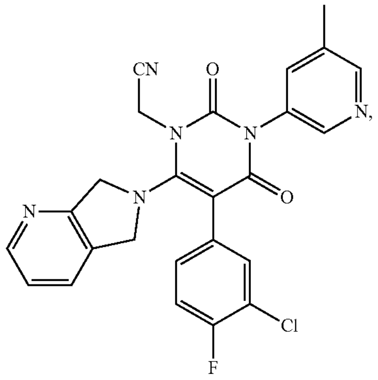
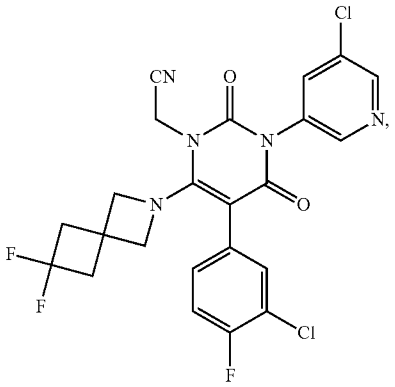 [SMILES: N#CCn1c(N2CC3(C2)CC(F)(F)C3)c(-c2ccc(F)c(Cl)c2)c(=O)n(-c2cncc(Cl)c2)c1=O]
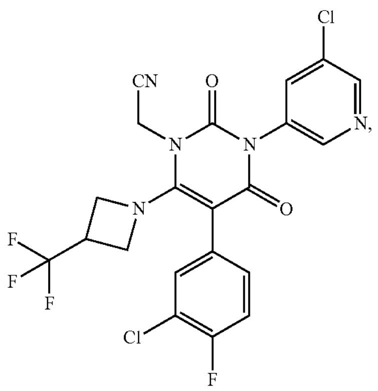

-continued
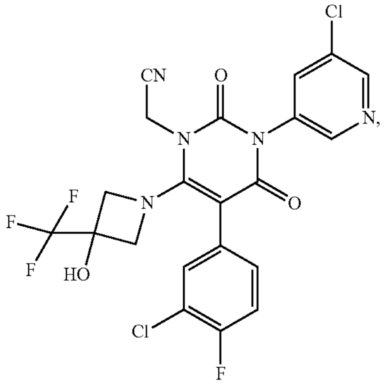
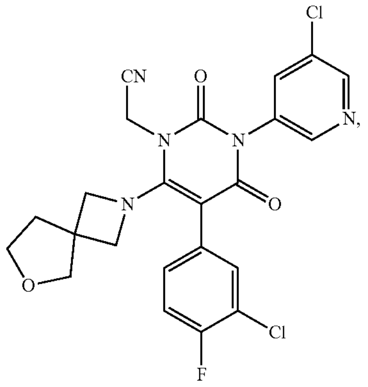
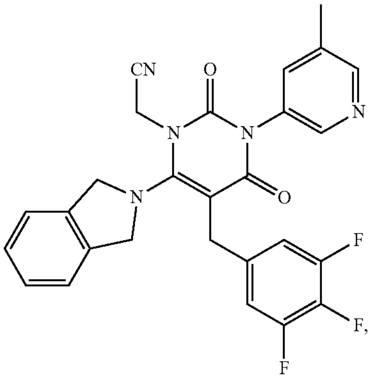
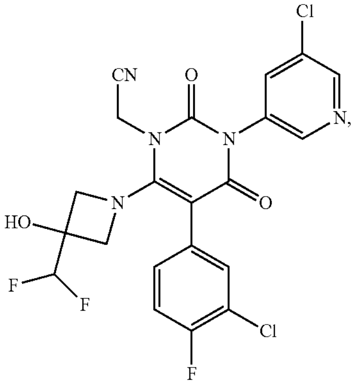
-continued
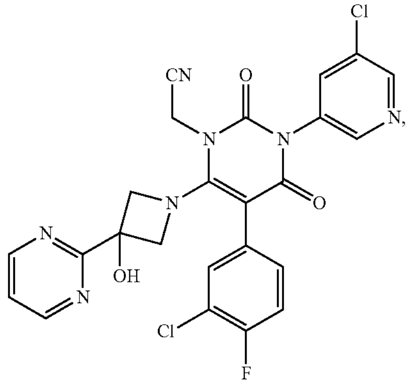
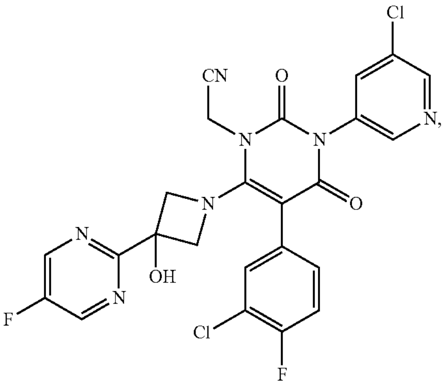
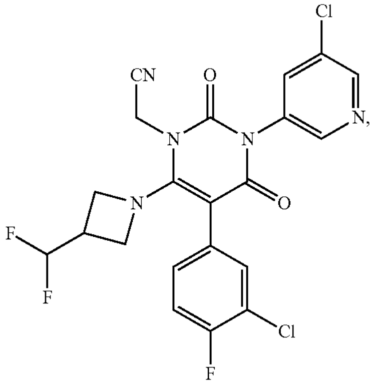
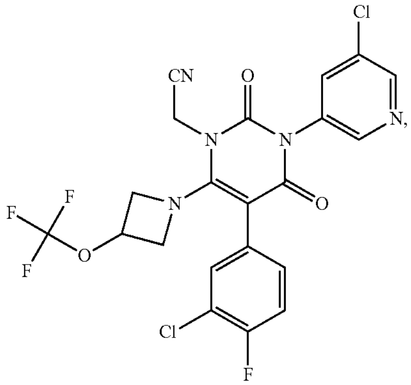

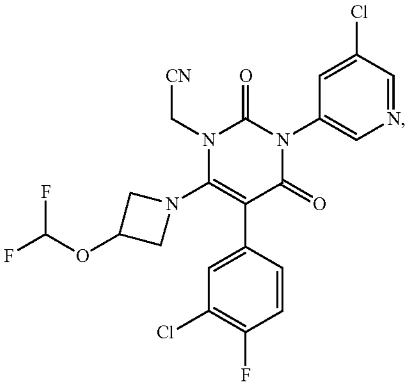
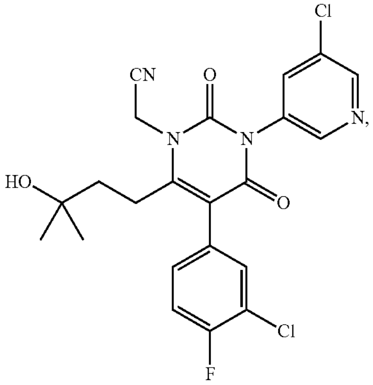
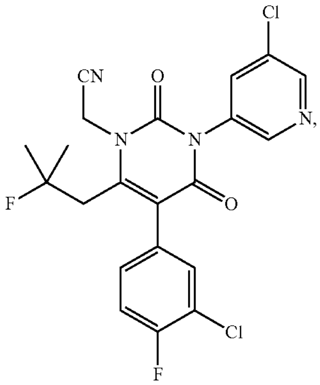
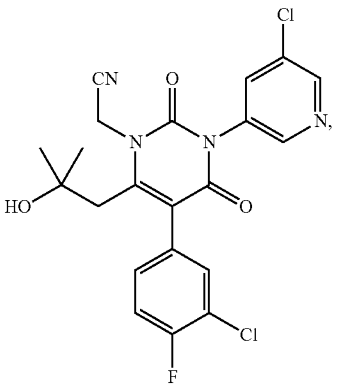
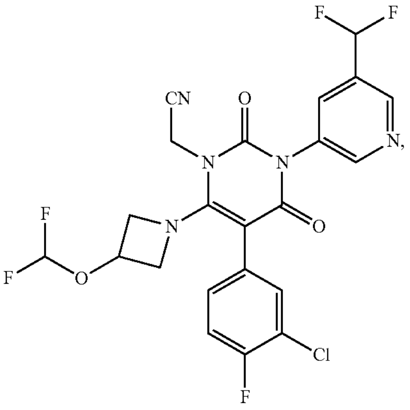
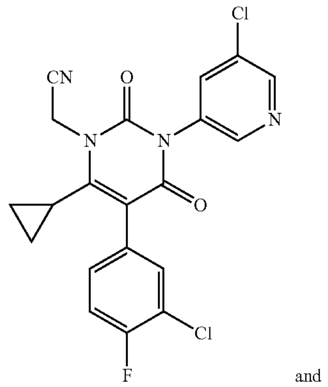
and
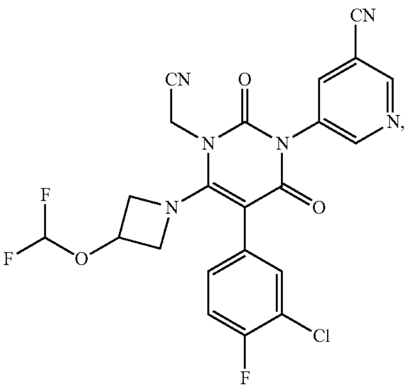
or a pharmaceutically acceptable salt thereof.

2. The compound according to claim 1 represented by the formula,

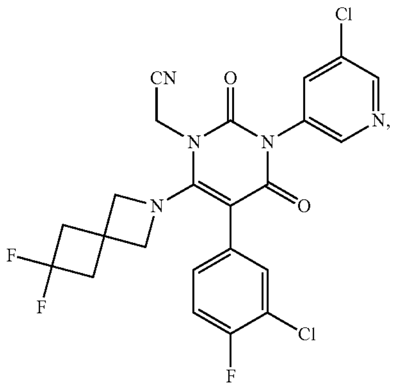

or a pharmaceutically acceptable salt thereof.

3. A method for treating a coronavirus selected from the group consisting of HCoV-229E, HCoV-NL63, HCoV-HKU1, HCoV-OC43, SARS-COV, MERS-CoV, and SARS-COV-2, the method comprising administering a therapeutically effective amount of a compound or a pharmaceutically acceptable salt thereof according to claim 1 to a human in need thereof.

4. A method for treating a coronavirus selected from the group consisting of HCoV-229E, HCoV-NL63, HCoV-HKU1, HCoV-OC43, SARS-COV, MERS-CoV, and SARS-COV-2, the method comprising administering a therapeutically effective amount of the compound or a pharmaceutically acceptable salt thereof according to claim 2 to a human in need thereof.

5. A pharmaceutical composition comprising the compound or a pharmaceutically acceptable salt thereof according to claim 1, and a pharmaceutically acceptable carrier or diluent.

6. A pharmaceutical composition comprising the compound or a pharmaceutically acceptable salt thereof according to claim 2, and a pharmaceutically acceptable carrier or diluent.

* * * * *